US009925621B2

(12) United States Patent
Sahler et al.

(10) Patent No.: US 9,925,621 B2
(45) Date of Patent: Mar. 27, 2018

(54) INTRAOCULAR LENS (IOL) FABRICATION SYSTEM AND METHOD

(71) Applicant: LASER LENS, LLC, Dallas, TX (US)

(72) Inventors: Ruth Sahler, Irvine, CA (US); Josef F. Bille, Heidelberg (DE)

(73) Assignee: PERFECT IP, LLP, Dallas, TX (US)

( * ) Notice: Subject to any disclaimer, the term of this patent is extended or adjusted under 35 U.S.C. 154(b) by 320 days.

(21) Appl. No.: 14/928,798

(22) Filed: Oct. 30, 2015

(65) Prior Publication Data

US 2016/0074967 A1 Mar. 17, 2016

Related U.S. Application Data

(60) Continuation-in-part of application No. 14/275,372, filed on May 12, 2014, now Pat. No. 9,186,242,
(Continued)

(51) Int. Cl.
*B23K 26/06* (2014.01)
*A61F 2/16* (2006.01)
(Continued)

(52) U.S. Cl.
CPC .......... *B23K 26/0648* (2013.01); *A61F 2/16* (2013.01); *B23K 26/0624* (2015.10);
(Continued)

(58) Field of Classification Search
CPC .......... B23K 26/0648; B23K 26/0624; B23K 26/0626; B23K 26/361; A61F 2/16; B29D 11/00461; B29D 11/023
See application file for complete search history.

(56) References Cited

U.S. PATENT DOCUMENTS

| 5,100,689 A | 3/1992 | Goldberg et al. |
| 5,256,853 A | 10/1993 | McIntyre |

(Continued)

FOREIGN PATENT DOCUMENTS

| CN | 101058403 A | 10/2007 |
| CN | 100534892 C | 9/2009 |
| CN | 101563212 A | 10/2009 |

OTHER PUBLICATIONS

ISA/US, International Search Report and Written Opinion for PCT/US2013/064098 dated Dec. 16, 2013.
(Continued)

*Primary Examiner* — Mathieu Vargot
(74) *Attorney, Agent, or Firm* — David W. Carstens; Carstens & Cahoon, LLP

(57) ABSTRACT

A system/method allowing intraocular lens (IOL) fabrication using a femtosecond laser is disclosed. The system and method generate a stream of pulses at a rate of at least 1 million pulses per second and a pulse length of 300 femtoseconds or less to sculpt a polymeric material blank (PMB) to form an IOL. The high repetition rate and short pulse length combine to permit IOL fabrication in less than 10 minutes. During this fabrication procedure a lens may be formed within the IOL by incorporating a refractive index shaping (RIS) structure within the IOL. Additionally, IOL haptics may be formed during this IOL formation process. This combination of physical feature generation and RIS structure generation permits per-patient customization of the IOL as it relates to sphere, cylinder, asphericity, multifocality, and/or higher optical aberrations (HOAs).

100 Claims, 128 Drawing Sheets

Related U.S. Application Data which is a division of application No. 13/843,464, filed on Mar. 15, 2013, now Pat. No. 9,023,257.

(60) Provisional application No. 61/726,383, filed on Nov. 14, 2012.

(51) Int. Cl.

| | |
|---|---|
| *B23K 26/0622* | (2014.01) |
| *B29D 11/00* | (2006.01) |
| *B29D 11/02* | (2006.01) |
| *B23K 26/361* | (2014.01) |
| *B29L 11/00* | (2006.01) |

(52) U.S. Cl.
CPC ........ *B23K 26/0626* (2013.01); *B23K 26/361* (2015.10); *B29D 11/00461* (2013.01); *B29D 11/023* (2013.01); *A61F 2/1613* (2013.01); *A61F 2002/1681* (2013.01); *A61F 2240/002* (2013.01); *B29L 2011/0016* (2013.01)

(56) References Cited

U.S. PATENT DOCUMENTS

| | | | |
|---|---|---|---|
| 5,260,093 | A | 11/1993 | Kamel et al. |
| 6,011,082 | A | 1/2000 | Wang et al. |
| 6,086,204 | A | 7/2000 | Magnante |
| 7,789,910 | B2 | 9/2010 | Knox et al. |
| 8,115,792 | B2 | 2/2012 | Petsch et al. |
| 8,337,553 | B2 | 12/2012 | Knox et al. |
| 9,023,257 | B2 | 5/2015 | Sahler et al. |
| 9,107,746 | B2 | 8/2015 | Sahler et al. |
| 9,186,242 | B2 | 11/2015 | Sahler et al. |
| 2002/0117624 | A1 | 8/2002 | Katayama et al. |
| 2006/0092519 | A1 | 5/2006 | Hasei |
| 2006/0213880 | A1 | 9/2006 | Tanaka et al. |
| 2008/0001320 | A1 | 1/2008 | Knox et al. |
| 2009/0143858 | A1 | 6/2009 | Knox et al. |
| 2010/0228345 | A1 | 9/2010 | Bille |
| 2010/0294749 | A1 | 11/2010 | Kempe et al. |
| 2011/0118836 | A1 | 5/2011 | Jain et al. |
| 2012/0310340 | A1 | 12/2012 | Knox et al. |
| 2013/0268072 | A1 | 10/2013 | Smith et al. |
| 2013/0289543 | A1 | 10/2013 | Mordaunt |

OTHER PUBLICATIONS

Abbasi et al., "Bulk and surface modification of silicone rubber for biomedical applications". Polym Int 51:882-888 (2002)—the entire document.

Correa et al., "Femtosecond Laser in Polymeric Materials: Microfabrication of Doped Structures and Micromachining". IEEE Journal of Selected Topics in Quantom Electronics, vol. 18, No. 1, Jan./Feb. 2012; p. 176-186; p. 176, col. 2, para 1; p. 177, col. 1, para 1-2; p. 177, col. 2, para 4; p. 178, col. 1, para 2-3; p. 178, col. 2, para 2; p. 178, col. 2, para 4; p. 181, col. 1, para 1; figres 2, 3 and 5; abstract.

Introduction to Modulation Transfer Function, Edmund Optics, pp. 1-5, downloaded Oct. 2, 2015, http://www. edmundoptics.com/techical-resources-center/optics/modulation-transfer-function/.

Li Ding, et al., "Large enhancement of femtosecond laser mircromachining speed in dye-doped hydrogel polymers"; Dec. 22, 2008 / vol. 16, No. 26/Optics Express 21914.

Objektive, Ernst Leitz Wetzlar GmbH, 1985.

Oujja et al., "Three Dimensional Microstructuring of Biopolymers by Femtosecond Laser Irradiation". Applied Physics Letters 95, 263730 (Dec. 2009), p. 1-3; p. 1, col.

P. J. Scully, et al., "Femtosecond laser irradiation of polymethylmethacrylte for refractive index gratings"; Journal of Optics A: Pue Appl Opt. 5 (2003) S92-S96.

Schaffer et al., Micromachining bulk glass by use of femtosecond laser pulses with nanojoule energy:. Optic Letters, vol. 26, No. 2, Jan. 15, 2001—the entire document.

Wang et al., "Polymer Hydrophilicity and Hydrophobicity Inducted by Femtosecond Laser". Applied Physics Letters 95, 111110 (2009), p. 1-3; p. 2, col. 2, para 2-3.

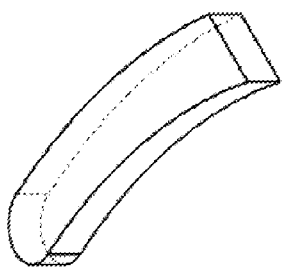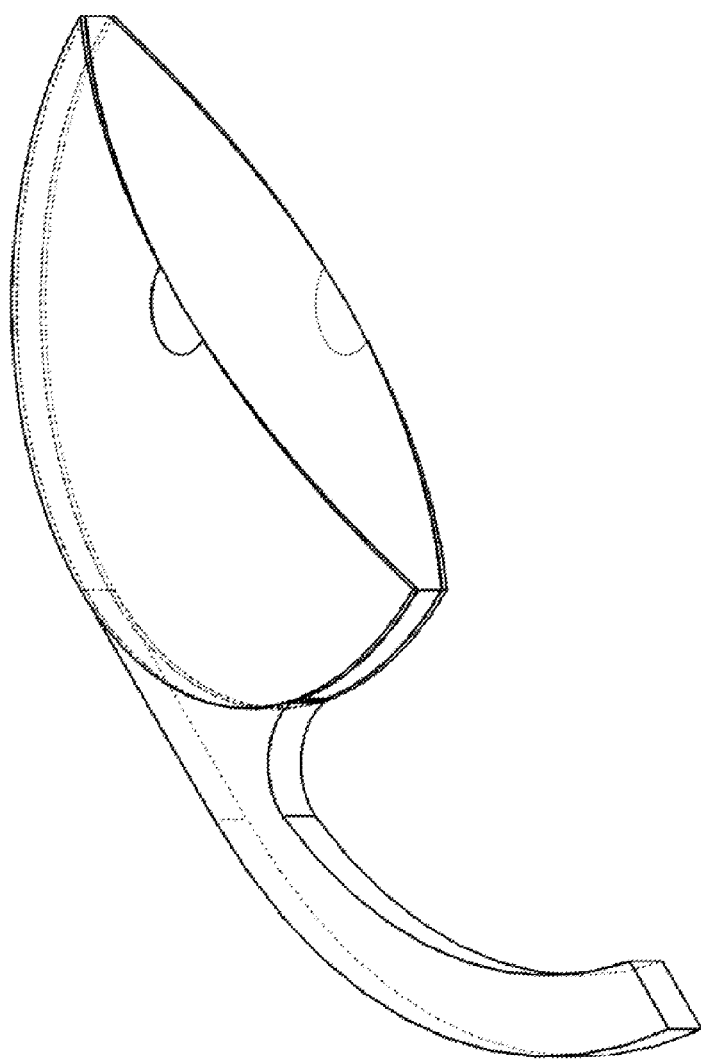
FIG. 118
11800

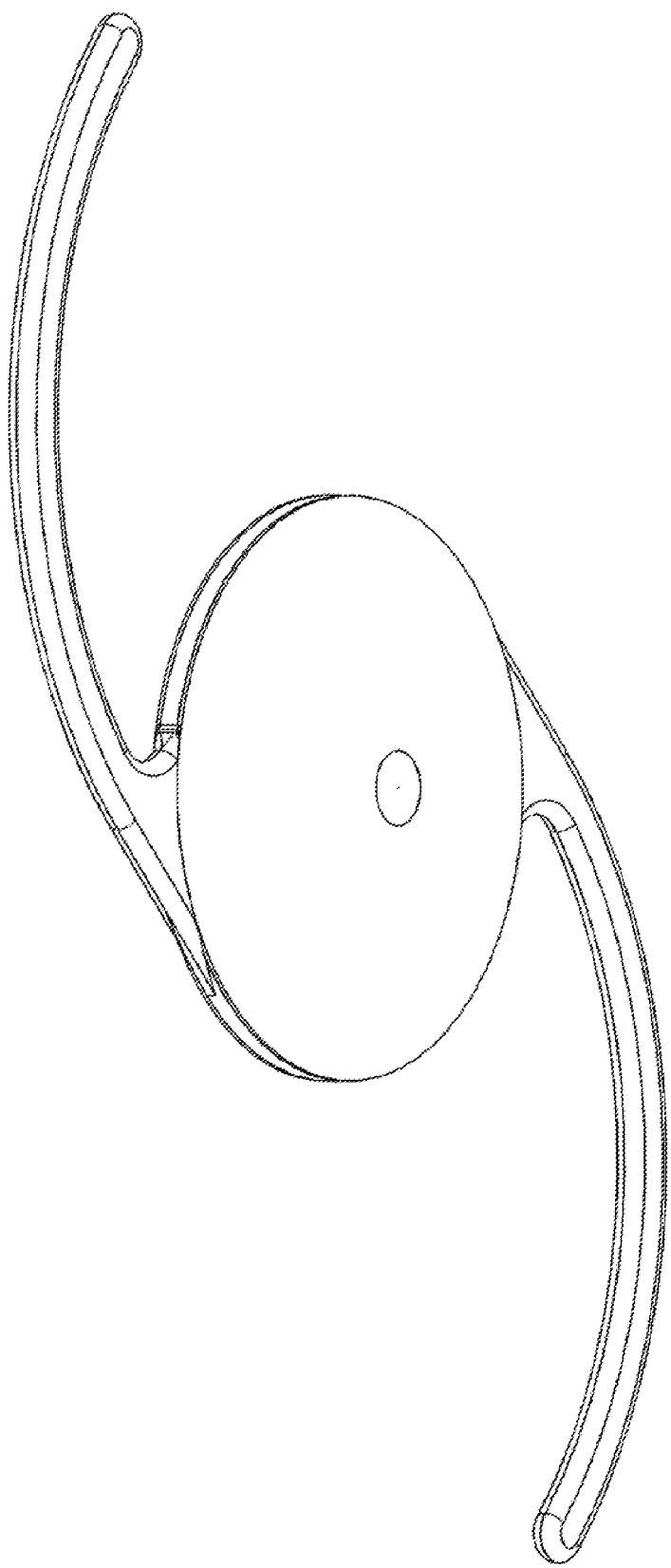

INTRAOCULAR LENS (IOL) FABRICATION SYSTEM AND METHOD

CROSS REFERENCE TO RELATED APPLICATIONS

Continuation-in-Part Patent Application

This is a continuation-in-part (CIP) patent application of and incorporates by reference United States Utility patent application for HYDROPHILICITY ALTERATION SYSTEM AND METHOD by inventors Ruth (nmn) Sahler, Stephen Q. Zhou, and Josef F. Bille, filed electronically with the USPTO on May 12, 2014, with Ser. No. 14/275,372, EFS ID 19007591, confirmation number 7435, and issued on Nov. 17, 2015 as U.S. Pat. No. 9,186,242.

UTILITY PATENT APPLICATIONS

United States Utility patent application for HYDROPHILICITY ALTERATION SYSTEM AND METHOD by inventors Ruth (nmn) Sahler, Stephen Q. Zhou, and Josef F. Bille, filed electronically with the USPTO on May 12, 2014, with Ser. No. 14/275,372, EFS ID 19007591, confirmation number 7435, issued on Nov. 17, 2015 as U.S. Pat. No. 9,186,242 is a divisional patent application (DPA) of and incorporates by reference United States Utility patent application for HYDROPHILICITY ALTERATION SYSTEM AND METHOD by inventors Ruth (nmn) Sahler, Stephen Q. Zhou, and Josef F. Bille, filed electronically with the USPTO on May 15, 2013, with Ser. No. 13/843,464, EFS ID 15272084, confirmation number 4167, now U.S. Pat. No. 9,023,257.

UTILITY PATENT APPLICATIONS

This application claims benefit under 35 U.S.C. §120 and incorporates by reference United States Utility patent application for HYDROPHILICITY ALTERATION SYSTEM AND METHOD by inventors Ruth (nmn) Sahler, Stephen Q. Zhou, and Josef F. Bille, filed electronically with the USPTO on May 12, 2014, with Ser. No. 14/275,372, EFS ID 19007591, confirmation number 7435, and issued on Nov. 17, 2015 as U.S. Pat. No. 9,186,242.

This application claims benefit under 35 U.S.C. §120 and incorporates by reference United States Utility patent application for HYDROPHILICITY ALTERATION SYSTEM AND METHOD by inventors Ruth (nmn) Sahler, Stephen Q. Zhou, and Josef F. Bille, filed electronically with the USPTO on Mar. 15, 2013, with Ser. No. 13/843,464, EFS ID 15272084, confirmation number 4167, now U.S. Pat. No. 9,023,257.

PROVISIONAL PATENT APPLICATIONS

This application claims benefit under 35 U.S.C. §119 and incorporates by reference United States Provisional patent application for HYDROPHILICITY ALTERATION SYSTEM AND METHOD by inventors Ruth (nmn) Sahler, Stephen Q. Zhou, and Josef F. Bille, filed electronically with the USPTO on Nov. 14, 2012, with Ser. No. 61/726,383, EFS ID 14230078, confirmation number 5116.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates to the creation of intraocular lenses (IOLs) from a polymeric material blank (PMB) using laser cutting of surface and internal features of the PMB. The use and control of a femtosecond laser in this context permits automation of this process to allow formation of customized lens structures including haptics.

PRIOR ART AND BACKGROUND OF THE INVENTION

There are two common techniques used for forming intraocular lenses. One technique is molding, where an optical polymeric material is formed into a desired shape having a predetermined dioptic power. These lenses are available in steps of about 0.5 diopter power. A problem with the molding technique is it is a very expensive way to make a customized lens, and thus for most patients, only an approximate approach to clear vision can be obtained.

The other technique used is lathing and milling, where a disc shaped blank is ground to a desired shape. Due to the properties of the materials used for intraocular lenses, it is preferable to machine lenses at a reduced temperature such as −10° F. A problem with lathing and milling is that optical properties of a lens at −10° F. may be different than the optical properties of the lens at body temperature, and thus such a lens only approximates optimal vision. In addition, as the lens warms it absorbs moisture and dimensions of the lens may change, thus altering the diopter power of the lens.

Accordingly, there is a need for a system and method for forming intraocular lenses that overcomes the disadvantages of prior art manufacturing techniques, and also allows for customization of lenses to provide multiple corrective features to approach optimum vision such as toricity, asphericity, multifocality, and the correction of higher order optical aberrations (HOAs).

DEFICIENCIES IN THE PRIOR ART

While the prior art as detailed above can theoretically be used to form optical lenses, it suffers from the following deficiencies:
  Prior art IOL formation systems and methods generate lenses with discrete steps of diopter that are not fully corrective of patient sight deficiencies.

Prior art IOL formation systems and methods fail to correct for temperature differences in the manufacturing process.

Prior art IOL formation systems and methods fail to correct for toricity, asphericity, and multifocality irregularities in patient vision.

Prior art IOL formation systems and methods fail to correct for higher order optical aberrations (HOAs) in patient vision.

To date the prior art has not fully addressed these deficiencies.

OBJECTIVES OF THE INVENTION

Accordingly, the objectives of the present invention are (among others) to circumvent the deficiencies in the prior art and affect the following objectives:

(1) provide for a system and method that generate lenses with linear ranges of diopter that are fully corrective of patient sight deficiencies;

(2) provide for a system and method that correct for temperature differences in the manufacturing process;

(3) provide a system and method that correct for toricity, asphericity, and multifocality irregularities in patient vision; and (4) provide a system and method that correct higher order optical aberrations (HOAs) in patient vision.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention pertains to a system, method, and product-by-process wherein a pulsed laser system is used to fabricate a polymeric material blank (PMB) into an intraocular lens (IOL).

The invention generally describes an apparatus and method to generate a stream of pulses having a repetition rate of at least 0.1 million pulses per second and a pulse length (duration) of less than 400 femtoseconds, that is configured to scan and focus the stream of pulses to an output light pattern and sculpt an optical polymeric material in the form of an IOL. This optical fabrication procedure uses a high number of pulses to complete the fabrication procedure in a few seconds (e.g., 7.5 million pulses in less than 5 seconds with an estimated cutting time to processing time to be ¼ cutting and ¾ processing). Some invention embodiments create an intraocular lens (IOL), including the optical fabrication of associated haptics. Other embodiments additionally incorporate a Refractive Index Shaping (RIS) lens inside the intraocular lens (IOL), before sculpting the intraocular lens (IOL) exterior. The total optical manufacturing procedure allows for the customization of the IOL, as related to sphere, cylinder, asphericity, multifocality, and Higher Optical Aberrations (HOAs).

The present invention incorporates a high-repetition rate femtosecond laser coupled to a high-speed scanner, which results in an exquisitely fine granularity in forming cuts inside a polymeric material, and an adequately short duration of an optical manufacturing procedure of intraocular lenses (IOLs).

In some embodiments, the individual spots are created in a pattern, where the temporal separation of spots is adjusted (by varying the pulse repetition rate) in order to comply with limitations in commercially available scanning components (for example, galvanometrically driven scanning mirrors). This is of importance in assuring the quality of optical cuts sculpting the central cap of a lenticule inside a polymeric material blank (PMB). A lenticule is a disc-shaped piece of corneal tissue or a piece of synthetic material manufactured to produce a given curvature and thickness. It is implanted into or on top of the cornea to change its anterior curvature.

In other embodiments, the optical sculpting procedure is augmented by an additional optical procedure to modify the refractive properties of an IOL, by creating a Refractive Index Shaping (RIS) lens inside the IOL, thus customizing the IOL by Modulation Transfer Function (MTF) engineering.

BRIEF DESCRIPTION OF THE DRAWINGS

For a fuller understanding of the advantages provided by the invention, reference should be made to the following detailed description together with the accompanying drawings wherein:

Figure 60:
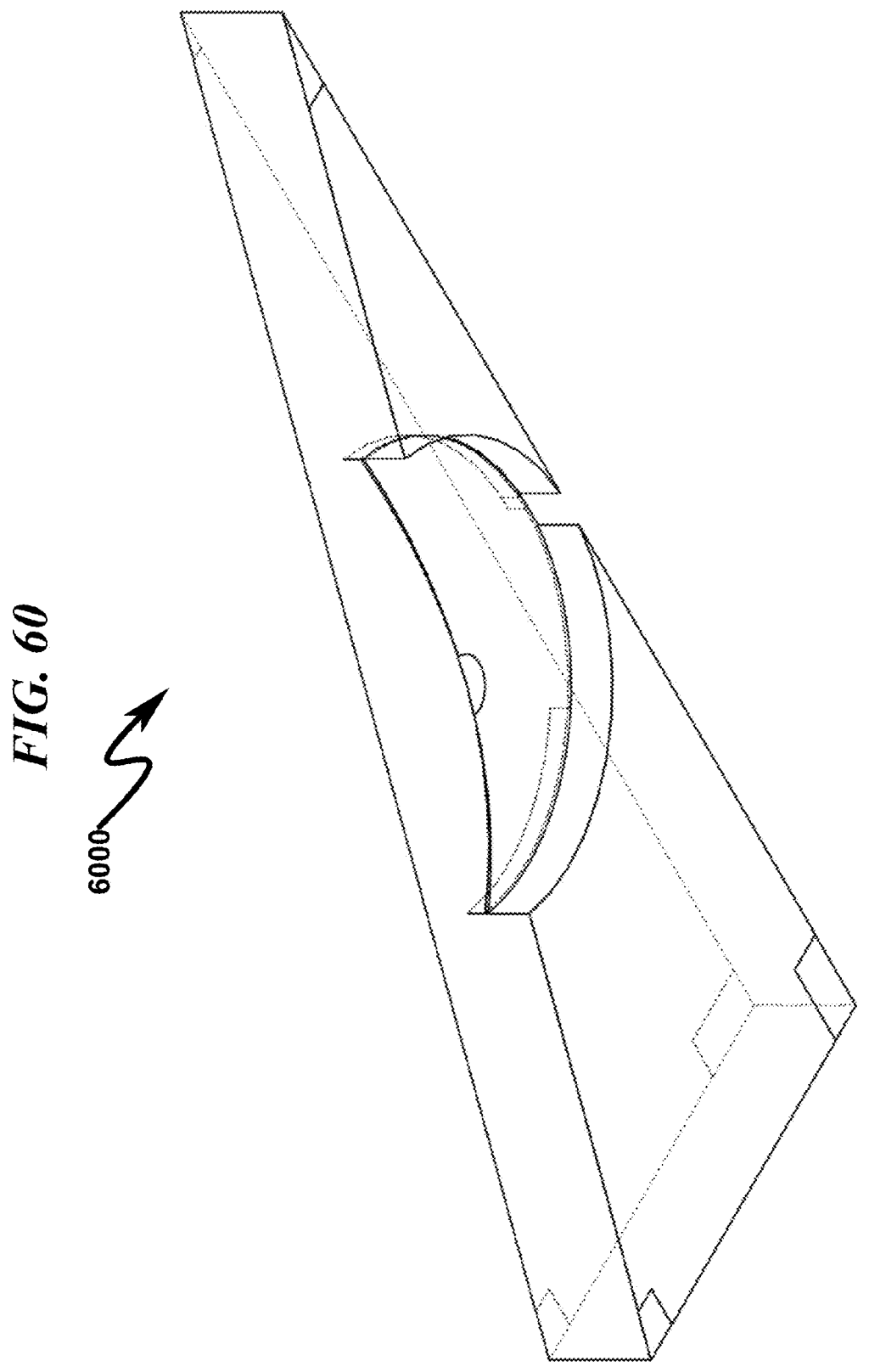

FIG. 60 illustrates a bottom right perspective diagonal section view of removal of the posterior lens cutout in an exemplary present invention IOL fabrication sequence formed using a PMS;

FIG. 118 illustrates a top left perspective front section view depicting removal of the right haptic interior PMS material in an exemplary present invention IOL fabrication sequence formed using a PMS;

FIG. 119 illustrates a top left perspective right section view depicting removal of the right haptic interior PMS material in an exemplary present invention IOL fabrication sequence formed using a PMS;

FIG. 120 illustrates a top left perspective diagonal section view depicting removal of the right haptic interior PMS material in an exemplary present invention IOL fabrication sequence formed using a PMS;

FIG. 121 illustrates a top front perspective view of an exemplary IOL fabrication step depicting additional edge processing of the left posterior haptic;

FIG. 122 illustrates a bottom front perspective view of an exemplary IOL fabrication step depicting additional edge processing of the left posterior haptic;

FIG. 123 illustrates a top front perspective view of an exemplary IOL fabrication step depicting additional edge processing of the left anterior haptic;

FIG. 124 illustrates a bottom front perspective view of an exemplary IOL fabrication step depicting additional edge processing of the left anterior haptic;

FIG. 125 illustrates a top front perspective view of an exemplary IOL fabrication step depicting additional edge processing of the right posterior haptic;

FIG. 126 illustrates a bottom front perspective view of an exemplary IOL fabrication step depicting additional edge processing of the right posterior haptic;

FIG. 127 illustrates a top front perspective view of an exemplary IOL fabrication step depicting additional edge processing of the right anterior haptic; and FIG. 128 illustrates a bottom front perspective view of an exemplary IOL fabrication step depicting additional edge processing of the right anterior haptic.

DESCRIPTION OF THE PRESENTLY PREFERRED EXEMPLARY EMBODIMENTS

Figure 1:
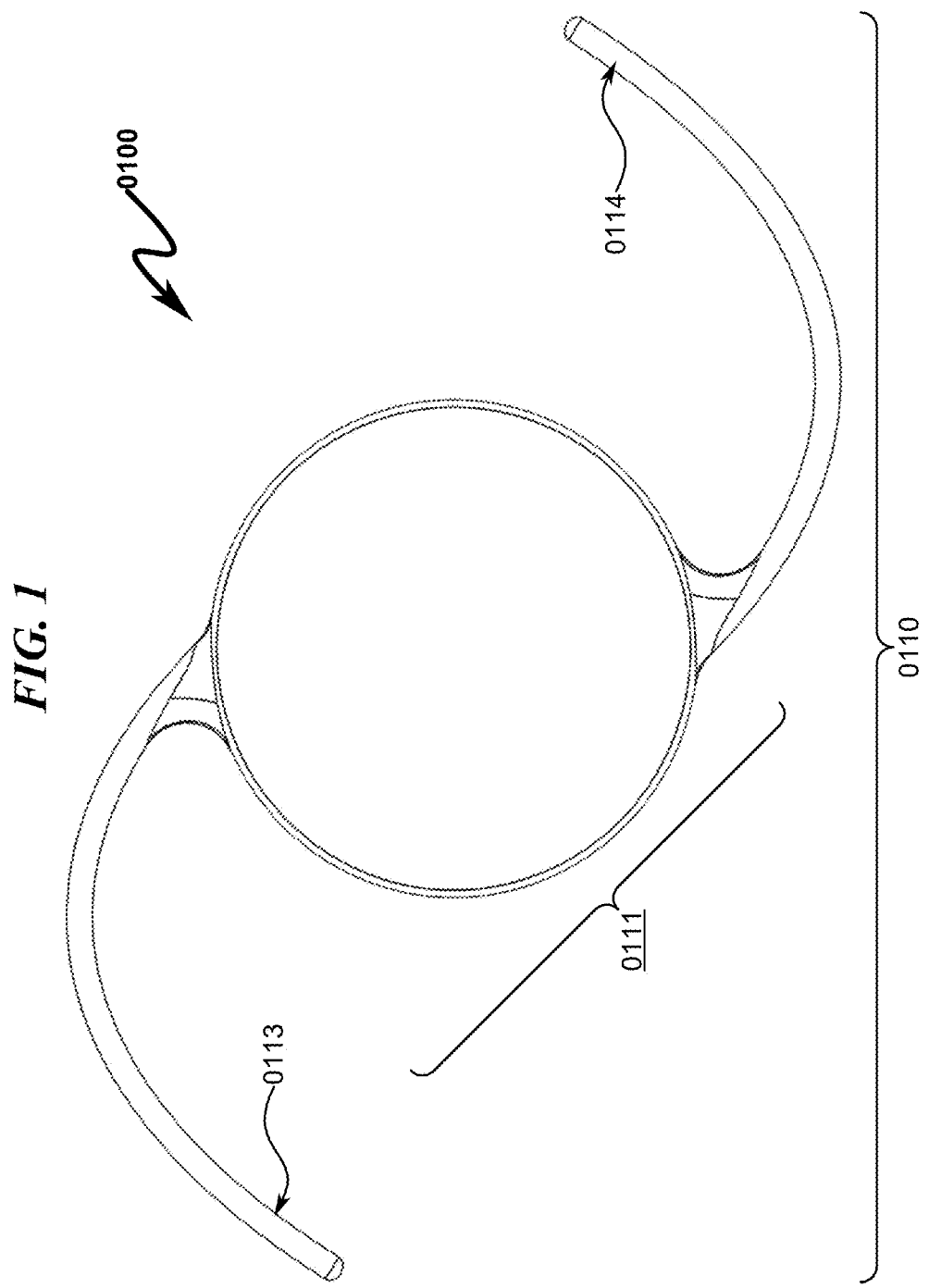
FIG. 1 illustrates a top view of an exemplary intraocular lens (IOL) with simplified haptics.
Figure 2:
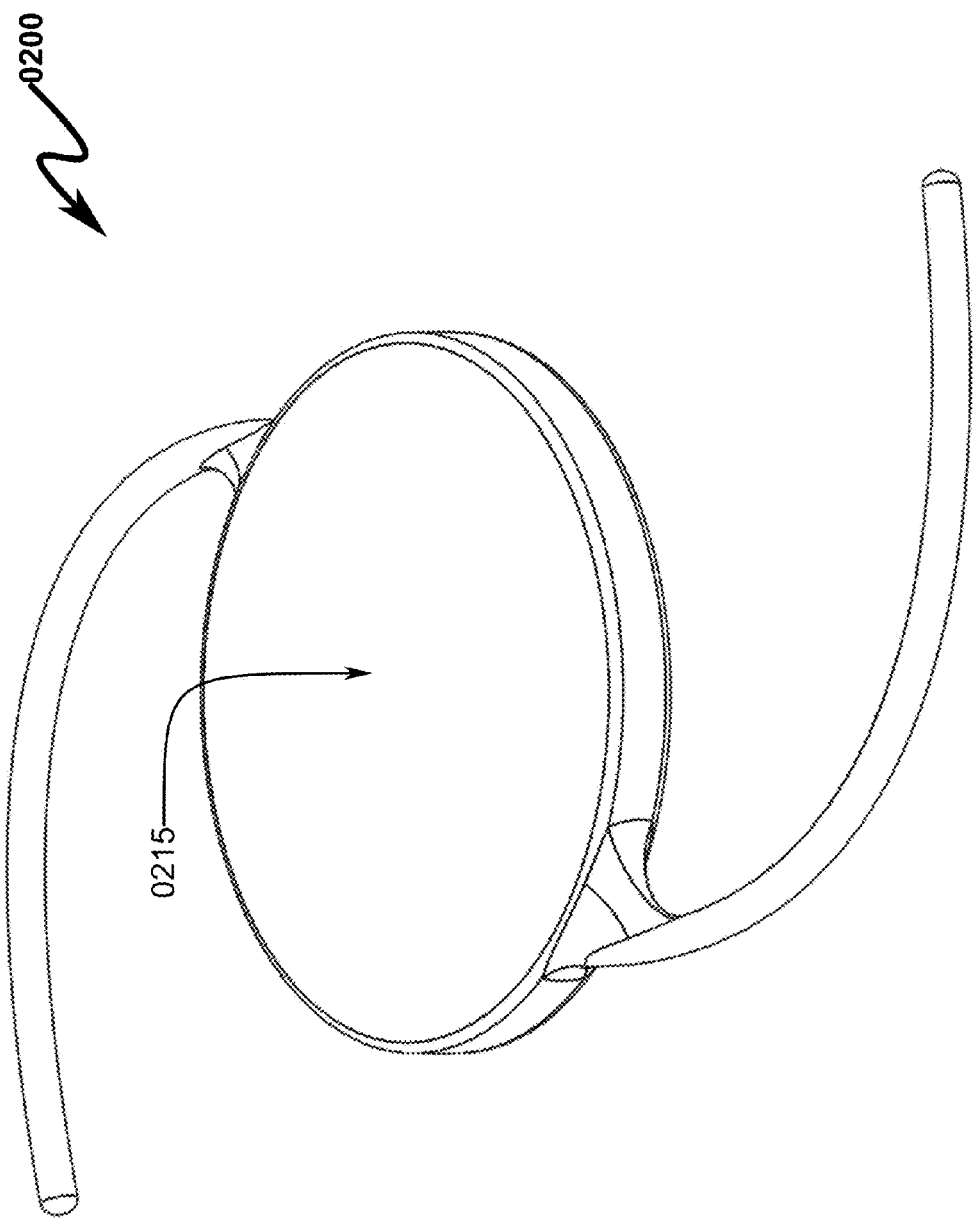
FIG. 2 illustrates a bottom view of an exemplary intraocular lens (IOL) with simplified haptics.
Figure 3:
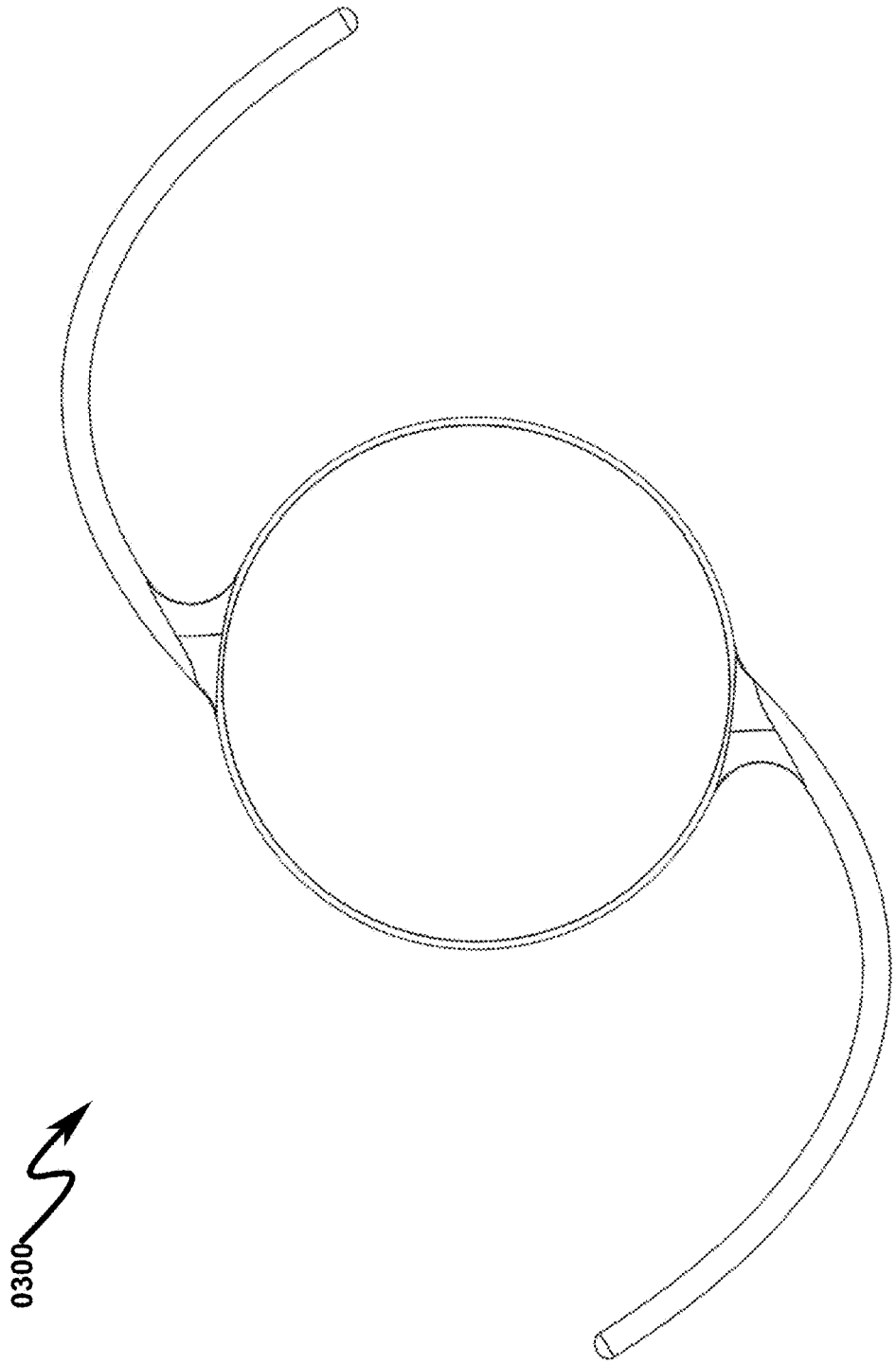
FIG. 3 illustrates a front view of an exemplary intraocular lens (IOL) with simplified haptics.
Figure 4:
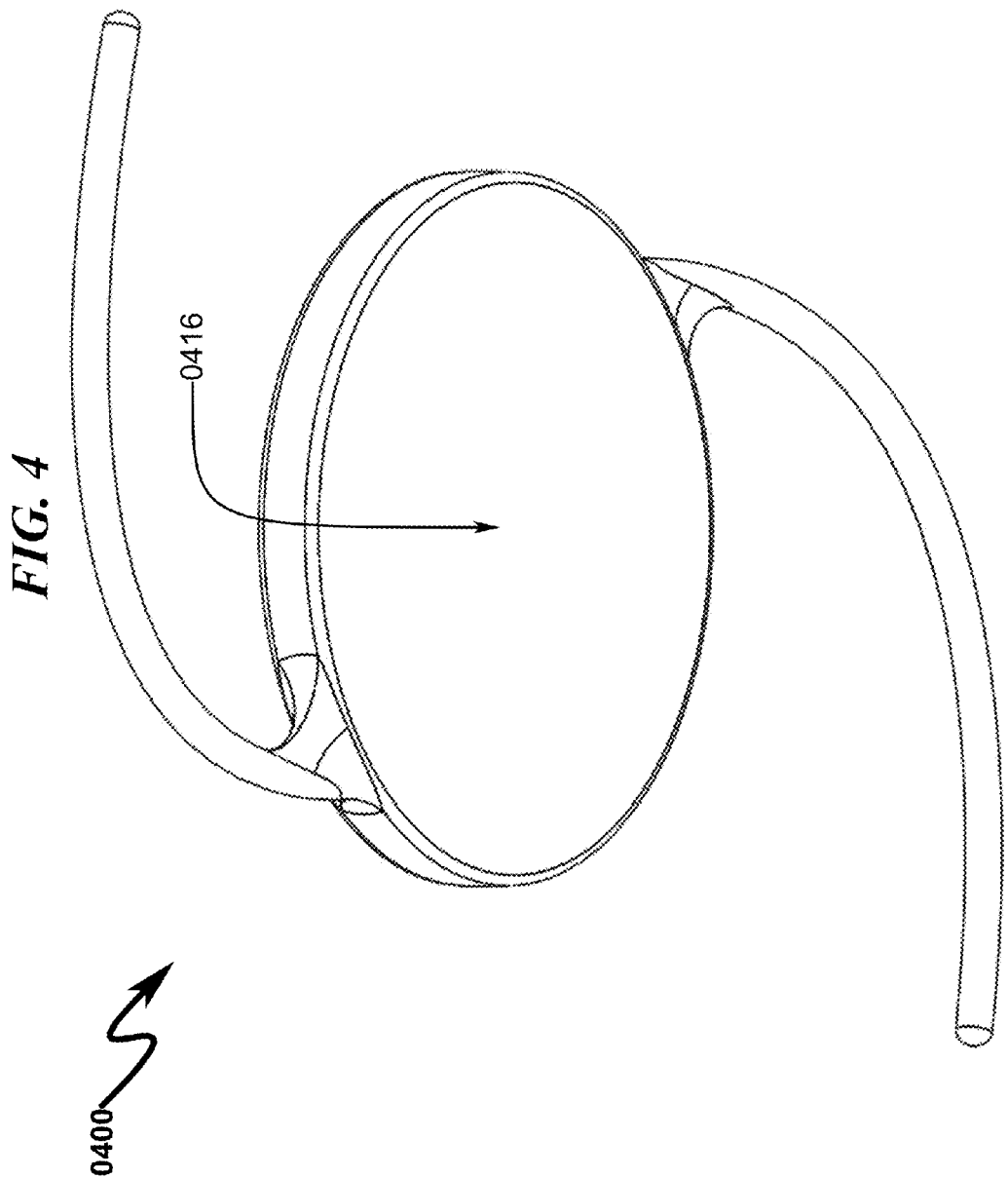
FIG. 4 illustrates a side view of an exemplary intraocular lens (IOL) with simplified haptics.
Figure 5:
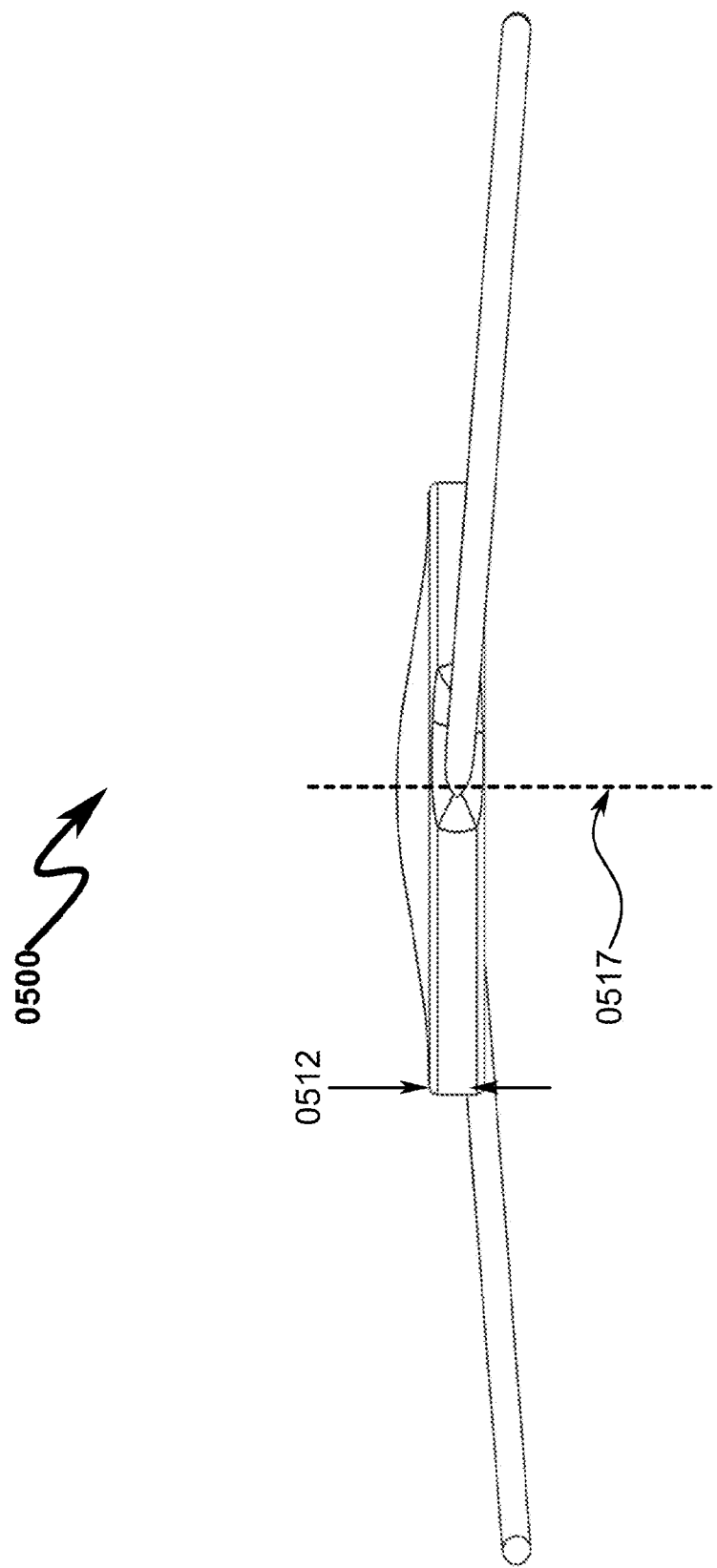
FIG. 5 illustrates a top perspective view of an exemplary intraocular lens (IOL) with simplified haptics.
Figure 6:
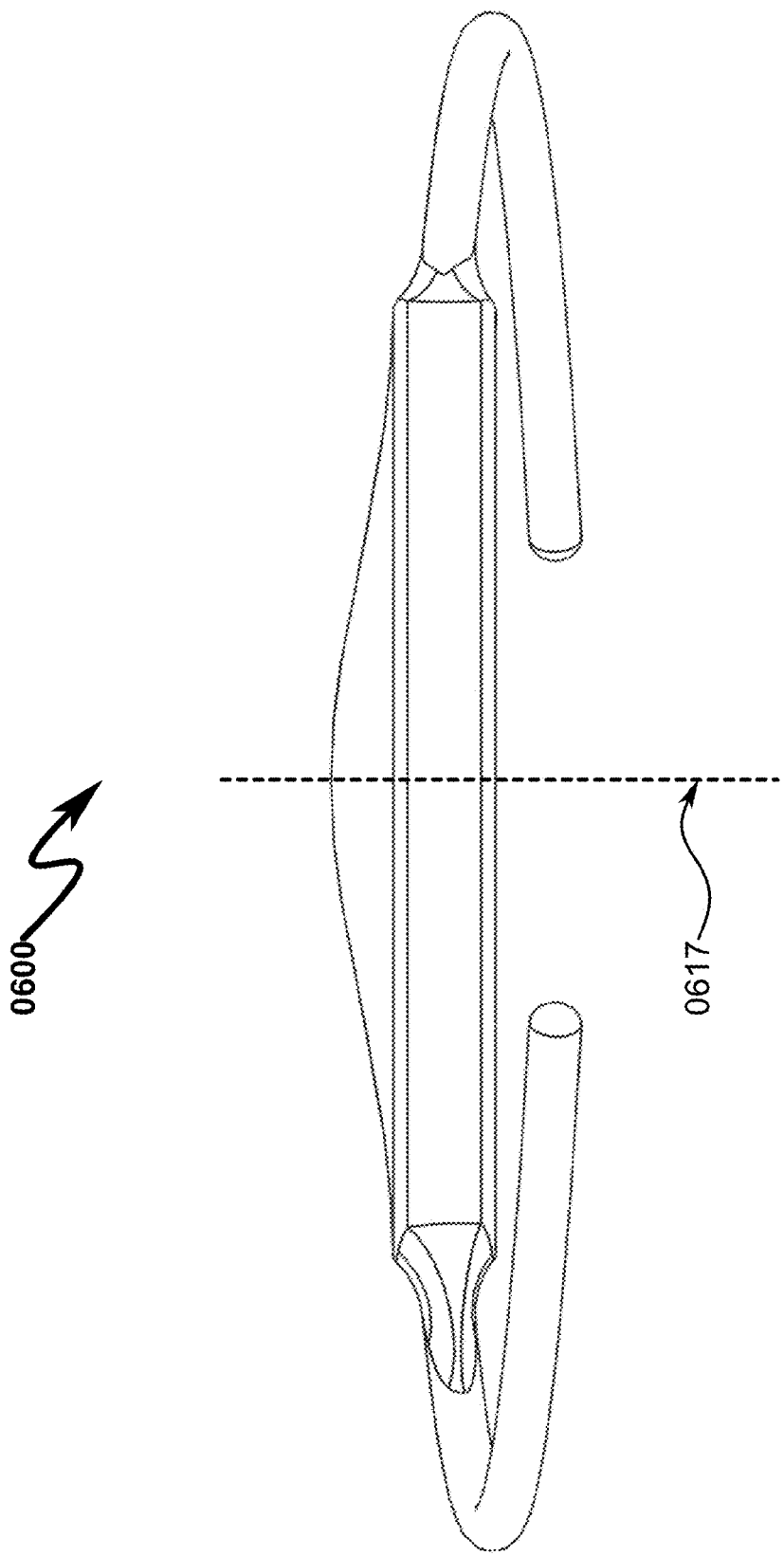
FIG. 6 illustrates a bottom perspective view of an exemplary intraocular lens (IOL) with simplified haptics.
Figure 7:
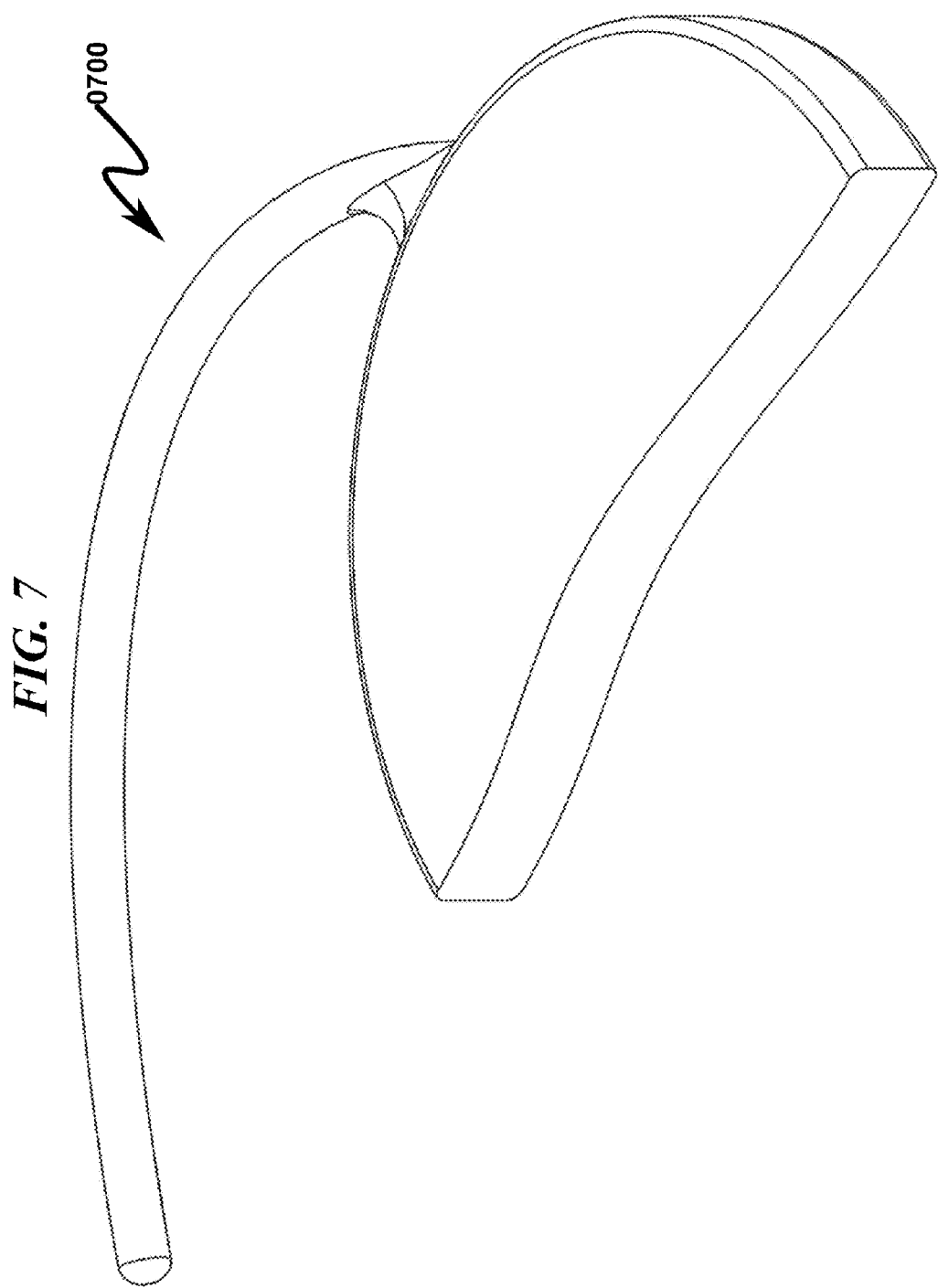
FIG. 7 illustrates a front perspective section view of an exemplary intraocular lens (IOL) with simplified haptics.
Figure 8:
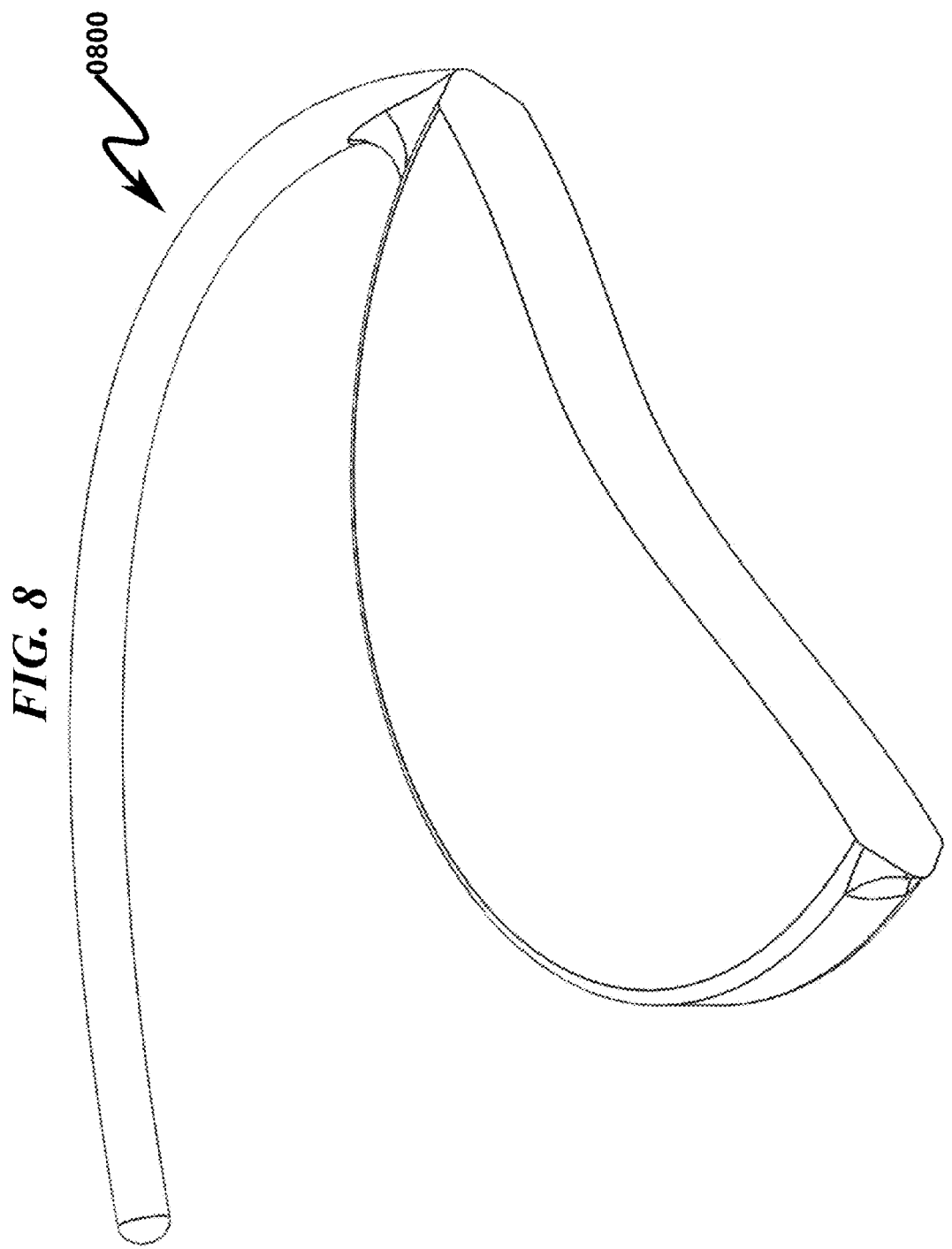
FIG. 8 illustrates a side perspective section view of an exemplary intraocular lens (IOL) with simplified haptics.
Figure 9:
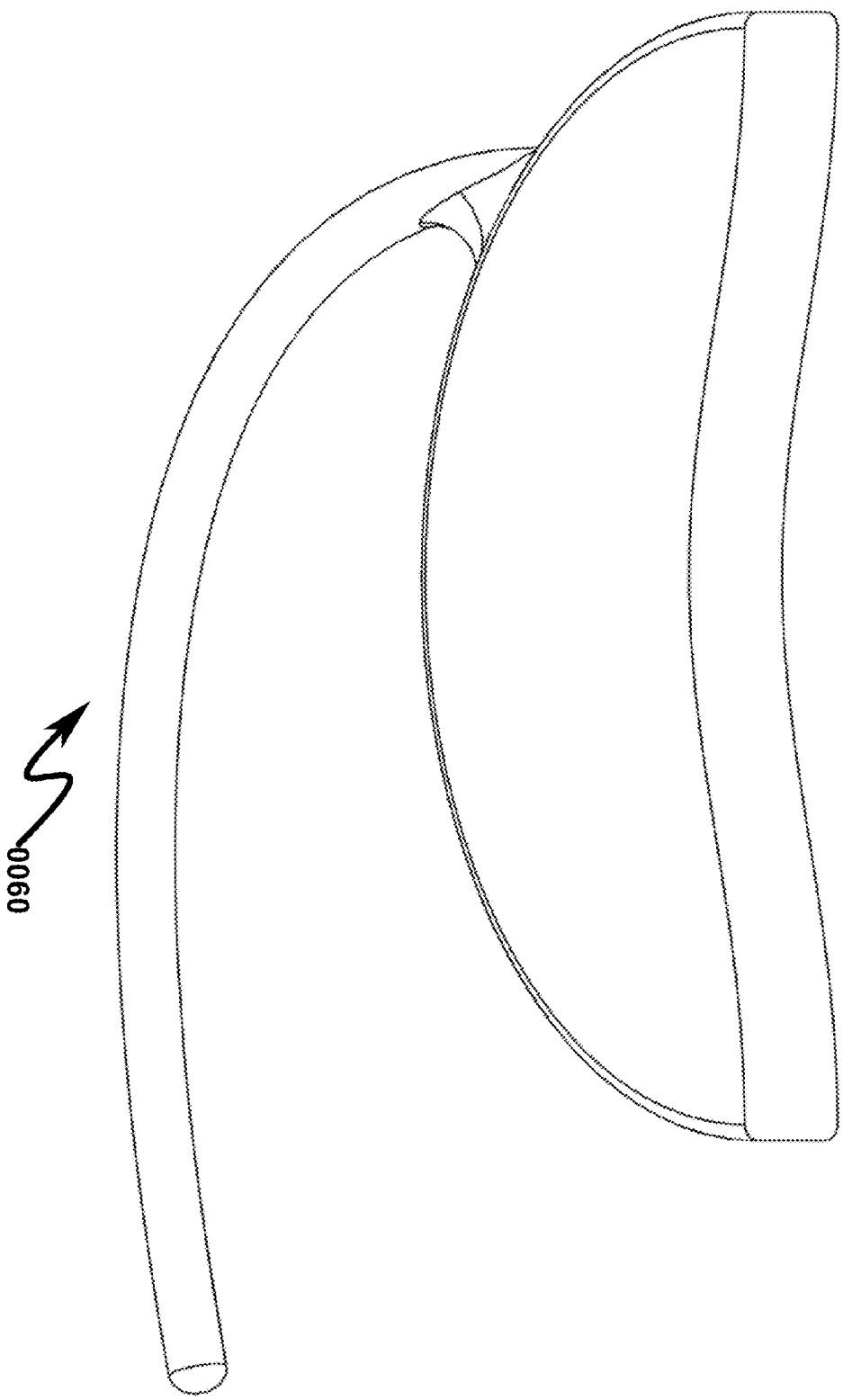
FIG. 9 illustrates a left diagonal perspective section (front top) view of an exemplary intraocular lens (IOL) with simplified haptics.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of an INTRAOCULAR LENS (IOL) FABRICATION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Polymeric Material Blank (PLB) not Limitive

The present invention may incorporate a wide range of materials within the scope of anticipated embodiments, many of which may be application specific. The polymeric material (PLM) from which the polymeric material blank is constructed for use in the disclosed system may in many preferred embodiments incorporate the use of an ultraviolet (UV) (generally 300-400 nm wavelength) absorbing material to augment the absorption of pulsed laser energy by the PLM and thus affect a change in refractive index of the PLM. PLM as used herein should not be constrained as limiting its use to materials that form optical lenses. Specifically, the term "polymeric material (PM)" may be used herein to denote applications of the invention system/method/product that are not necessarily limited to the production of optical lenses. Thus, "PM" may cover a broader application of the invention concepts than "PLM", although the materials may be identical. Therefore, the term "polymeric lens material (PLM)", "polymeric material (PM)", "polymeric material blank (PMB)", and their equivalents should be given the broadest possible meaning within this context.

Laser Radiation not Limitive

The present invention may incorporate a wide variety of laser radiation to affect changes in refractive index within the PLM described herein to form a lens. Therefore, the term "laser radiation" and its equivalents should be given the broadest possible meaning within this context, and not limited to near infrared light laser radiation.

Laser Wavelength not Limitive

Generally speaking, the laser wavelengths used in the present invention are in ranges greater than 500 nm (515-530 nm) and 1000 nm (1000 nm-1100 nm). These ranges can be approximated as 520 nm and 1040 nm respectively within the discussion of the present invention.

Laser Source not Limitive

The present invention may incorporate a wide variety of laser radiation sources provide the required pulsed laser radiation used within the disclosed invention. Within this context, the term "laser source" may also incorporate an Acousto-Optic Modulator (AOM) (also called a Bragg cell) that uses the acousto-optic effect to diffract and shift the frequency of laser light generated using sound waves (usually at radio-frequency). Within this context, the "laser source" may be globally defined as comprising a laser radiation source and optionally an AOM, whether or not the AOM is physically incorporated into the laser radiation source hardware. Therefore, the term "laser source" and its equivalents should be given the broadest possible meaning within this context.

Acousto-Optic Modulator (AOM) not Limitive

Various invention embodiments may make use of an Acousto-Optic Modulator (AOM) to act as a switch to enable/disable or moderate the quantity of laser radiation pulse stream as directed to the laser scanner within the context of the invention. Within this context the AOM may incorporate "greyscale" modulation wherein the switching function serves to switch a portion of the laser radiation pulse train to the laser scanner and therefore permit reductions in effective laser power as applied to the targeted PLM to which the refractive index is to be modified. Thus, the utilization of "greyscale AOM" components to modulate laser radiation intensity is specifically anticipated within the scope of the invention.

The AOM as depicted in the present invention is used as a shutter and as variable attenuator and as such could therefore be replaced with another equivalent component which simulates the same functionality as described above.

Laser Scanner not Limitive

The use of a laser scanner within the preferred invention embodiments described herein may incorporate many different varieties of scanner, including but not limited to flying spot scanners (generally vector-based modes) and raster scanners (generally raster-based modes). The scanner is used to distribute the laser pulse to the correct location within the objective field size. The present invention makes no limitation on the type of laser scanner that may be used in this context.

Microscope Objective not Limitive

References herein to a "microscope objective" may equivalently utilize a "microscope objective or other focusing device" to achieve these functions. Thus, the term "microscope objective" should be given its broadest possible interpretation within this application context.

Lens Form not Limitive

The present invention may incorporate a wide variety of lenses formed to affect optical light bending and thus the construction of an overall lens formation. While exemplary embodiments of the present invention are described herein as being used to construct convex, biconvex, concave, biconcave, and plano lens structures, these structures are only exemplary of a plethora of lens forms that may be constructed with the present invention. Therefore, the term "lens formation" and its equivalents should be given the broadest possible meaning within this context.

Intraocular Lens not Limitive

The present invention may be advantageously applied to the construction of dynamically adjustable optical lenses incorporating a wide range of materials. The mechanisms of incorporation of a wide variety of materials within the optical lens are not limited by the present invention. Therefore, the term "intraocular lens" and "optical lens (which would include contact lenses)" and its equivalent construction embodiments should be given the broadest possible meaning within this context.

Spiral/Circular Cutting not Limitive

The present invention in some embodiments may be discussed in terms of "spiral" cutting patterns. In many preferred embodiments these spiral cutting patterns may in fact be circular for improved performance and lens formation. Thus, circular patterns having a constant radius should be considered as being anticipated by any spiral cutting pattern discussed herein. Furthermore, some discussions below may incorporate partial arcs rather than full circles. These discussions may in some cases incorporate full circles to improve overall lens formation performance and cutting time.

Intraocular Lens (IOL) Structure (0100)-(1000)

Figure 10:
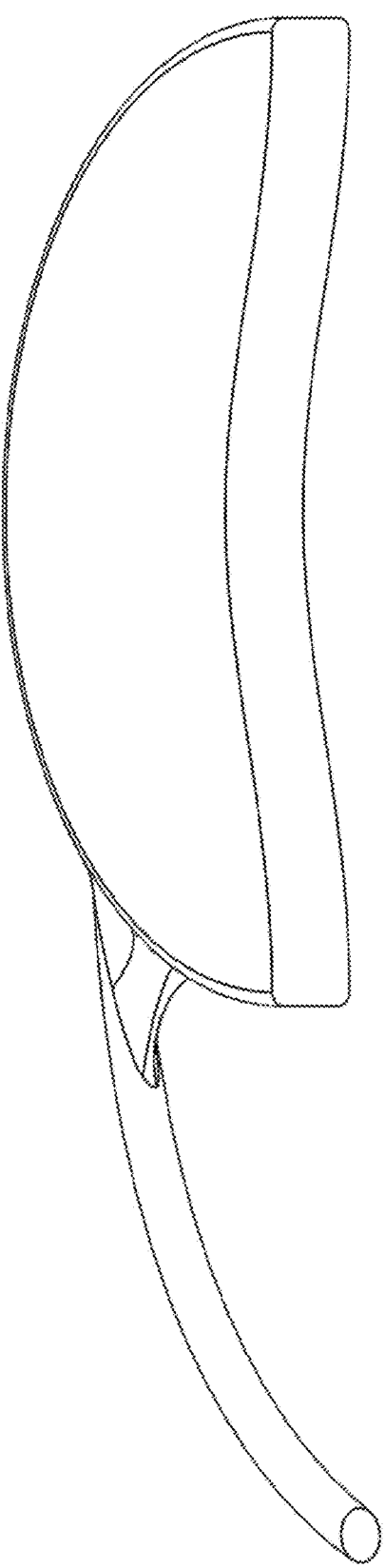
FIG. 10 illustrates a right diagonal perspective section (rear top) view of an exemplary intraocular lens (IOL) with simplified haptics.

Typical intraocular lens (IOL) structures to which the present invention applies are generally depicted in FIG. 1 (0100)-FIG. 10 (1000). With regard to FIG. 1 (0100)-FIG. 10 (1000), an IOL (0110) comprising a central disc/lens shaped body (0111) having simplified haptics (0113, 0114) is depicted. This exemplary IOL (0110) central disc/lens shaped body (0111) has an associated thickness (0512) and incorporates an anterior surface (0215) and posterior surface (0416). The present invention discloses a means to cut the anterior surface (0215) and posterior surface (0416) by employing focused femtosecond laser pulses of high repetition rate. In addition, use of the techniques of the present invention allows introduction of additional refractive capabilities within the IOL by modifying a central portion of the polymeric lens blank (PMB) material. As is conventional with many intraocular lenses, there can be a pair of haptics (0113, 0114) for holding the lens in the posterior chamber of the patient's eye. The present invention also discloses a means to create the haptics with the femtosecond laser.

The terms "anterior" and "posterior" refer to surfaces of a lens as it is normally placed in the human eye, with the anterior surface (0215) facing outwardly, and the posterior surface (0416) facing inwardly toward the retina. The lens (0111) has an axis (0517, 0617), which is an imaginary line which defines the path along which light propagates through the lens (0111). In the invention embodiment depicted, the optical axis (0517, 0617) is coincident with the mechanical axis of the lens, but this is not a strict requirement of the invention. The lens (0111) as depicted may be formed in a spherically symmetric fashion, or in some embodiments be formed asymmetrically or in a custom pattern that corresponds to specific topical irregularities of the eye of an individual patient.

Elongated Y-Axis Lens (1100)-(1200)

Figure 11:
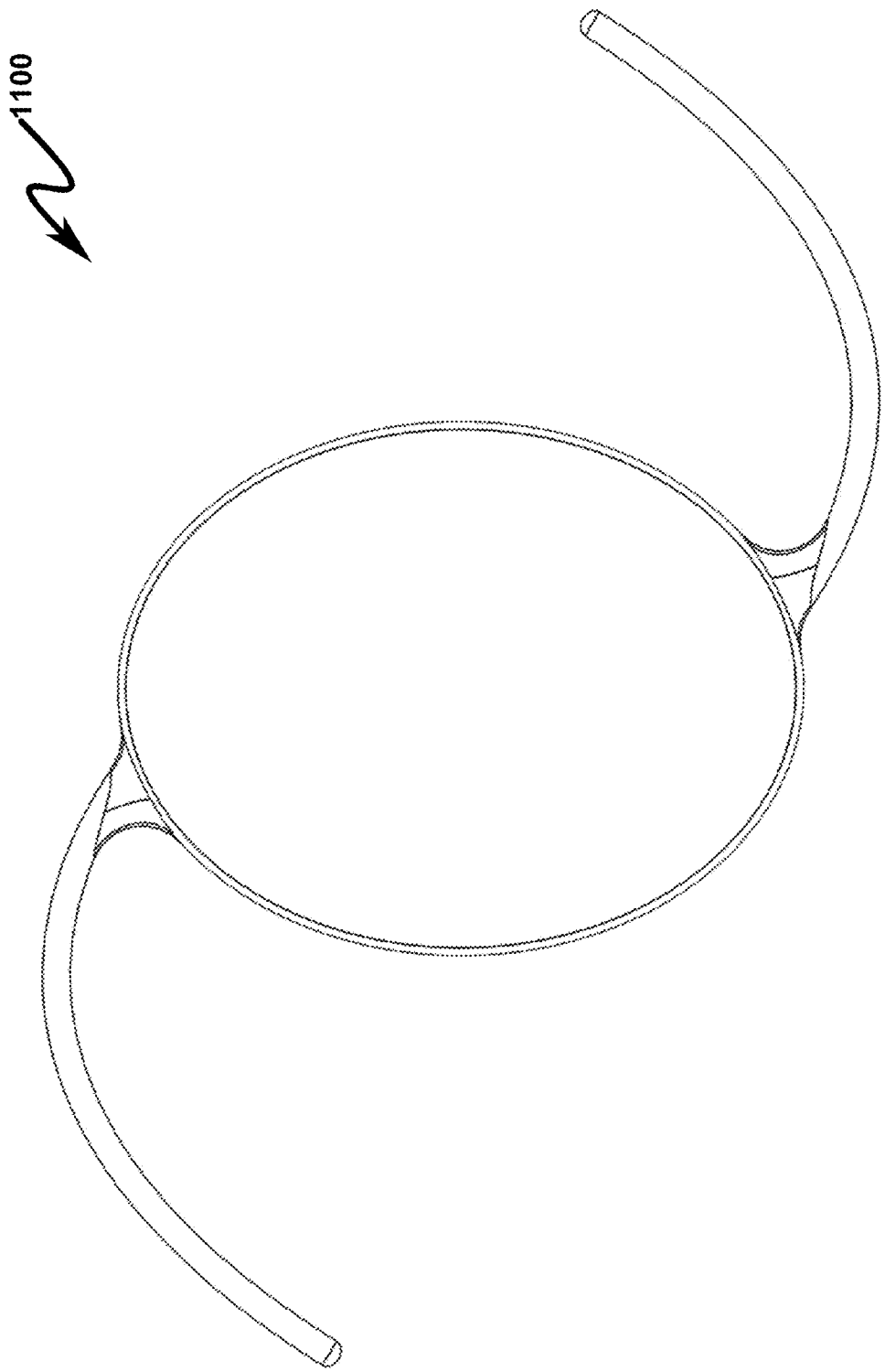
FIG. 11 illustrates a top view of an exemplary intraocular lens (IOL) with simplified haptics and elongated Y-axis geometry.
Figure 12:
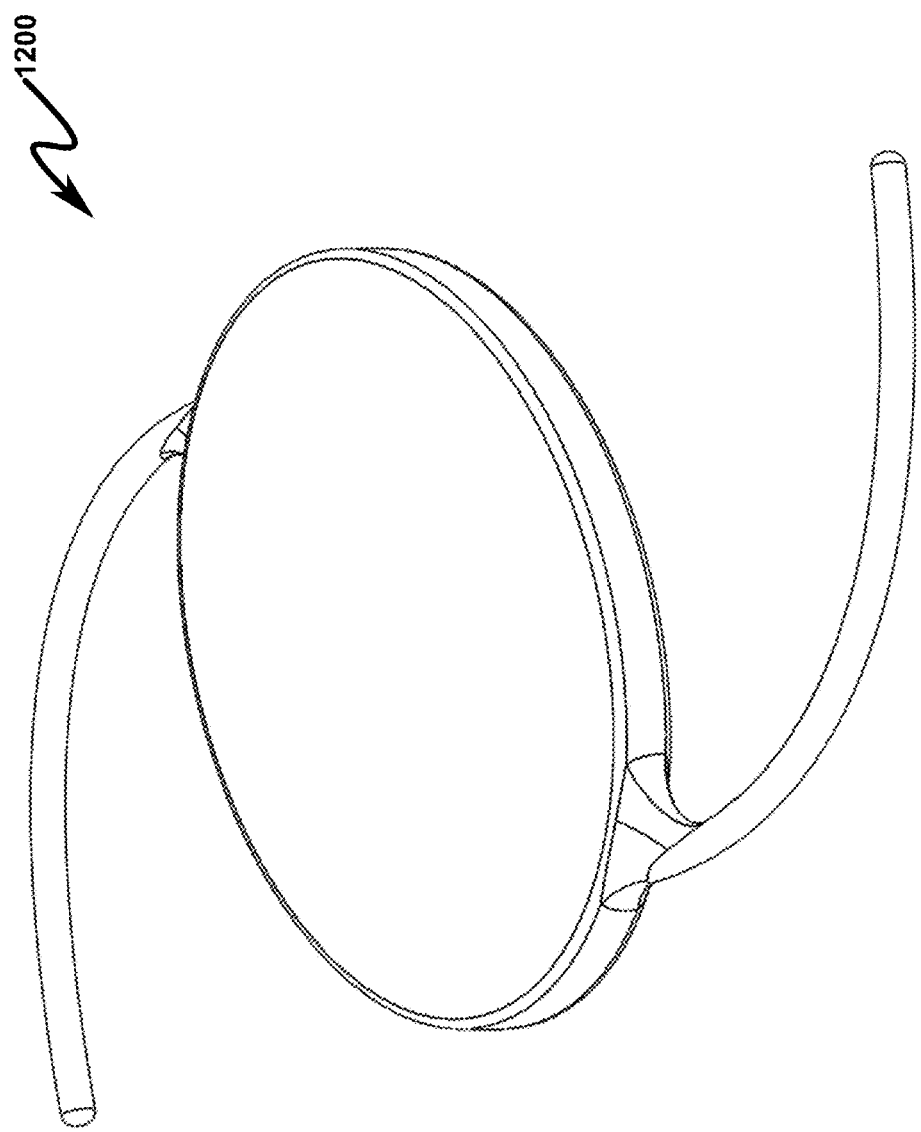
FIG. 12 illustrates a top perspective view of an exemplary intraocular lens (IOL) with simplified haptics and elongated Y-axis geometry.

As generally depicted in FIG. 11 (1100)-FIG. 12 (1200), the present invention may generate IOL structures having elongated Y-axis lens structures. This elongated lens structure may be rotated about an arbitrarily positioned vertical Z-axis to form non-orthogonal lens structures, or may be combined with elongated X-axis lens structures as described below.

Elongated X-Axis Lens (1300)-(1400)

Figure 13:
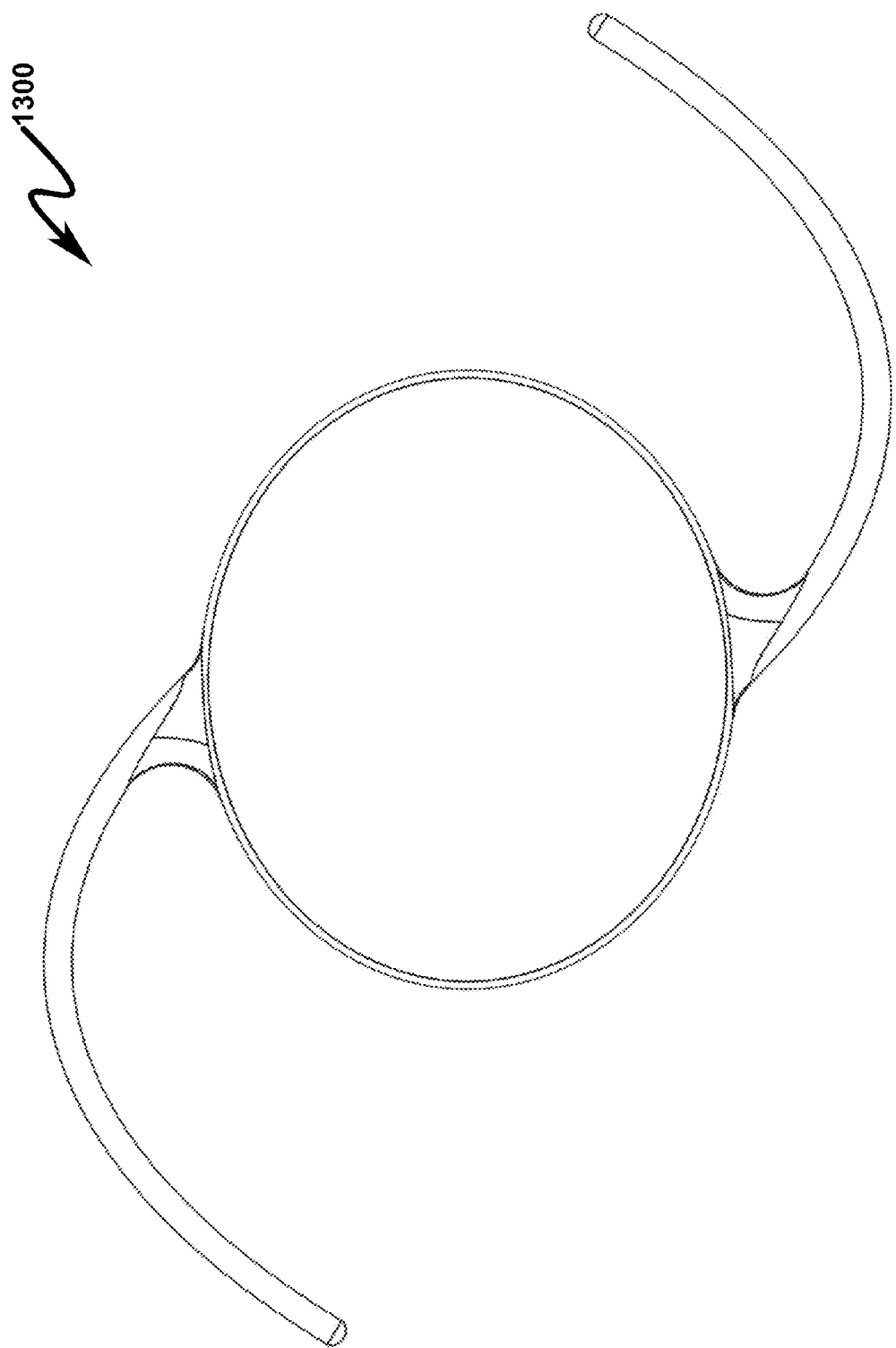
FIG. 13 illustrates a top view of an exemplary intraocular lens (IOL) with simplified haptics and elongated X-axis geometry.
Figure 14:
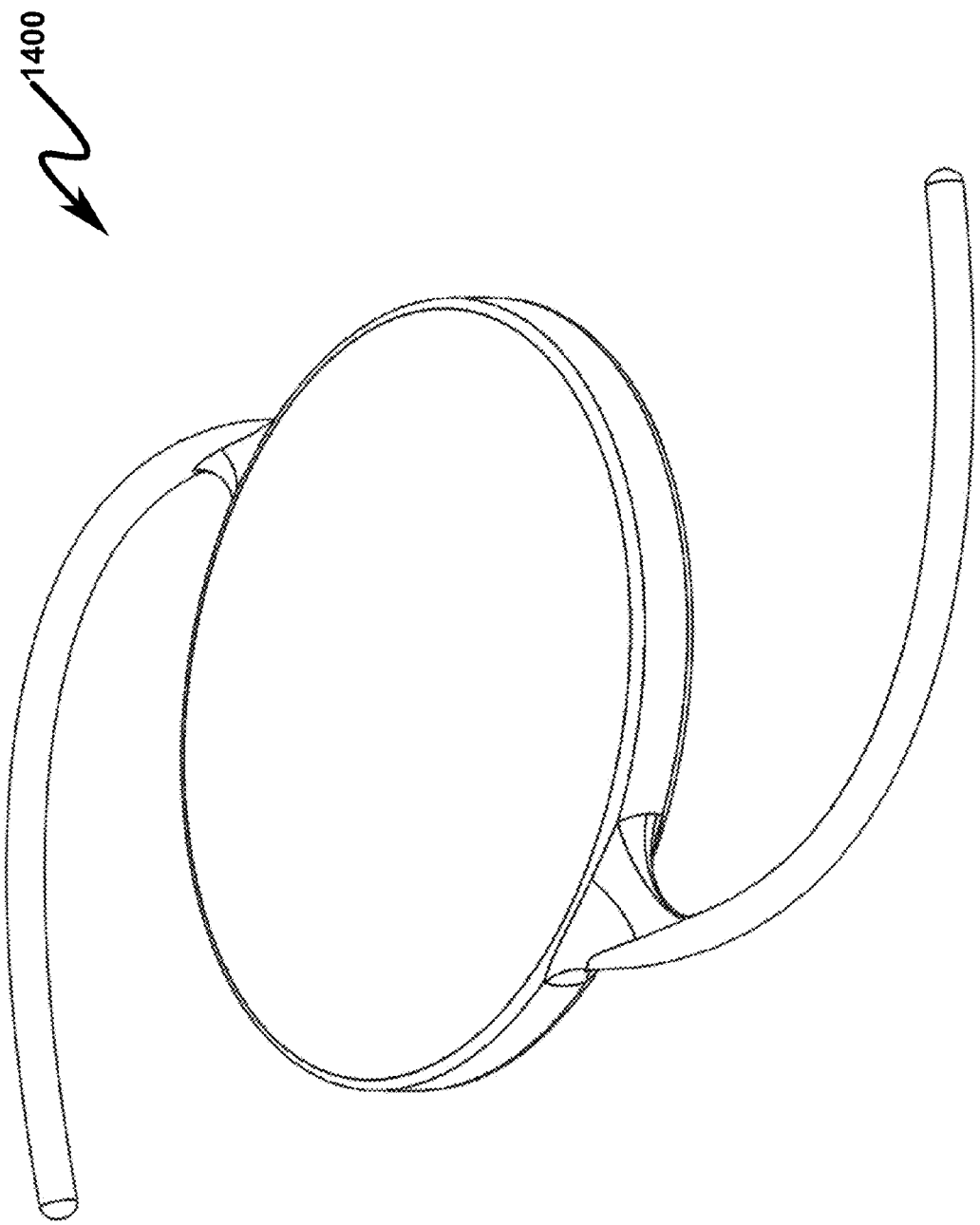
FIG. 14 illustrates a top perspective view of an exemplary intraocular lens (IOL) with simplified haptics and elongated X-axis geometry.

As generally depicted in FIG. 13 (1300)-FIG. 14 (1400), the present invention may generate IOL structures having elongated X-axis lens structures. This elongated lens structure may be rotated about an arbitrarily positioned vertical Z-axis to form non-orthogonal lens structures, or may be combined with elongated Y-axis lens structures as described above.

Customized Anterior/Posterior Surface Curvatures (1500)-(1600)

Figure 15:
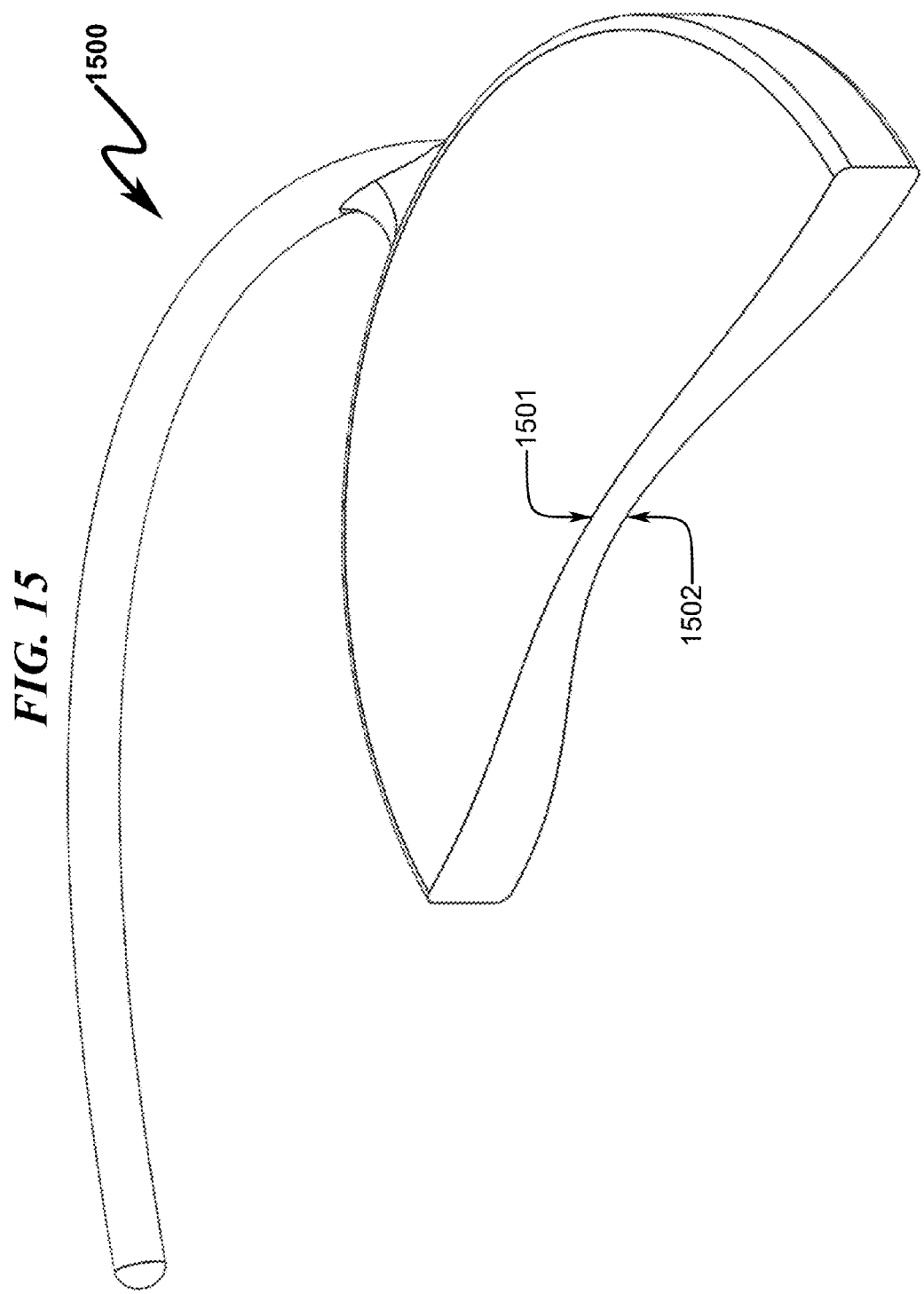
FIG. 15 illustrates a front sectional view of an exemplary intraocular lens (IOL) with simplified haptics and different anterior and posterior surface geometries.
Figure 16:
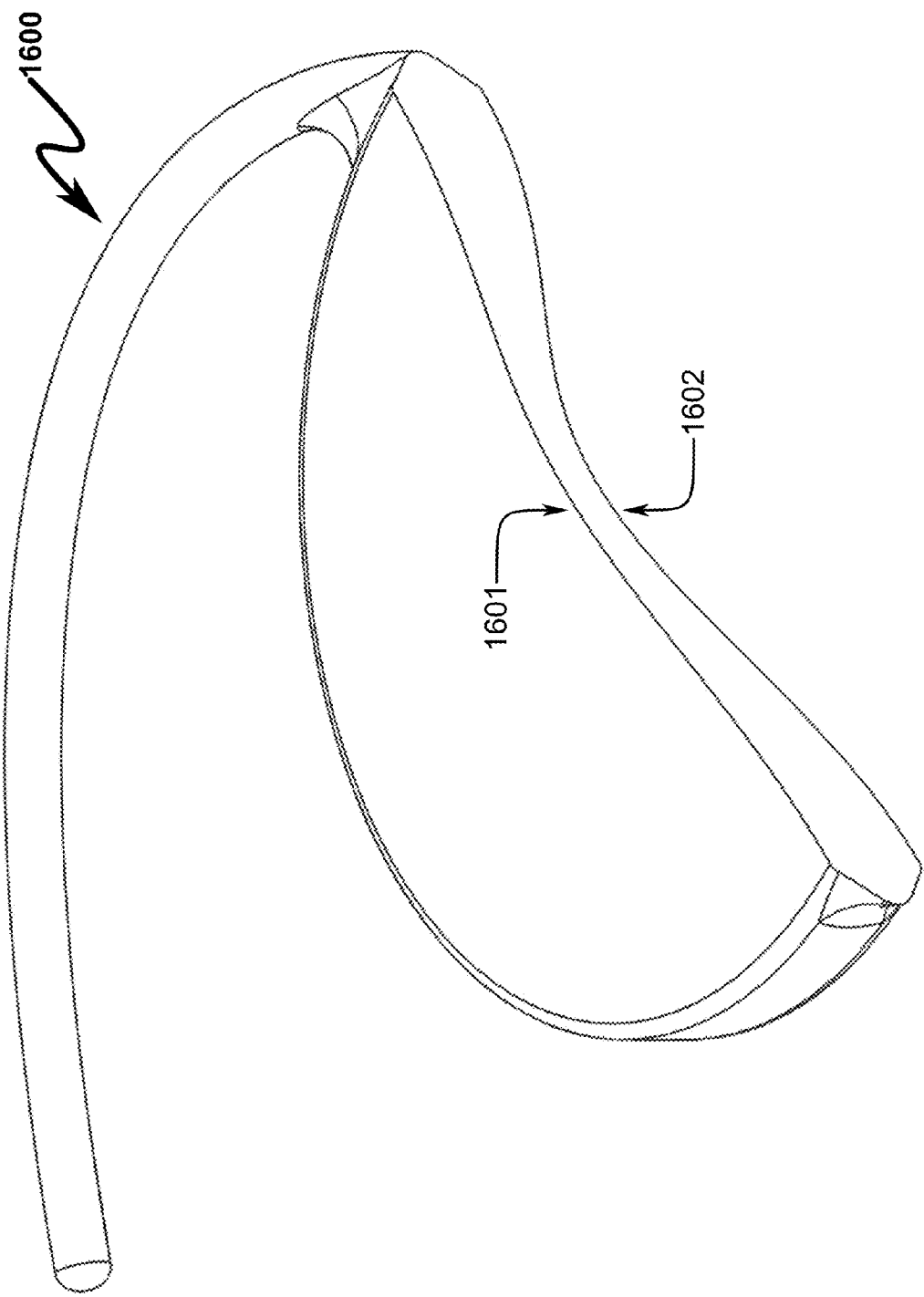
FIG. 16 illustrates a top perspective view of an exemplary intraocular lens (IOL) with simplified haptics and different anterior and posterior surface geometries.

The use of one or more custom surface curvatures is possible for the anterior and posterior surfaces of the lens as generally depicted in FIG. 15 (1500)-FIG. 16 (1600). Here the anterior (1501, 1601)/posterior (1502, 1602) surface curvatures and/or contours can be customized to fit the exact physical properties of an individual patient. This customized fitting of lens provide a better fit and more comfort to the patient as compared to the use of a generic lens structure that may have curvatures and contours that may cause irritation to the patient's eye.

Polymeric Material Slab (PMS) (1700)-(2000)

Figure 17:
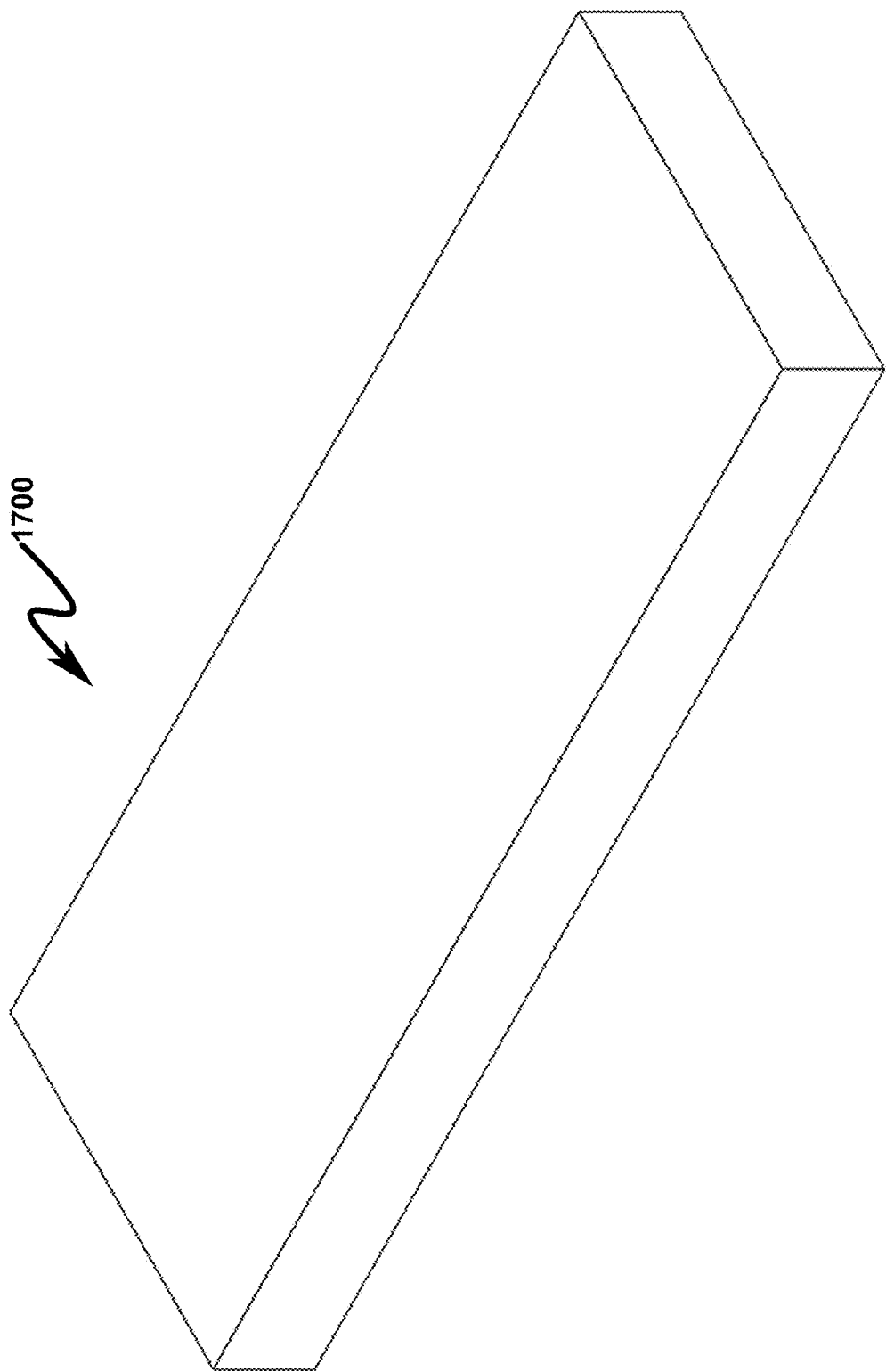
FIG. 17 illustrates top perspective view of an exemplary intraocular lens (IOL) polymeric lens slab (PMS)
Figure 18:
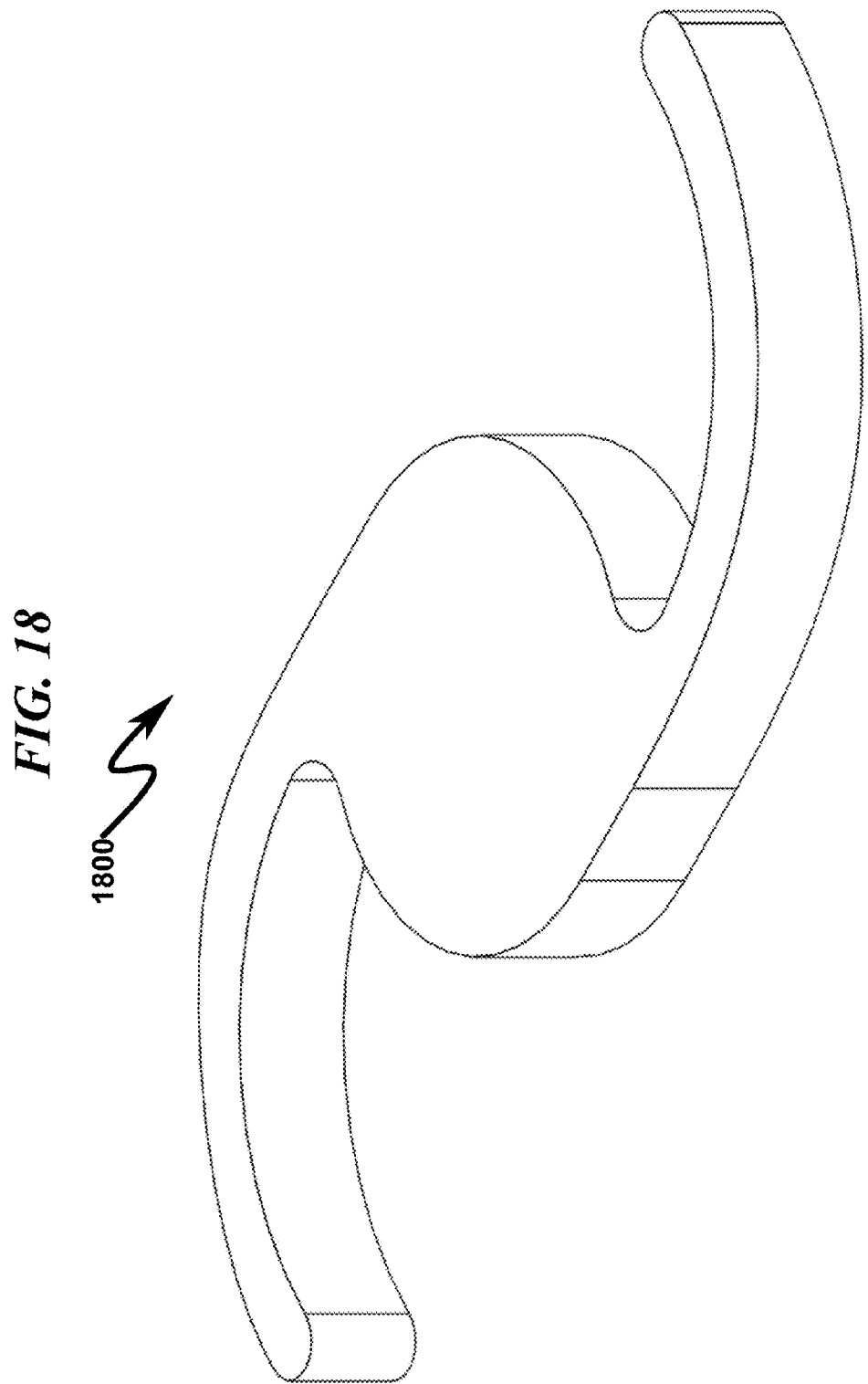
FIG. 18 illustrates a top perspective view of an exemplary intraocular lens (IOL) polymeric lens slab (PMS) that has been transformed into a polymeric lens blank (PMB)
Figure 19:
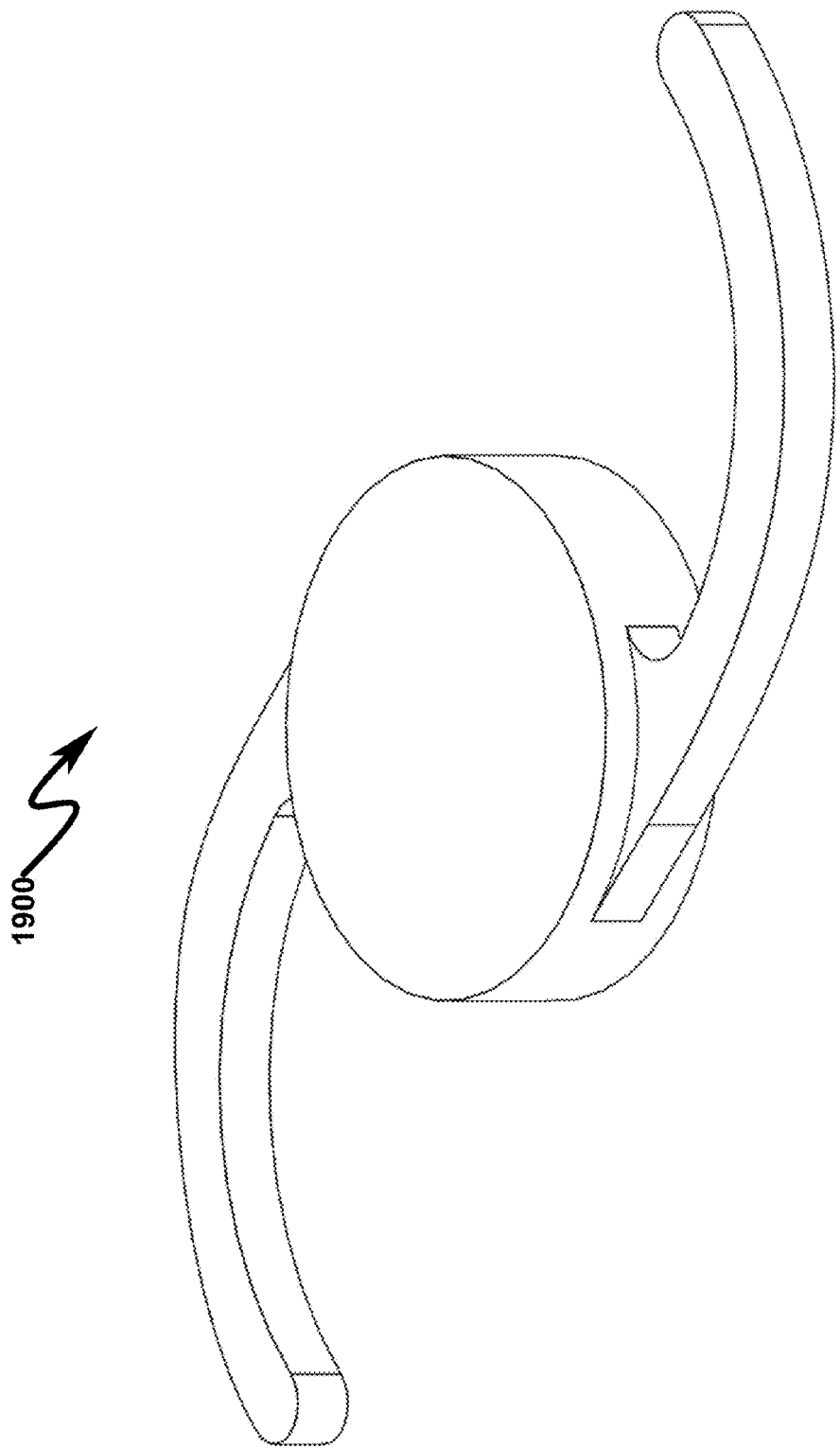
FIG. 19 illustrates a front perspective view of an exemplary intraocular lens (IOL) polymeric lens slab (PMS) that has been transformed into a polymeric lens blank (PMB)
Figure 20:
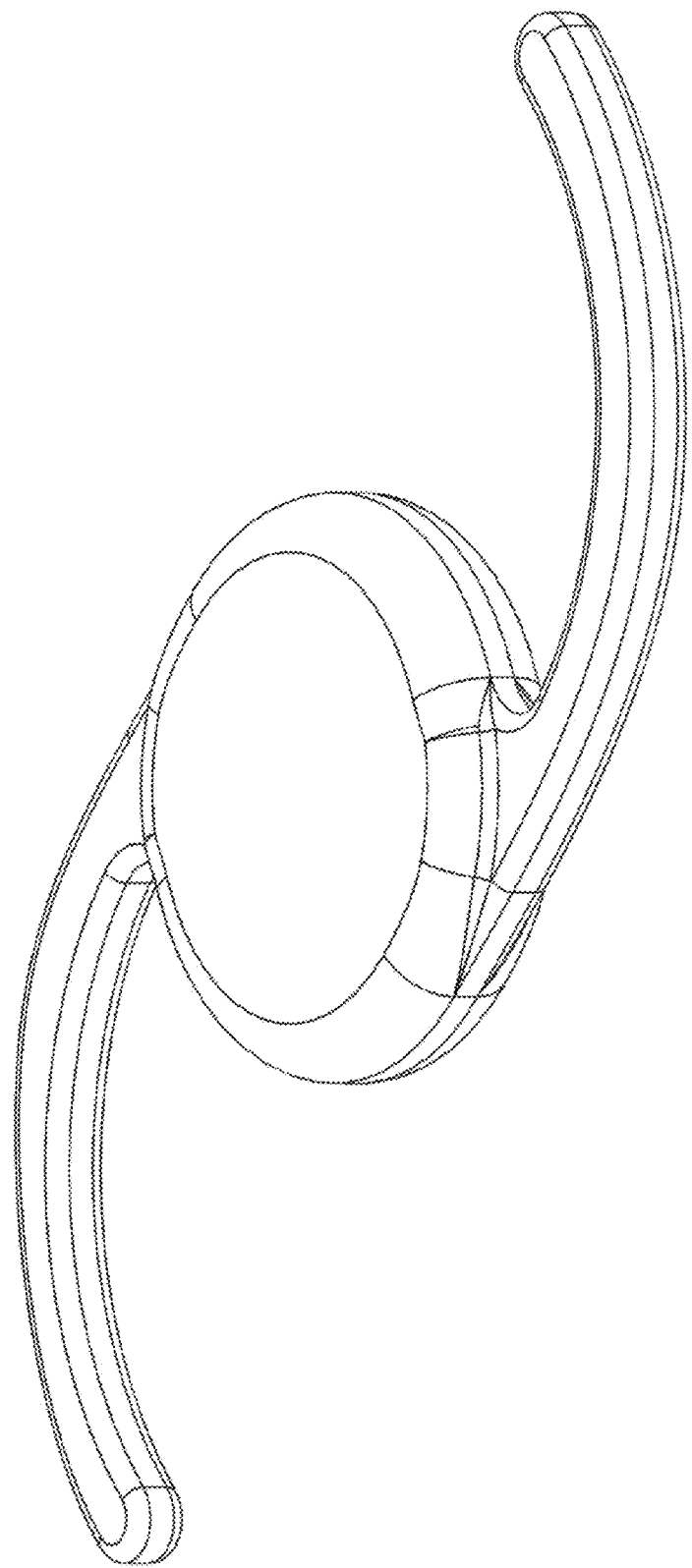
FIG. 20 illustrates a side perspective view of an exemplary intraocular lens (IOL) polymeric lens slab (PMS) that has been transformed into a polymeric lens blank (PMB)

FIG. 17 (1700)-FIG. 20 (2000) depict a polymeric material slab (PMS) with associated transformations that may be made to form a polymeric material blank (PMB). Generally speaking, the present invention may start with a "slab" of polymeric material as generally depicted in FIG. 17 (1700) and then perform a series of cuts on the material to eventually form lens/haptic structures as depicted in FIG. 1 (0100)-FIG. 16 (1600). These "slabs" may be in some circumstances be roughly formed into "blanks" that contain some of the basic form elements of the lens/haptic structures. FIG. 18 (1800) depicts a PMS that has been transformed into a rough PMB having a central lens portion and haptics. FIG. 19 (1900) illustrates a further refinement of this PMB structure in which basic thicknesses of the lens structure and haptics are pre-formed. FIG. 20 (2000) illustrates an additional refinement in which additional material in the lens and haptics are removed in the PMB pre-formation.

The transition from PMS to PMB can take many forms as generally illustrated in FIG. 17 (1700)-FIG. 20 (2000). As additional material is removed from the PMS to PMB, less material is required to be removed from the PMB to eventually form the final lens structure. This reduction in material to be removed by the present invention can significantly reduce the time to manufacture a fully-formed lens/haptic structure.

Polymeric Material Blank (PMB) (2100)-(2400)

Figure 21:
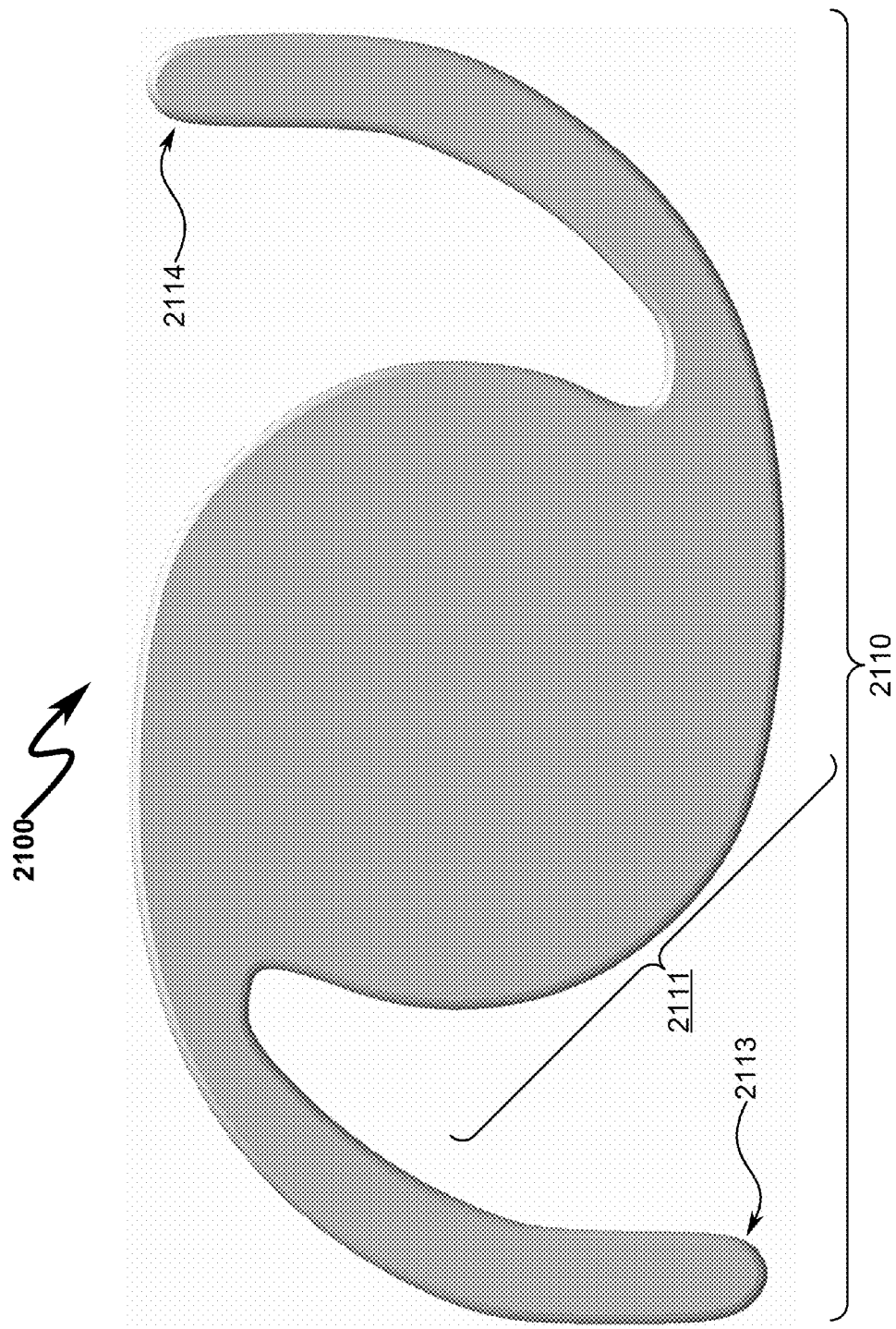
FIG. 21 illustrates a top view of an exemplary intraocular lens (IOL) polymeric lens blank (PMB)
Figure 22:
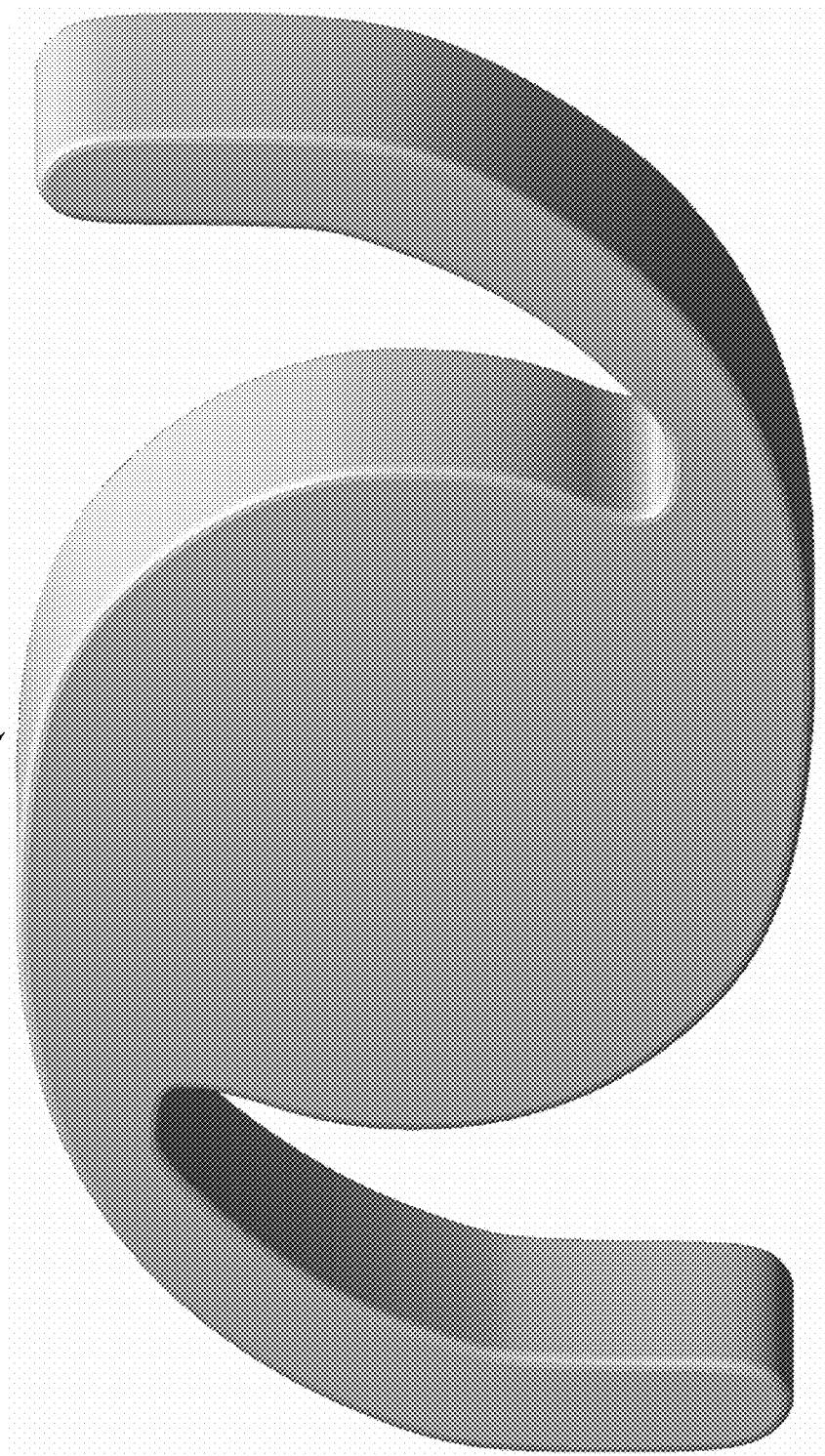
FIG. 22 illustrates a top perspective view of an exemplary intraocular lens (IOL) polymeric lens blank (PMB)
Figure 23:
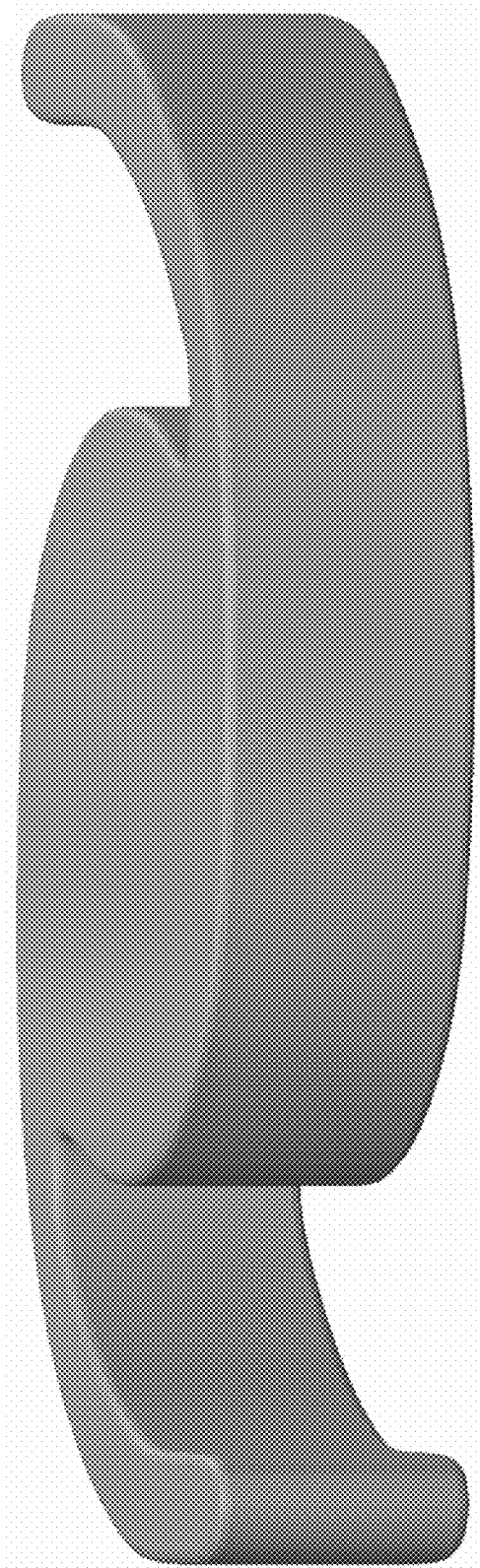
FIG. 23 illustrates front perspective view of an exemplary intraocular lens (IOL) polymeric lens blank (PMB)
Figure 24:
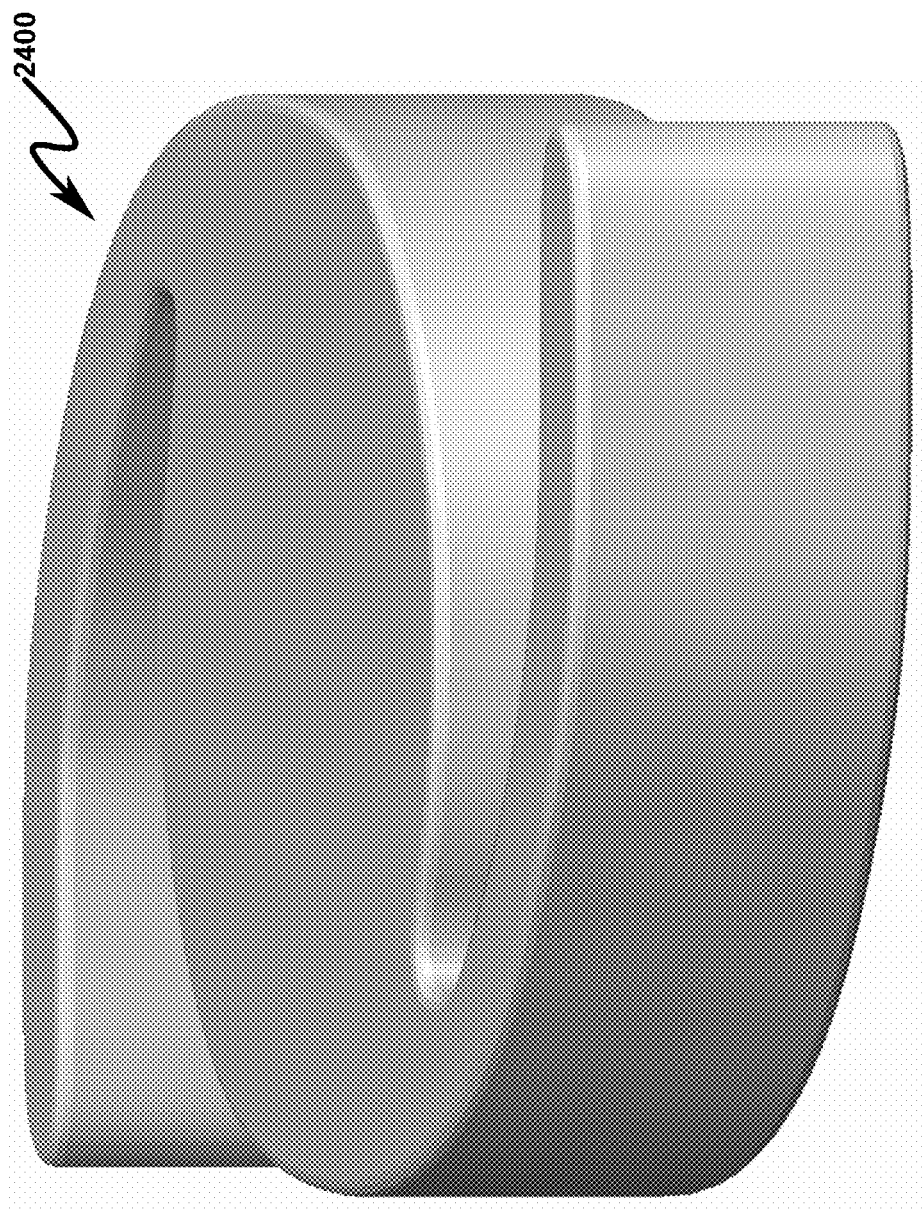
FIG. 24 illustrates right front perspective view of an exemplary intraocular lens (IOL) polymeric lens blank (PMB)

With regard to FIG. 21 (2100)-FIG. 24 (2400), the IOL (1310) as formed may start with a wide variety of baseline polymeric material blank (PMB) formations. In the illustrated PMB the central lenticule (2111) is roughly formed along with the lateral haptics (2113, 2114) and both features are later laser cut to form the final IOL structure. Within this process an additional refractive index shaping (RIS) lens structure may be formed within the IOL by use of the femtosecond layer being focused within the body of the PMB.

Polymeric Lens Blank (PLB) Modification (2500)

Figure 25:
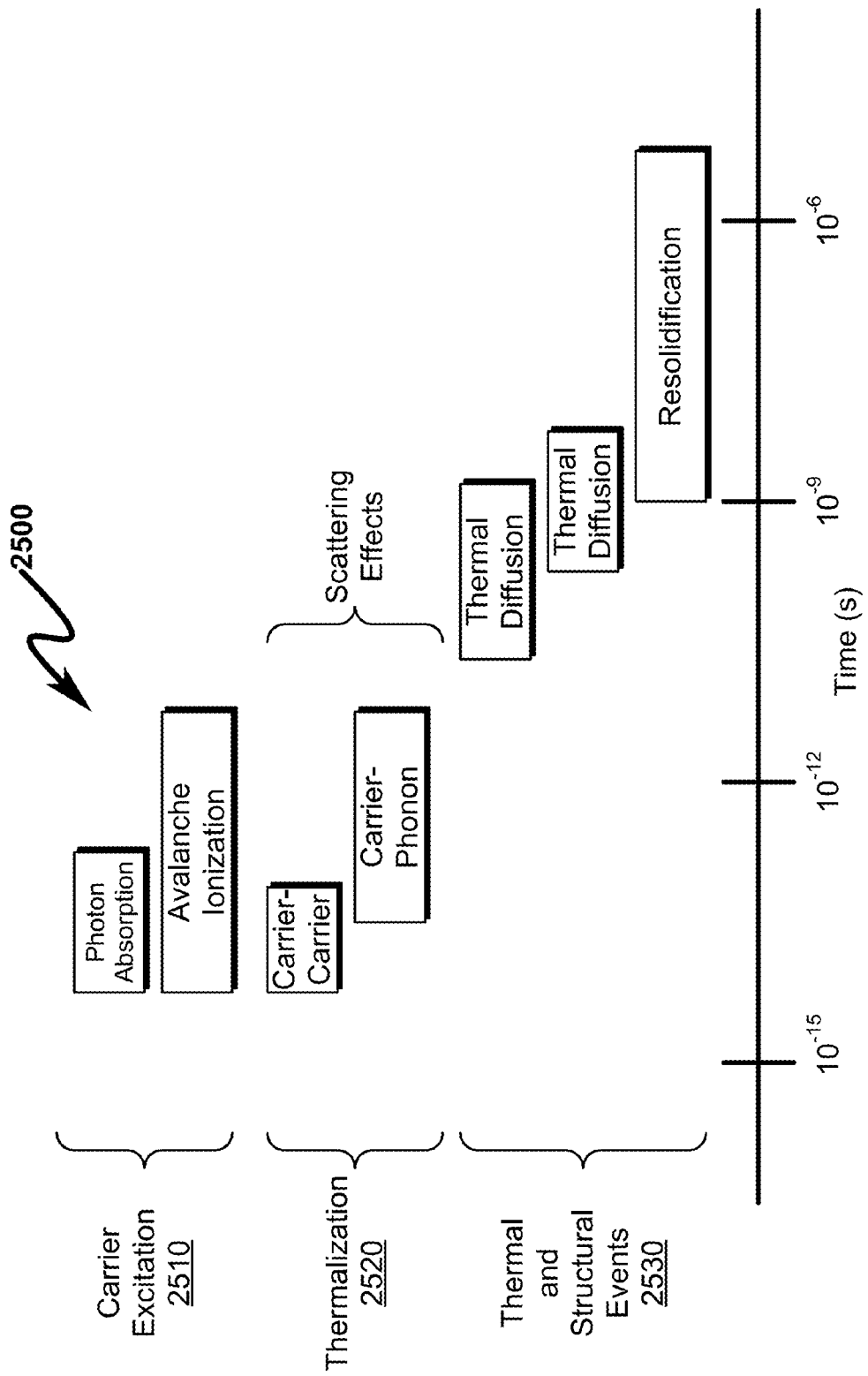
FIG. 25 illustrates exemplary various mechanisms by which a polymeric lens blank (PLB) may be modified by a femtosecond laser and summarizes the processes occurring in a polymeric material after femtosecond laser irradiation.

The interaction of the laser radiation with the polymeric material blank (PLB) involves several processes that determine the energy dissipation in the matter-carrier excitation, thermalization, thermal and structural processes As generally depicted in FIG. 25 (2500), these may include carrier excitation (2510), thermalization (2520), and thermal/structural events (2530).

These processes occur on time scales of femtoseconds to nanoseconds after the excitation. First, the photons are absorbed in the material (photon-electron interaction) in about 10 femtoseconds, followed by the interaction with carriers. Then, in a few picoseconds, the electrons start to transfer their energy to the lattice, e.g. polymeric material, which can last up to nanoseconds by phonon-phonon interaction. See R. Gattass and E. Mazur: Femtosecond Laser Micromachining in Transparent Materials, Nature Photonics, Vol. 2, 2008.

To produce small localized defects without cracks, a strongly focused femtosecond laser radiation has to be used to reach the threshold intensity for the optical breakdown. With this configuration the short pulse length (duration) causes fast energy transfer to the lattice. Above a certain threshold intensity a plasma is formed, incurring material damage. Together with shock-wave propagation, a minute cavity with micrometer dimensions surrounded by compacted material is created.

Femtosecond Laser Configuration

The following table summarizes typical configuration parameters of the femtosecond laser systems employed in the present invention:

| Laser Parameter | Minimum | Maximum |
|---|---|---|
| Wavelength | 520 nm | 1040 nm |
| Pulse Duration | 400 fs | 900 fs |
| Frequency | 0.1 MHz | 2 MHz |
| Pulse Energy | 5 µJ | 10 µJ |
| Peak Pulse Power | 50 MW | 50 MW |
| $M^2$ (Beam Quality Factor | 1.1 | 1.1 |

For sculpting of polymeric material, a laser wavelength of 1040 nm is typically chosen. The laser system exhibits a pulse duration between <900 fs, a pulse repetition rate of 1 MHz, pulse energies up to 10 µJ, resulting in pulse peak power of around 50 MW. The beam quality factor $M^2$ amounts to 1.1, allowing for close to diffraction-limited optical focusing performance. For creating a Refractive Index Shaping (RIS) lens inside an intraocular lens (before lens sculpting) the laser output is frequency-doubled, to generate a green laser beam with a wavelength of 515 nm. This green laser light favourably generates refractive index changes inside the polymeric material through multi-photon excitation. The green laser exhibits a pulse length (duration) of <900 fs, a pulse repetition rate of 1 MHz, pulse energies up to 5.0 µJ, resulting in pulse peak power of around 50 MW. The green laser beam allows for close to diffraction-limited optical focusing performance, too, due to the beam quality factor $M^2$ of 1.1.

Exemplary Microscope Objective (2600)

Figure 26:
FIG. 26 illustrates an exemplary microscope objective useful in some preferred invention embodiments (e.g. LEITZ WETZLAR LL20X/0.40), comprising a field size of 6 mm, a focal length of 8 mm, and a working distance of approximately 10 mm.

FIG. 26 (2600) depicts a microscope objective, as appropriate for the optical sculpting process inside the PMB. A commercially available microscope objective (such as a LL 20X/0.40 objective (or equivalent) with large working distance (LWD)) supporting a field of view of larger than 6 mm diameter, with a focal length of 8 mm. For optimized sculpting performance, a custom cutting objective may be used in many preferred invention embodiments.

Light Inducted Optical Breakdown (LiOB) Cutting Parameters

The following table presents the experimental parameters to induce the process of Light induced Optical Breakdown (LiOB) in the PMB:

| LiOB Parameter | Value |
|---|---|
| Laser Wavelength | ~520 nm (515 nm-530 nm)/ ~1040 nm (1000 nm-1100 nm) |
| Numerical Aperture | 0.4 |
| Focal Diameter | 2.6 µm |
| Depth of Focus | 12 µm |
| Energy per Pulse | ≤10 µJ |
| Pulse-Width | ≤900 fs |
| Pulse Frequency | ≤2 MHz |
| Average Laser Power | ≤10 W |
| Minimum Pulse Energy to Achieve Cutting | ~1.0 µJ (e.g. 10 µJ/ 1 MHz) |
| Typical Pulse Energy for Cutting | 5 µJ |

The LiOB process facilitates the sculpting procedure in the PMB. The achieved cutting pitch may optimally comprises a lateral width of 2.6 µm and a cutting depth of 12 µm. The pulse intensity amounts to approximately 250 TW/cm². The width and length of the cutting pitch can be optimized by choosing the pulse energy appropriately, at a level from approximately 1.0 µJ±25% to 5.0 µJ±25%.

Basic Cutting Element (2700)-(2800)

Figure 27:
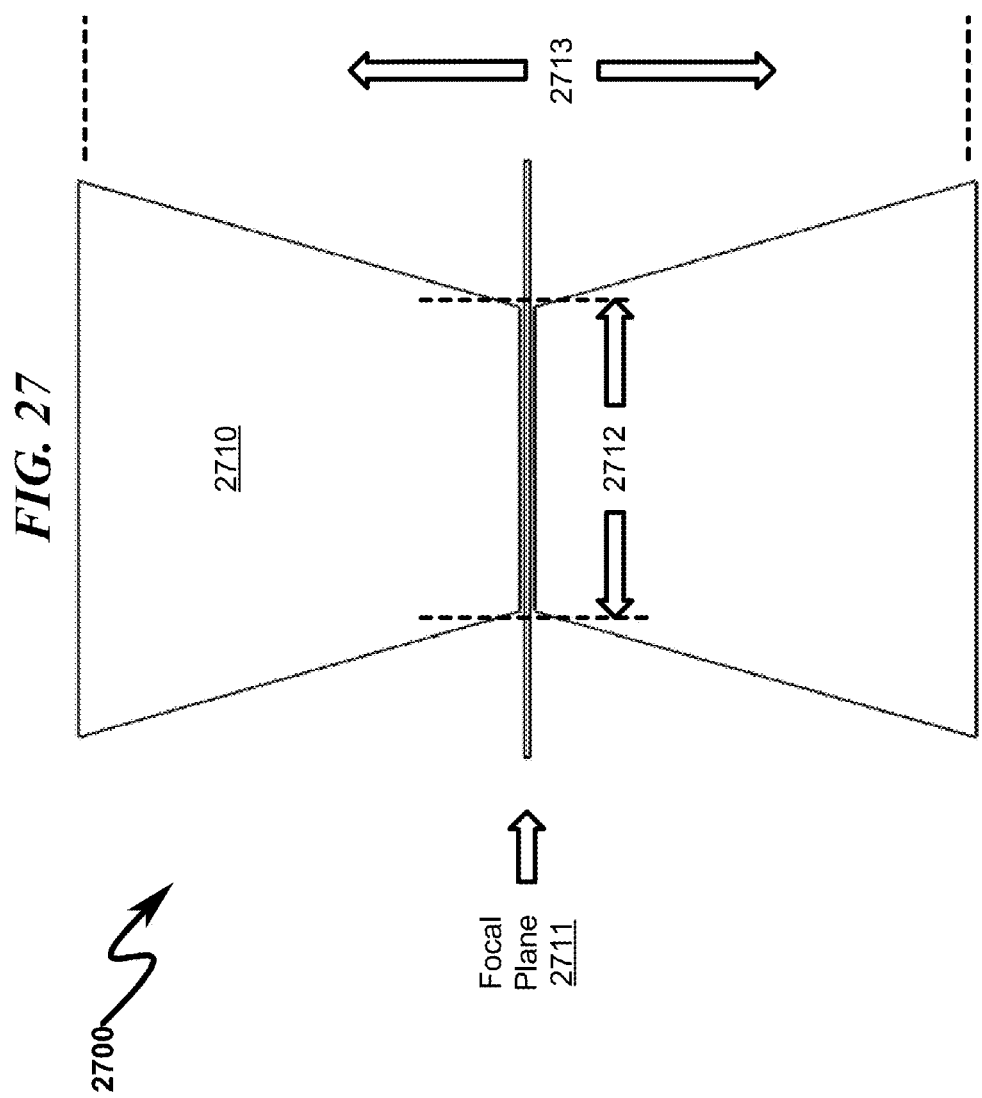
FIG. 27 illustrates a side view of a Basic Cutting Element (BCE) used to fabricate the PMB around the focal plane with the femtosecond laser and shows the focal-volume of the laser-spot, which resembles the basic cutting element ($\lambda$=1040 nm) for sculpting the polymeric material.
Figure 28:
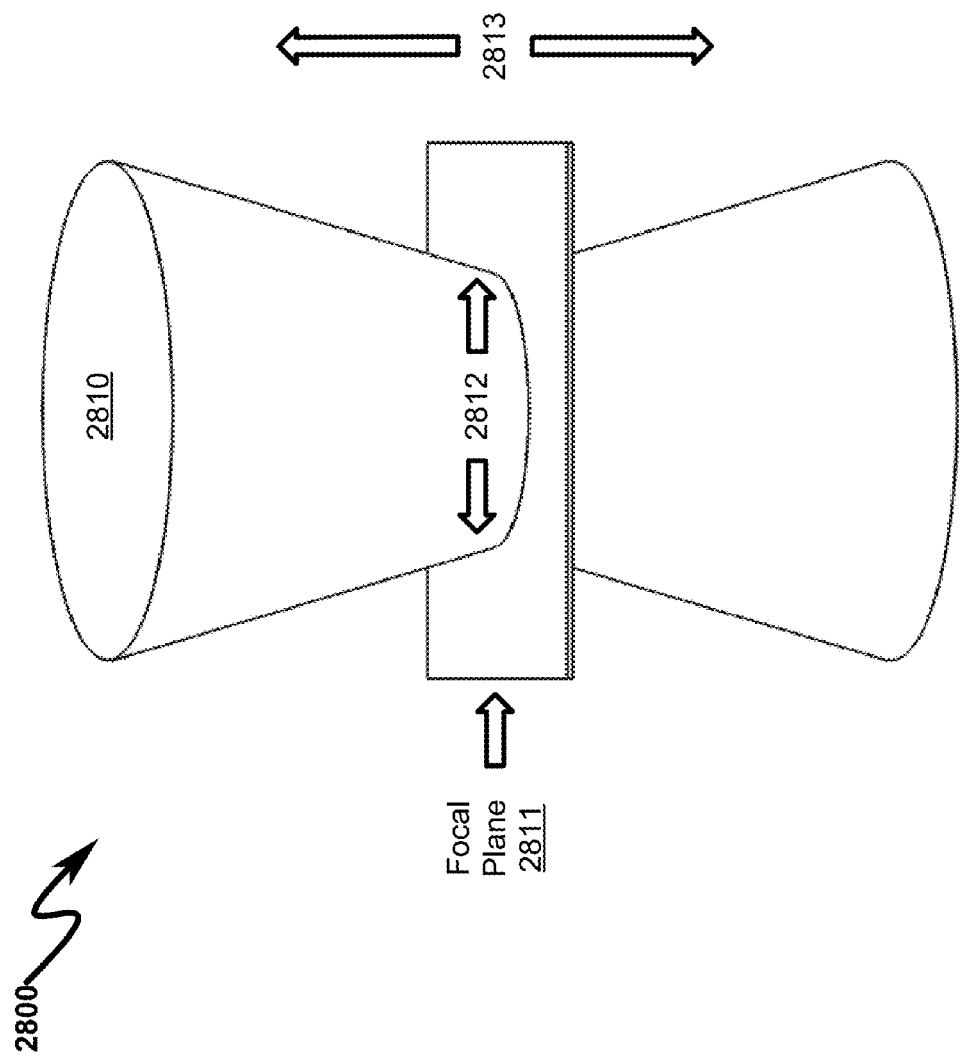
FIG. 28 illustrates a perspective view of a Basic Cutting Element (BCE) used to fabricate the PMB around the focal plane with the femtosecond laser and shows the focal-volume of the laser-spot, which resembles the basic cutting element ($\lambda$=1040 nm) for sculpting the polymeric material.

FIG. 27 (2700)-FIG. 28 (2800) depict the cutting pitch (2710, 2810) of Basic Cutting Element (BCE) used to fabricate the PMB around the focal plane (2711, 2811) with the femtosecond laser. This BCE closely resembles the focal-volume of the laser-spot. At a laser wavelength of ~520 nm (515 nm-530 nm)/~1040 nm (1000 nm-1100 nm), the diameter of the focal spot (1912, 2012) amounts to 2.6 µm, and the depth of focus (2713, 2813) extends to a depth of 12 µm. At threshold of optical breakdown, the cutting pitch is reduced to micrometer-dimensions, since only the center-caps of the Gaussian beam intensity distributions can create the desorption of the PMB.

Refractive Index Shaping Lens (RIS) (2900)

Figure 29:
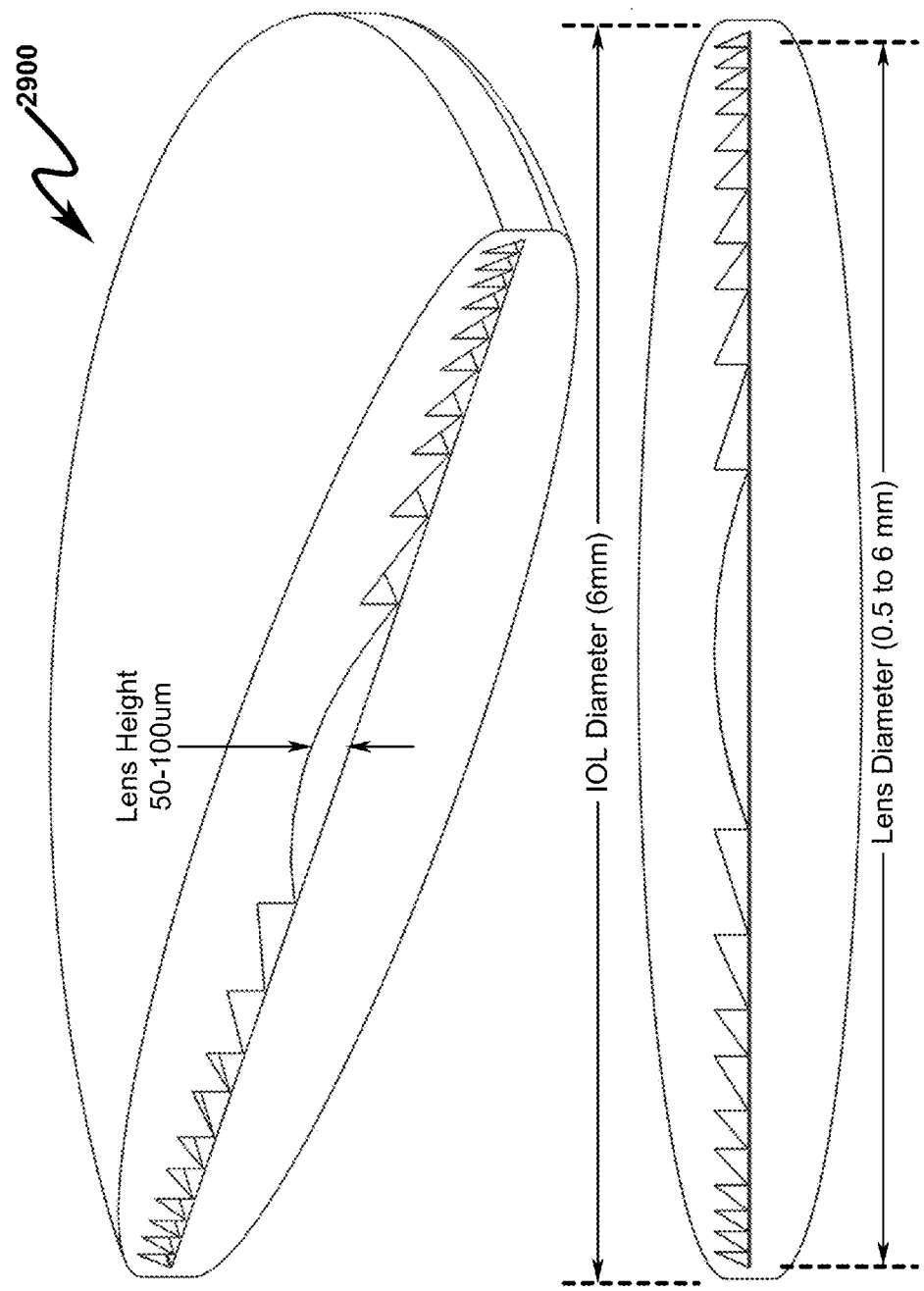
FIG. 29 illustrates the IOL-customization procedure through generating a secondary RIS-Lens ($\lambda$=515 nm) inside the IOL, before sculpting.

It is an objective of the current disclosure to provide a new manufacturing method for customized intraocular lenses (IOLs), based on a totally optical sculpting procedure. It is another objective of the current invention, to further optimize the optical performance of the sculpted intraocular lenses (IOLs) by incorporating a Refractive Index Shaping (RIS) lens, during the same manufacturing procedure. As illustrated in FIG. 29 (2900), the intended intraocular lens (IOL) can be customized through a secondary RIS-lens, which is incorporated into the PMB, before the sculpting procedure takes place. The RIS-lens is generated by a laser beam with a wavelength of 515 nm, which is obtained by frequency-doubling the sculpting laser beam with a wavelength of 1040 nm. The RIS-lens occupies a central slab-shaped volume of approximately 50 µm to 100 µm thickness, and extends over the 6 mm diameter of the sculpted intraocular lens (IOL). The RIS-lens formation system is described in further detail in U.S. Pat. No. 8,292,952 which is hereby incorporated by reference.

Optical Sculpting Processing Time

In the table below, typical processing time per IOL for the optical sculpting procedure is shown:

| Processing Parameter | Value |
|---|---|
| Posterior Surface Cutting | 5 seconds |
| Anterior Surface Cutting | 5 seconds |
| Cutting to PMB slab surface | 5 seconds |
| Total lens cutting time | 15 seconds |
| Haptic cutting time | 15 seconds |
| Customized RIS-lens | 30 seconds |
| Total Processing Time: | 1 minute |

Total lens cutting amounts to 15 seconds, cutting the haptics adds another 15 seconds, and finally, the creation of a customized RIS-lens consumes approximately 30 seconds. Thus, the overall all-optical IOL manufacturing procedure lasts approximately 1 minute. Extrapolating to a fully automated production laser machine, about 500000 IOLs could be optically manufactured annually, based on the total lens cutting time. Taking into consideration additional time periods for automatic feeding of the PMBs and loading of the software for customized production, still several hundred thousand of customized premium lenses can be fabricated with one laser system.

Death of Focus (DOF) Vs. Multifocality (3000)

Figure 30:
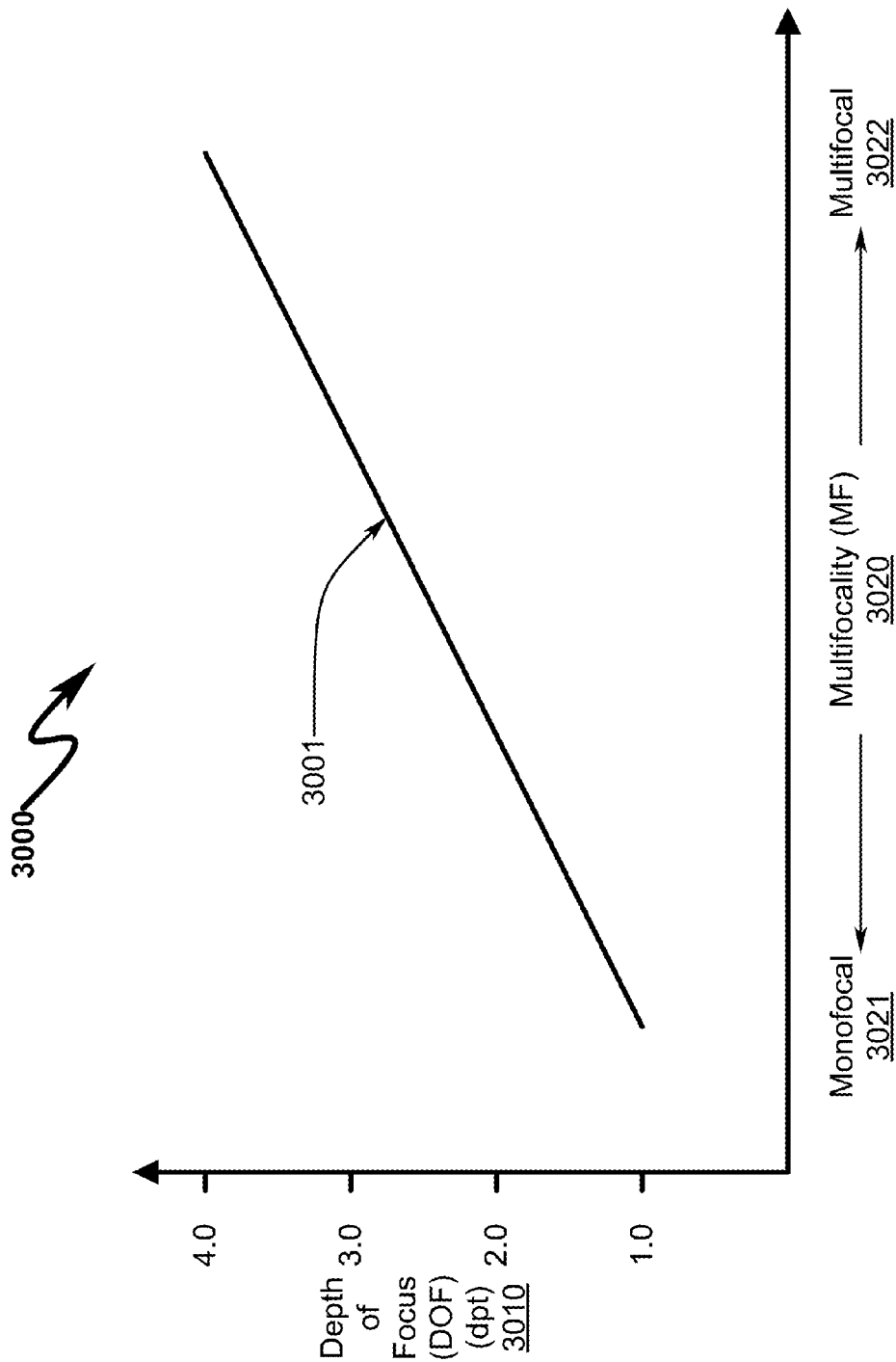
FIG. 30 illustrates a plot of the Depth of Focus (DoF) as a function of multifocality of a typical customized IOL.

FIG. 30 (3000) depicts a plot (3001) of the Depth of Focus (DoF) (3010) as a function of multifocality (3020) of a typical customized IOL. In general, the depth of focus (DoF) of a human eye increases with the multifocality of the eye's dioptric system. For the case of monofocality (3021) (e.g., a normal presbyopic human eye), a depth of focus of approximately one (1) diopter is usable. In the case of multifocality (3022), such as after implantation of e.g. a multifocal customized IOL in a pseudophakic eye, typically a depth of focus of four (4) diopters is achieved, allowing for simultaneous near and distant vision.

Death of Focus (DOF) Vs. Spherical Aberration (3100)

Figure 31:
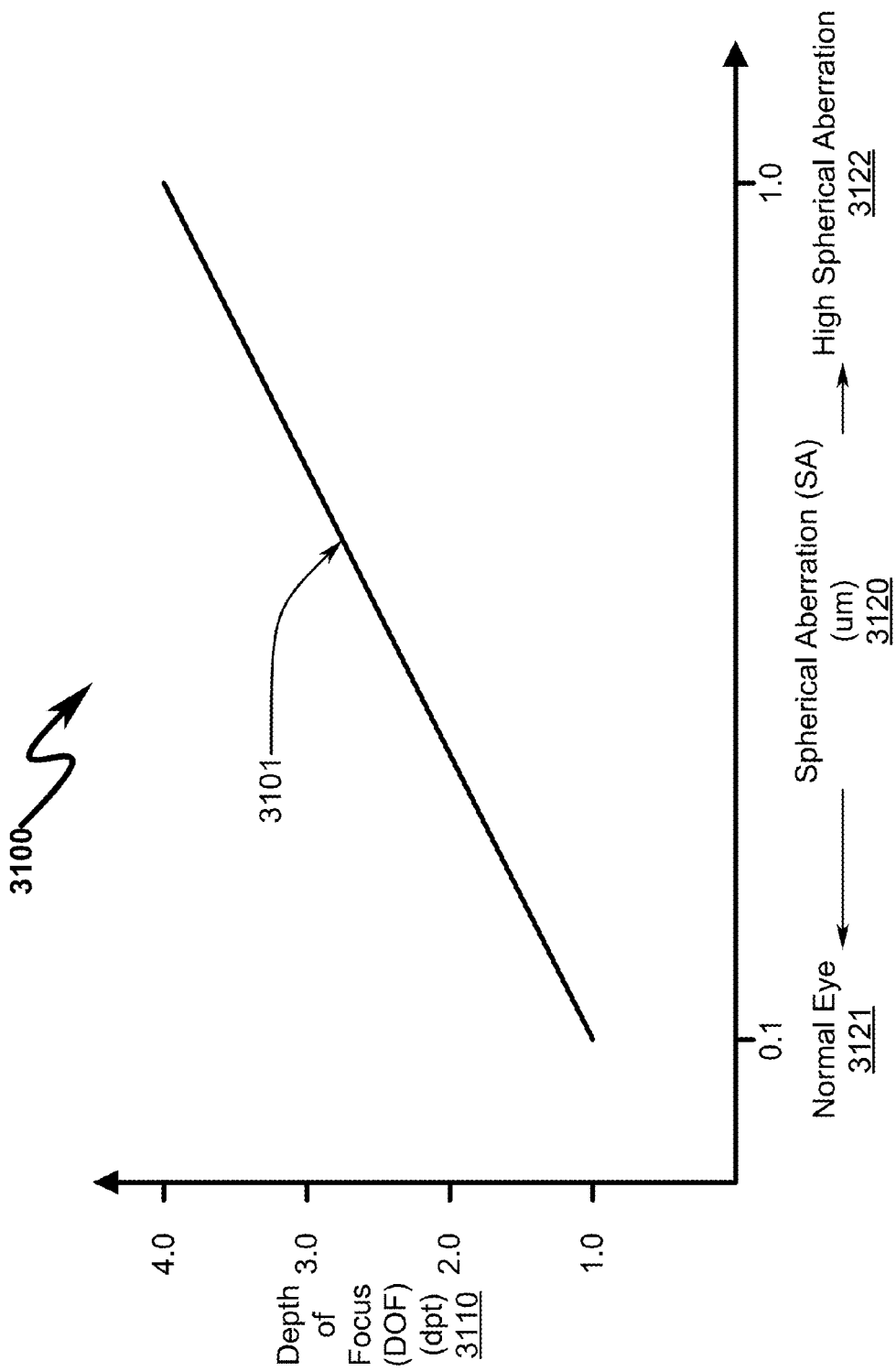
FIG. 31 illustrates a plot of the Depth of Focus (DoF) as a function of spherical aberration (asphericity) (SA) of a customized IOL.

FIG. 31 (3100) depicts a plot (3101) of the Depth of Focus (DoF) (3110) as a function of spherical aberration (SA) (3120) of a customized IOL. In normal eyes (3121), the amount of spherical aberration, which is described by a Zernike-polynomial (4,0) of fourth order, is less than 0.1 μm, corresponding to a negligible contribution to higher order aberrations and only slightly affecting the depth of focus (DoF) of the human eye. In eyes with a high level of spherical aberration (3122) (e.g., in monofocal pseudophakic eyes), an augmented depth of focus is present. In the framework of the present invention, a customized IOL can be manufactured to generate a predetermined amount of spherical aberration (i.e., depth of focus (DoF)), for achieving simultaneously near and distant vision, or reducing the amount of spherical aberration for a given human eye, applying a corresponding aspherical design of the customized IOL.

Modulation Transfer Function (3200)

Figure 32:
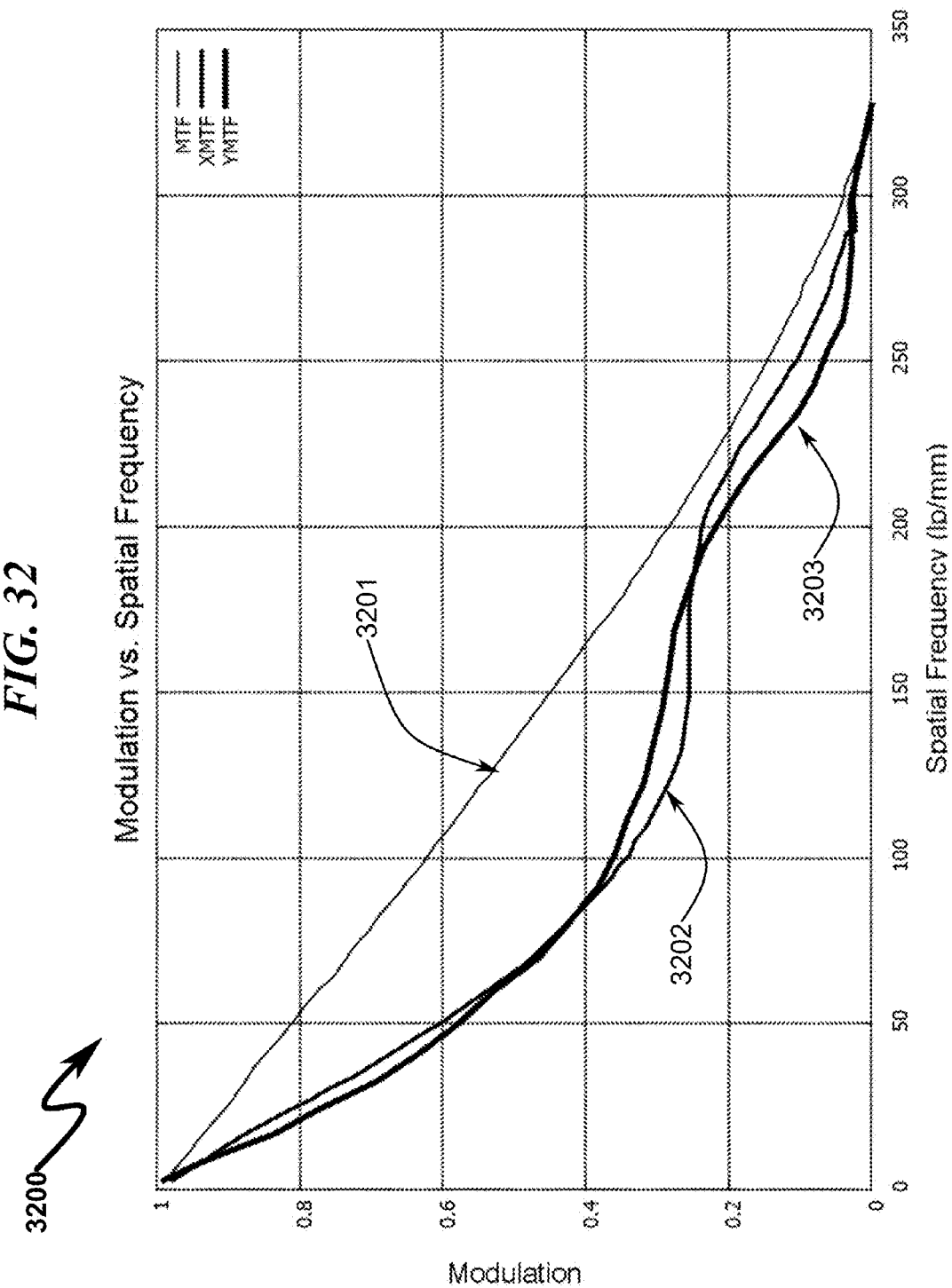
FIG. 32 illustrates the process of Modulation Transfer Function (MTF) engineering.

FIG. 32 (3200) illustrates a typical Modulation Transfer Function (MTF) of an aspheric lens (IOL). The MTF curve (3201) resembles the Modulation Transfer Function (MTF) of a diffraction-limited optical system. The numerical value of the Modulation Transfer Function (MTF) (3210) in decimal fractions of 1.0 is plotted as a function of the Spatial Frequency (3220), measured in line pairs per mm (lp/mm), with essential readings at 25 lp/mm (20/80 vision), 50 lp/mm (20/40 vision) and 100 lp/mm (20/20 vision). The components XMTF (3202) and YMTF (3203) of the Modulation Transfer Function (MTF) of the aspheric lens indicated as shown. As can be seen from FIG. 32 (3200), the asphericity of the lens (IOL) reduces the contrast at medium spatial frequencies, while augmenting the depth of focus (DoF). It is one objective of the present invention to allow for a specific engineering of the Modulation Transfer Function (MTF) of the customized IOL.

IOL Fabrication Method (3300)-(3600)

Figure 33:
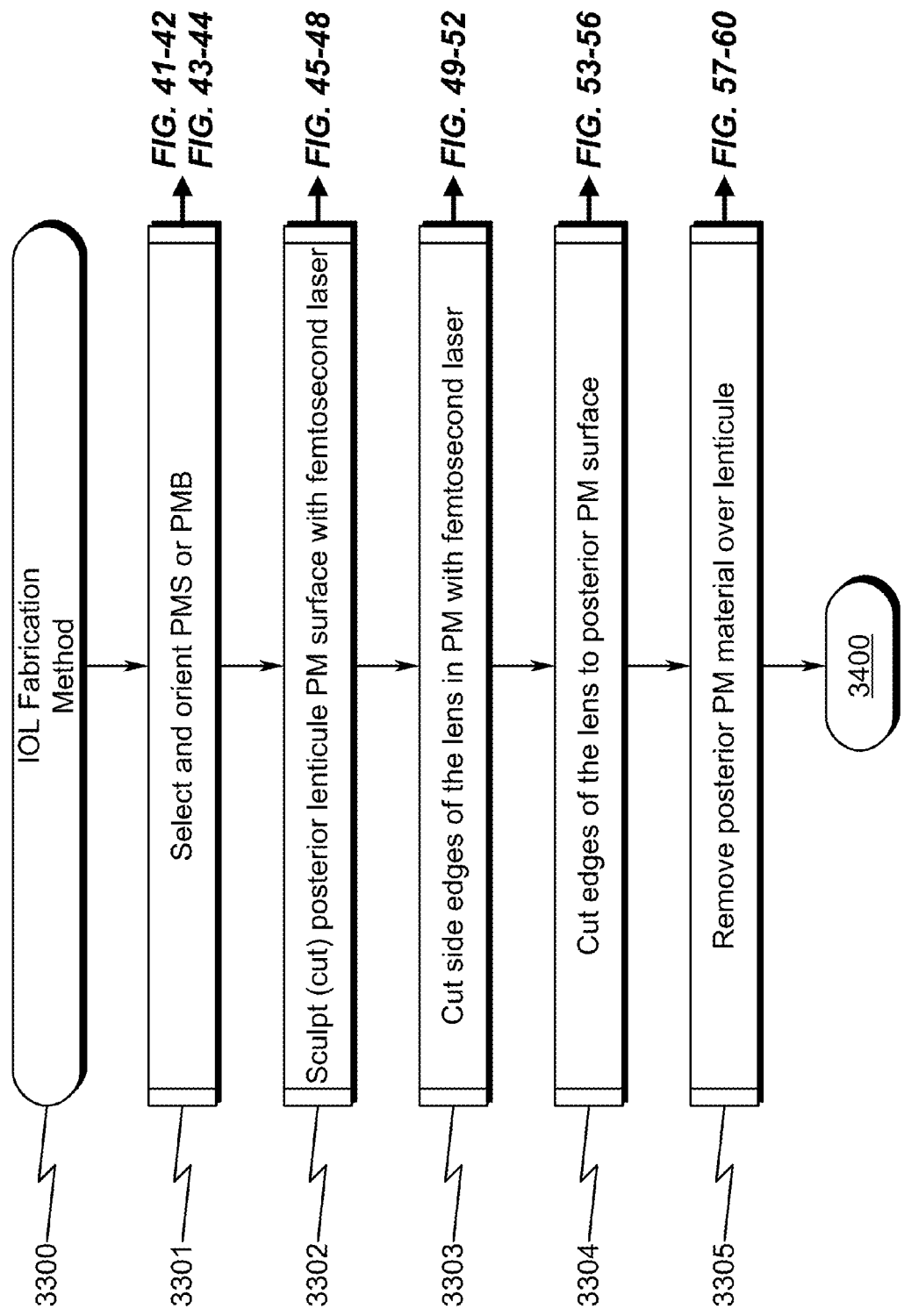
FIG. 33 illustrates a flowchart depicting an exemplary IOL fabrication method (1 of 4) and figure references to associated drawings depicting the fabrication steps.
Figure 34:
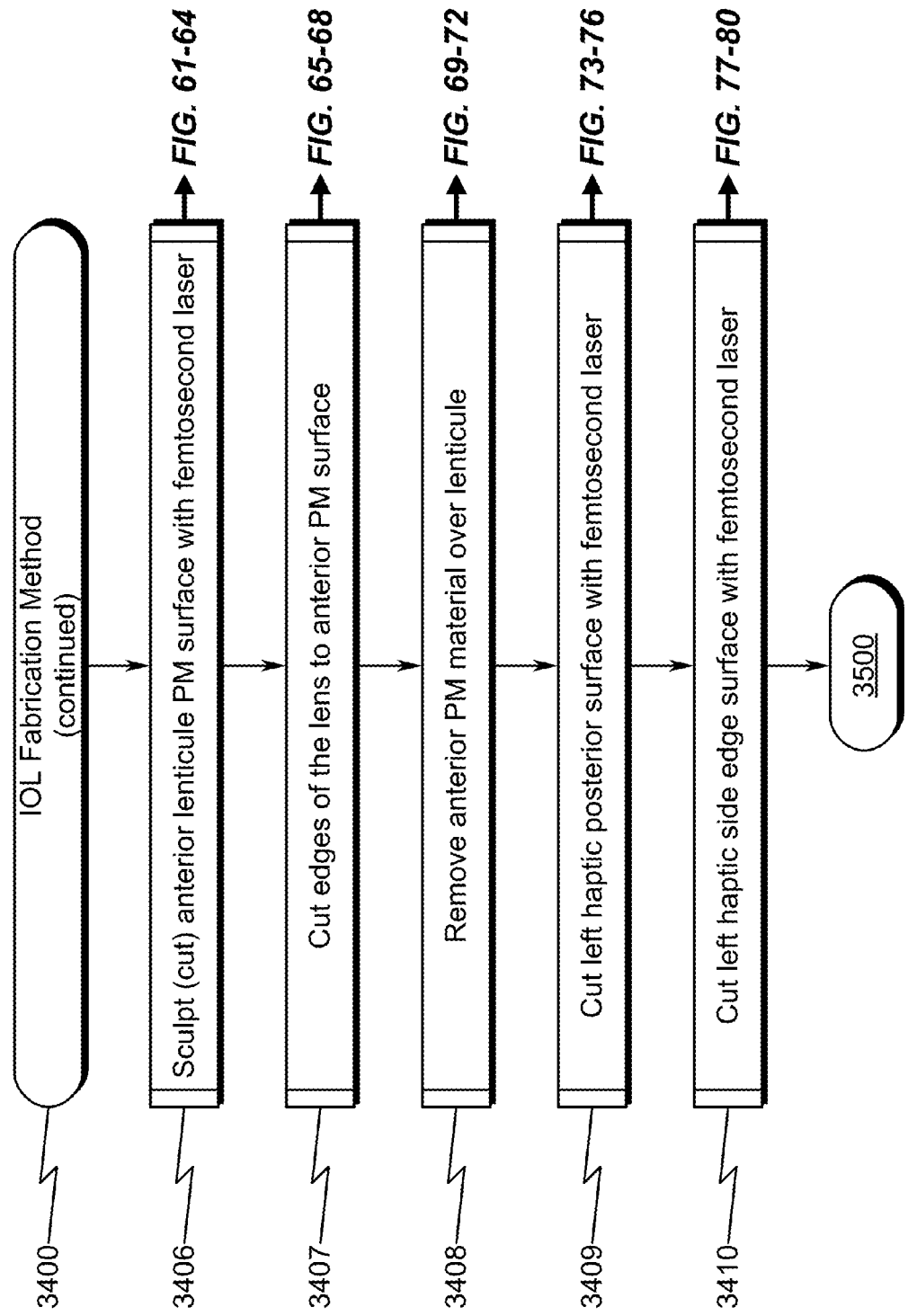
FIG. 34 illustrates a flowchart depicting an exemplary IOL fabrication method (2 of 4) and figure references to associated drawings depicting the fabrication steps.
Figure 35:
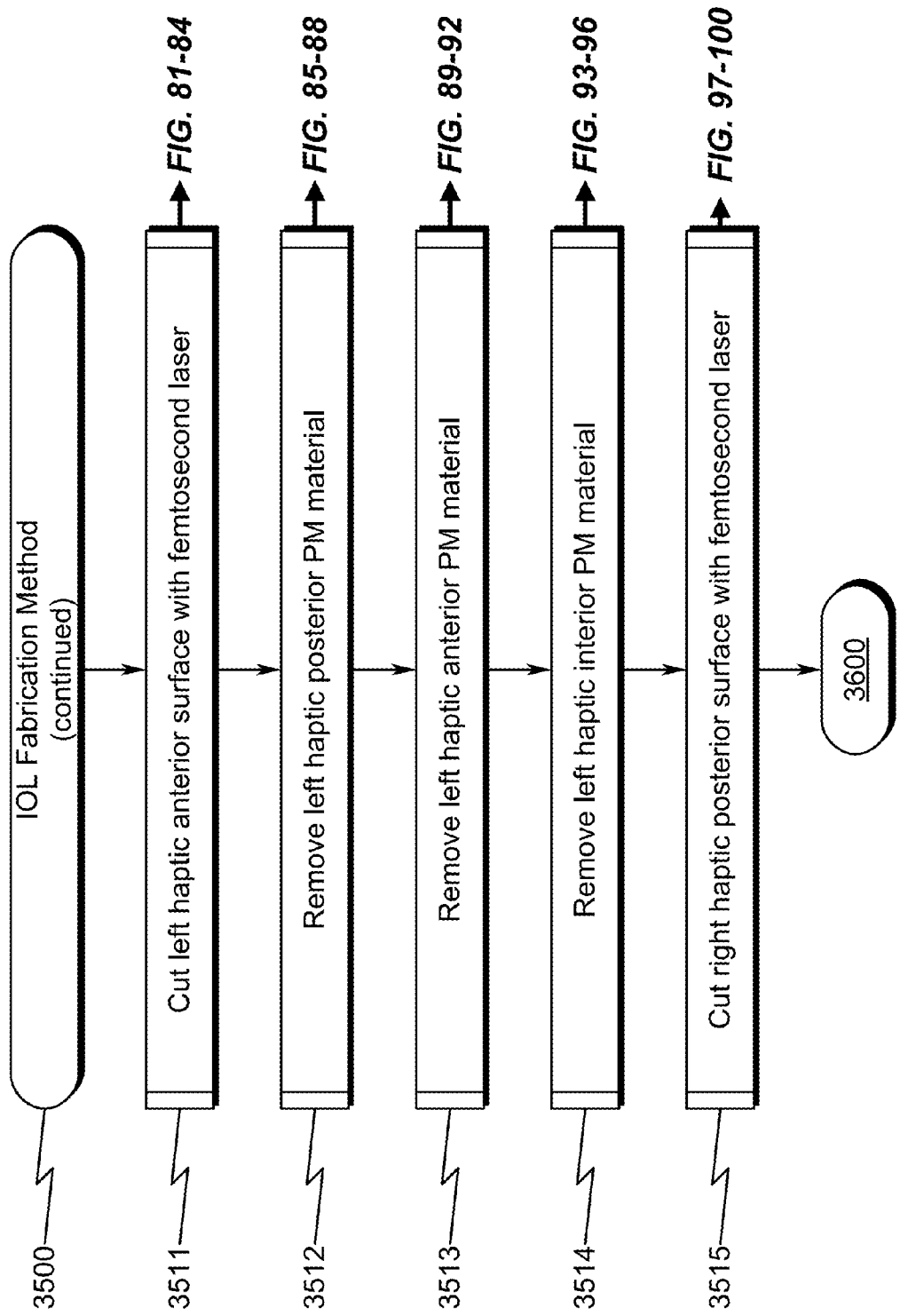
FIG. 35 illustrates a flowchart depicting an exemplary IOL fabrication method (3 of 4) and figure references to associated drawings depicting the fabrication steps.
Figure 36:
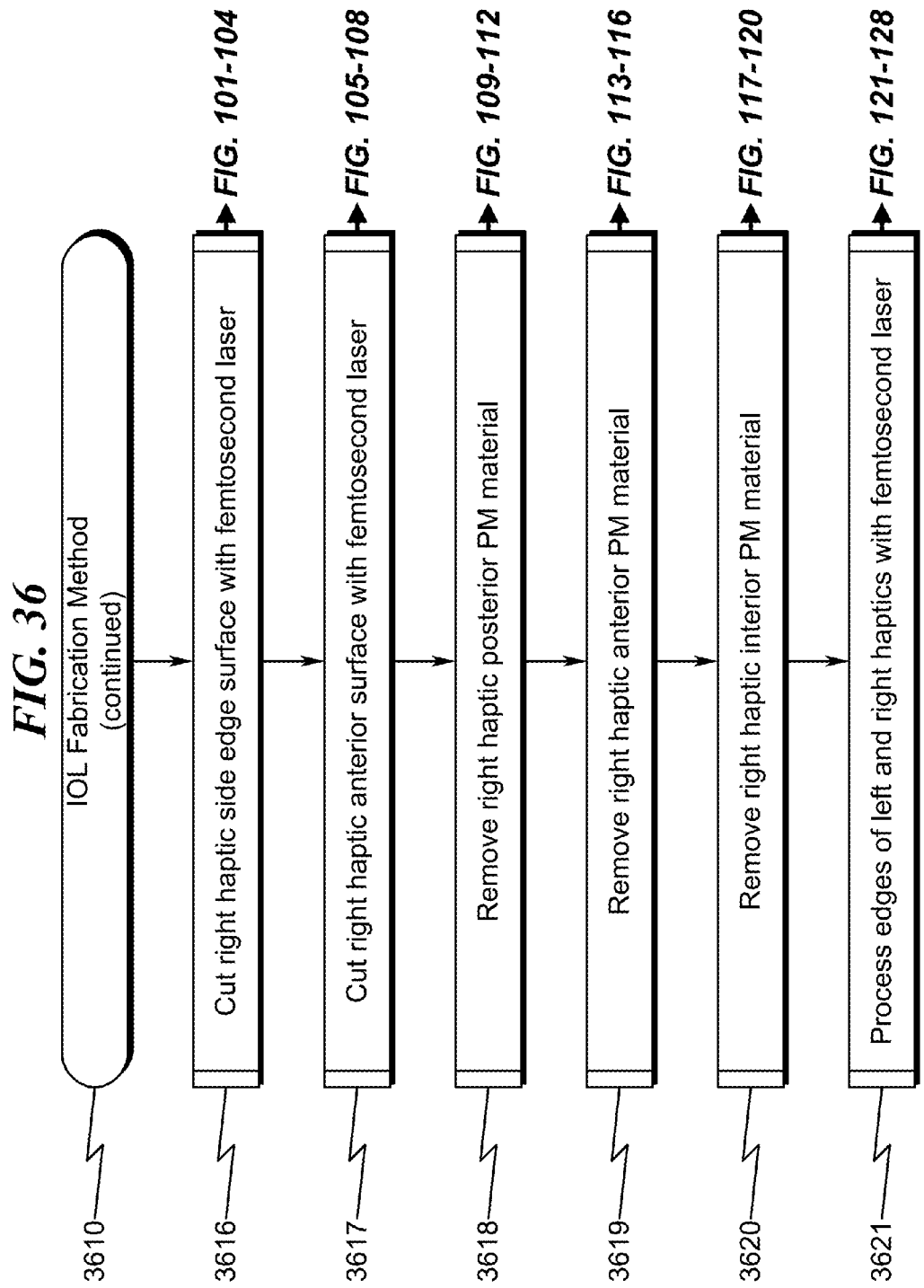
FIG. 36 illustrates a flowchart depicting an exemplary IOL fabrication method (4 of 4) and figure references to associated drawings depicting the fabrication steps.
Figure 41:
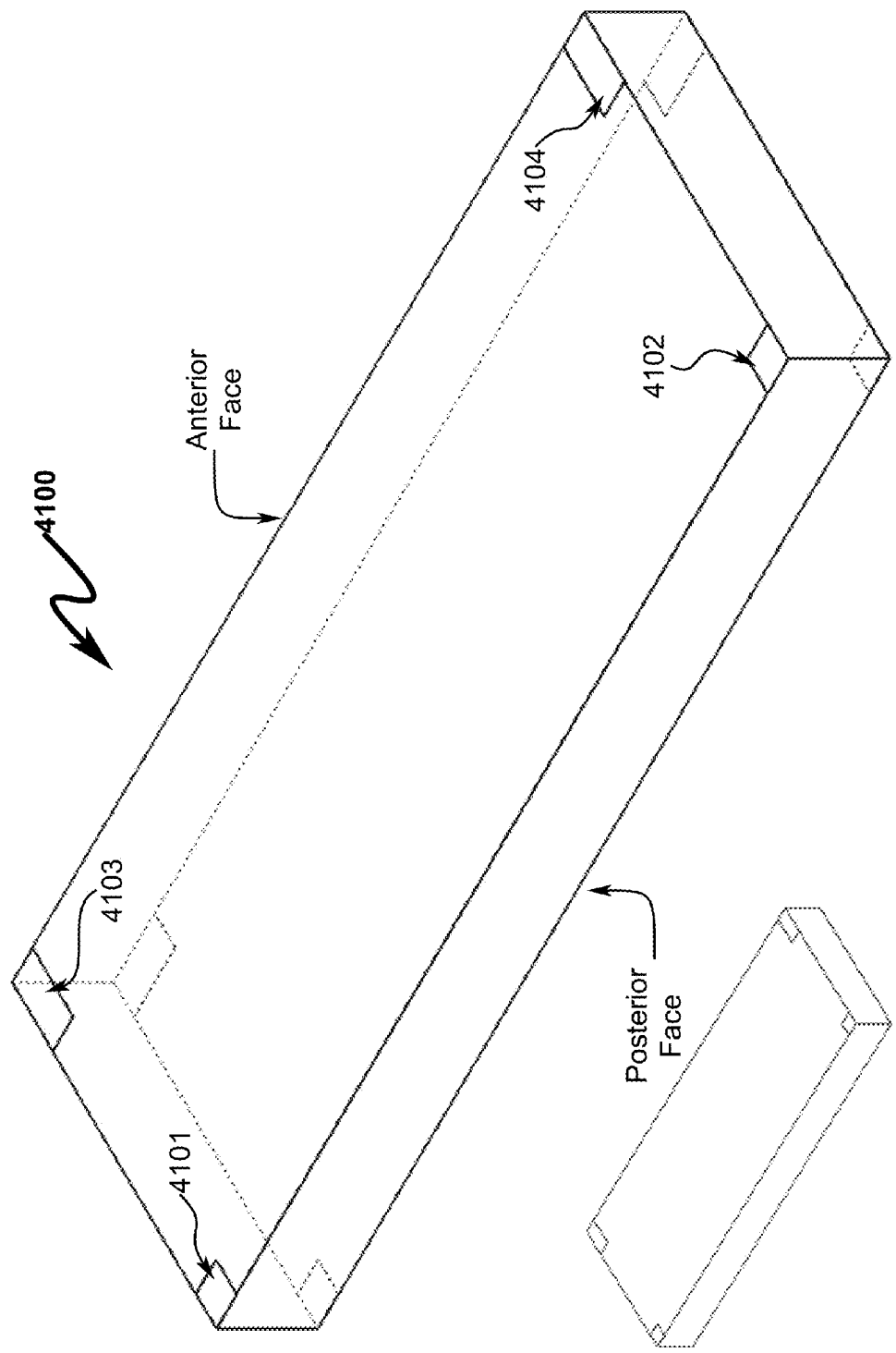
FIG. 41 illustrates a top right perspective view of a PMS used in an exemplary present invention IOL fabrication sequence.
Figure 52:
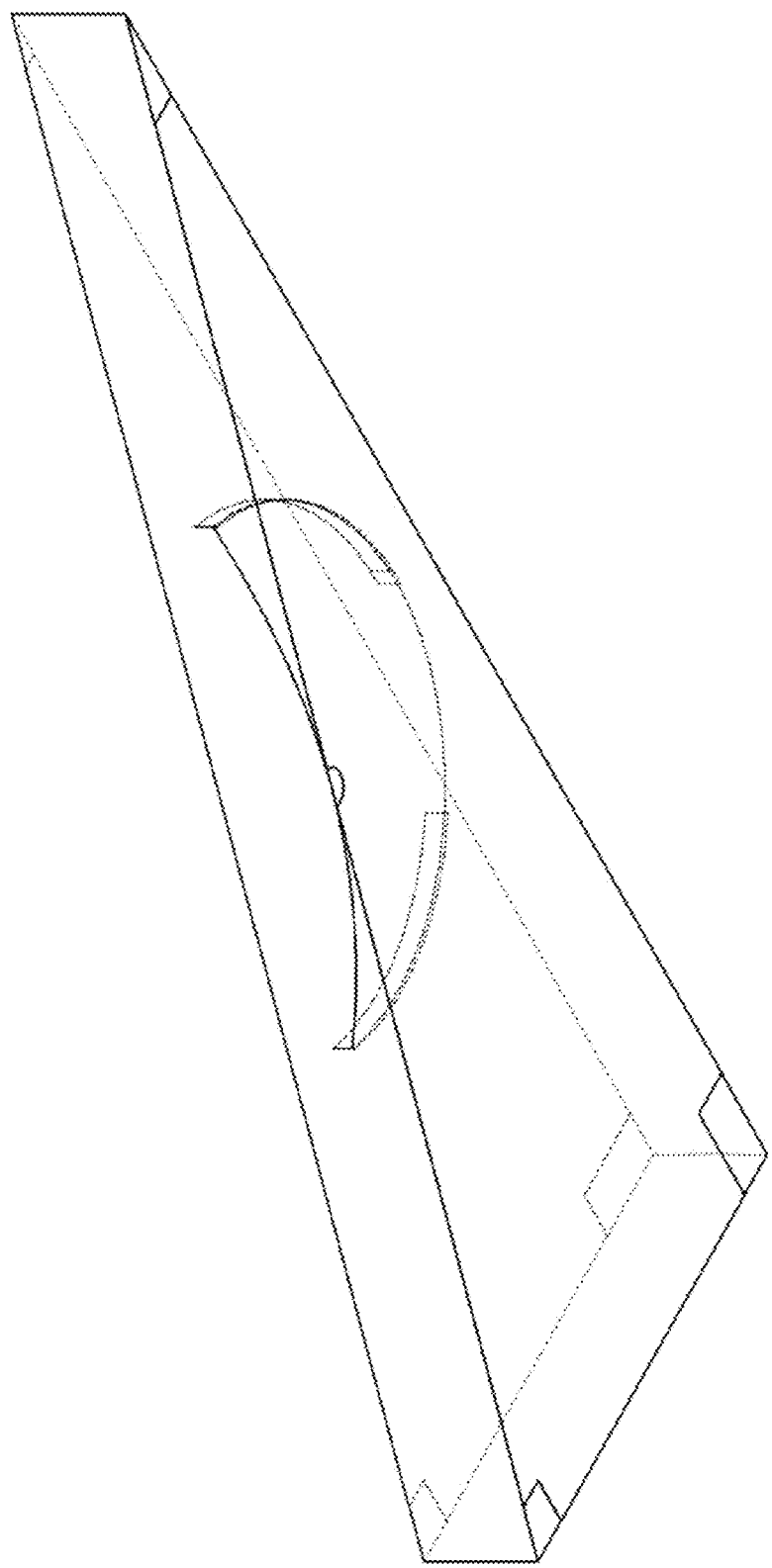
FIG. 52 illustrates a bottom right perspective diagonal section view of an interior edge lens cut in an exemplary present invention IOL fabrication sequence formed using a PMS.
Figure 53:
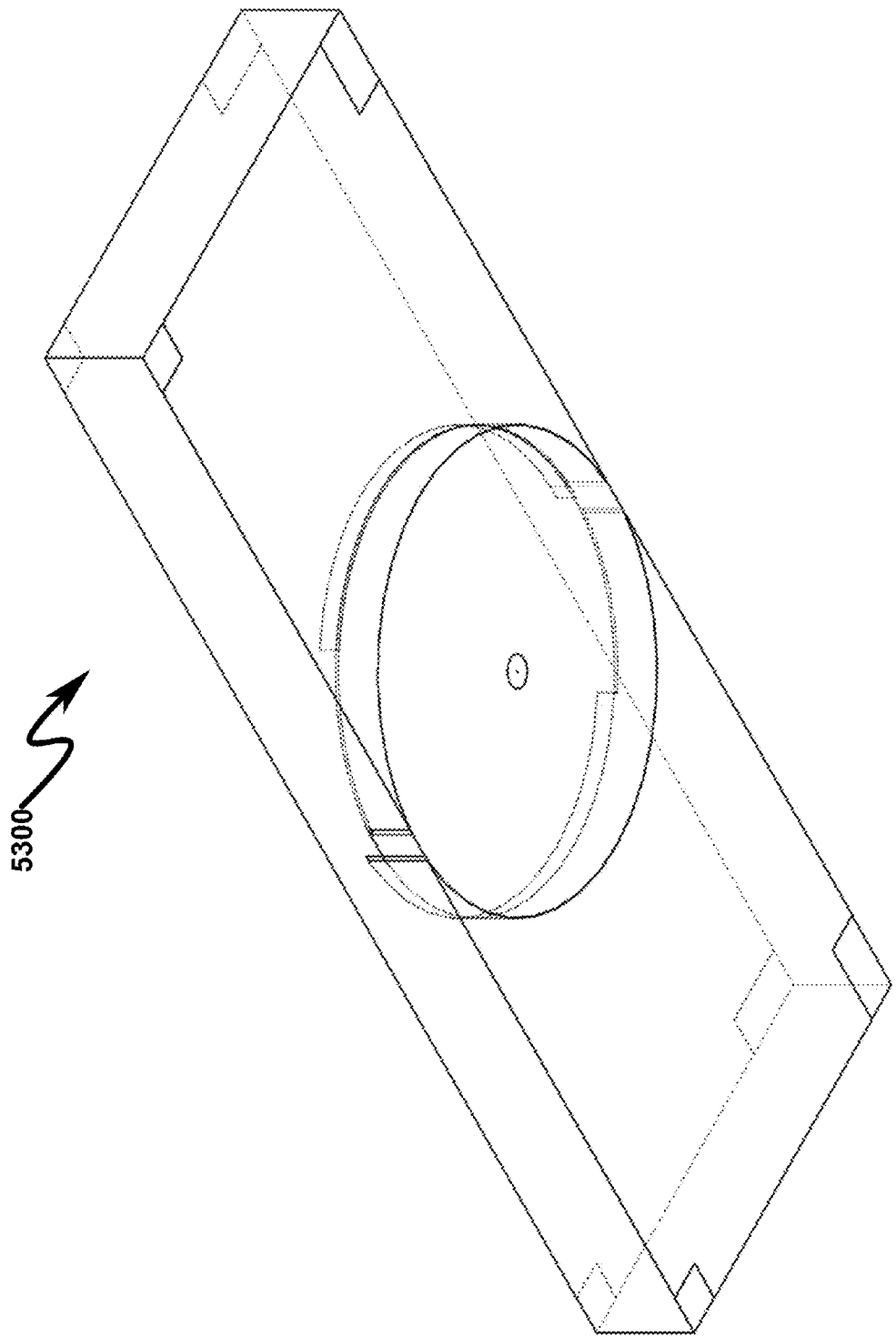
FIG. 53 illustrates a bottom right perspective view of an edge-to-posterior-surface lens cut in an exemplary present invention IOL fabrication sequence formed using a PMS.
Figure 54:
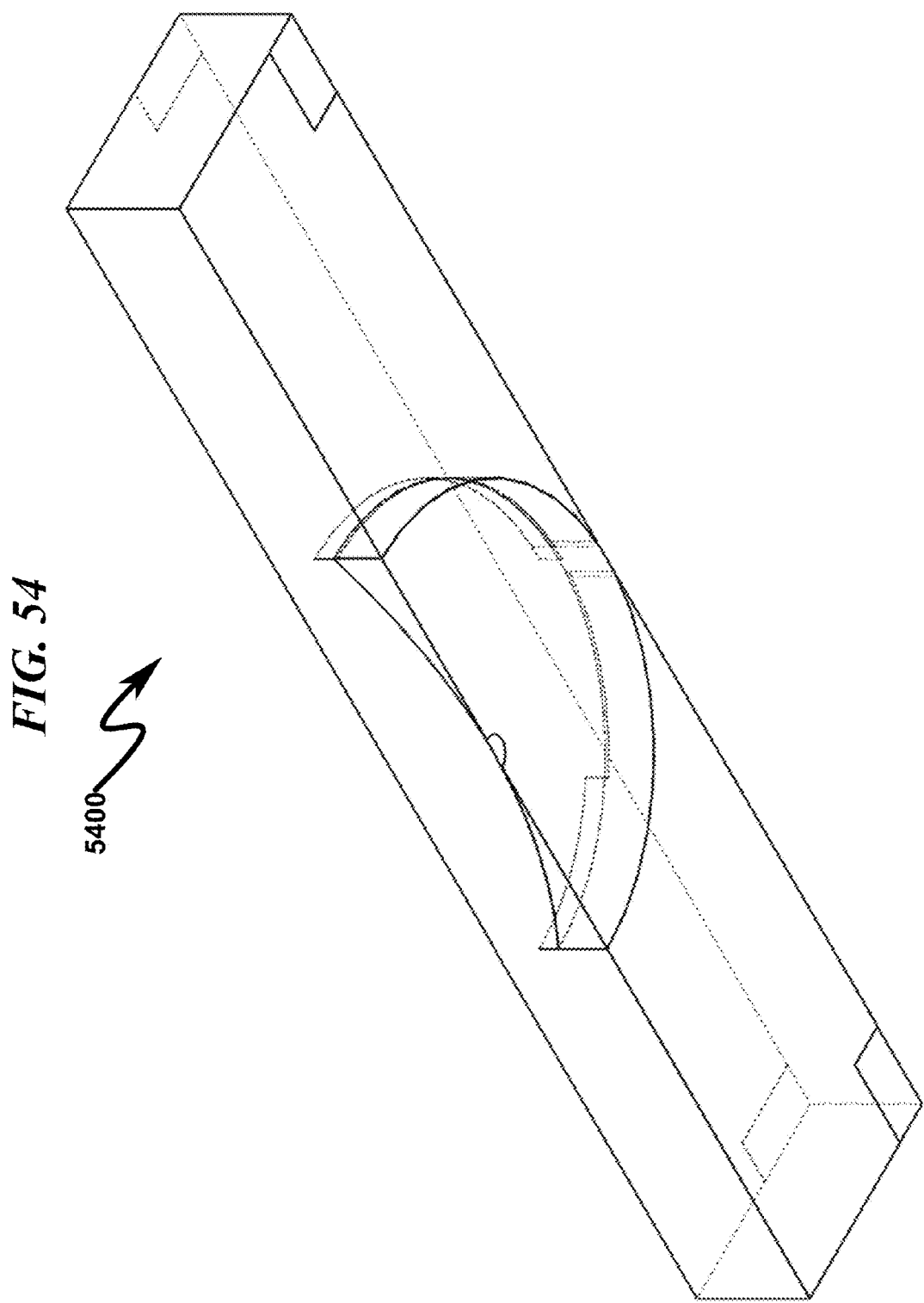
FIG. 54 illustrates a bottom right perspective front section view of an edge-to-posterior-surface lens cut in an exemplary present invention IOL fabrication sequence formed using a PMS.
Figure 55:
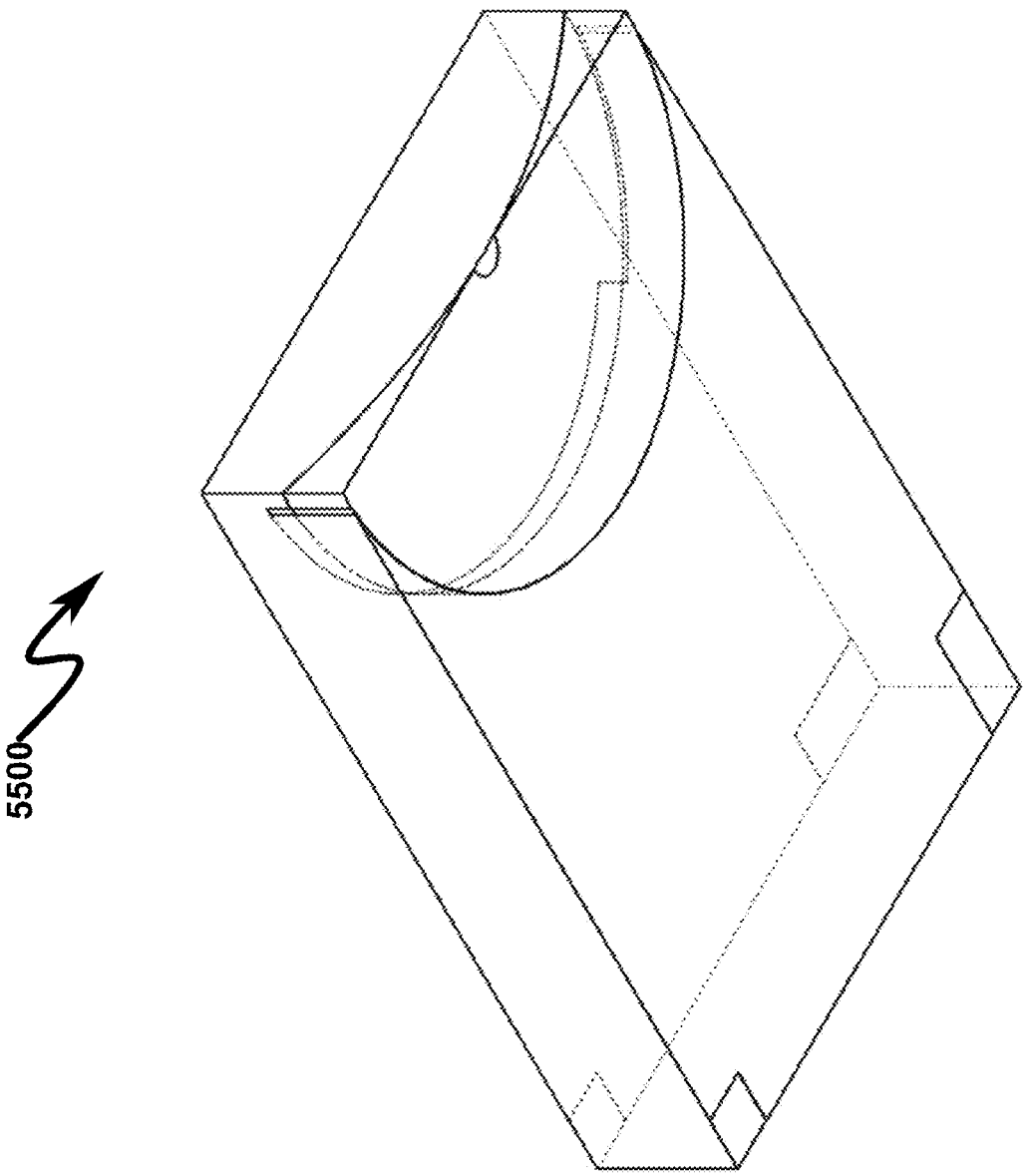
FIG. 55 illustrates a bottom right perspective right section view of an edge-to-posterior-surface lens cut in an exemplary present invention IOL fabrication sequence formed using a PMS.
Figure 56:
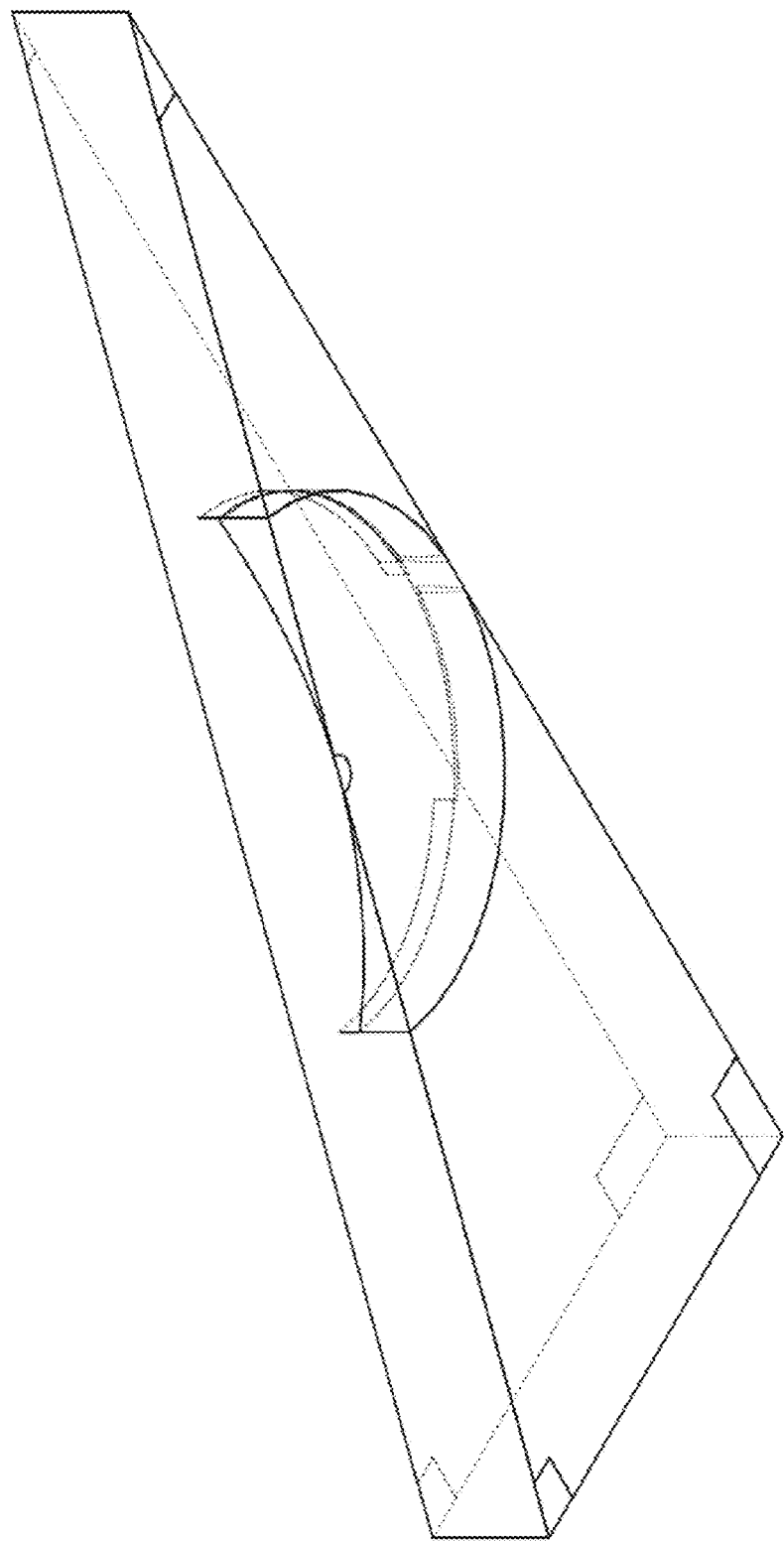
FIG. 56 illustrates a bottom right perspective diagonal section view of an edge-to-posterior-surface lens cut in an exemplary present invention IOL fabrication sequence formed using a PMS.
Figure 57:
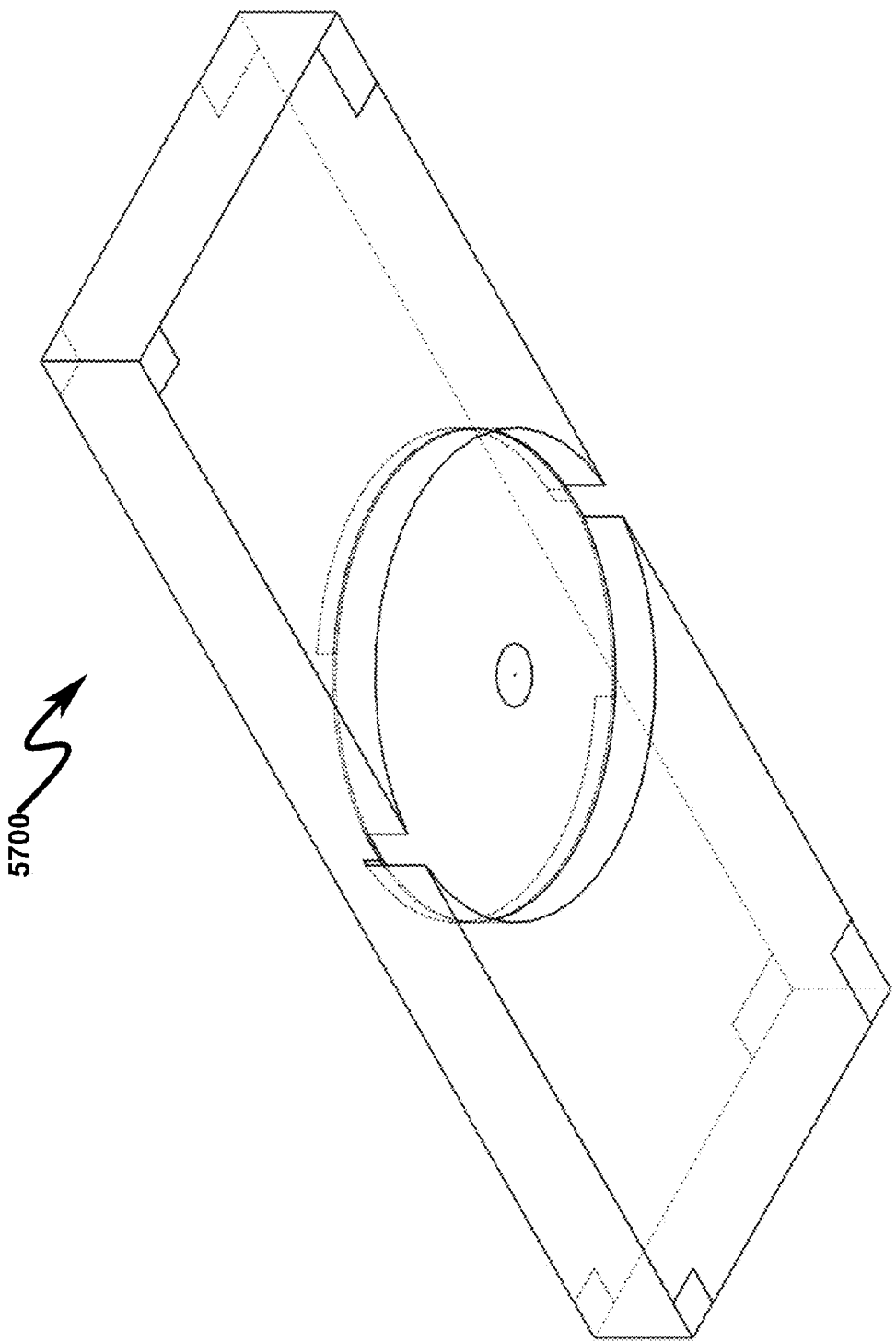
FIG. 57 illustrates a bottom right perspective view of removal of the posterior lens cutout in an exemplary present invention IOL fabrication sequence formed using a PMS.
Figure 58:
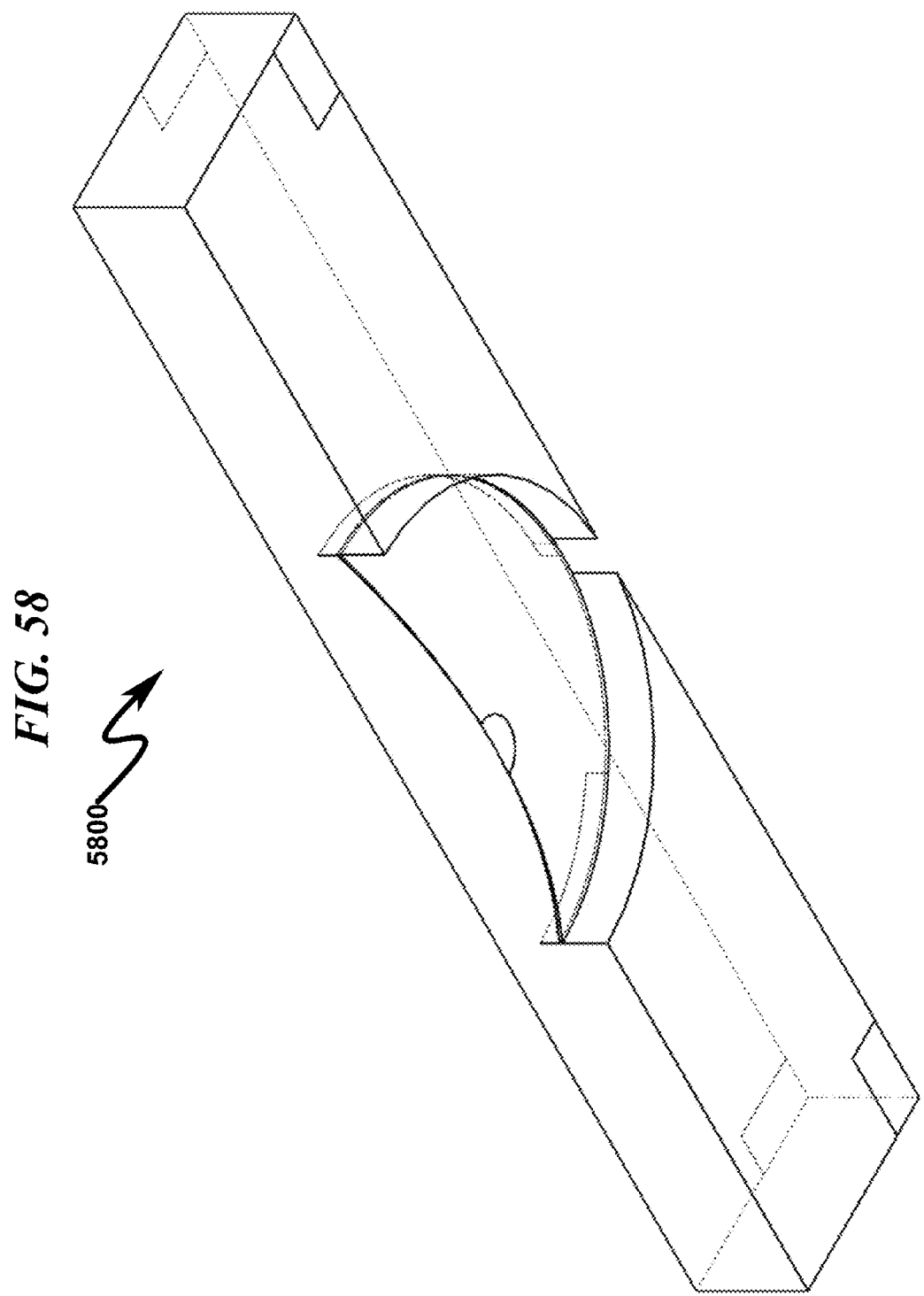
FIG. 58 illustrates a bottom right perspective front section view of removal of the posterior lens cutout in an exemplary present invention IOL fabrication sequence formed using a PMS.
Figure 59:
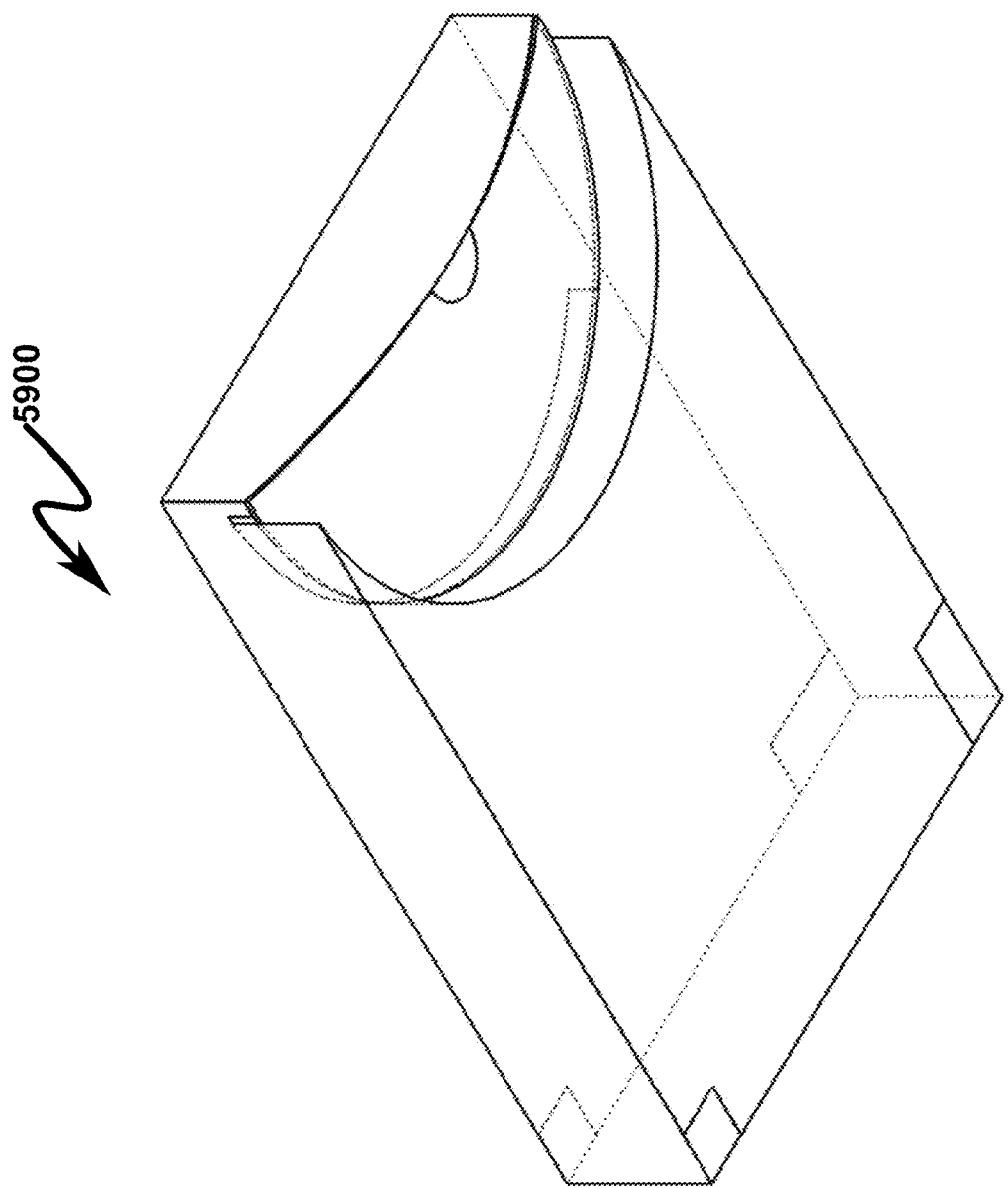
FIG. 59 illustrates a bottom right perspective right section view of removal of the posterior lens cutout in an exemplary present invention IOL fabrication sequence formed using a PMS.
Figure 61:
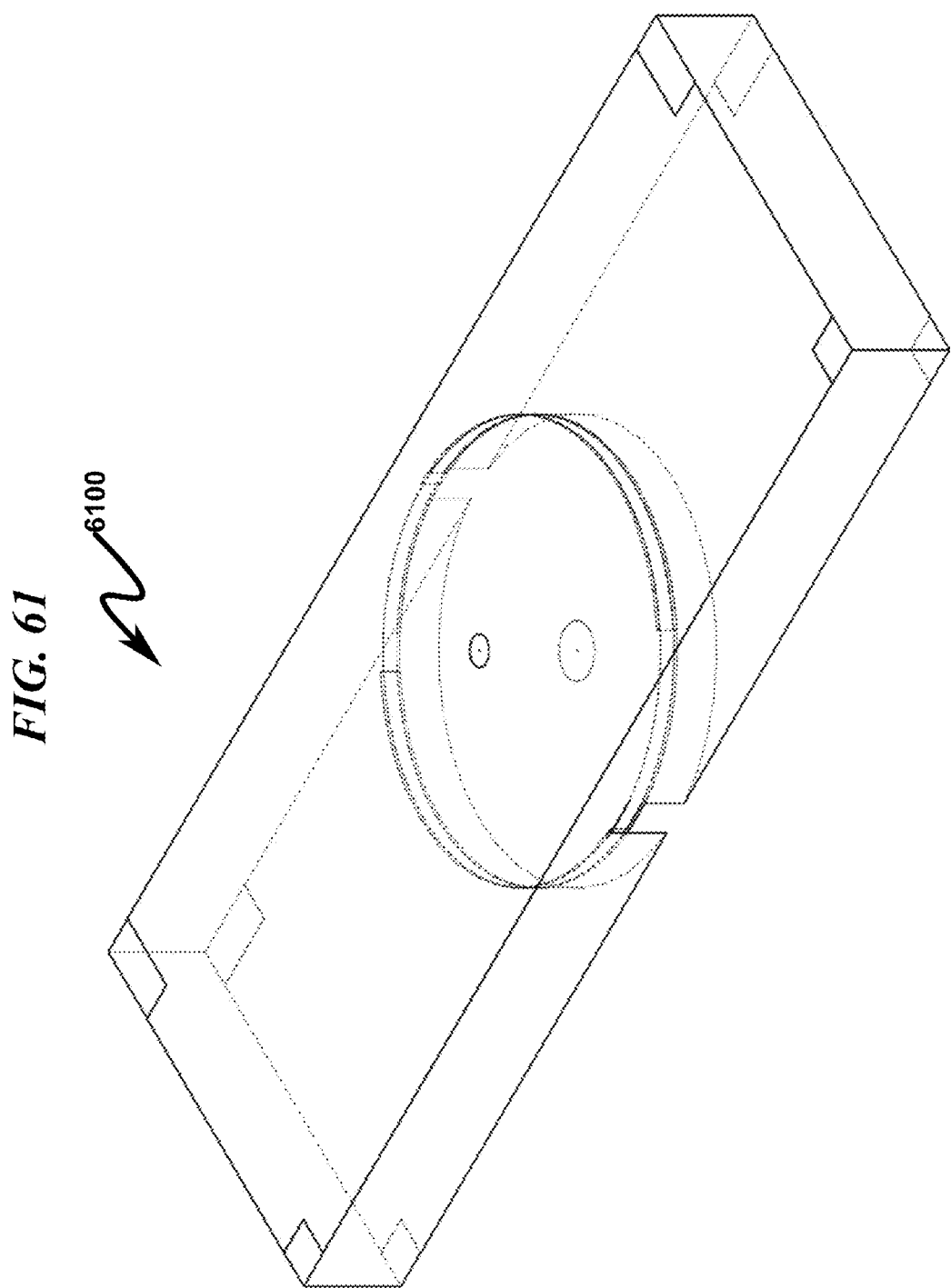
FIG. 61 illustrates a top right perspective view of an anterior lens cut in an exemplary present invention IOL fabrication sequence formed using a PMS.
Figure 62:
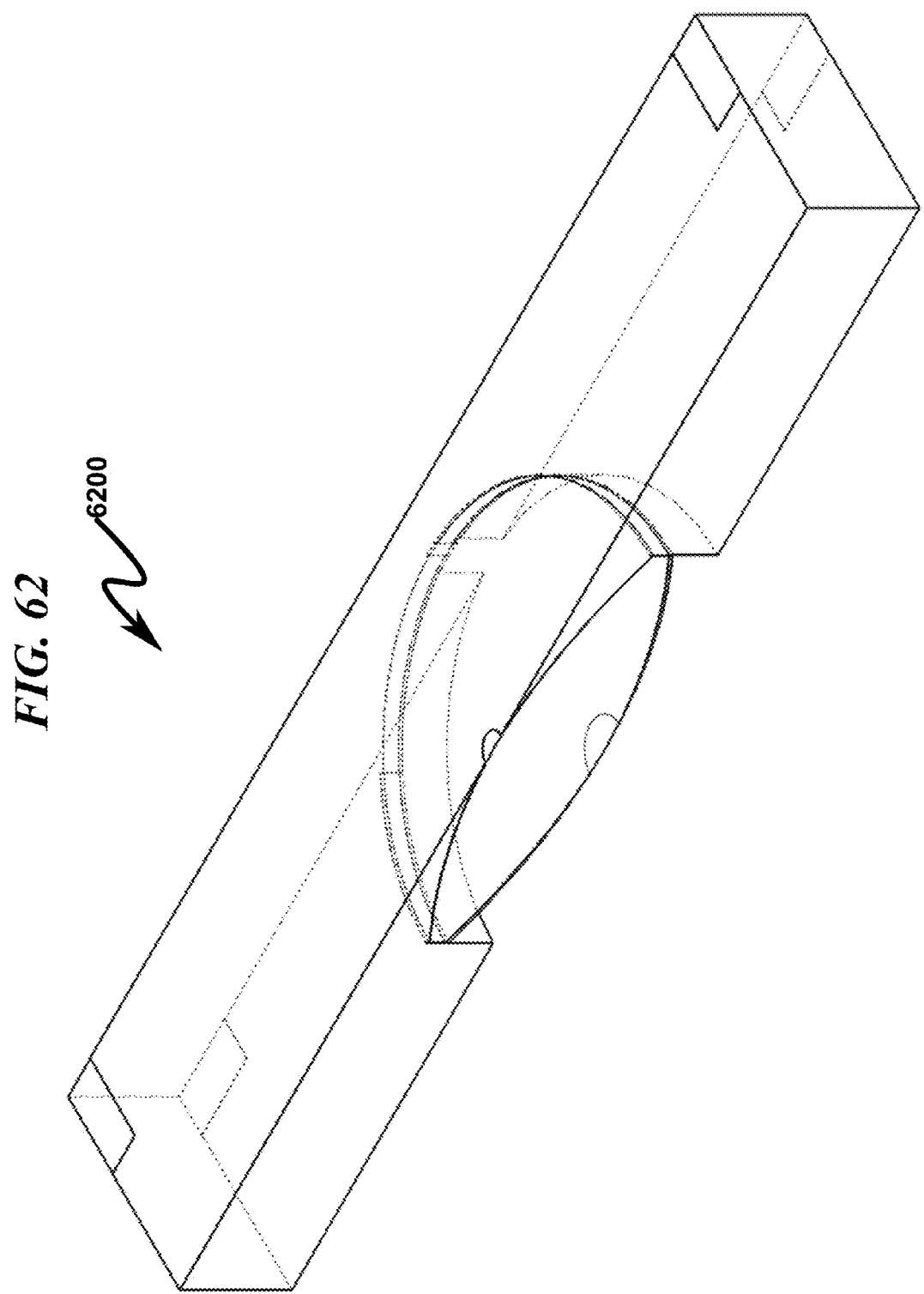
FIG. 62 illustrates a top right perspective front section view of an anterior lens cut in an exemplary present invention IOL fabrication sequence formed using a PMS.
Figure 63:
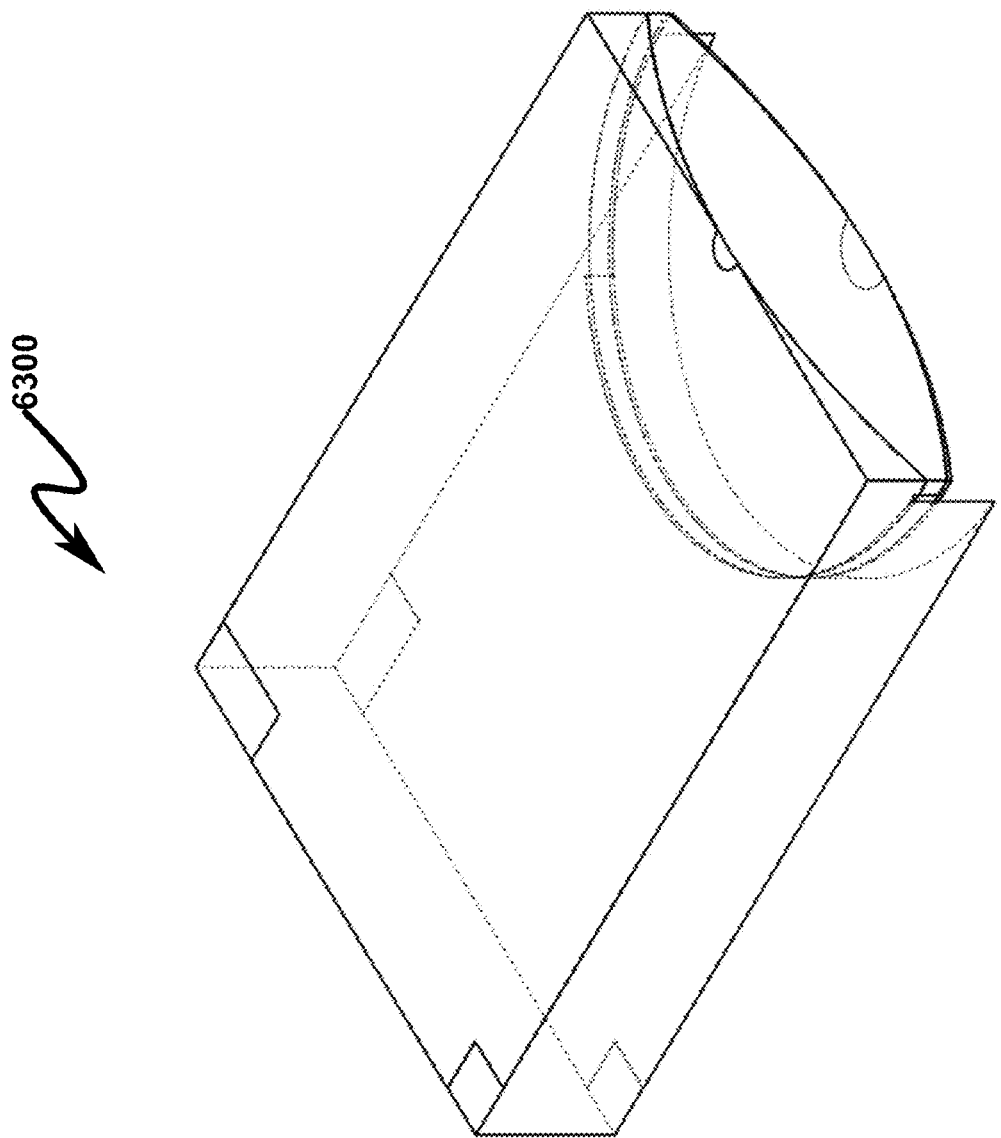
FIG. 63 illustrates a top right perspective right section view of an anterior lens cut in an exemplary present invention IOL fabrication sequence formed using a PMS.
Figure 64:
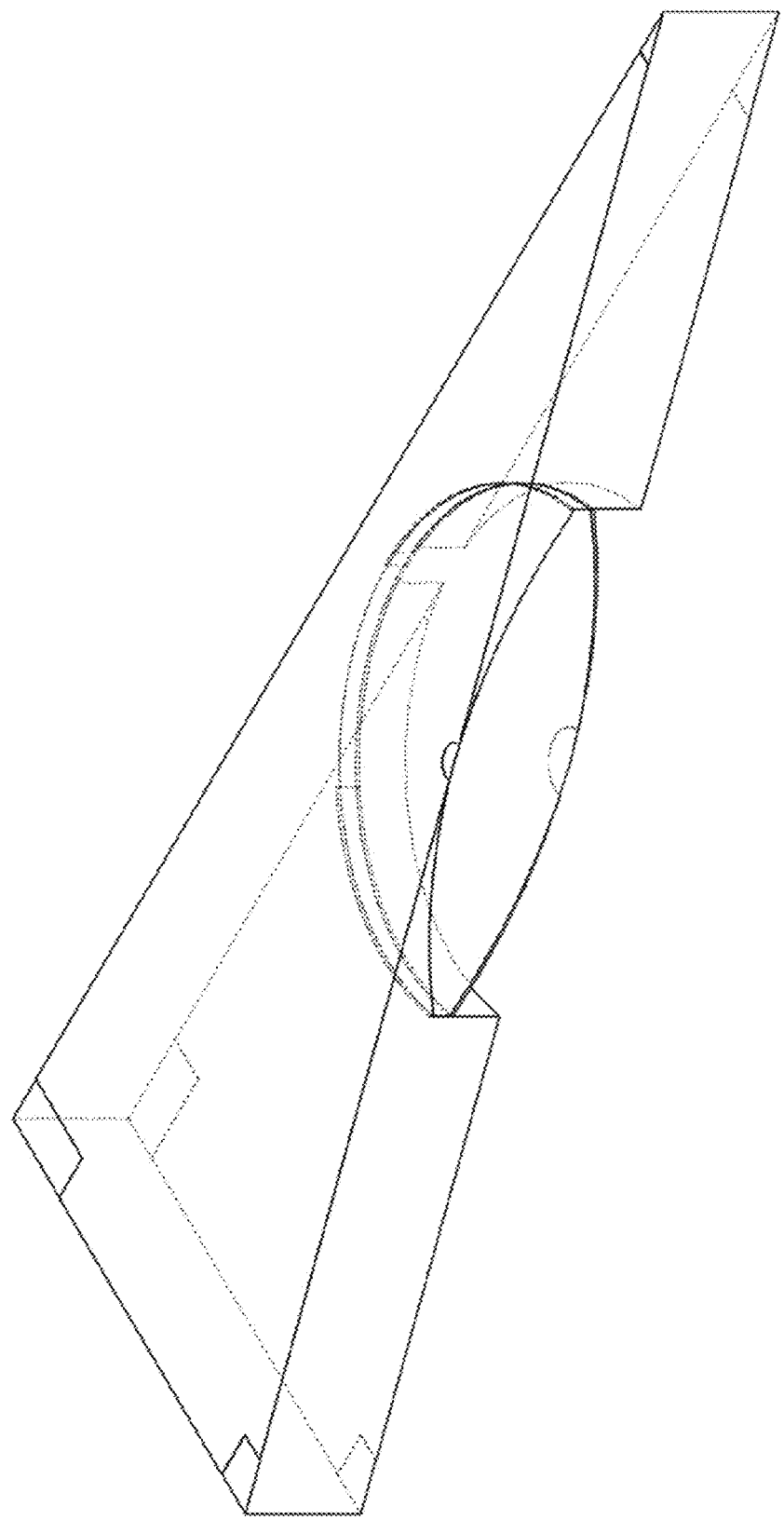
FIG. 64 illustrates a top right perspective diagonal section view of an anterior lens cut in an exemplary present invention IOL fabrication sequence formed using a PMS.
Figure 65:
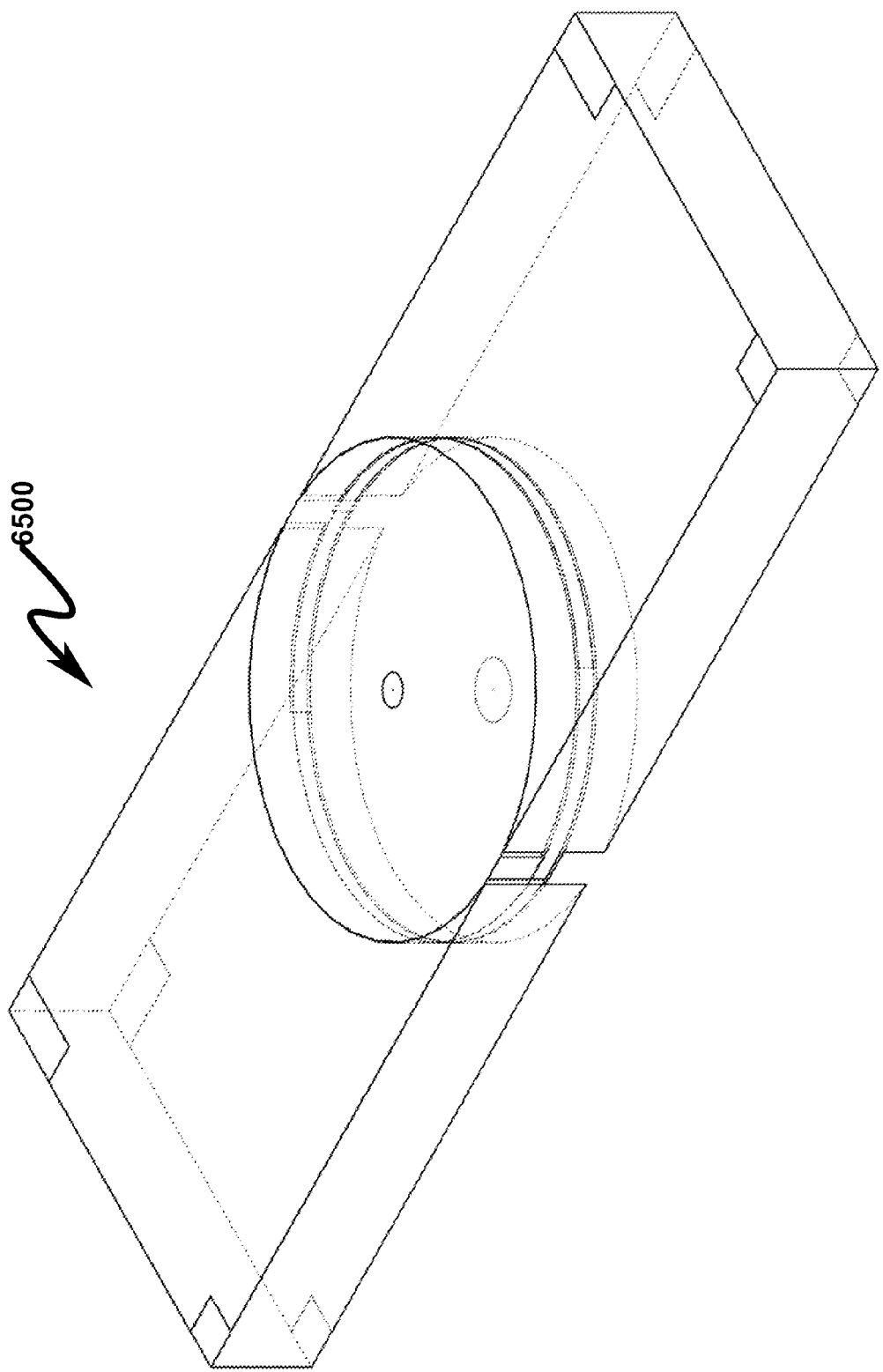
FIG. 65 illustrates a top right perspective view of an edge-to-anterior-surface lens cut in an exemplary present invention IOL fabrication sequence formed using a PMS.
Figure 66:
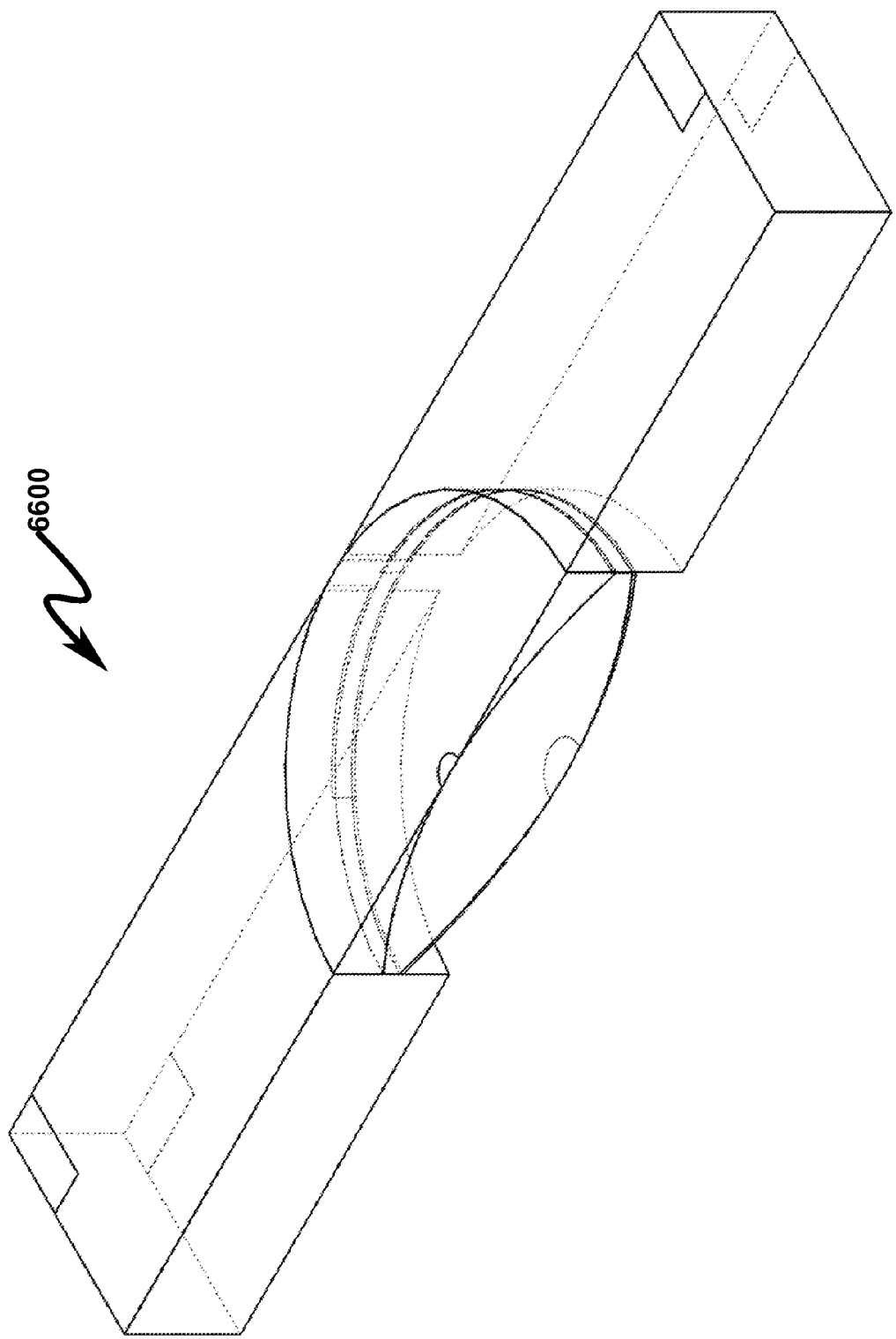
FIG. 66 illustrates a top right perspective front section view of an edge-to-anterior-surface lens cut in an exemplary present invention IOL fabrication sequence formed using a PMS.
Figure 67:
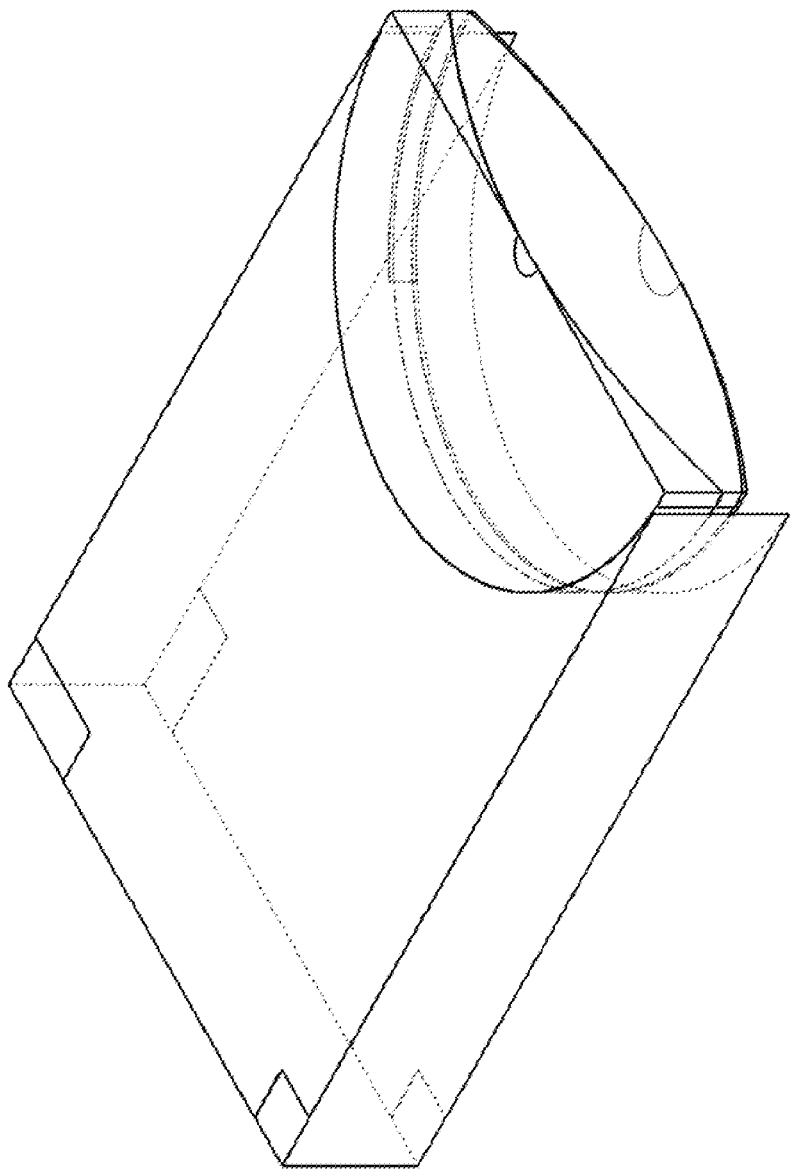
FIG. 67 illustrates a top right perspective right section view of an edge-to-anterior-surface lens cut in an exemplary present invention IOL fabrication sequence formed using a PMS.
Figure 68:
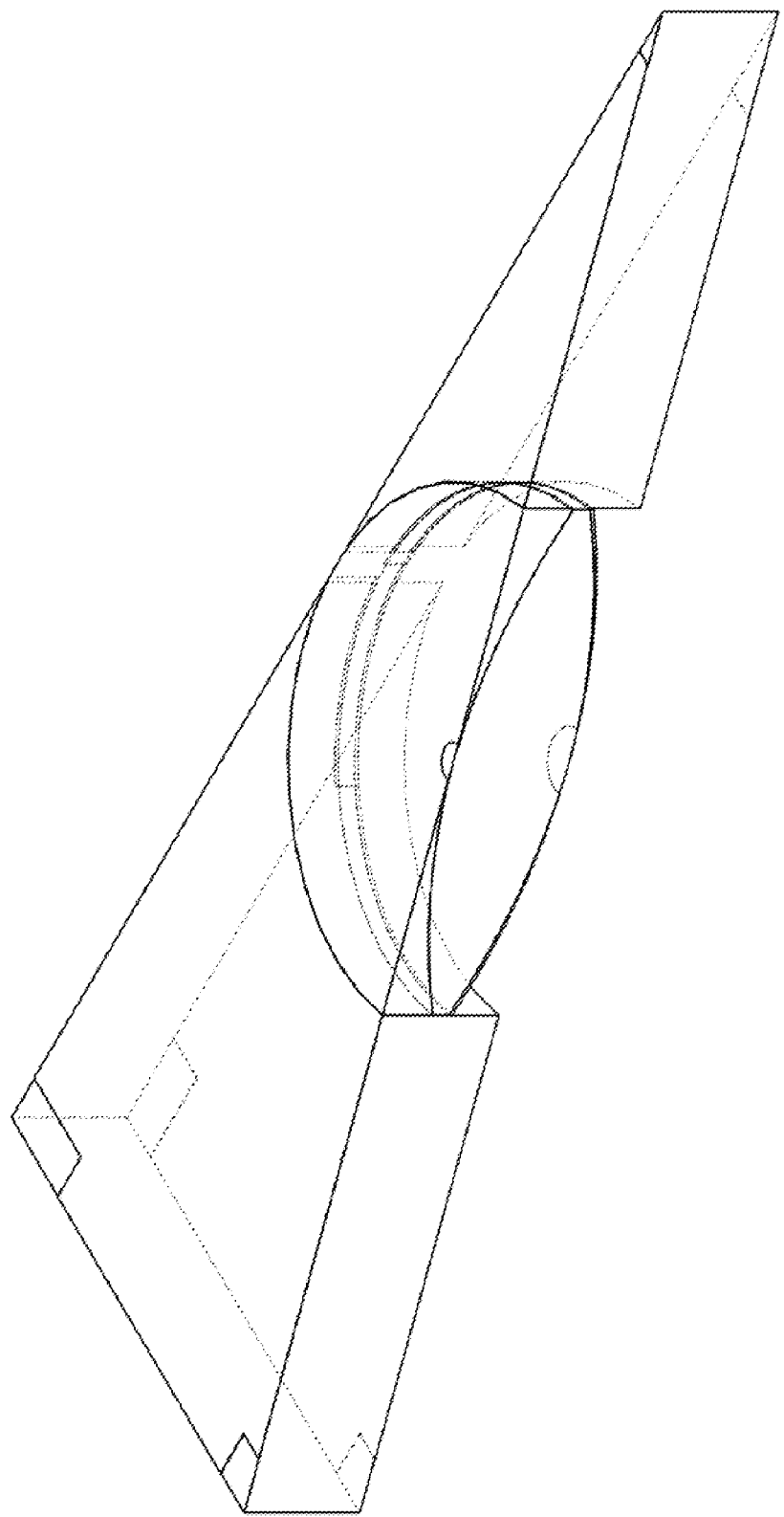
FIG. 68 illustrates a top right perspective diagonal section view of an edge-to-anterior-surface lens cut in an exemplary present invention IOL fabrication sequence formed using a PMS.
Figure 69:
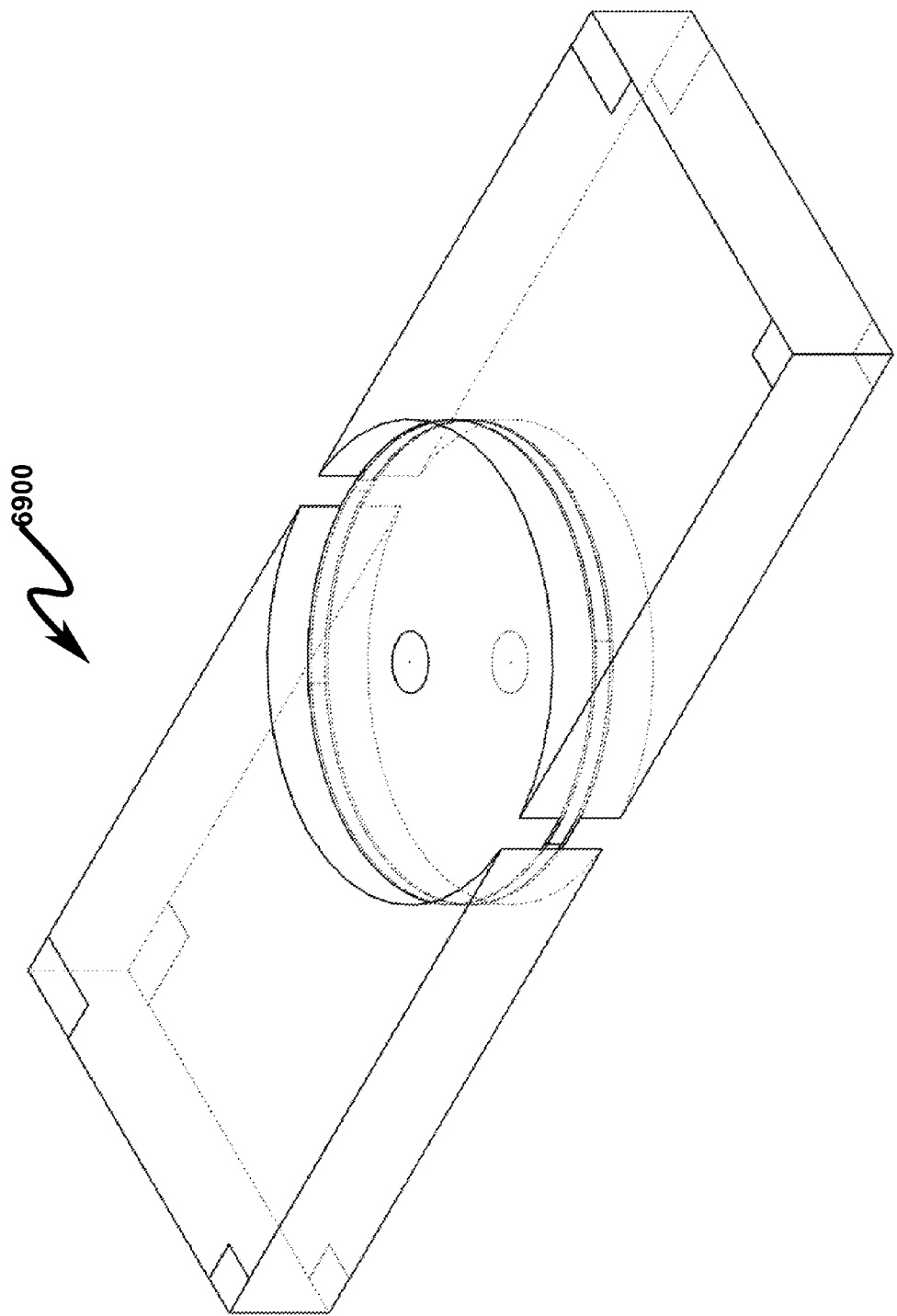
FIG. 69 illustrates a top right perspective view of removal of the anterior lens cutout in an exemplary present invention IOL fabrication sequence formed using a PMS.
Figure 70:
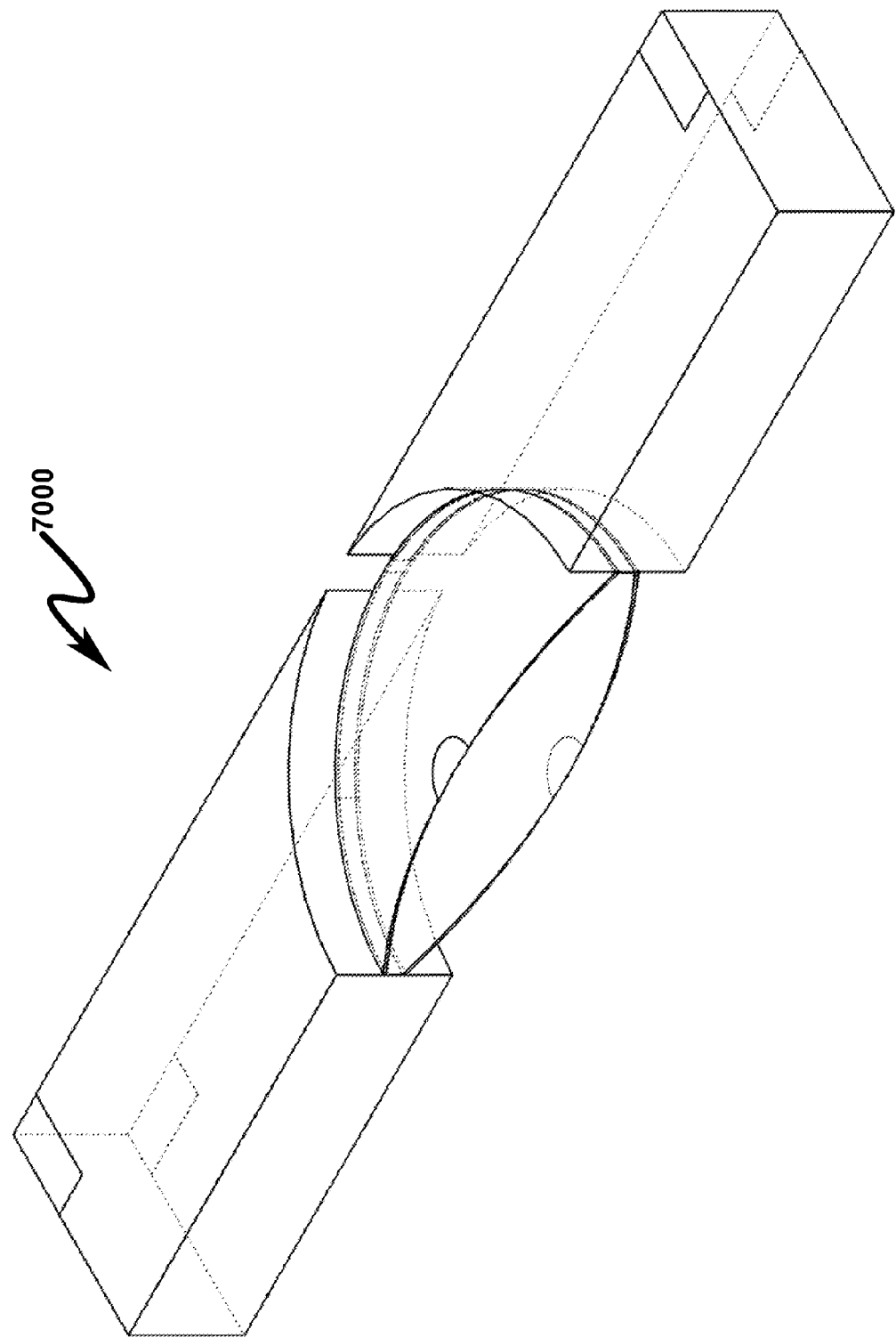
FIG. 70 illustrates a top right perspective front section view of removal of the anterior lens cutout in an exemplary present invention IOL fabrication sequence formed using a PMS.
Figure 71:
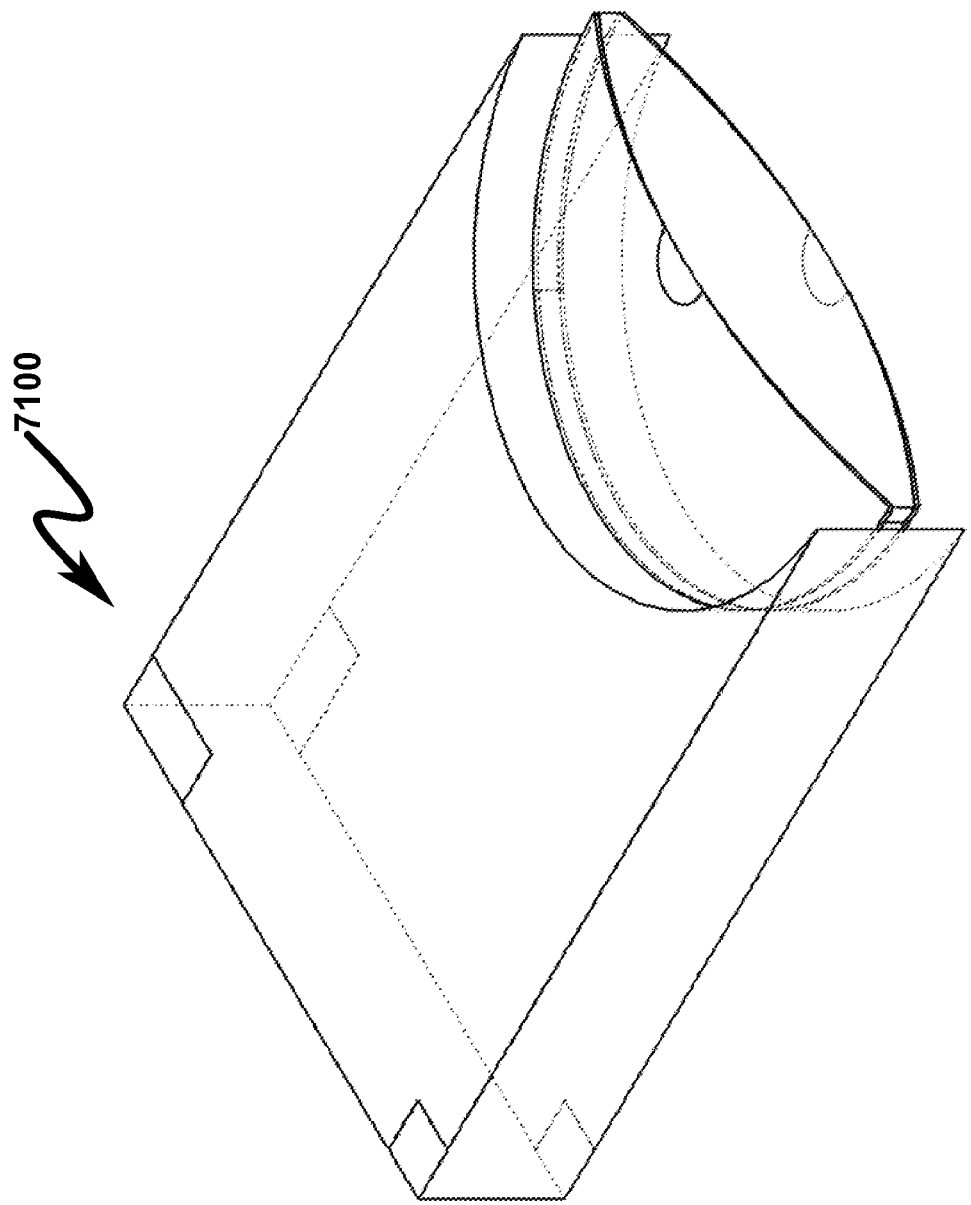
FIG. 71 illustrates a top right perspective right section view of removal of the anterior lens cutout in an exemplary present invention IOL fabrication sequence formed using a PMS.
Figure 72:
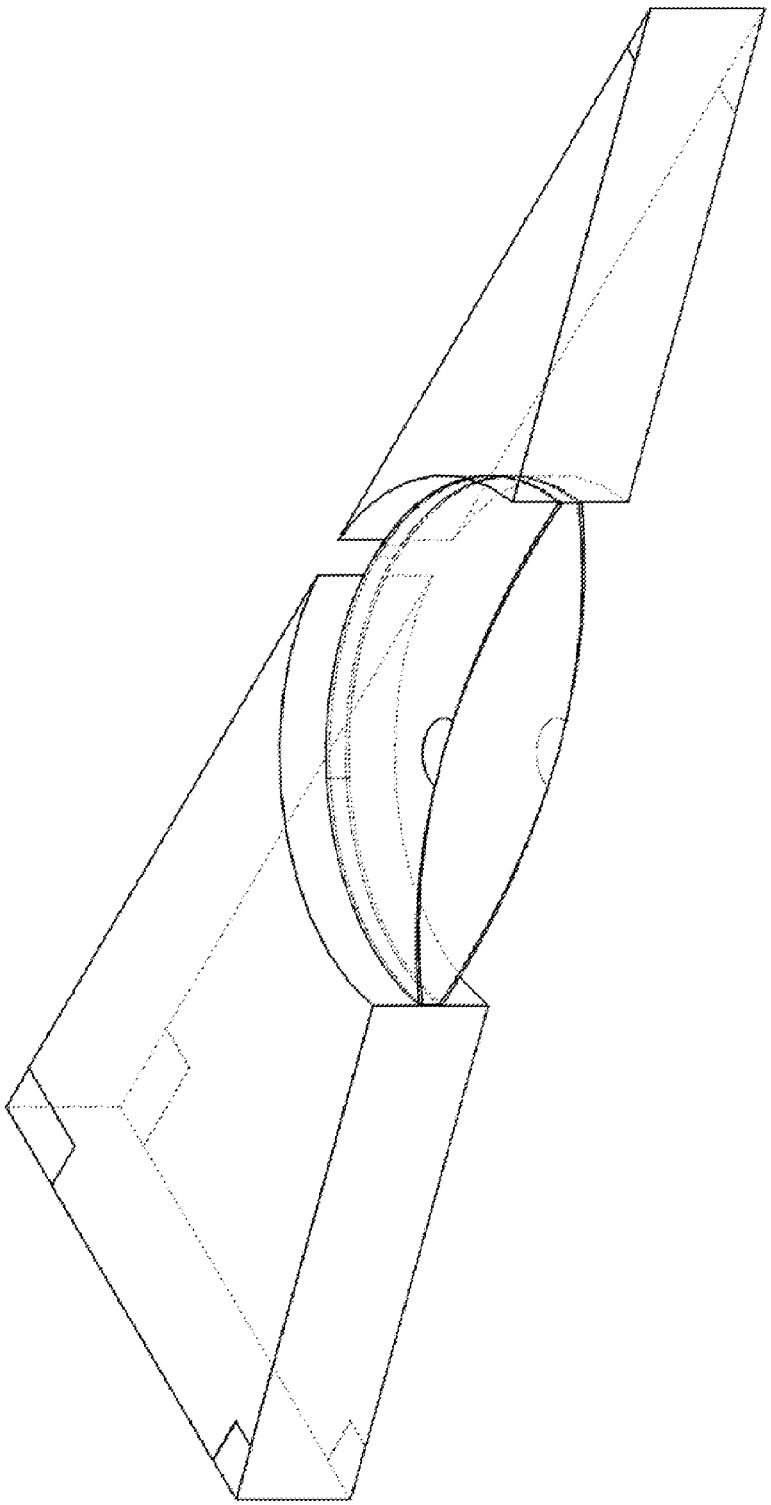
FIG. 72 illustrates a top right perspective diagonal section view of removal of the anterior lens cutout in an exemplary present invention IOL fabrication sequence formed using a PMS.
Figure 73:
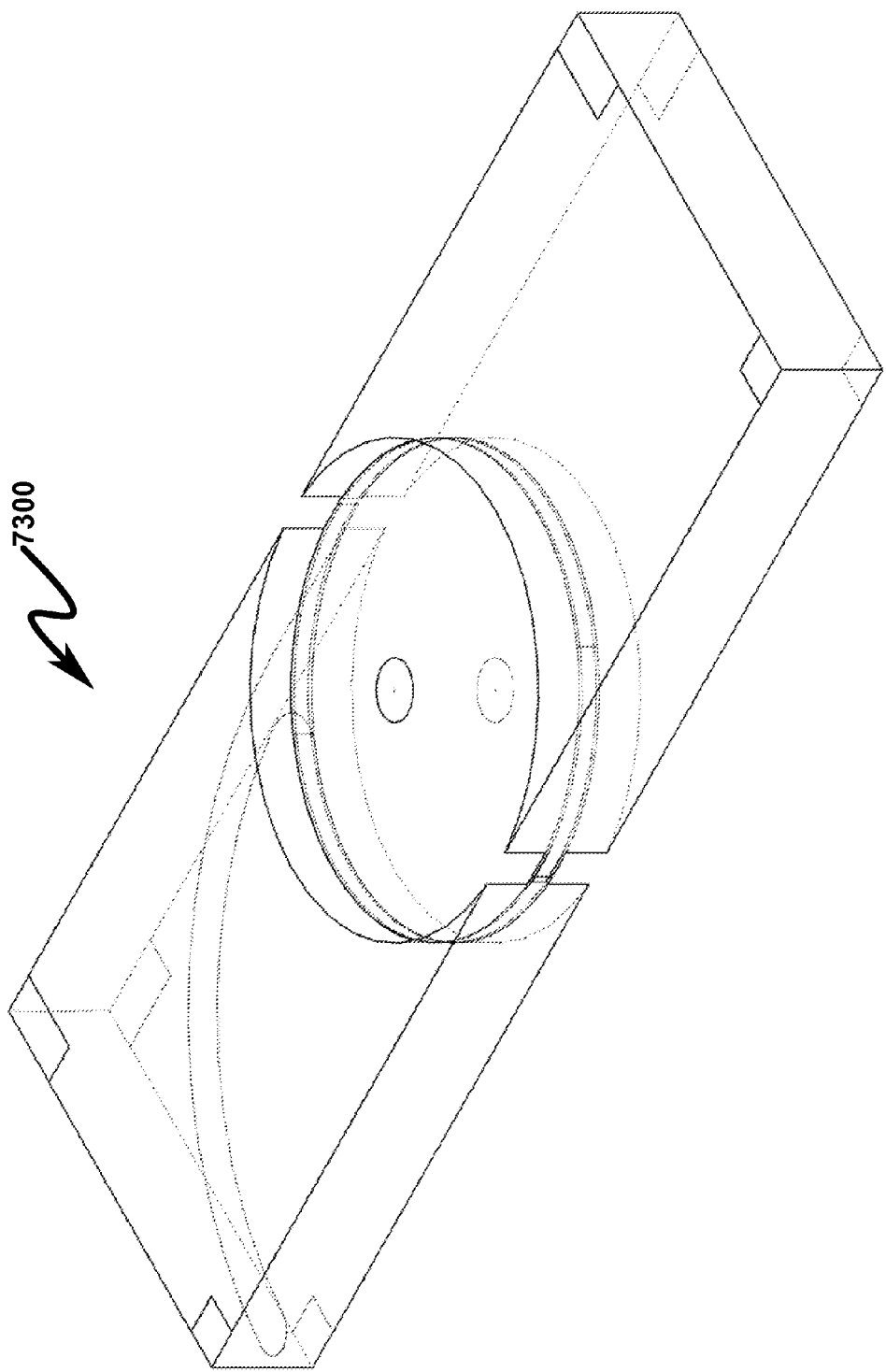
FIG. 73 illustrates a top right perspective view depicting cutting the left haptic posterior surface in an exemplary present invention IOL fabrication sequence formed using a PMS.
Figure 74:
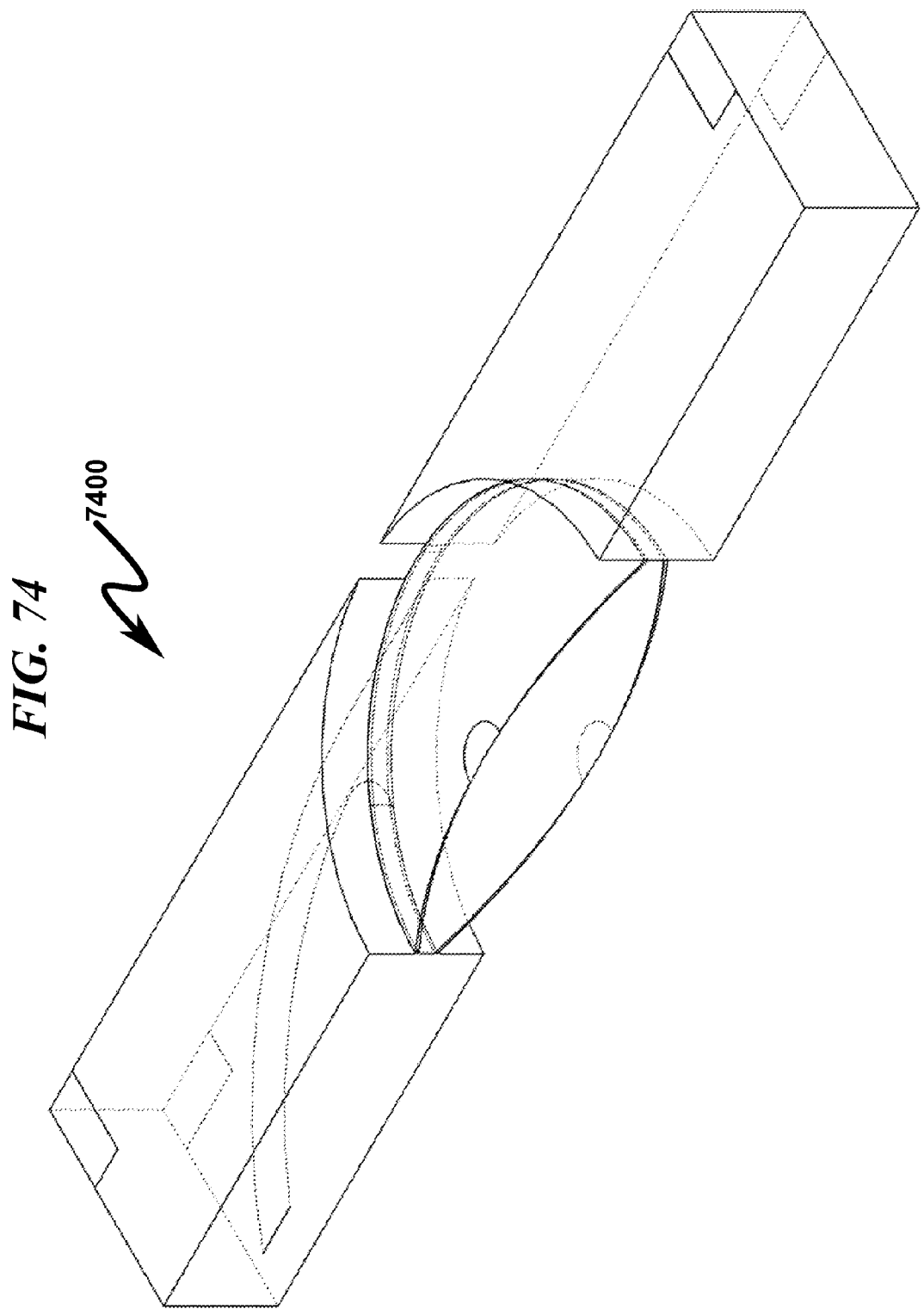
FIG. 74 illustrates a top right perspective front section view depicting cutting the left haptic posterior surface in an exemplary present invention IOL fabrication sequence formed using a PMS.
Figure 75:
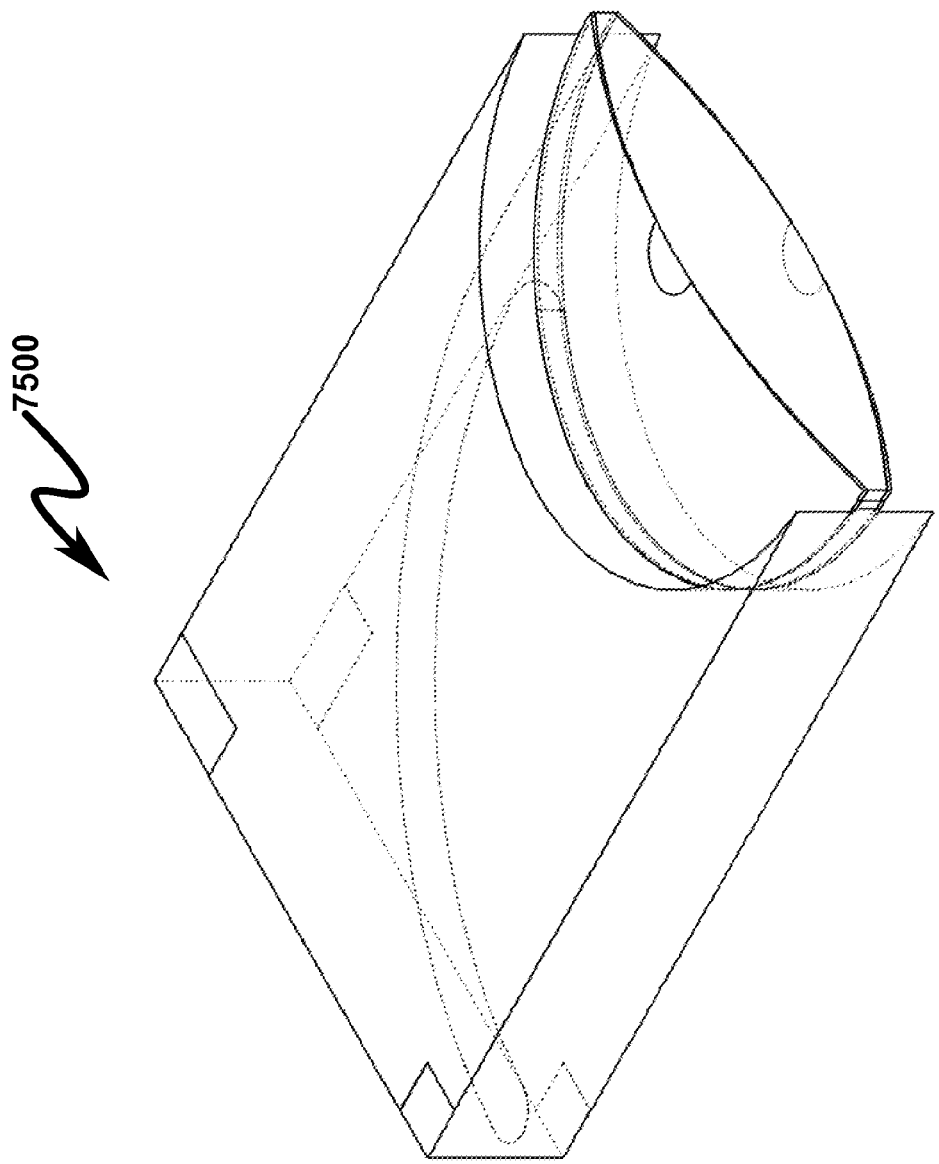
FIG. 75 illustrates a top right perspective right section view depicting cutting the left haptic posterior surface in an exemplary present invention IOL fabrication sequence formed using a PMS.
Figure 76:
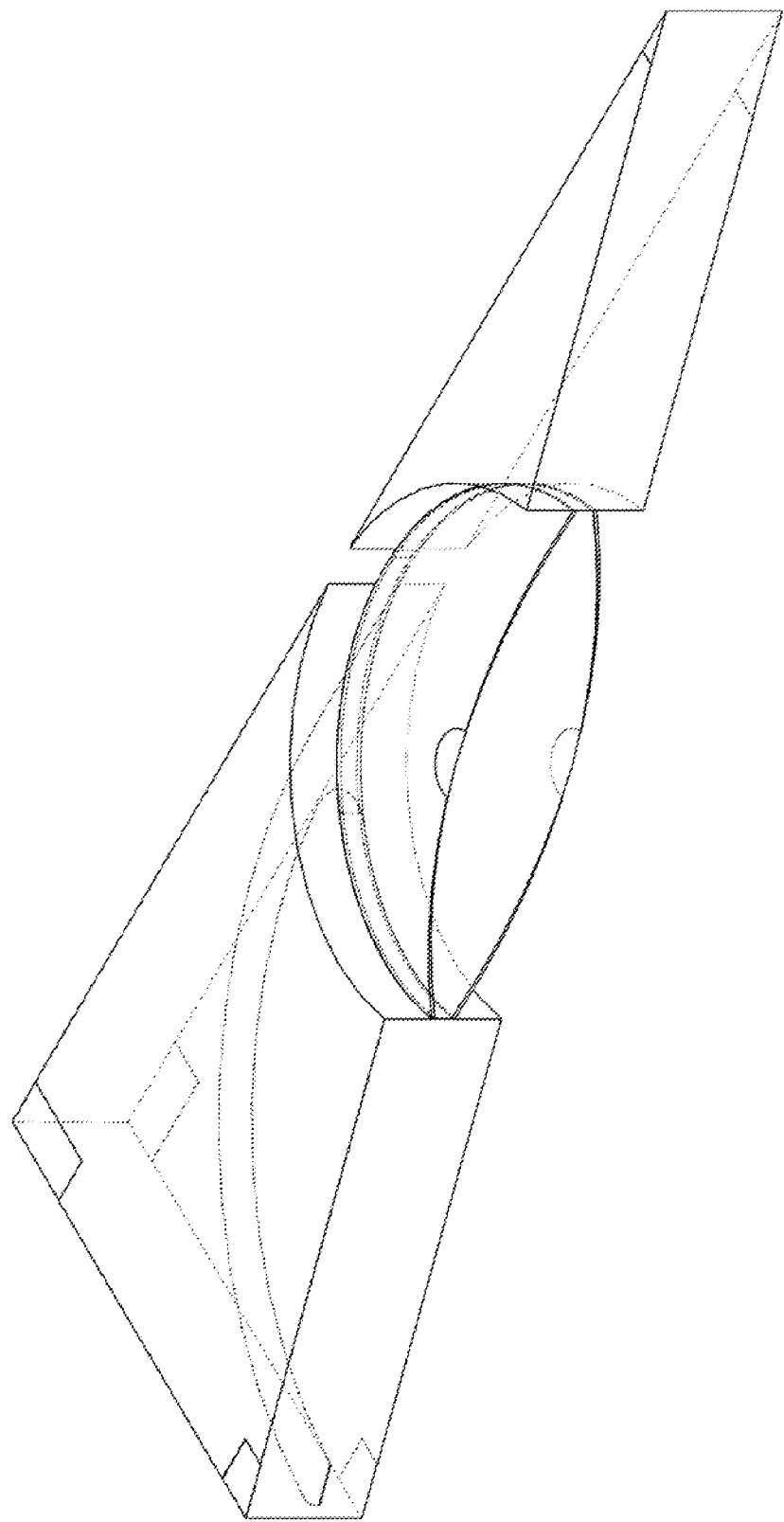
FIG. 76 illustrates a top right perspective diagonal section view depicting cutting the left haptic posterior surface in an exemplary present invention IOL fabrication sequence formed using a PMS.
Figure 77:
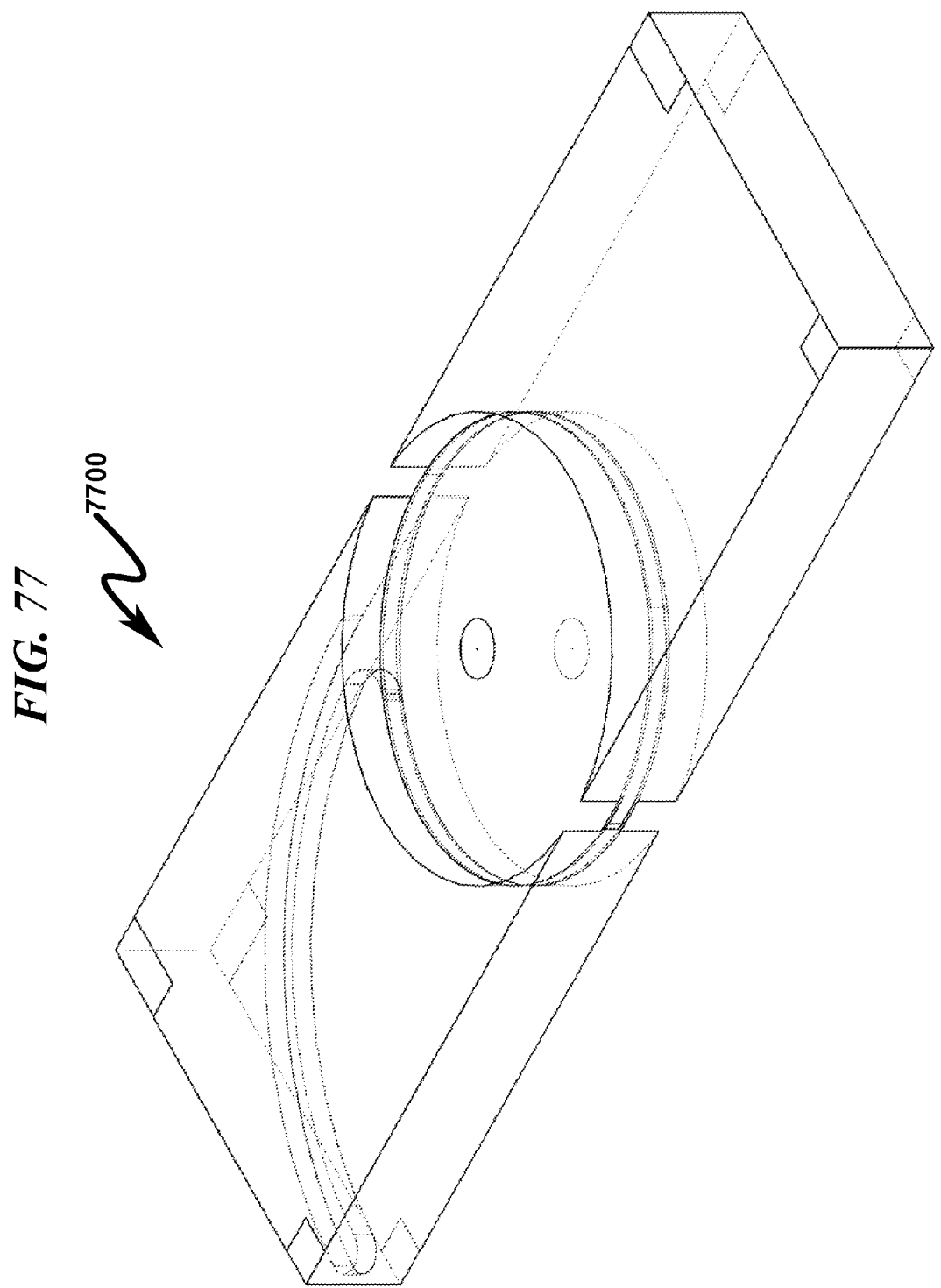
FIG. 77 illustrates a top right perspective view depicting cutting the left haptic side edge surface in an exemplary present invention IOL fabrication sequence formed using a PMS.
Figure 78:
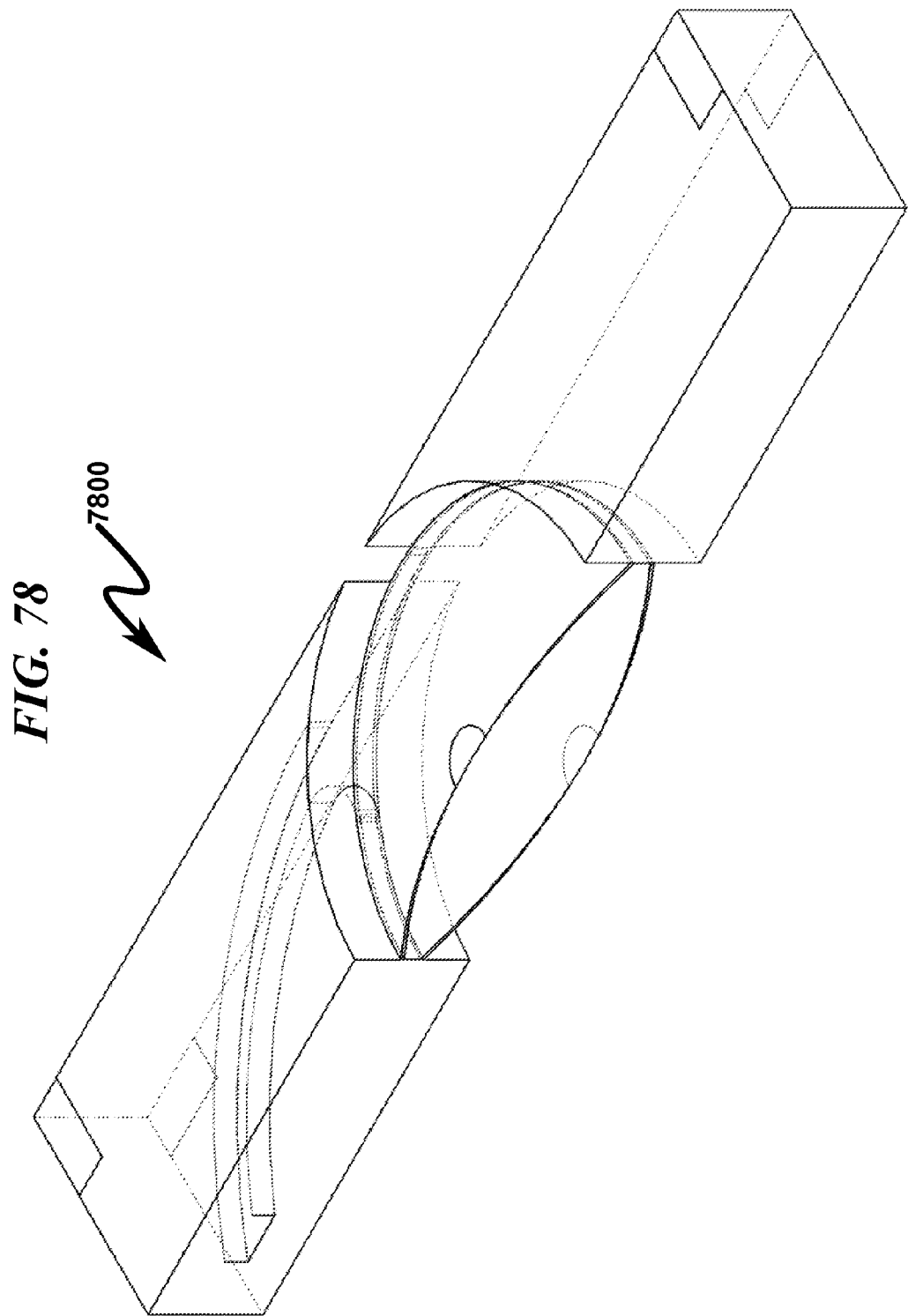
FIG. 78 illustrates a top right perspective front section view depicting cutting the left haptic side edge surface in an exemplary present invention IOL fabrication sequence formed using a PMS.
Figure 79:
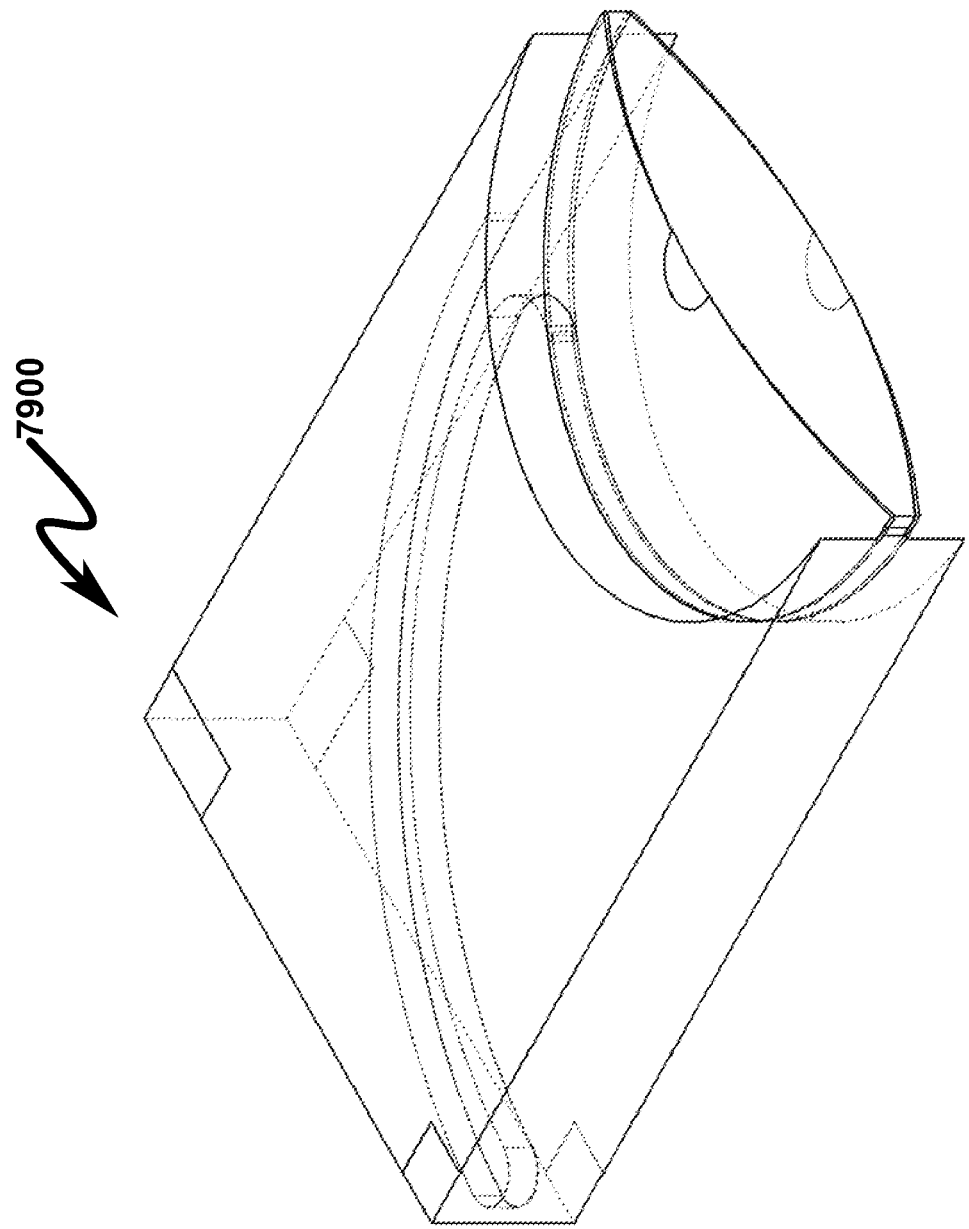
FIG. 79 illustrates a top right perspective right section view depicting cutting the left haptic side edge surface in an exemplary present invention IOL fabrication sequence formed using a PMS.
Figure 80:
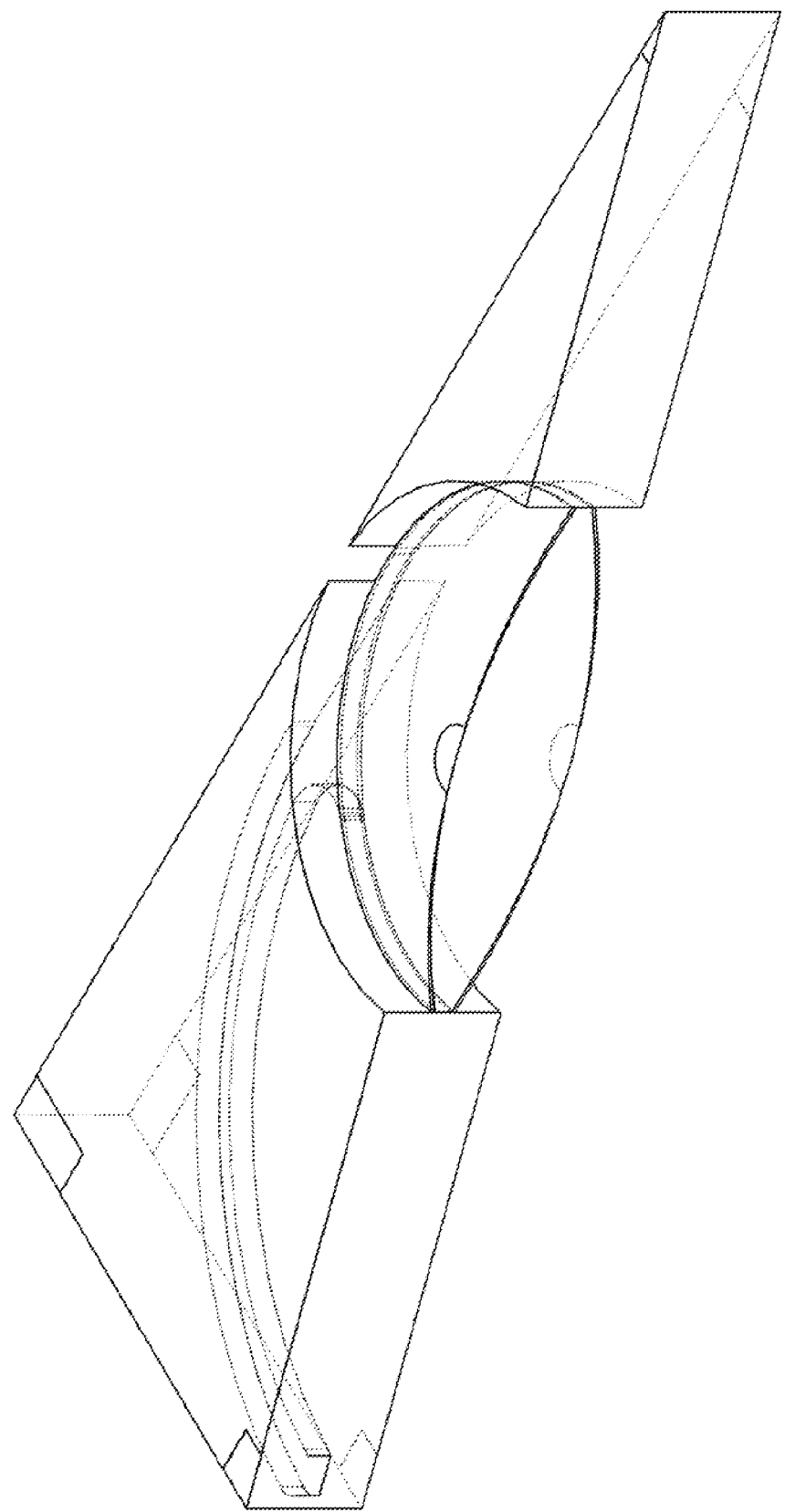
FIG. 80 illustrates a top right perspective diagonal section view depicting cutting the left haptic side edge surface in an exemplary present invention IOL fabrication sequence formed using a PMS.
Figure 81:
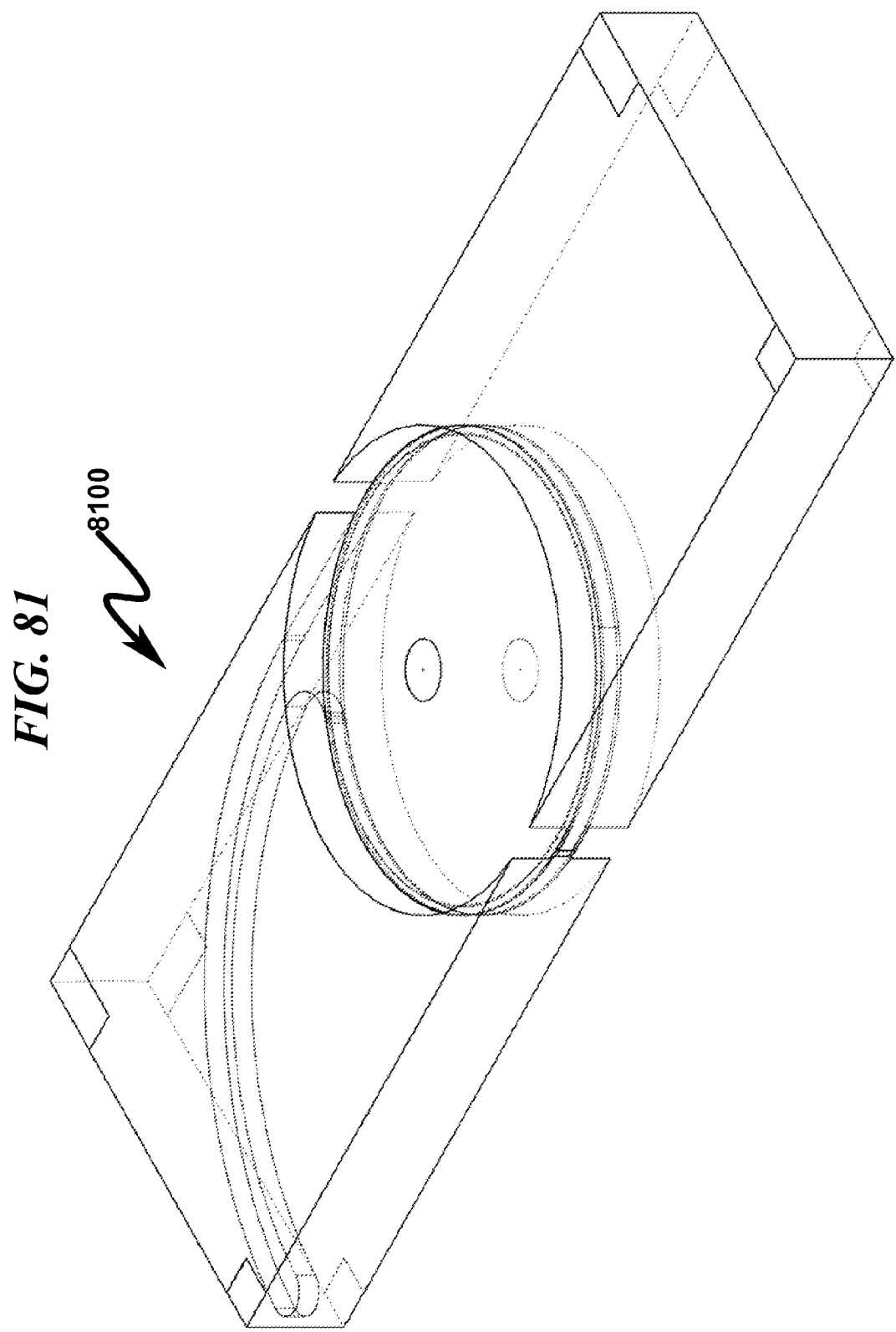
FIG. 81 illustrates a top right perspective view depicting cutting the left haptic anterior surface in an exemplary present invention IOL fabrication sequence formed using a PMS.
Figure 82:
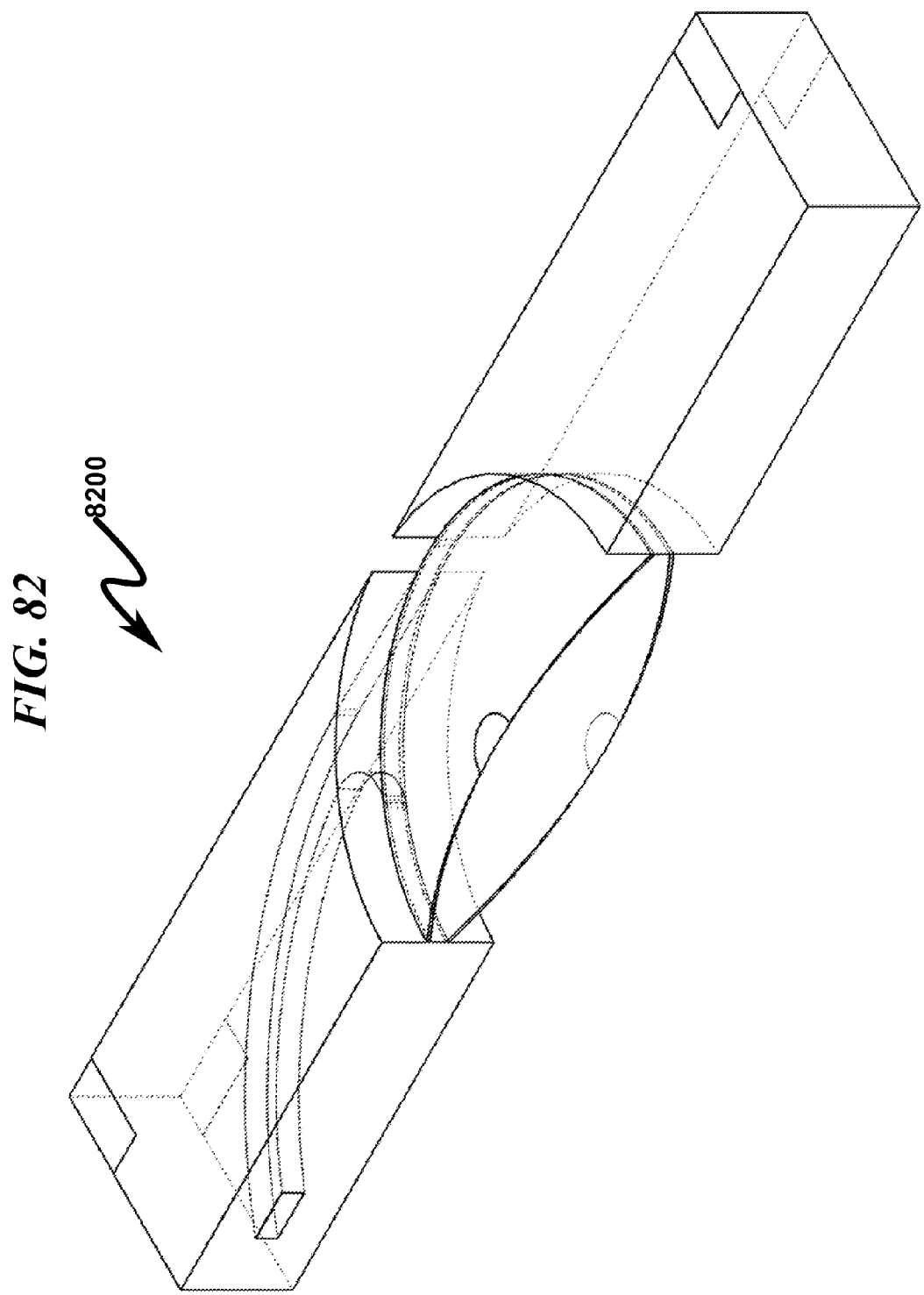
FIG. 82 illustrates a top right perspective front section view depicting cutting the left haptic anterior surface in an exemplary present invention IOL fabrication sequence formed using a PMS.
Figure 83:
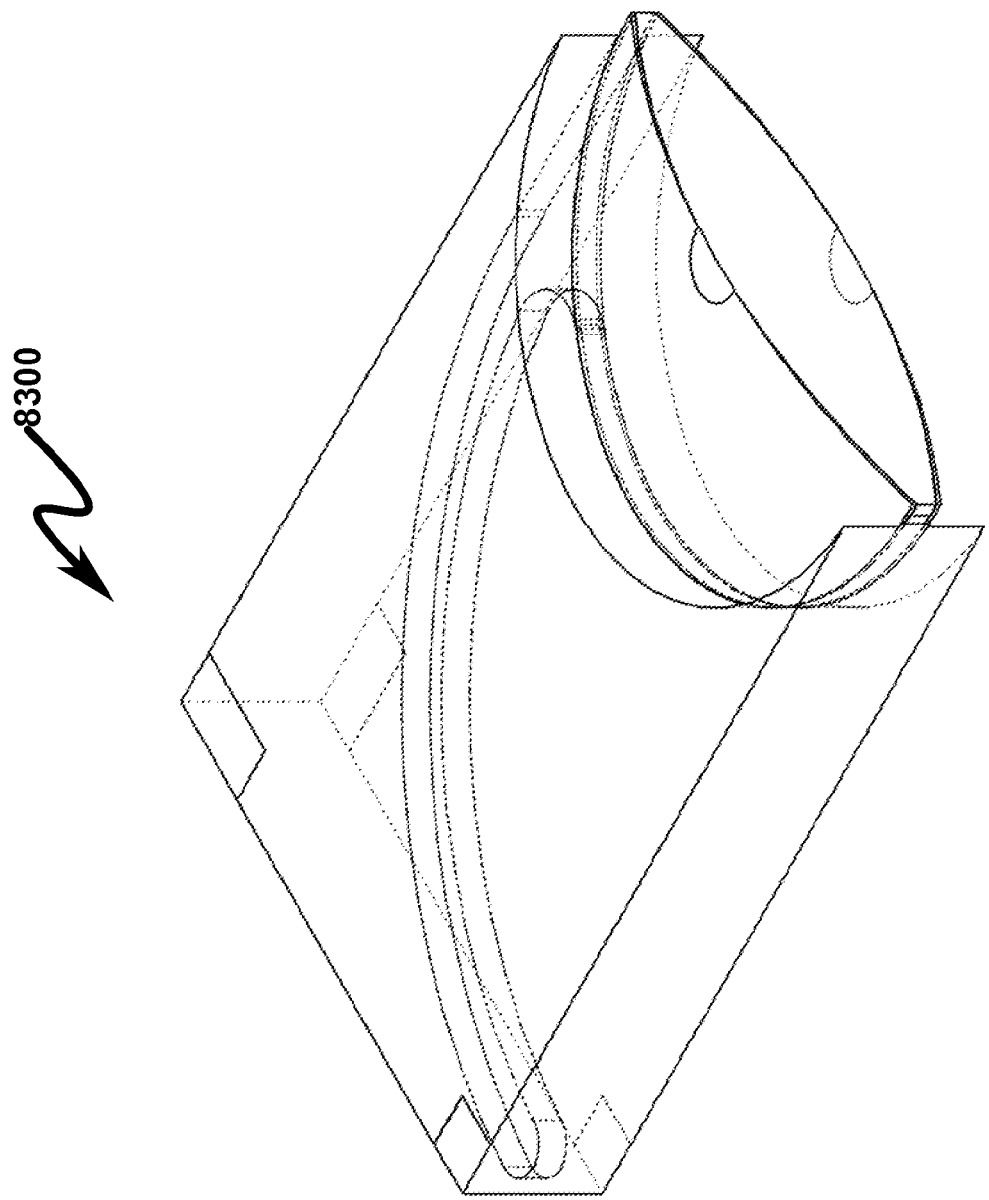
FIG. 83 illustrates a top right perspective right section view depicting cutting the left haptic anterior surface in an exemplary present invention IOL fabrication sequence formed using a PMS.
Figure 84:
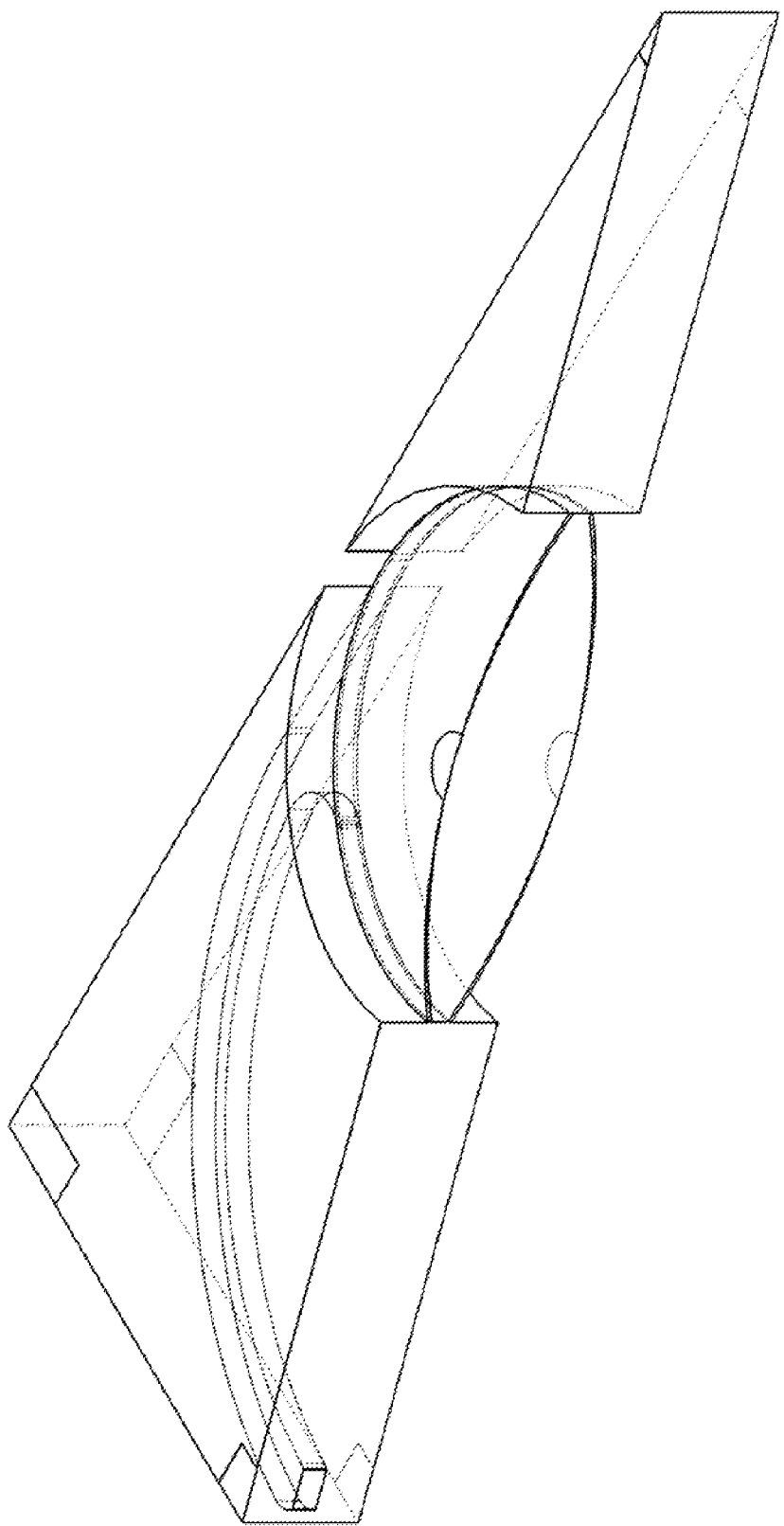
FIG. 84 illustrates a top right perspective diagonal section view depicting cutting the left haptic anterior surface in an exemplary present invention IOL fabrication sequence formed using a PMS.
Figure 85:
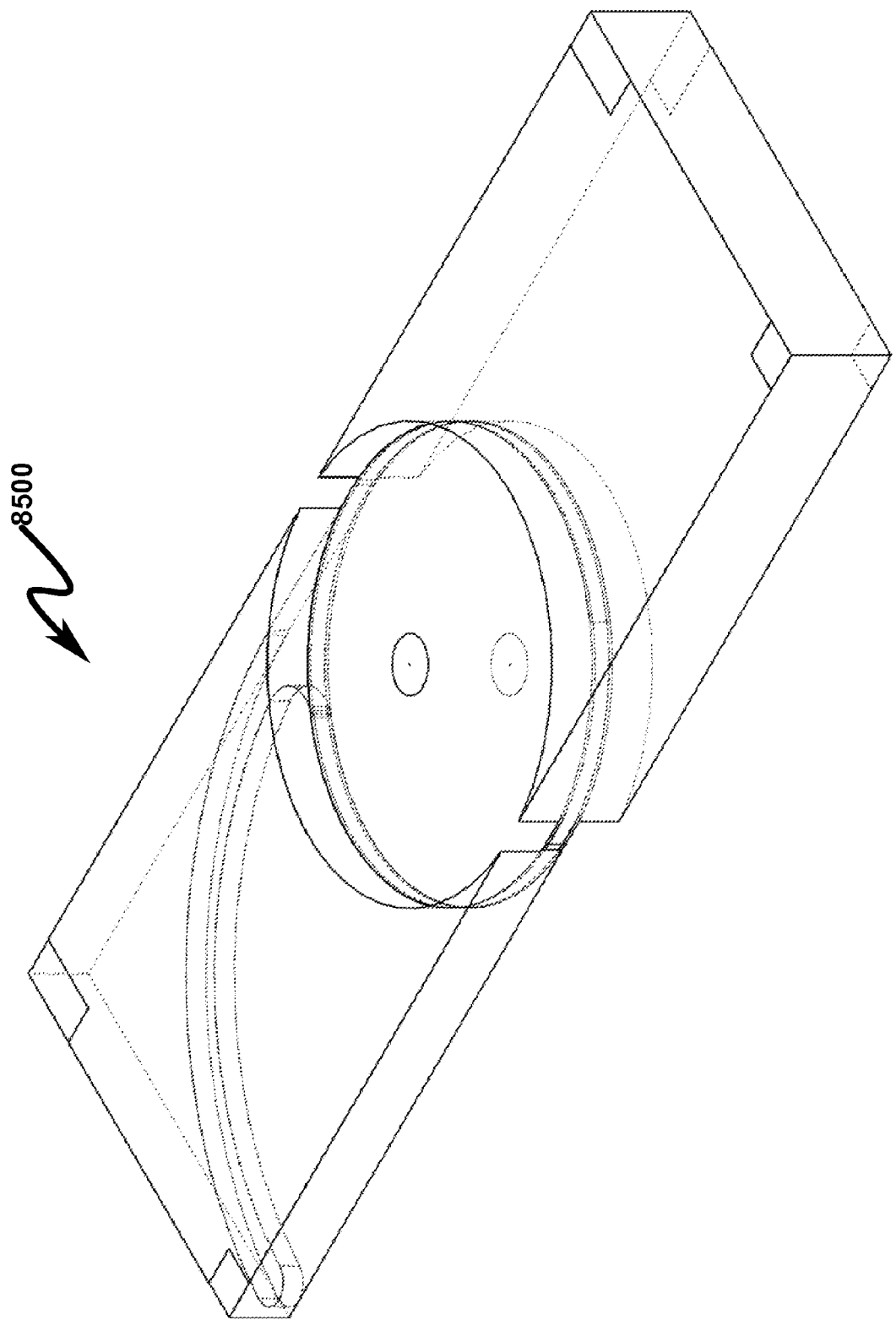
FIG. 85 illustrates a top right perspective view depicting removal of the left haptic posterior PMS material in an exemplary present invention IOL fabrication sequence formed using a PMS.
Figure 86:
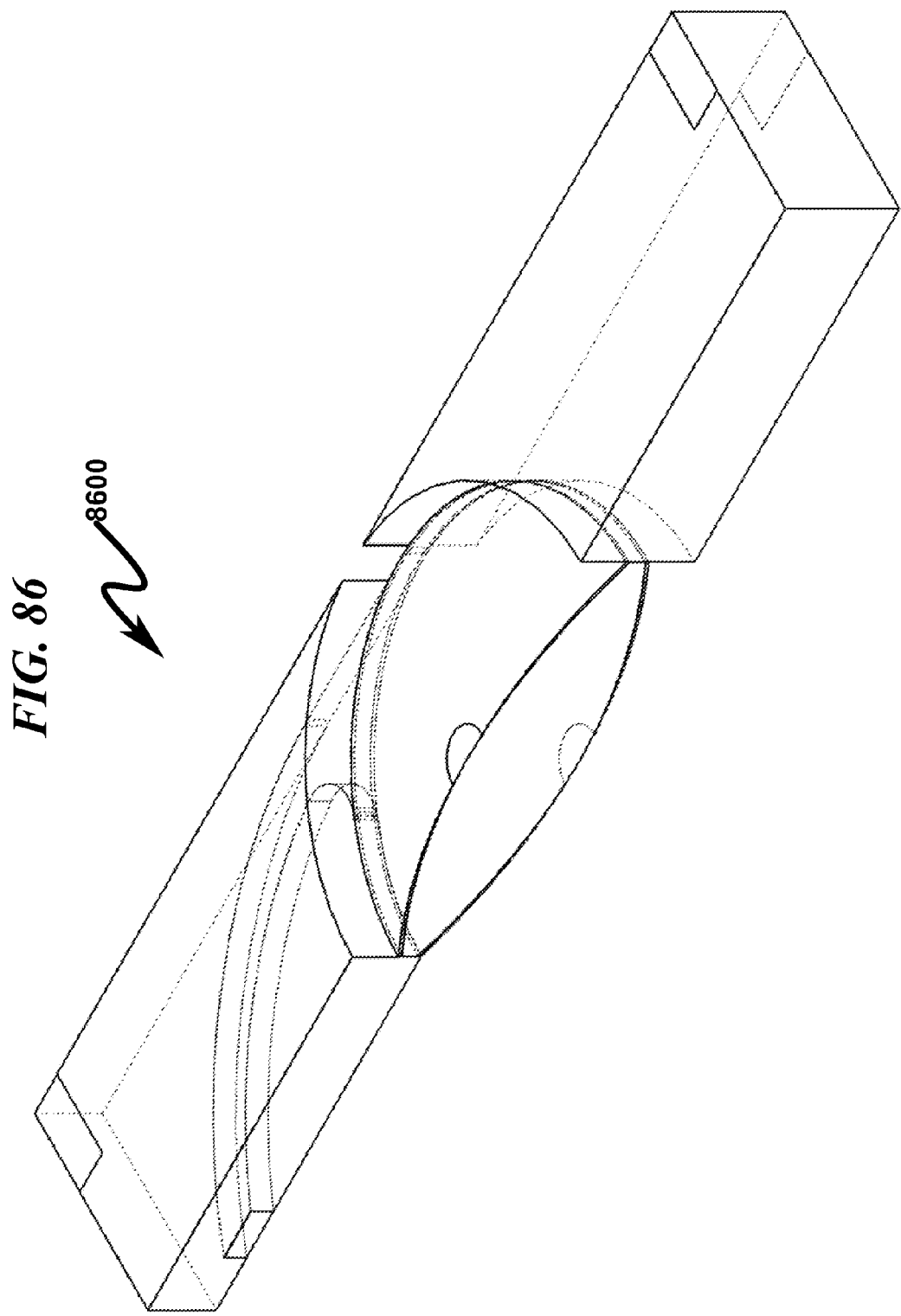
FIG. 86 illustrates a top right perspective front section view depicting removal of the left haptic posterior PMS material in an exemplary present invention IOL fabrication sequence formed using a PMS.
Figure 87:
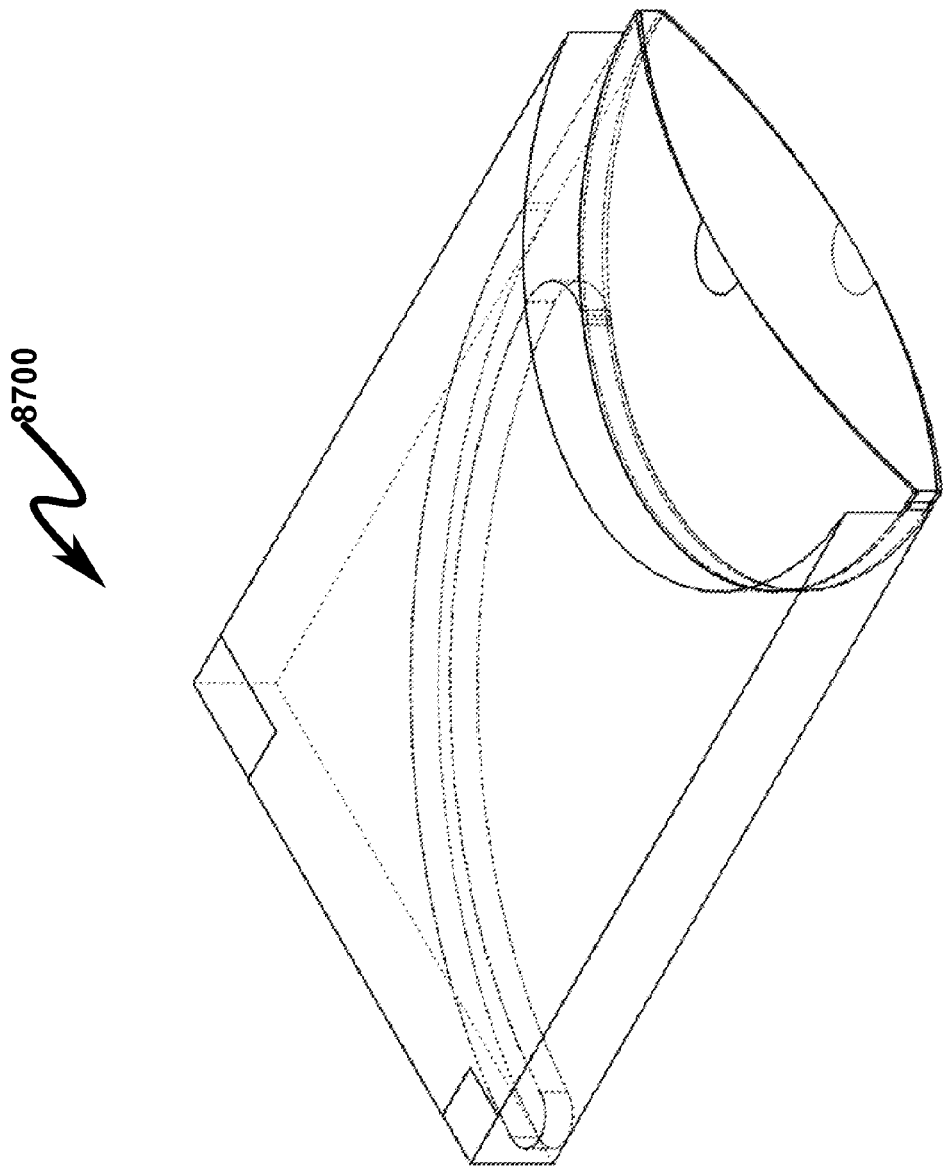
FIG. 87 illustrates a top right perspective right section view depicting removal of the left haptic posterior PMS material in an exemplary present invention IOL fabrication sequence formed using a PMS.
Figure 88:
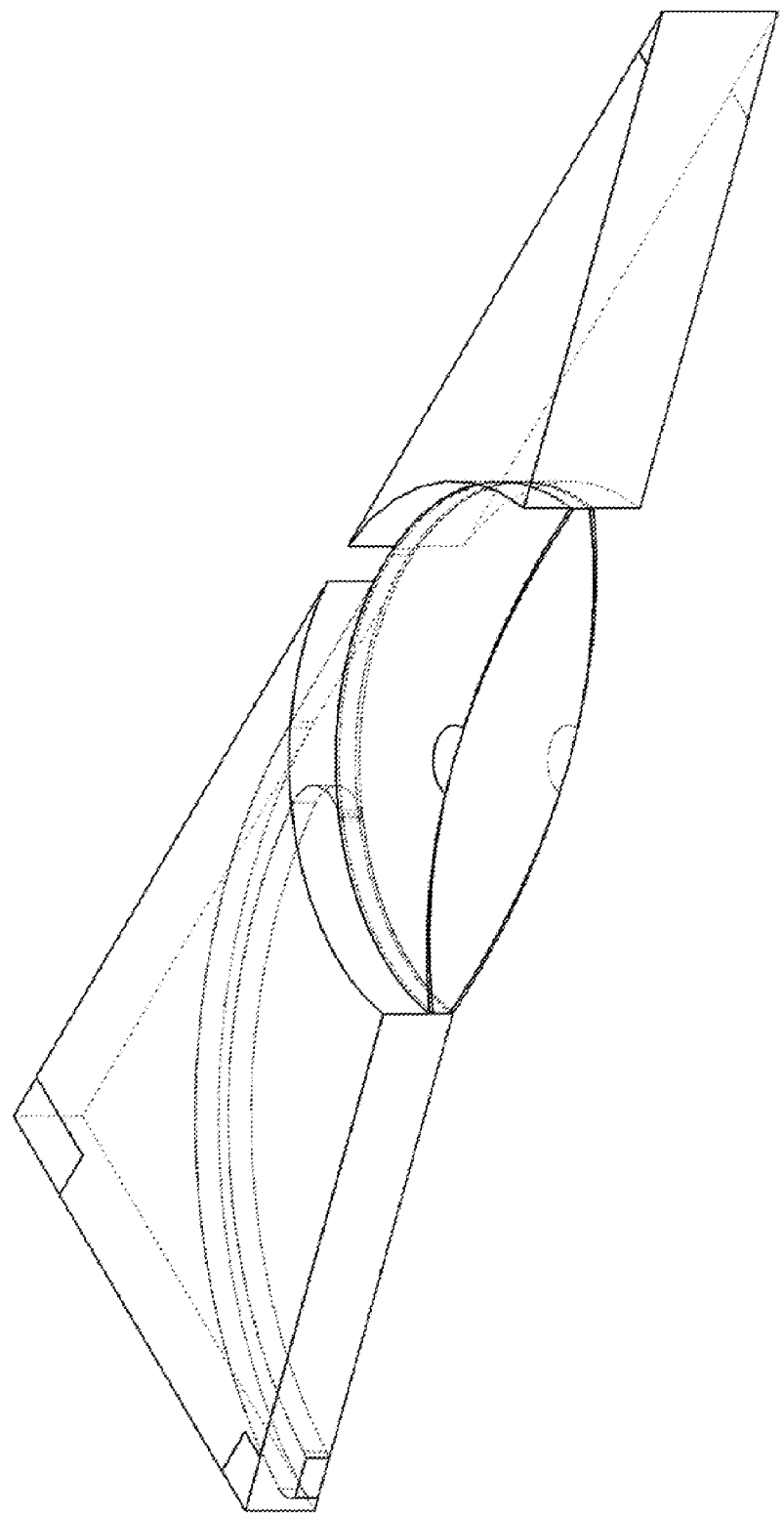
FIG. 88 illustrates a top right perspective diagonal section view depicting removal of the left haptic posterior PMS material in an exemplary present invention IOL fabrication sequence formed using a PMS.
Figure 89:
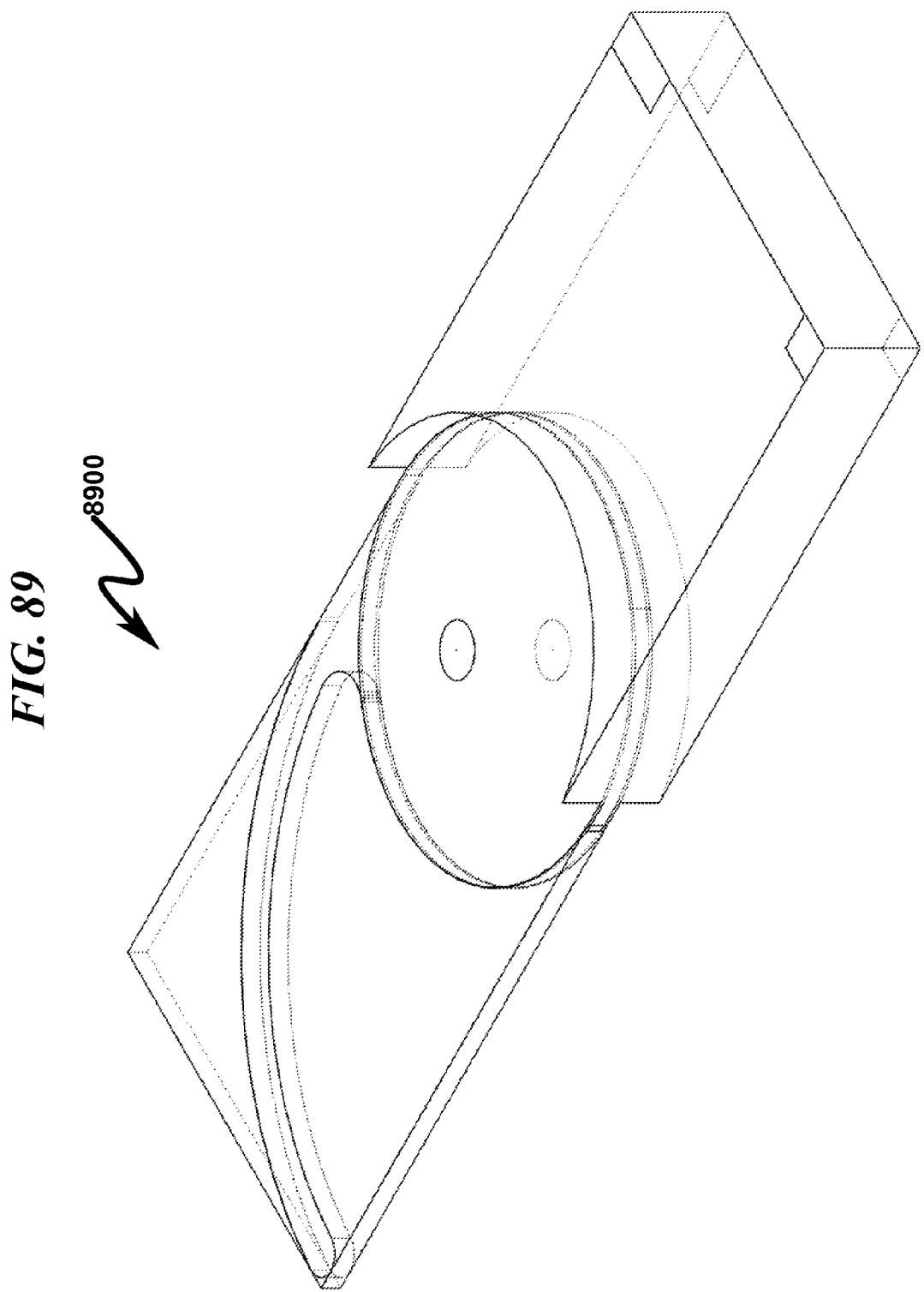
FIG. 89 illustrates a top right perspective view depicting removal of the left haptic anterior PMS material in an exemplary present invention IOL fabrication sequence formed using a PMS.
Figure 90:
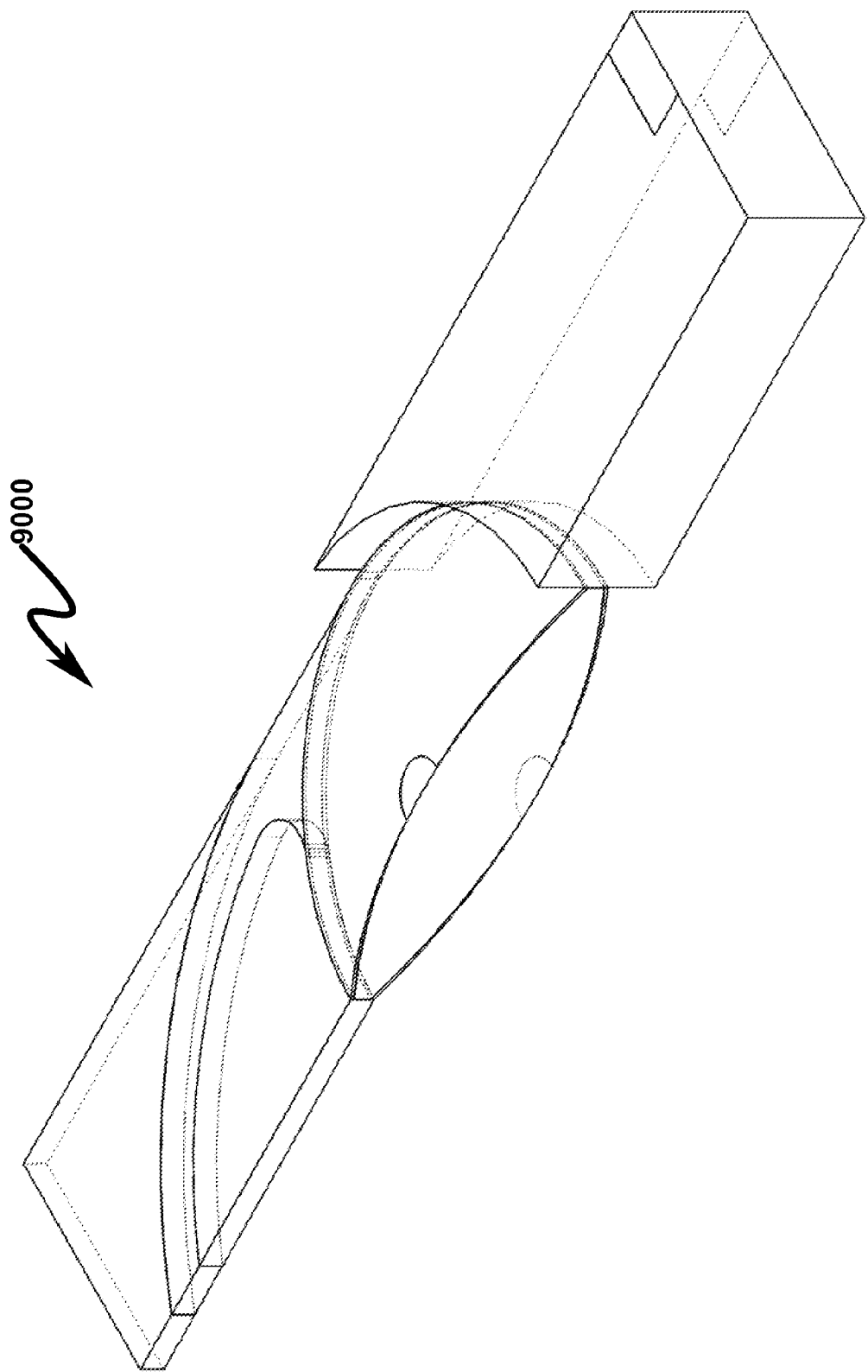
FIG. 90 illustrates a top right perspective front section view depicting removal of the left haptic anterior PMS material in an exemplary present invention IOL fabrication sequence formed using a PMS.
Figure 91:
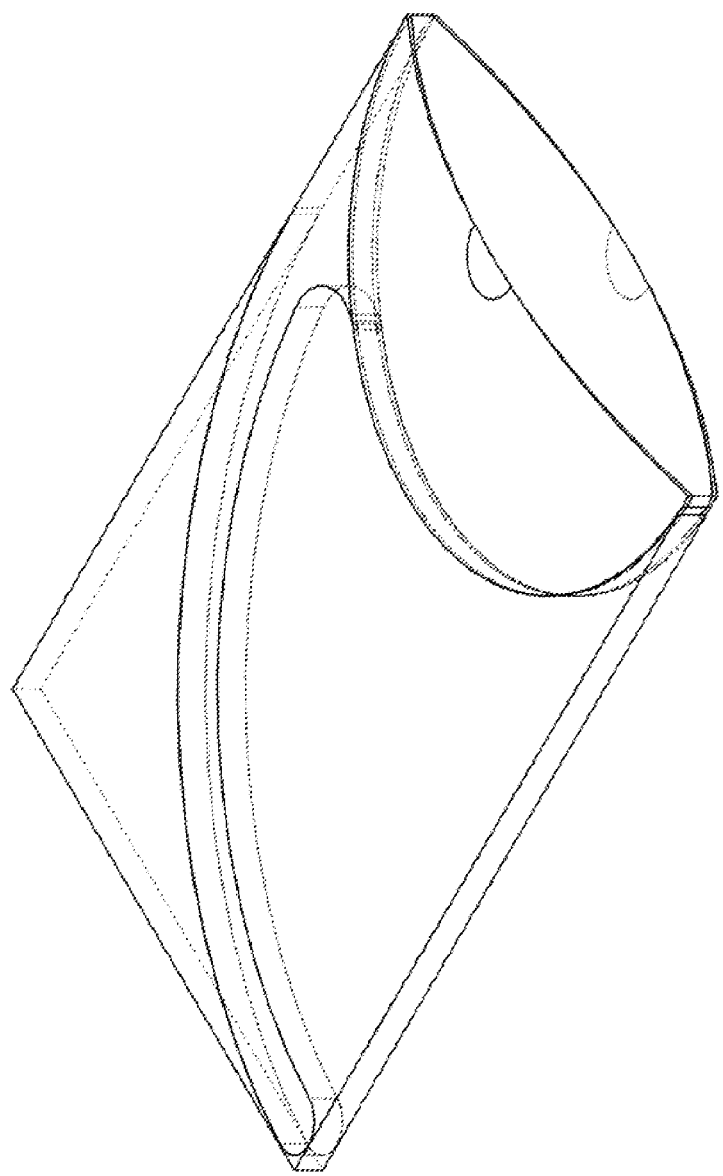
FIG. 91 illustrates a top right perspective right section view depicting removal of the left haptic anterior PMS material in an exemplary present invention IOL fabrication sequence formed using a PMS.
Figure 92:
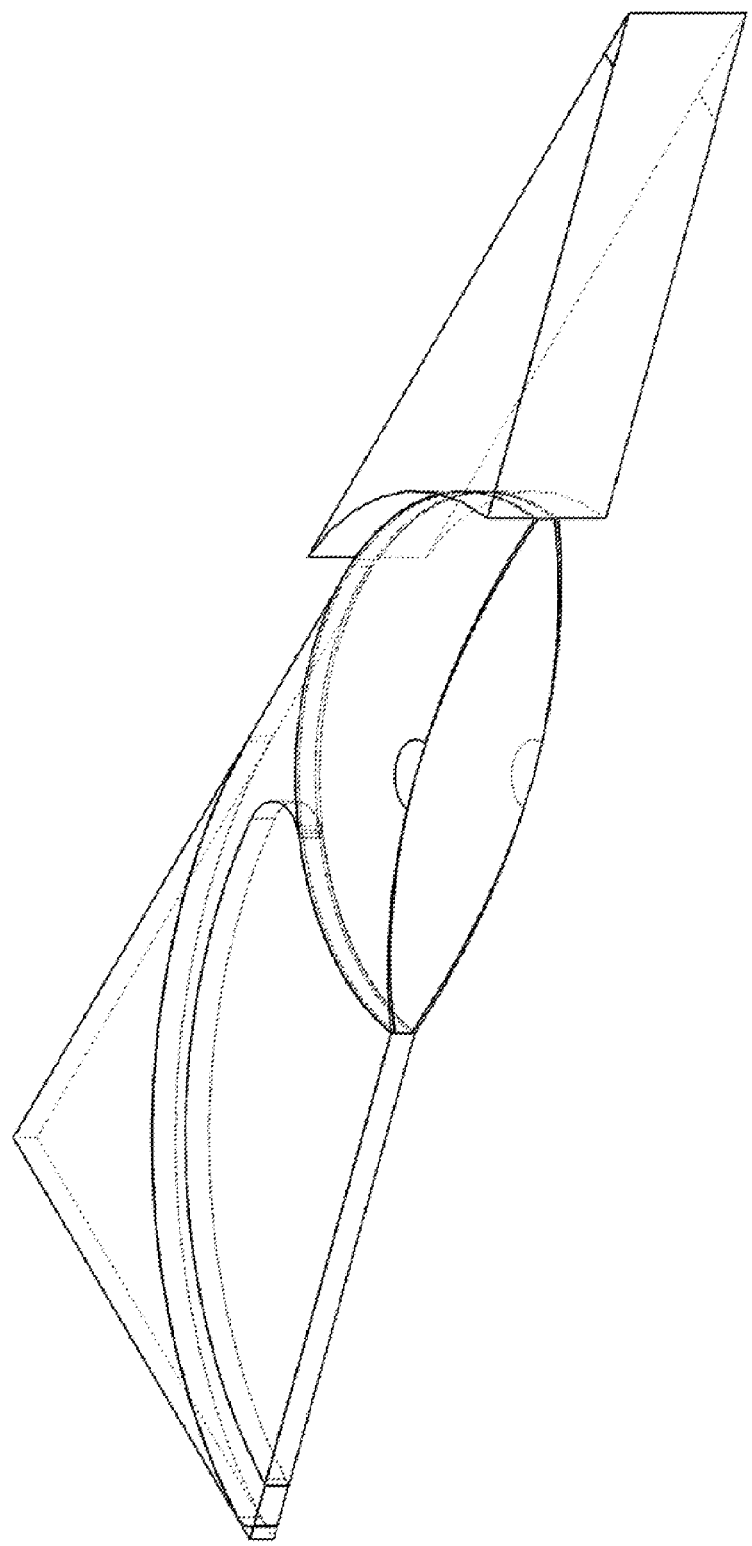
FIG. 92 illustrates a top right perspective diagonal section view depicting removal of the left haptic anterior PMS material in an exemplary present invention IOL fabrication sequence formed using a PMS.
Figure 93:
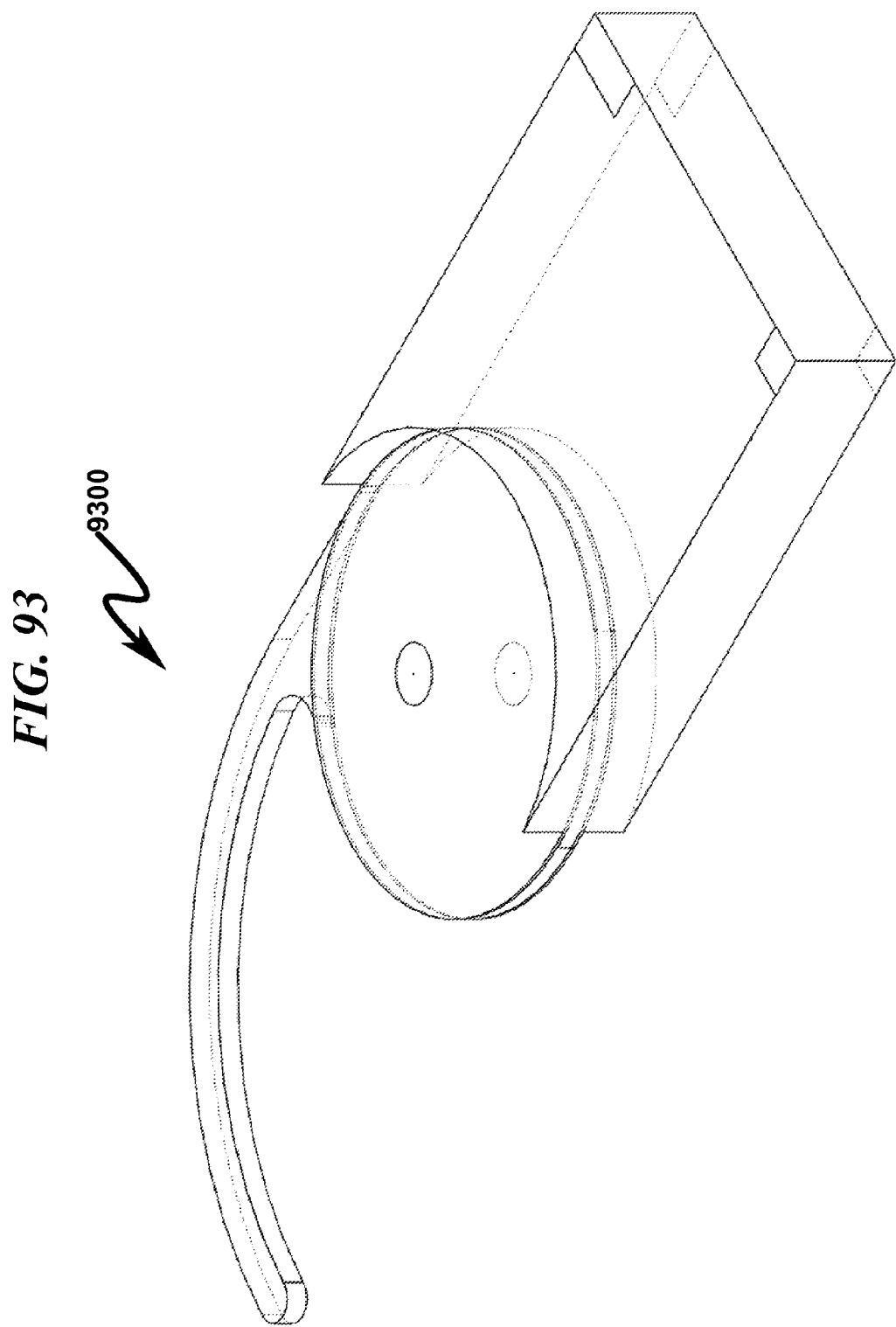
FIG. 93 illustrates a top right perspective view depicting removal of the left haptic interior PMS material in an exemplary present invention IOL fabrication sequence formed using a PMS.
Figure 94:
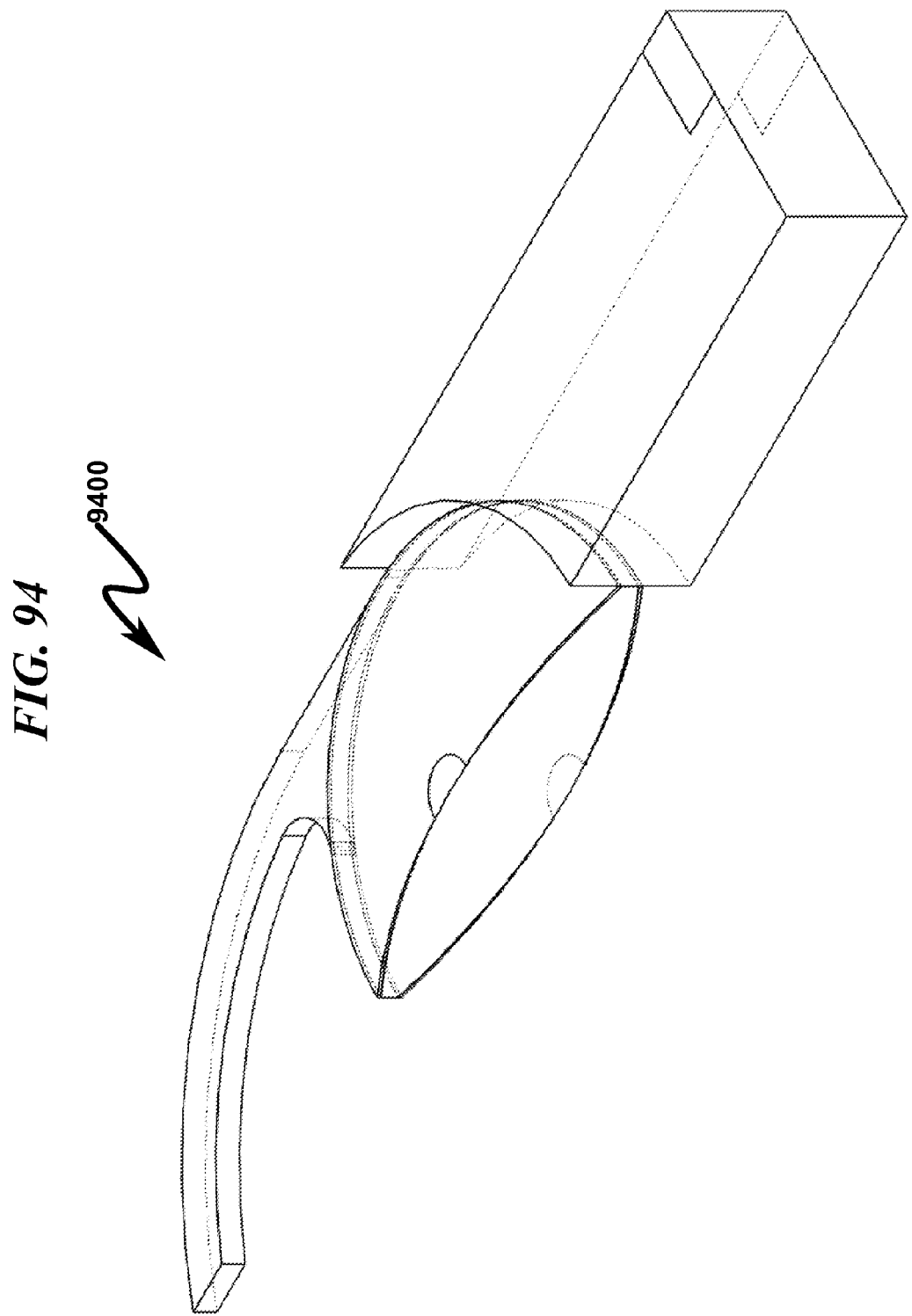
FIG. 94 illustrates a top right perspective front section view depicting removal of the left haptic interior PMS material in an exemplary present invention IOL fabrication sequence formed using a PMS.
Figure 95:
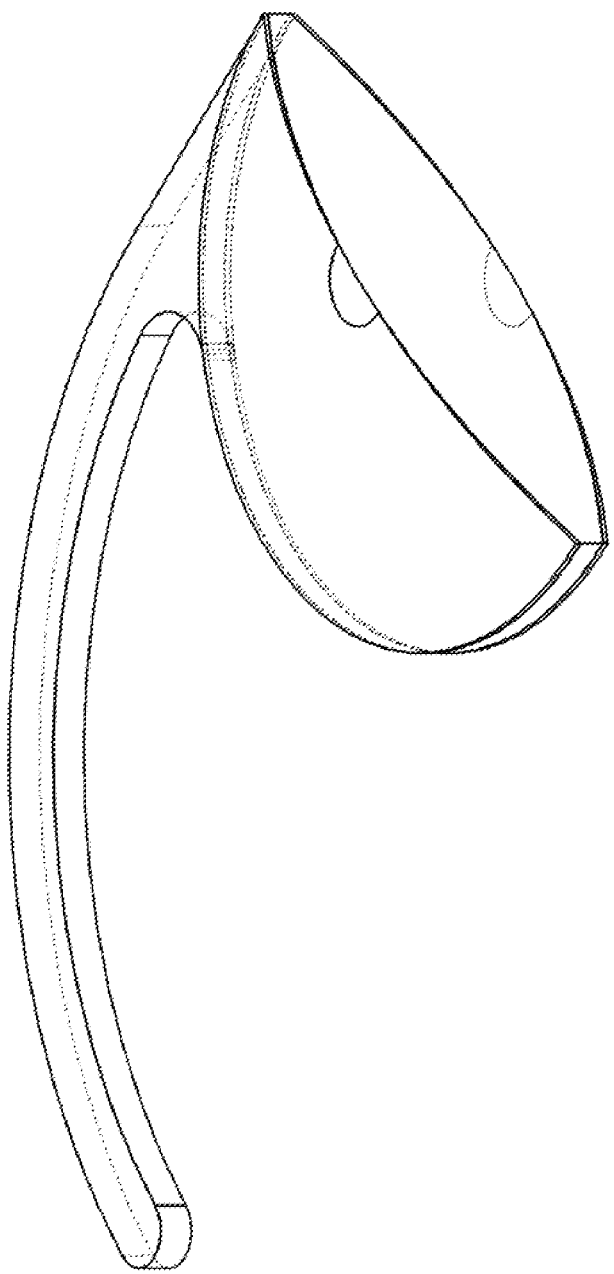
FIG. 95 illustrates a top right perspective right section view depicting removal of the left haptic interior PMS material in an exemplary present invention IOL fabrication sequence formed using a PMS.
Figure 96:
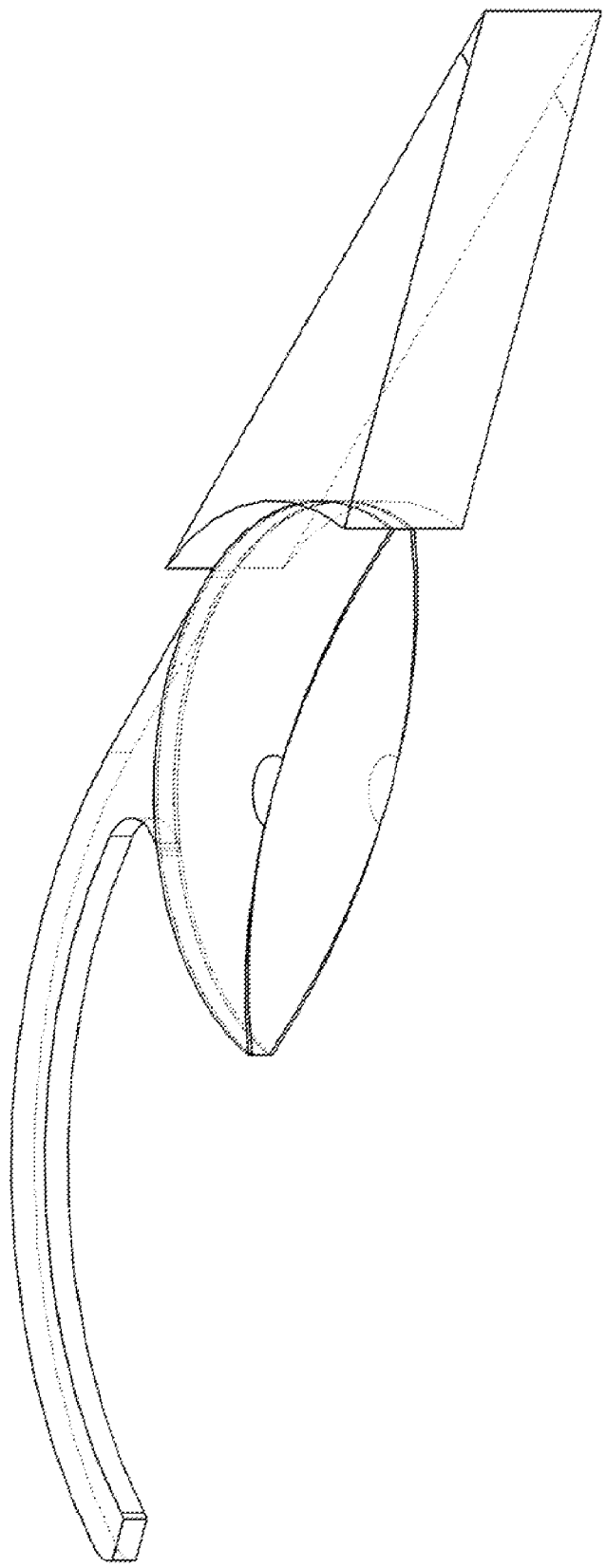
FIG. 96 illustrates a top right perspective diagonal section view depicting removal of the left haptic interior PMS material in an exemplary present invention IOL fabrication sequence formed using a PMS.
Figure 97:
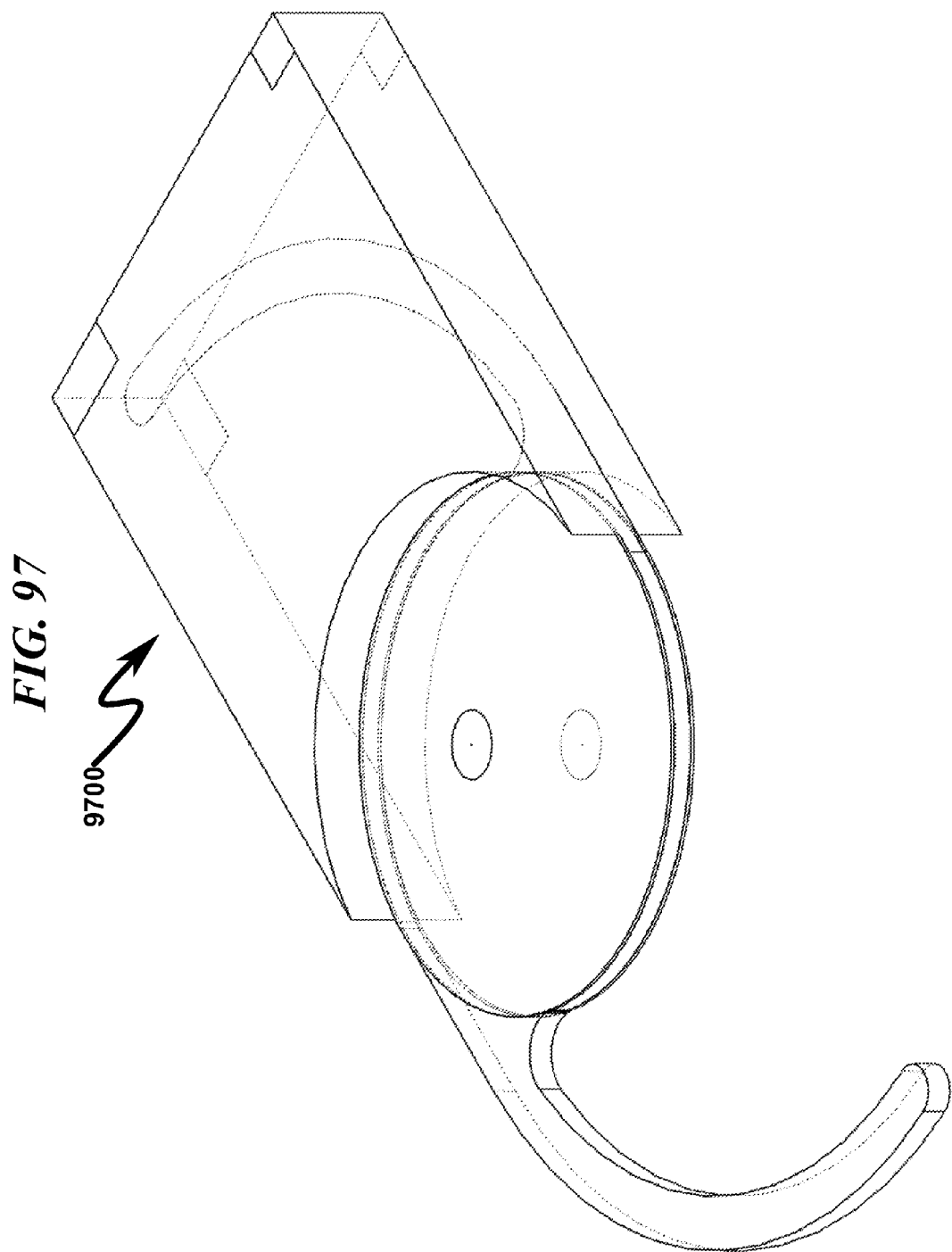
FIG. 97 illustrates a top left perspective view depicting cutting the right haptic posterior surface in an exemplary present invention IOL fabrication sequence formed using a PMS.
Figure 98:
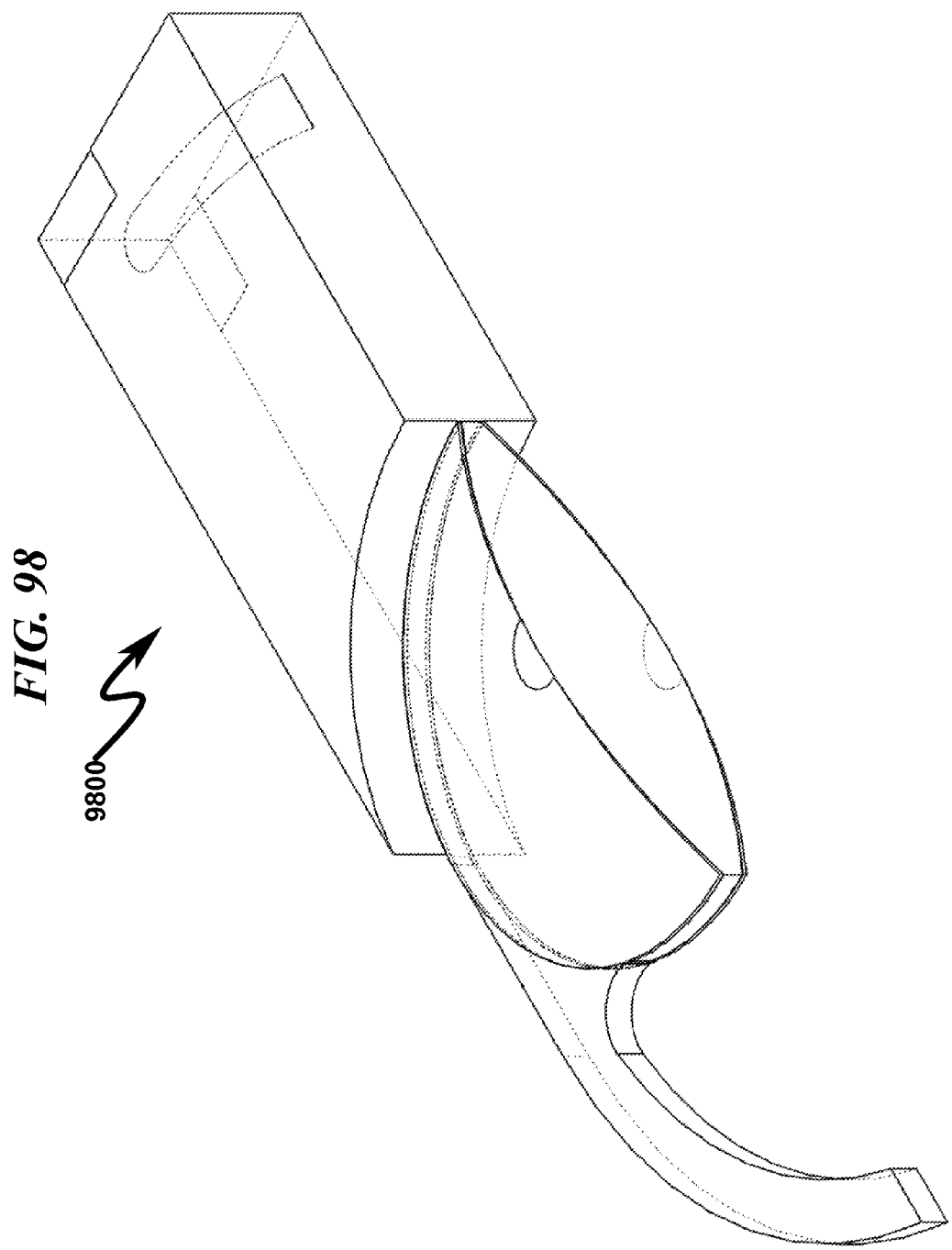
FIG. 98 illustrates a top left perspective front section view depicting cutting the right haptic posterior surface in an exemplary present invention IOL fabrication sequence formed using a PMS.
Figure 99:
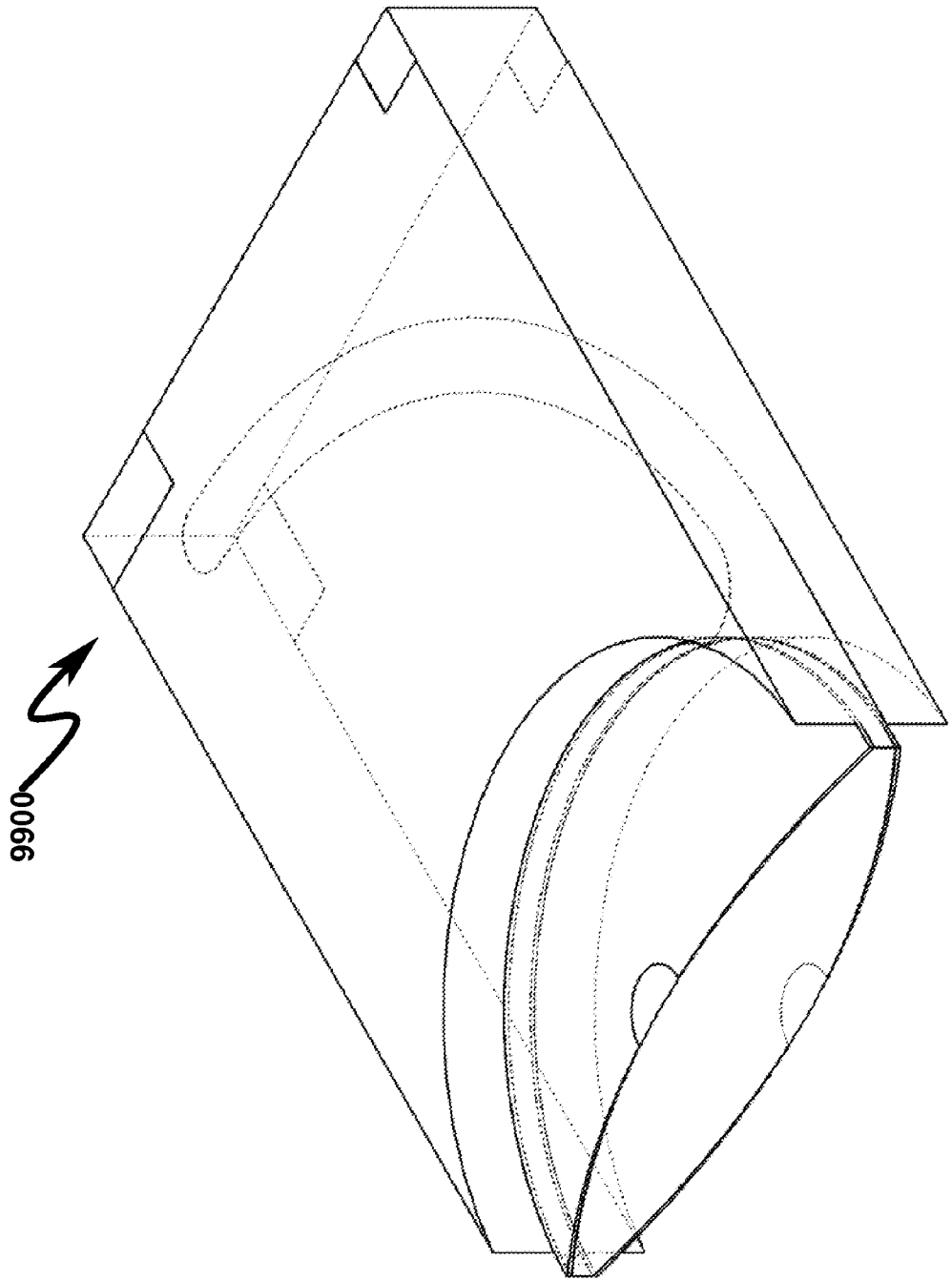
FIG. 99 illustrates a top left perspective right section view depicting cutting the right haptic posterior surface in an exemplary present invention IOL fabrication sequence formed using a PMS.
Figure 100:
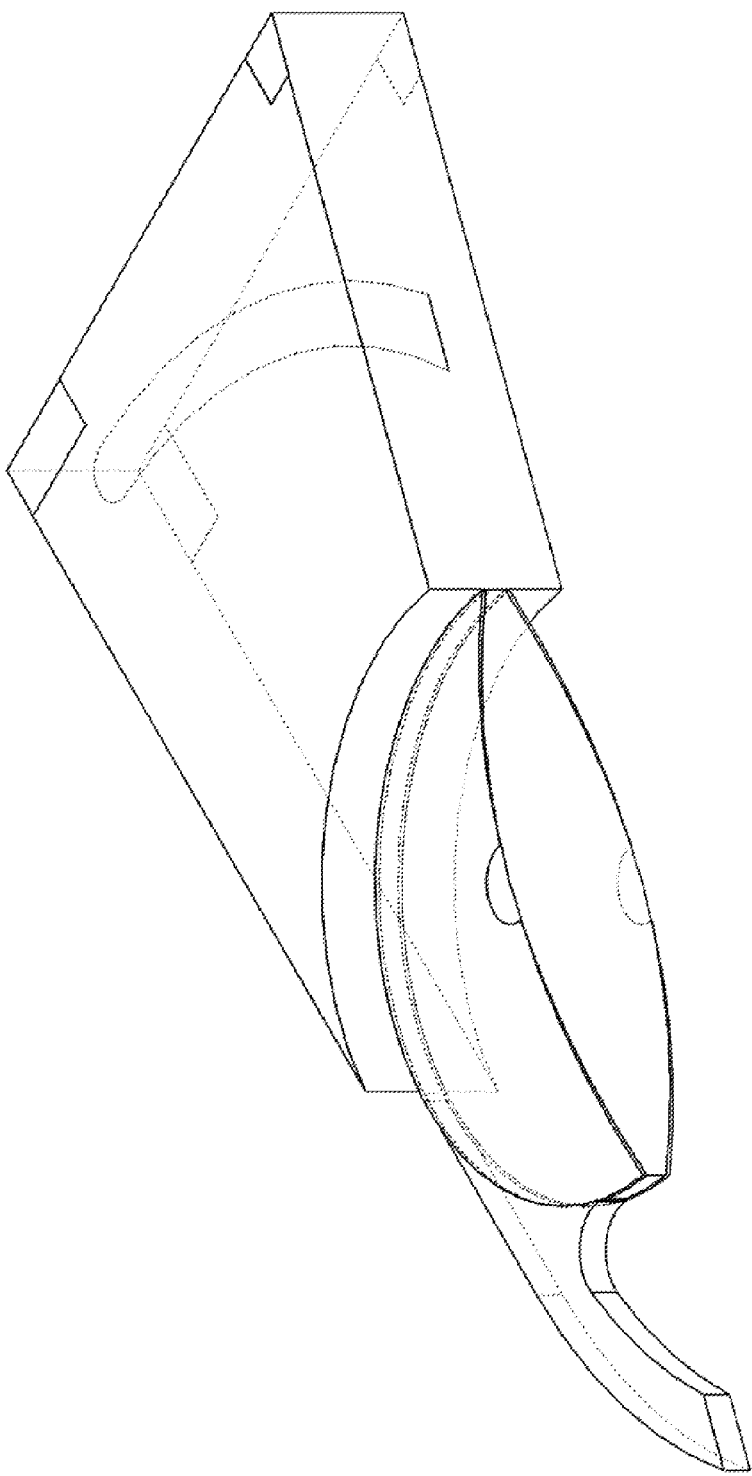
FIG. 100 illustrates a top left perspective diagonal section view depicting cutting the right haptic posterior surface in an exemplary present invention IOL fabrication sequence formed using a PMS.
Figure 101:
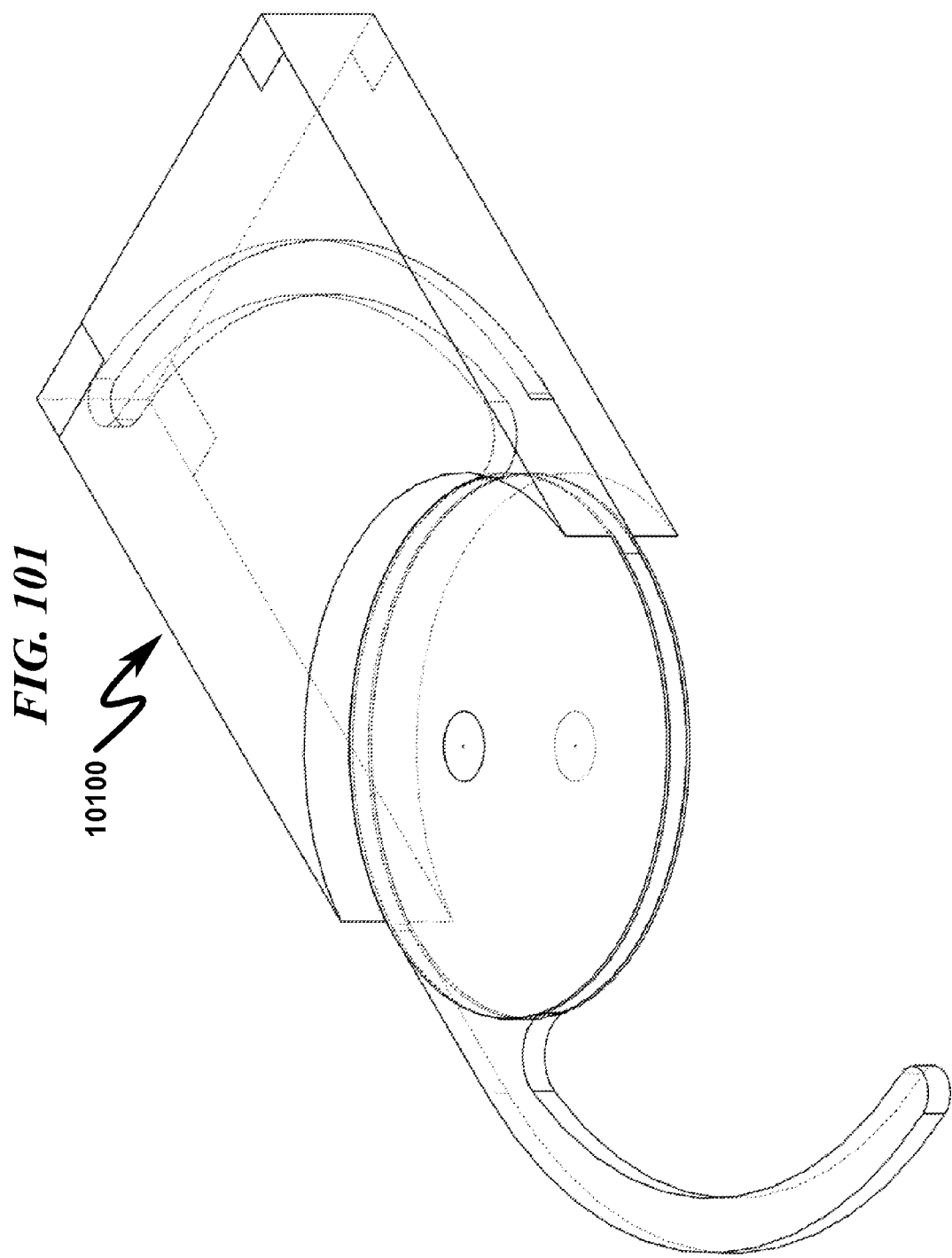
FIG. 101 illustrates a top left perspective view depicting cutting the right haptic side edge surface in an exemplary present invention IOL fabrication sequence formed using a PMS.
Figure 102:
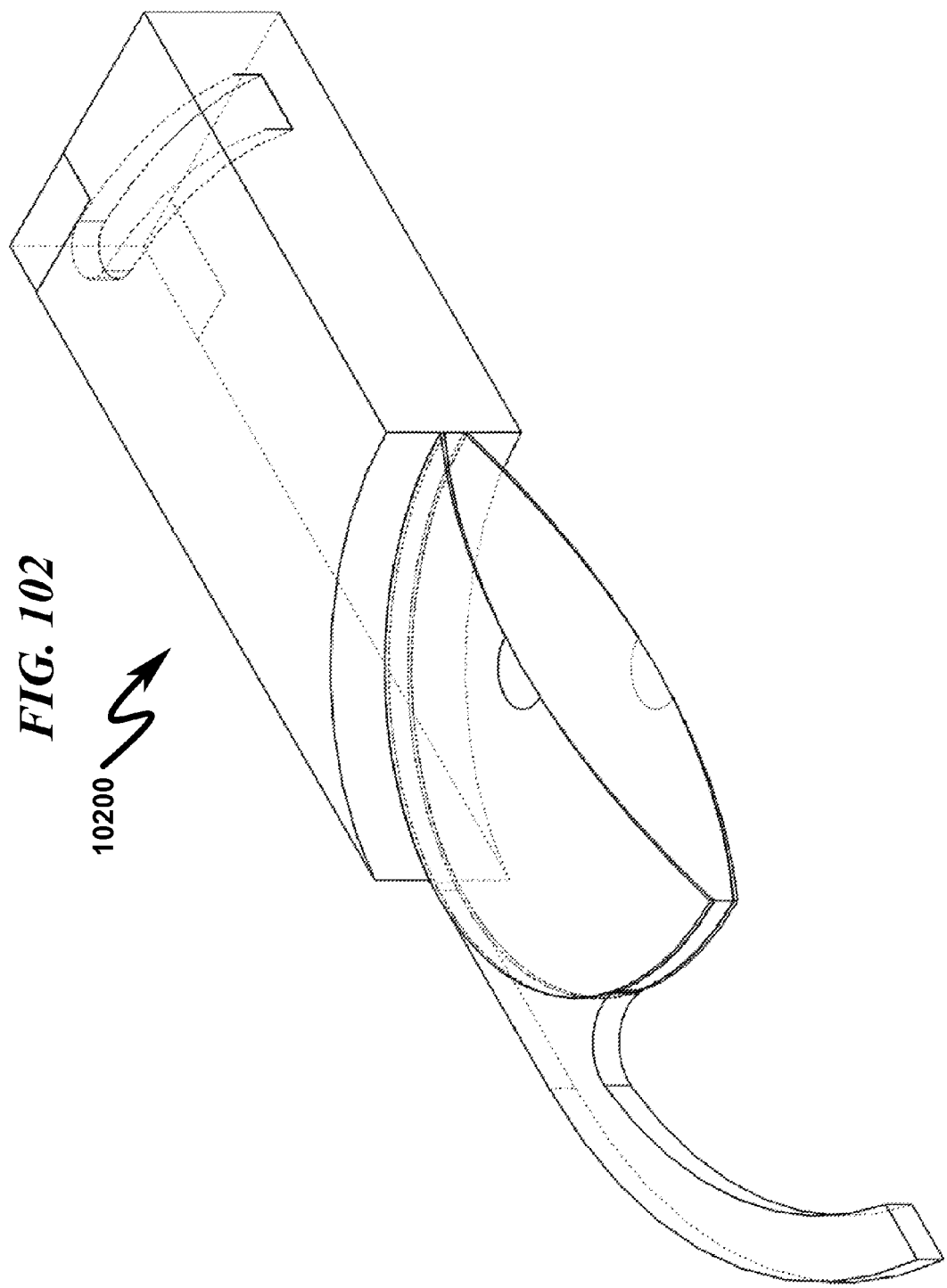
FIG. 102 illustrates a top left perspective front section view depicting cutting the right haptic side edge surface in an exemplary present invention IOL fabrication sequence formed using a PMS.
Figure 103:
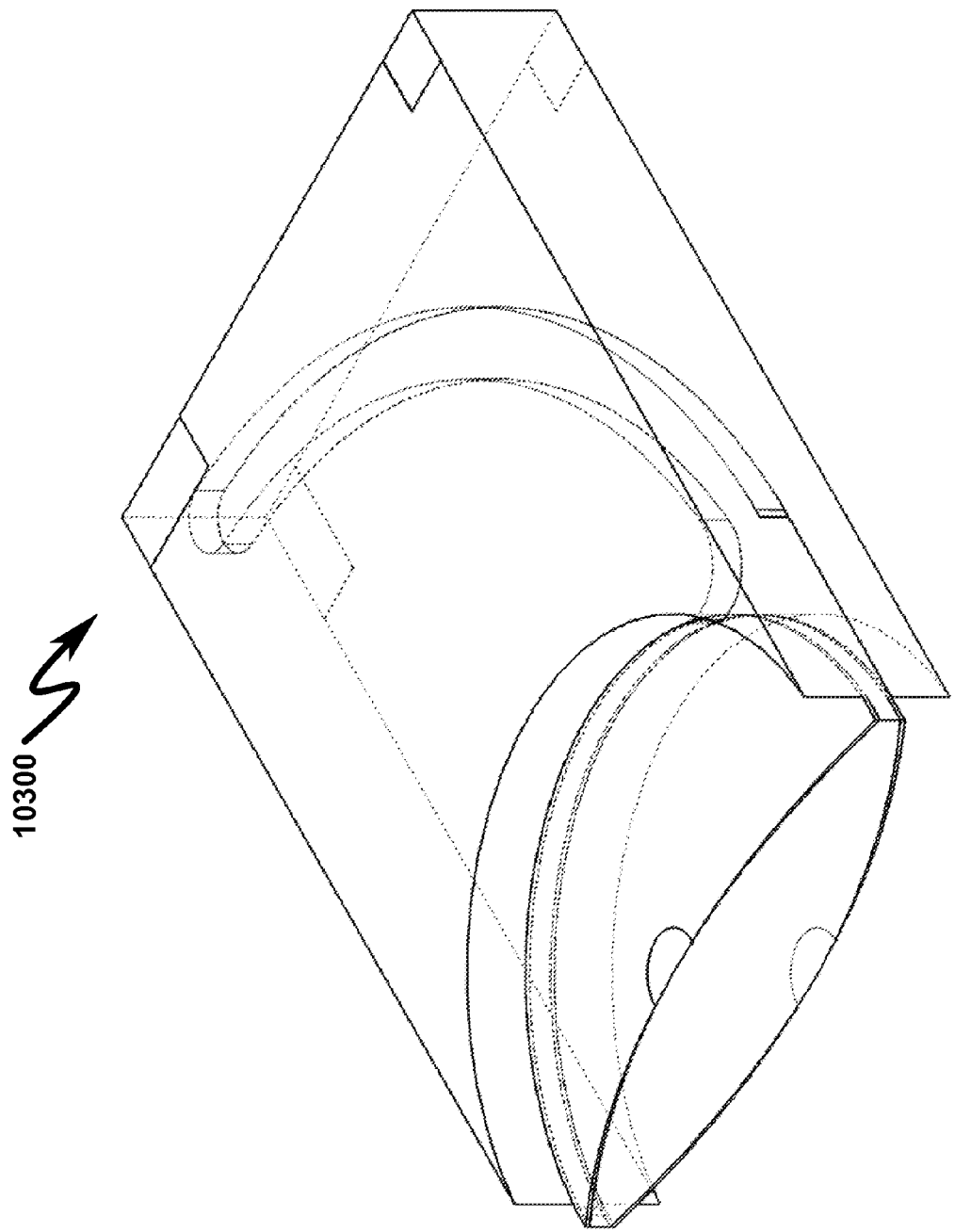
FIG. 103 illustrates a top left perspective right section view depicting cutting the right haptic side edge surface in an exemplary present invention IOL fabrication sequence formed using a PMS.
Figure 104:
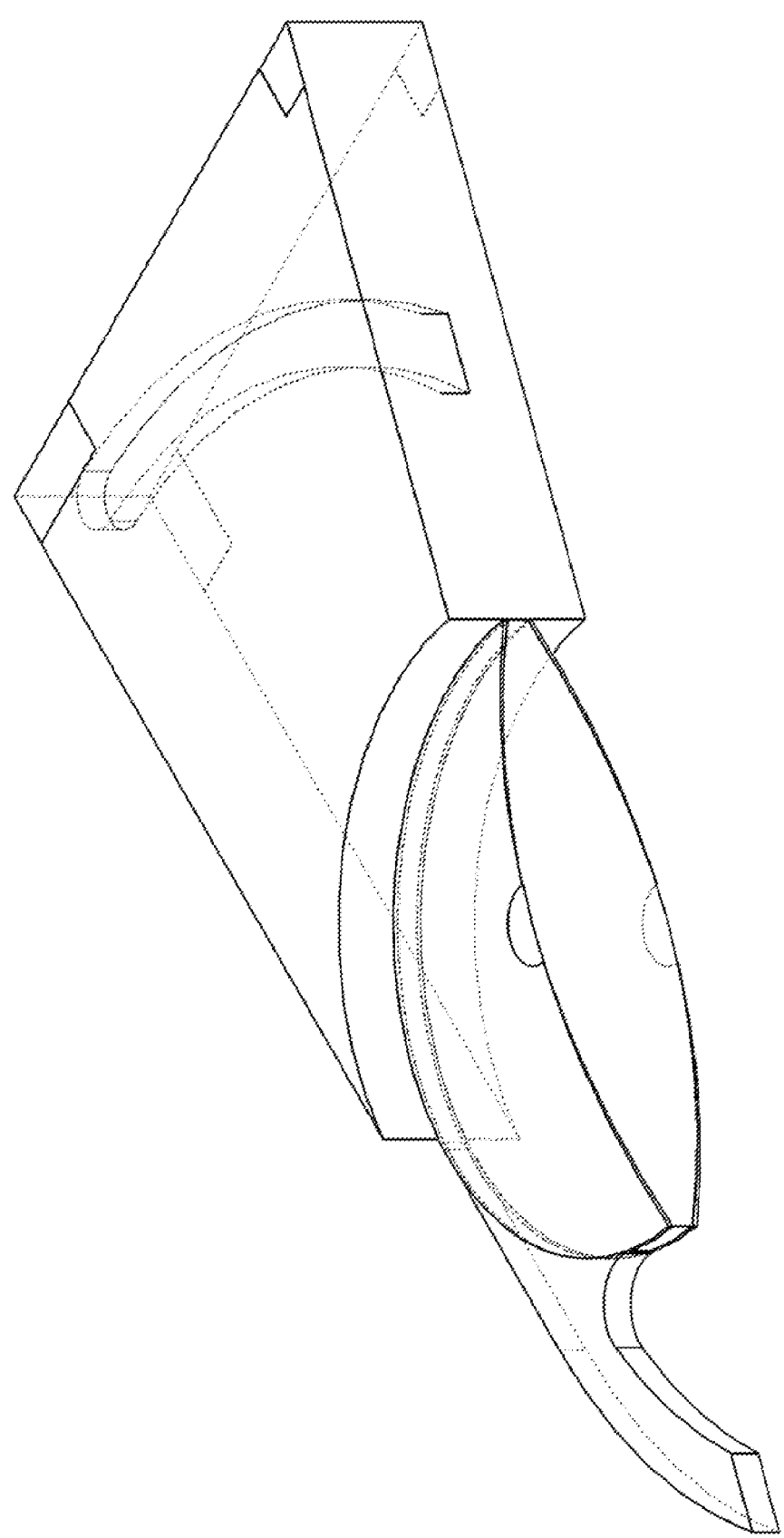
FIG. 104 illustrates a top left perspective diagonal section view depicting cutting the right haptic side edge surface in an exemplary present invention IOL fabrication sequence formed using a PMS.
Figure 105:
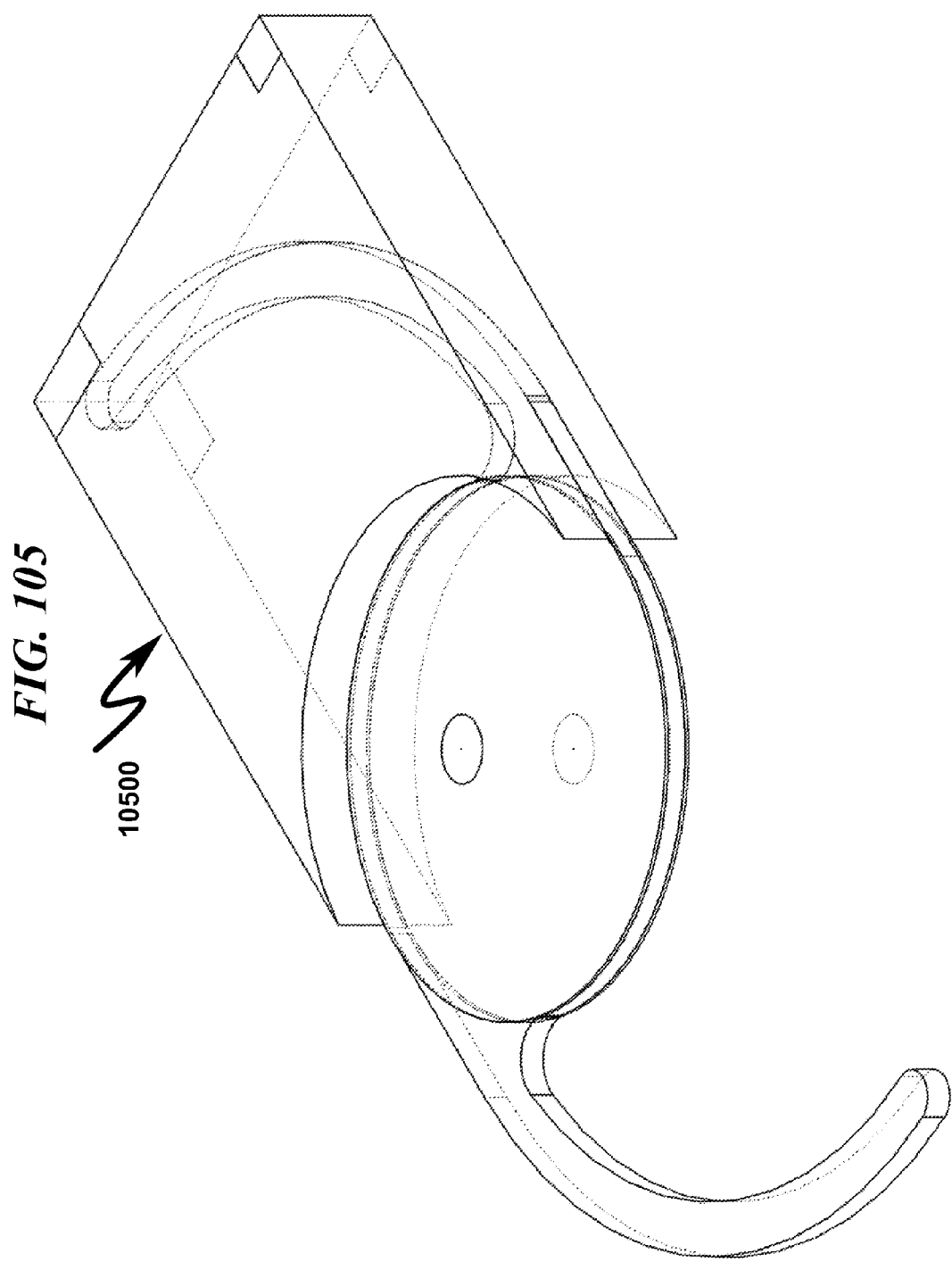
FIG. 105 illustrates a top left perspective view depicting cutting the right haptic anterior surface in an exemplary present invention IOL fabrication sequence formed using a PMS.
Figure 106:
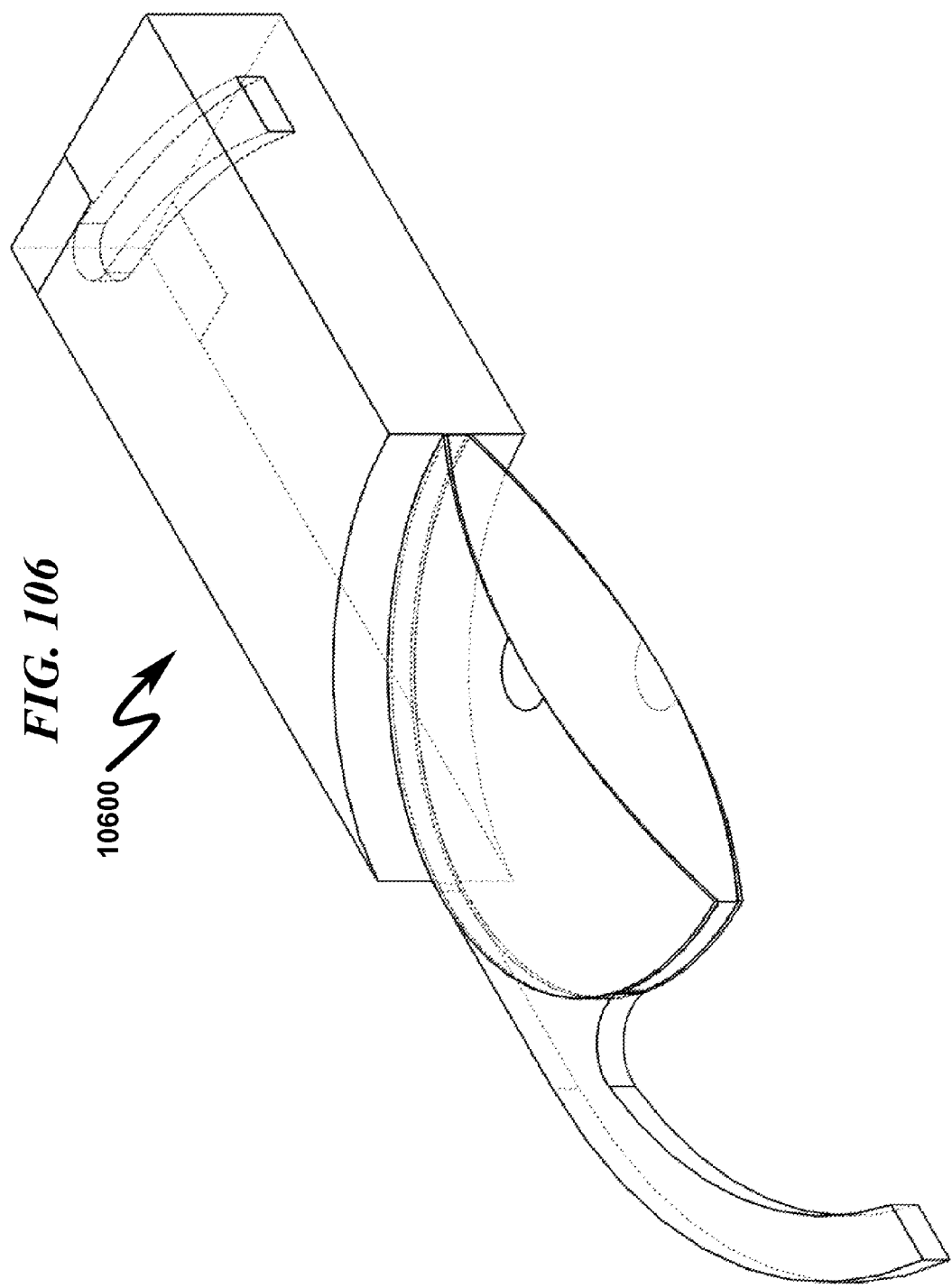
FIG. 106 illustrates a top left perspective front section view depicting cutting the right haptic anterior surface in an exemplary present invention IOL fabrication sequence formed using a PMS.
Figure 107:
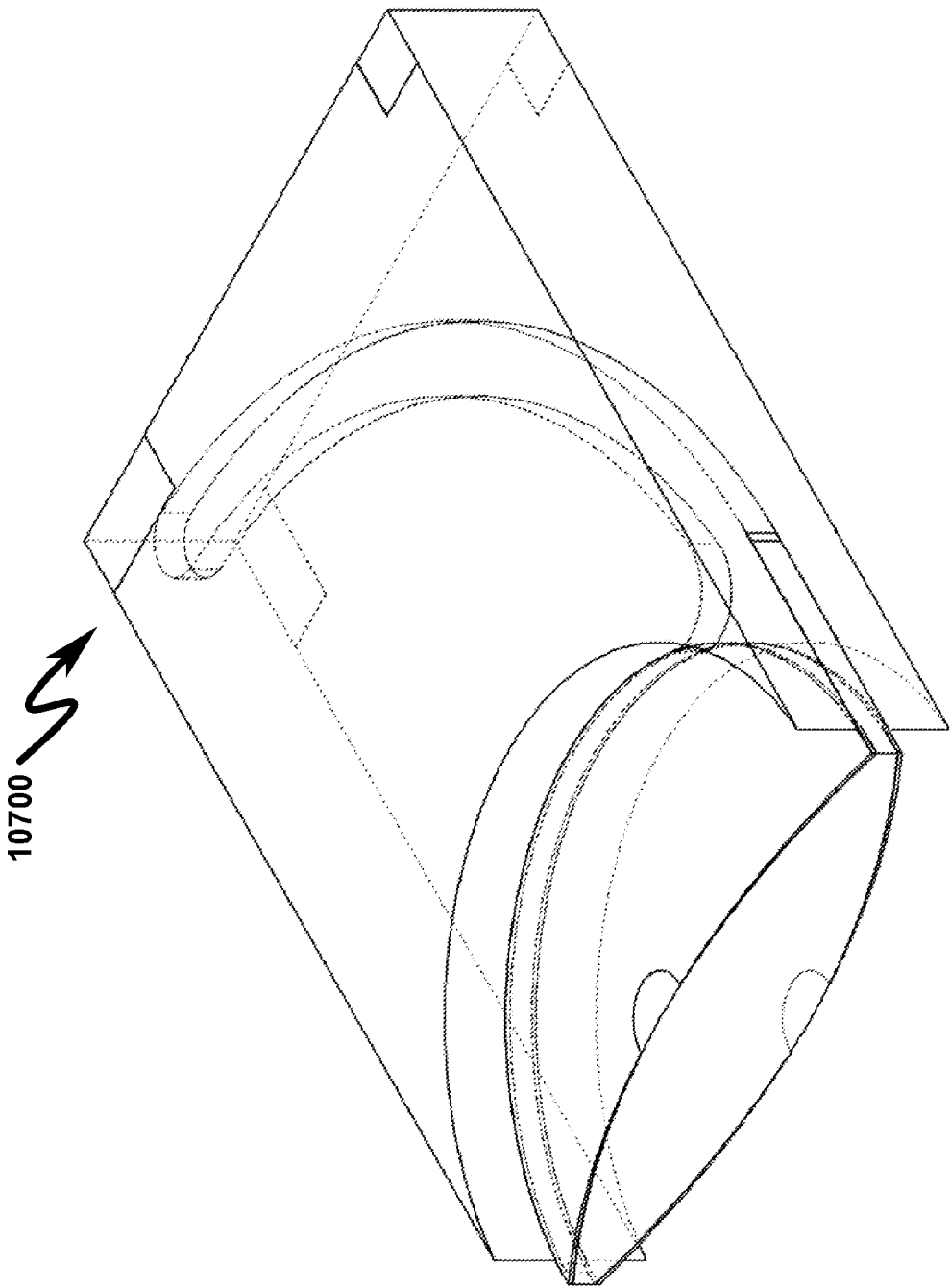
FIG. 107 illustrates a top left perspective right section view depicting cutting the right haptic anterior surface in an exemplary present invention IOL fabrication sequence formed using a PMS.
Figure 108:
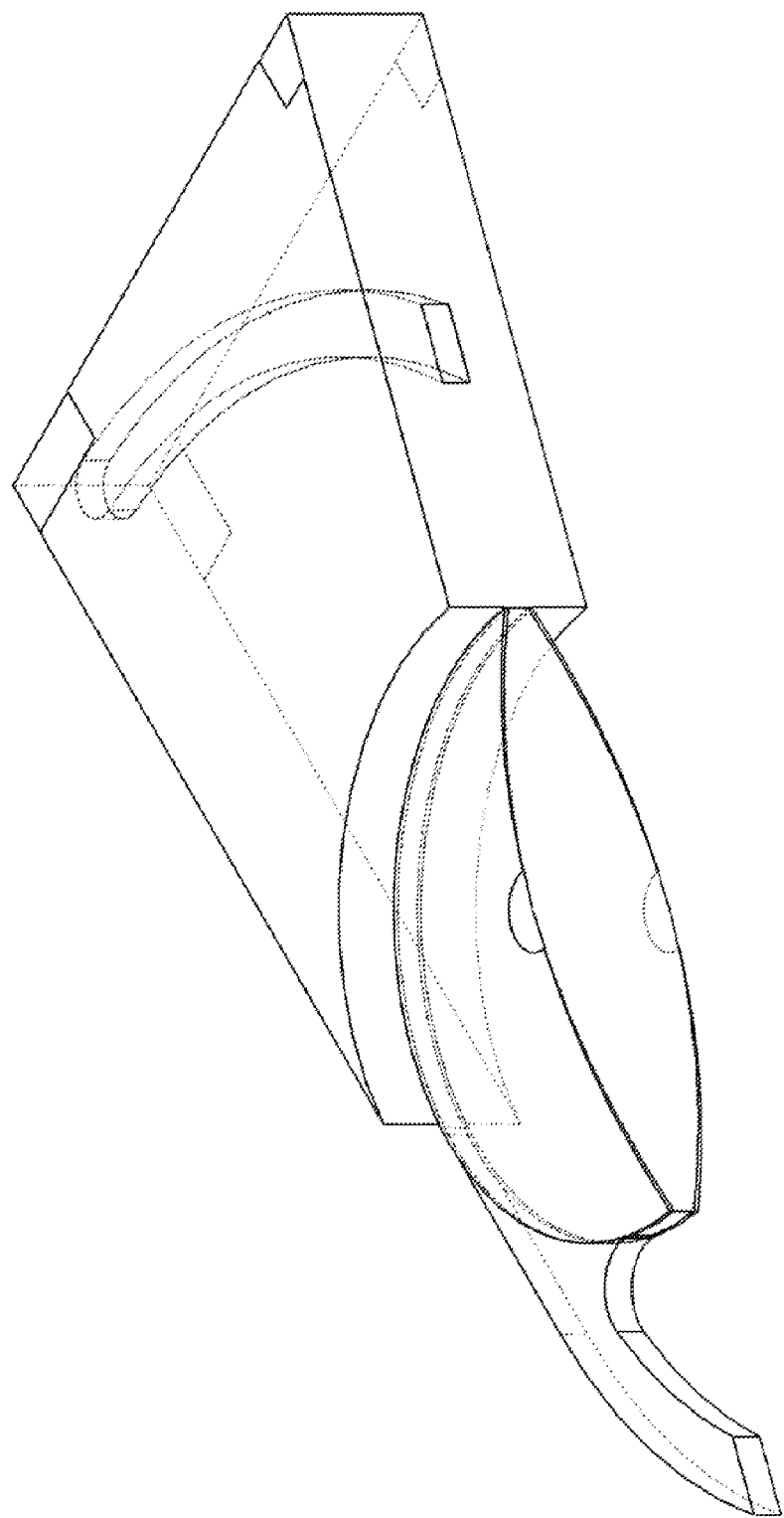
FIG. 108 illustrates a top left perspective diagonal section view depicting cutting the right haptic anterior surface in an exemplary present invention IOL fabrication sequence formed using a PMS.
Figure 109:
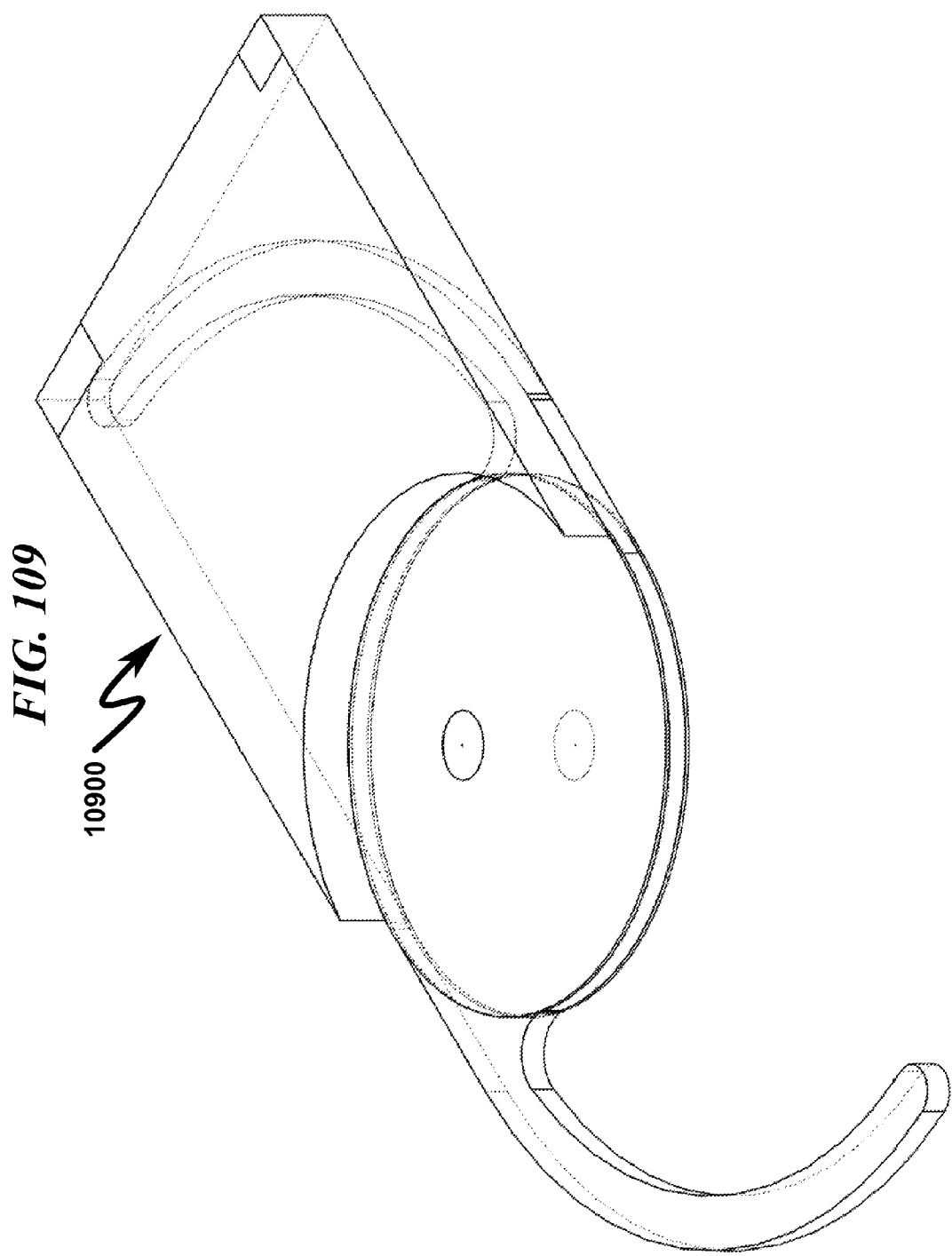
FIG. 109 illustrates a top left perspective view depicting removal of the right haptic posterior PMS material in an exemplary present invention IOL fabrication sequence formed using a PMS.
Figure 110:
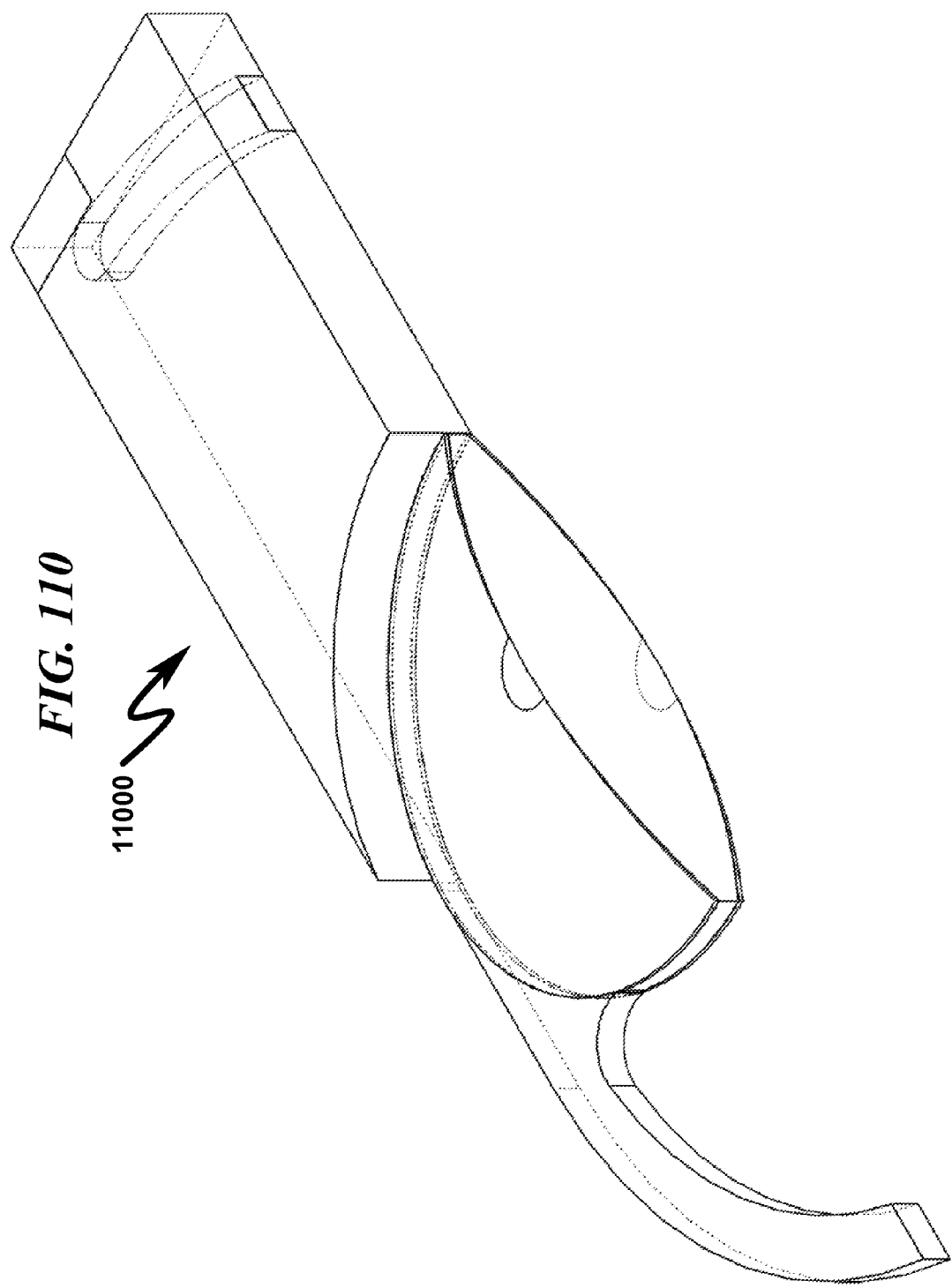
FIG. 110 illustrates a top left perspective front section view depicting removal of the right haptic posterior PMS material in an exemplary present invention IOL fabrication sequence formed using a PMS.
Figure 111:
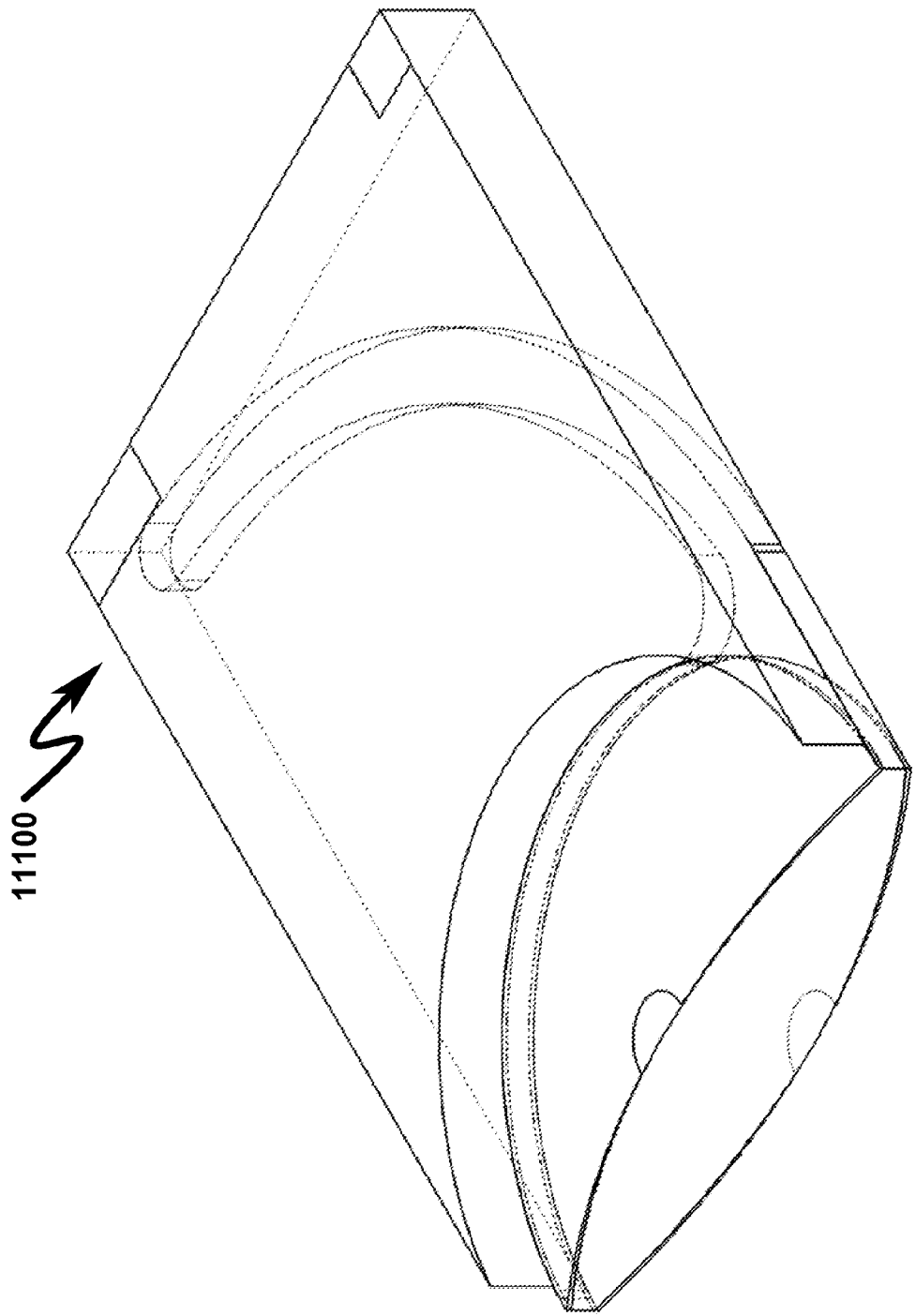
FIG. 111 illustrates a top left perspective right section view depicting removal of the right haptic posterior PMS material in an exemplary present invention IOL fabrication sequence formed using a PMS.
Figure 112:
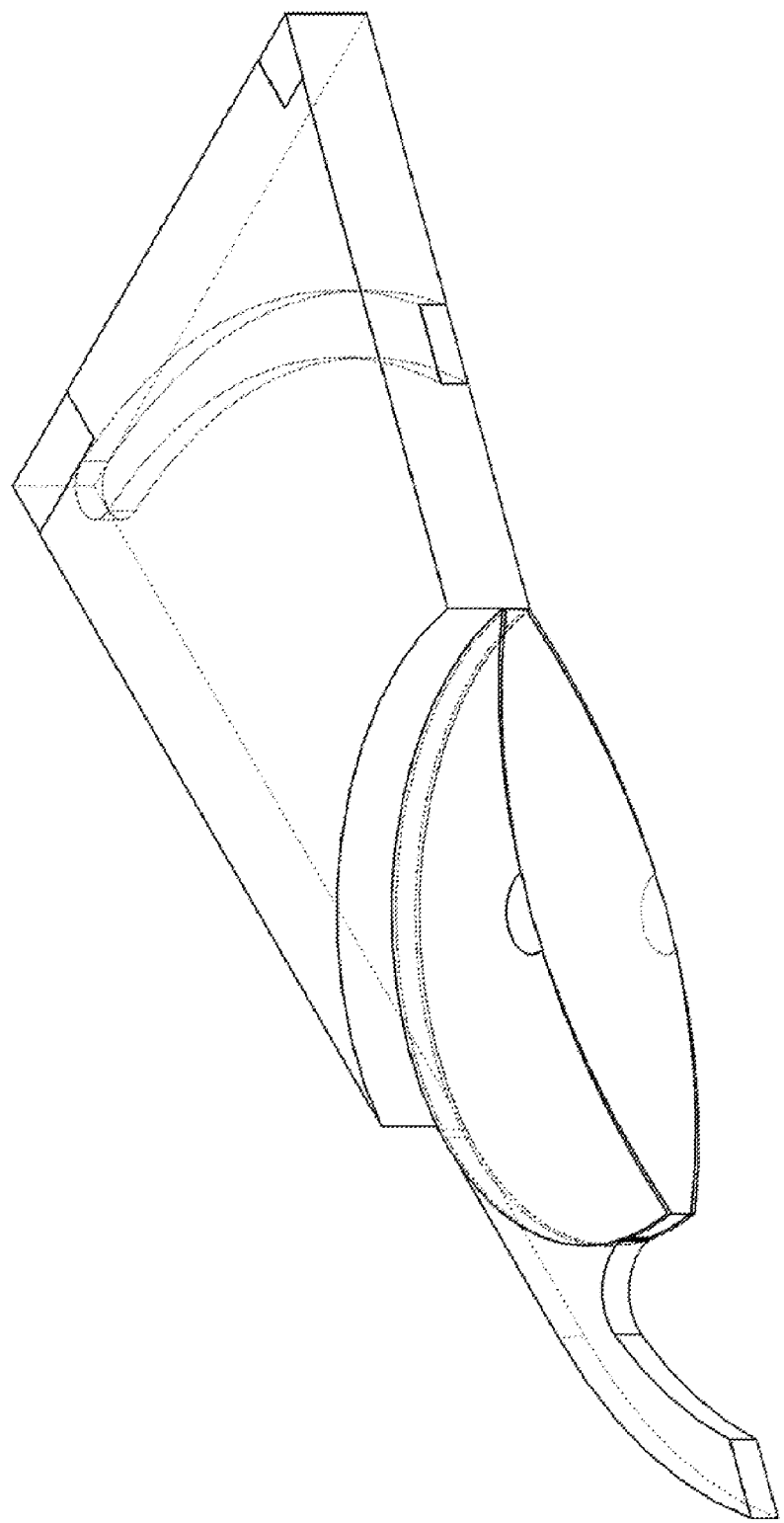
FIG. 112 illustrates a top left perspective diagonal section view depicting removal of the right haptic posterior PMS material in an exemplary present invention IOL fabrication sequence formed using a PMS.
Figure 113:
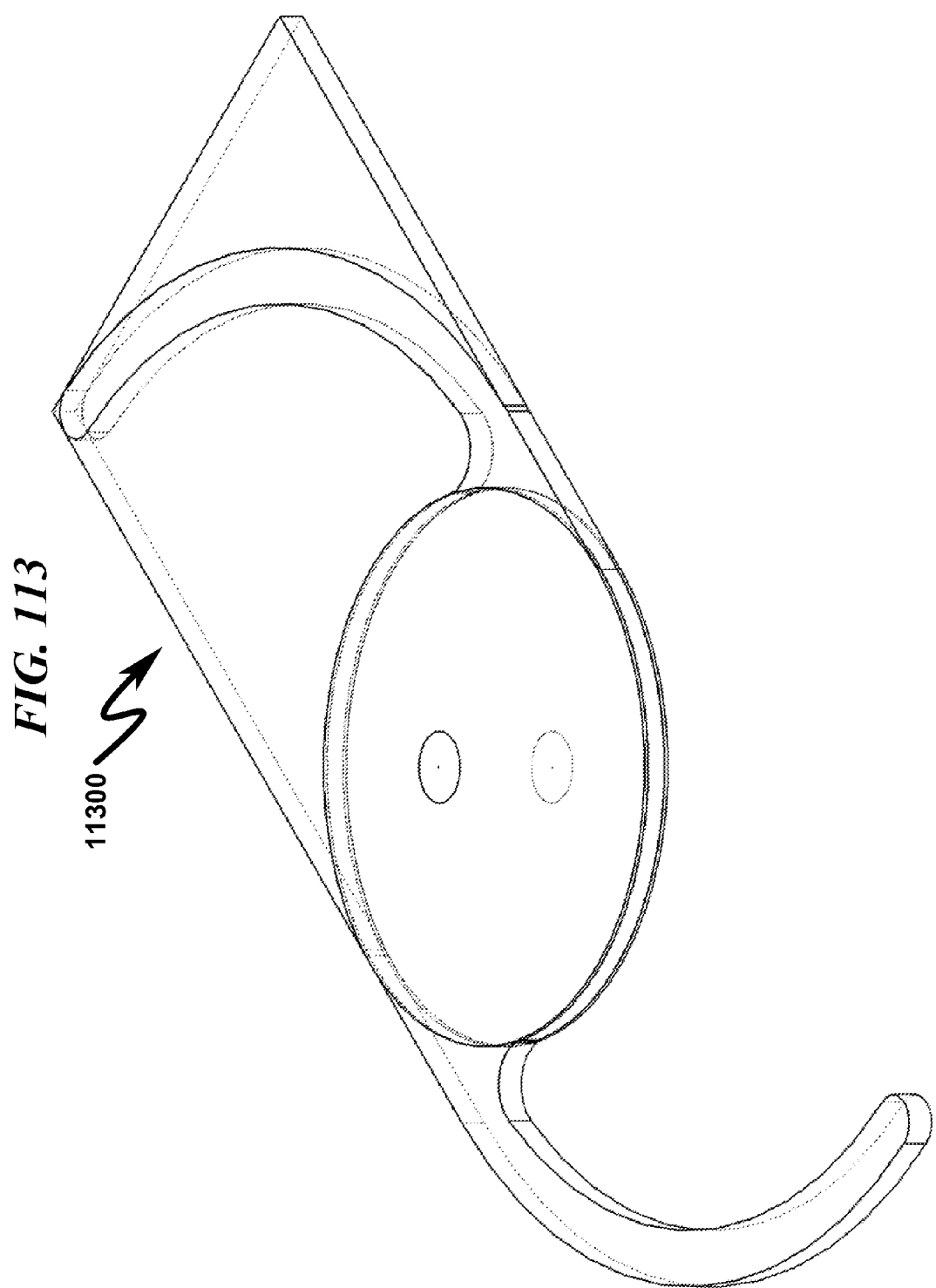
FIG. 113 illustrates a top left perspective view depicting removal of the right haptic anterior PMS material in an exemplary present invention IOL fabrication sequence formed using a PMS.
Figure 114:
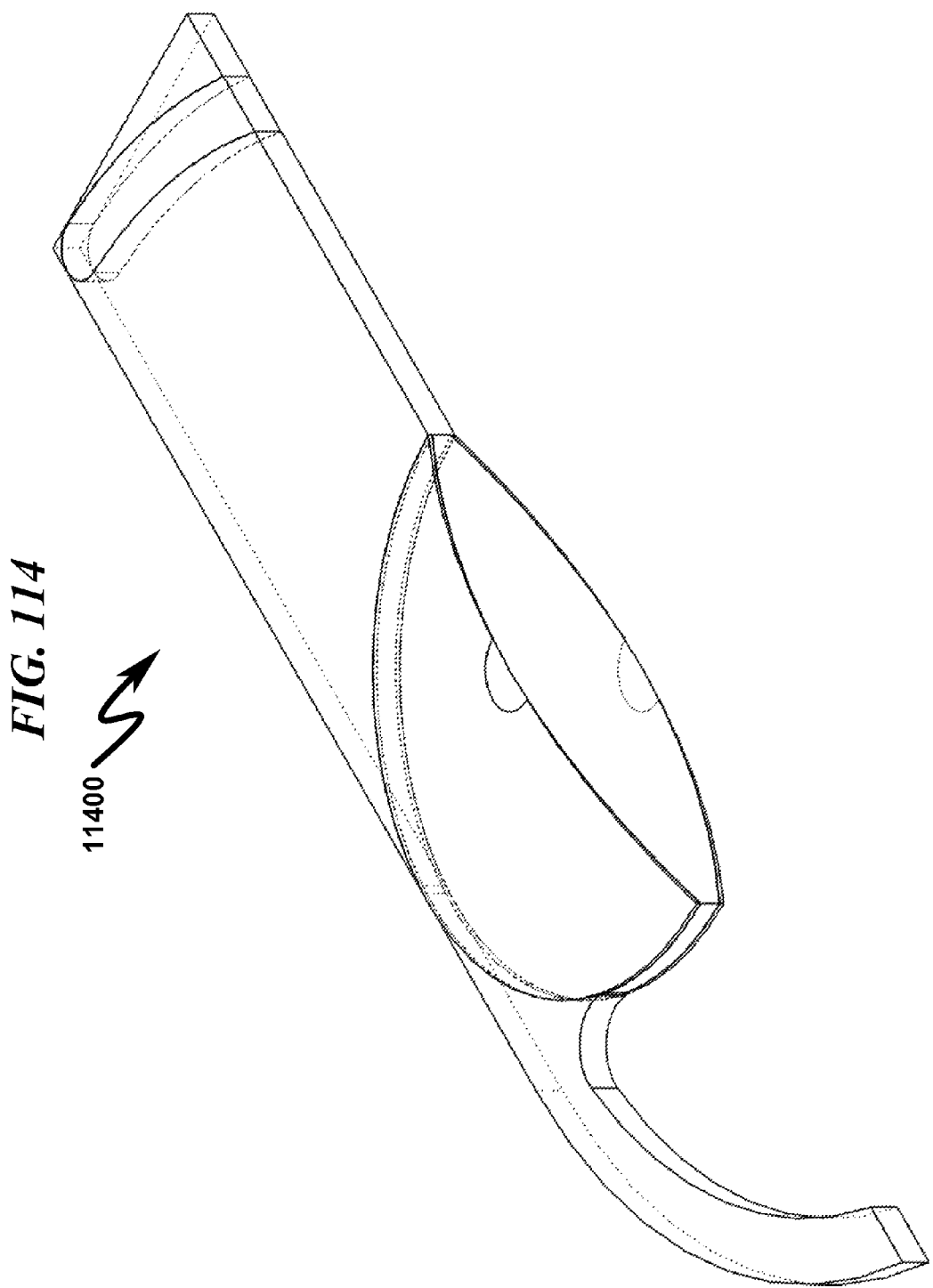
FIG. 114 illustrates a top left perspective front section view depicting removal of the right haptic anterior PMS material in an exemplary present invention IOL fabrication sequence formed using a PMS.
Figure 115:
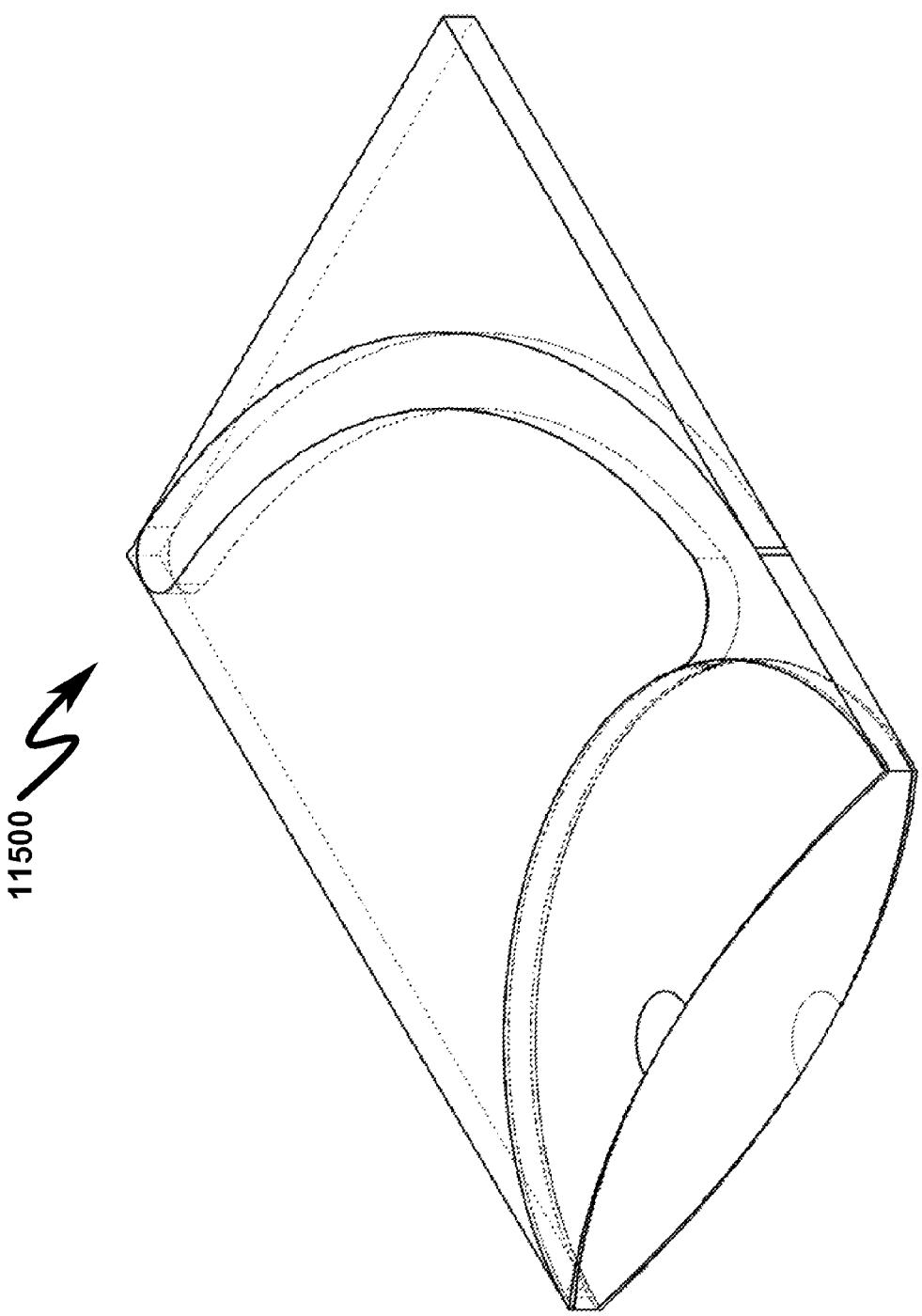
FIG. 115 illustrates a top left perspective right section view depicting removal of the right haptic anterior PMS material in an exemplary present invention IOL fabrication sequence formed using a PMS.
Figure 116:
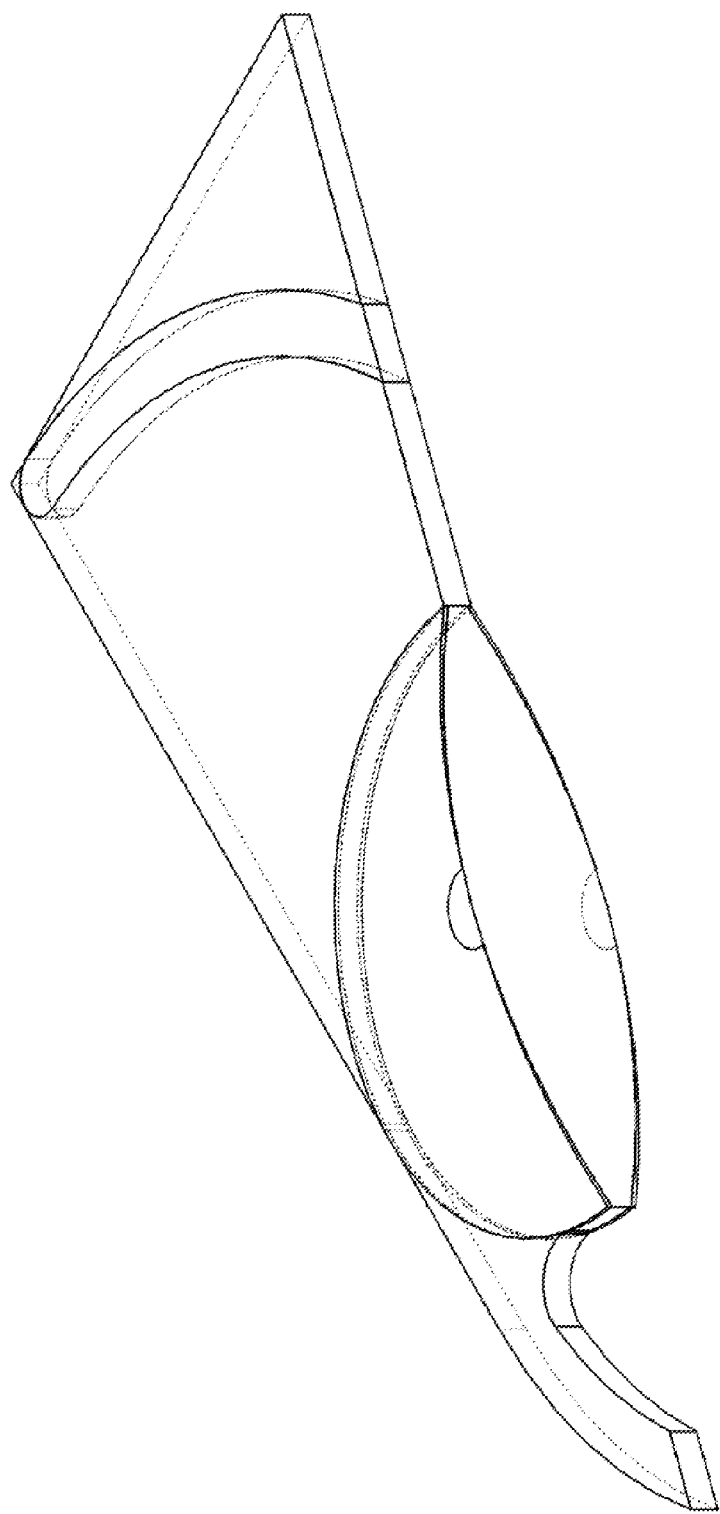
FIG. 116 illustrates a top left perspective diagonal section view depicting removal of the right haptic anterior PMS material in an exemplary present invention IOL fabrication sequence formed using a PMS.
Figure 117:
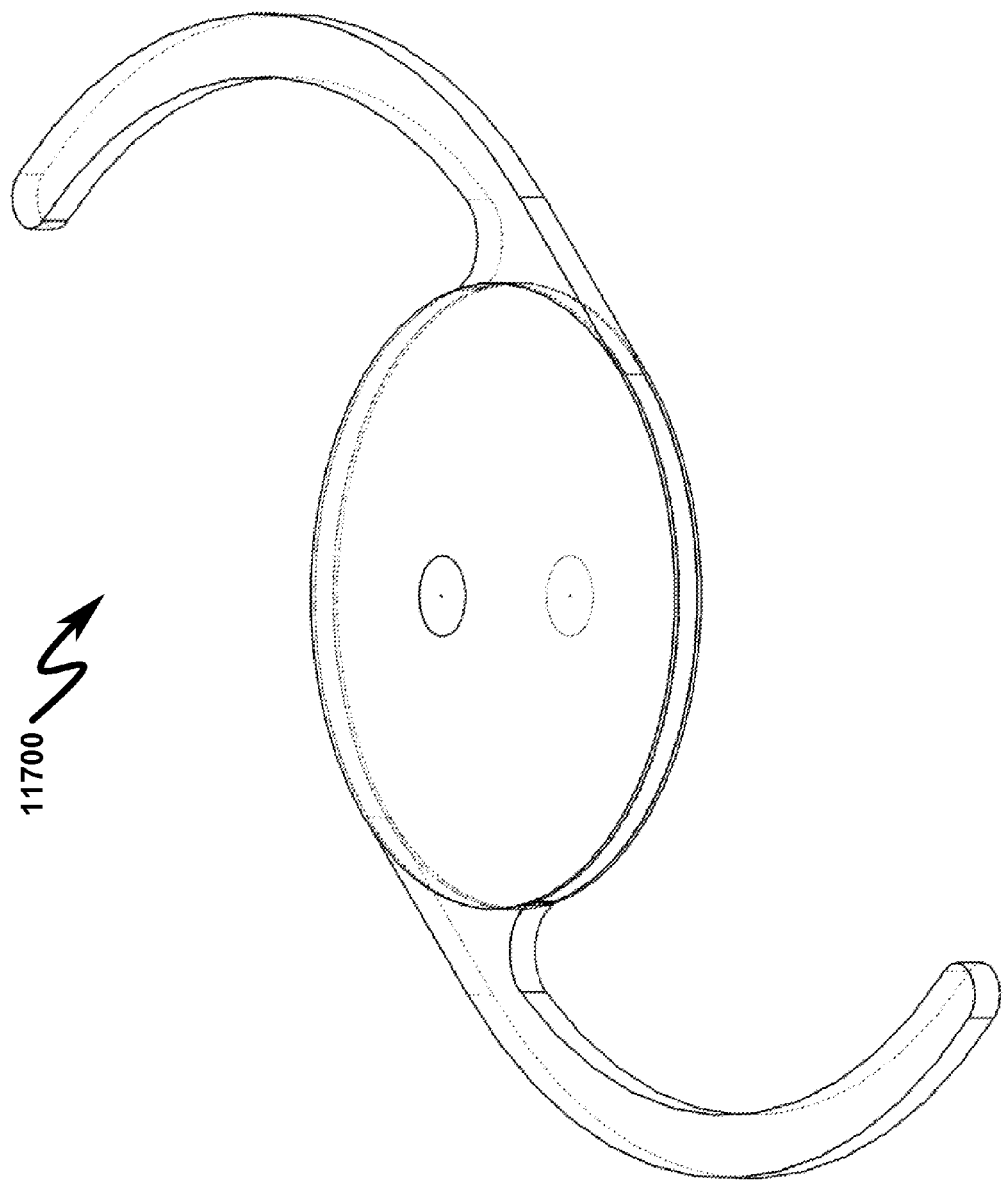
FIG. 117 illustrates a top left perspective view depicting removal of the right haptic interior PMS material in an exemplary present invention IOL fabrication sequence formed using a PMS.
Figure 119:
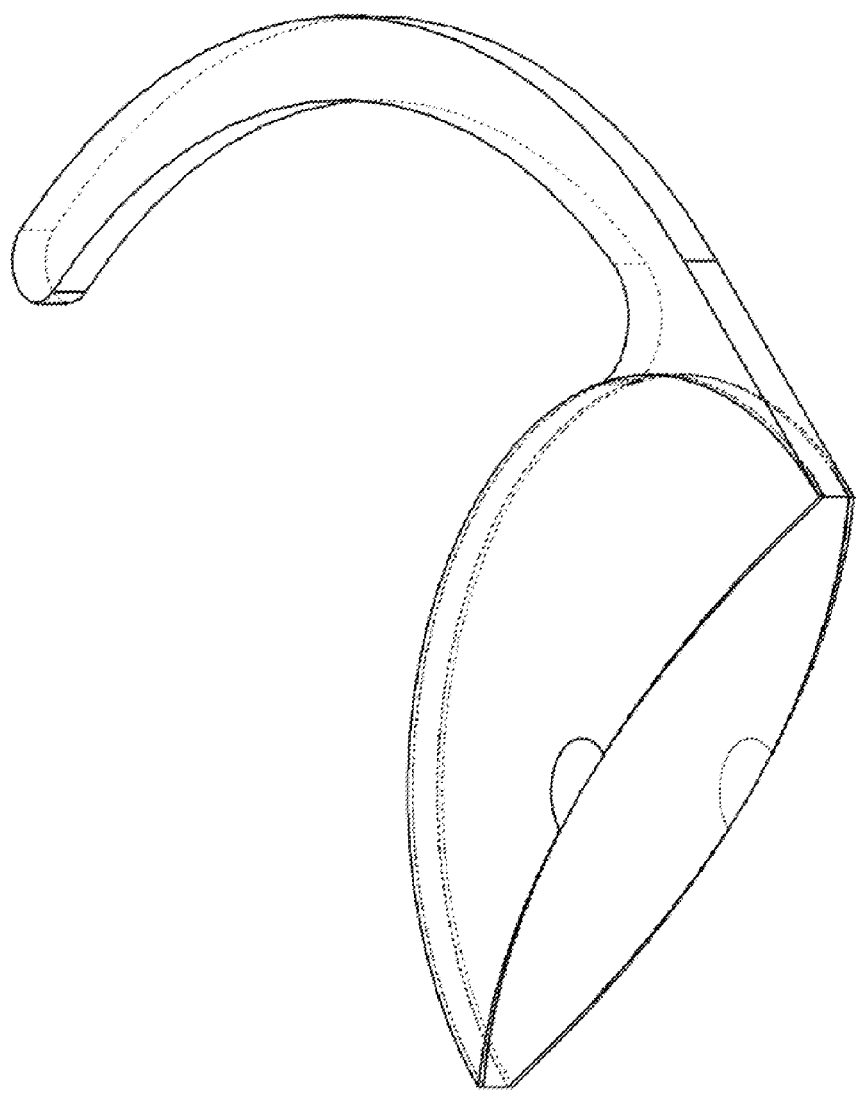
Figure 120:
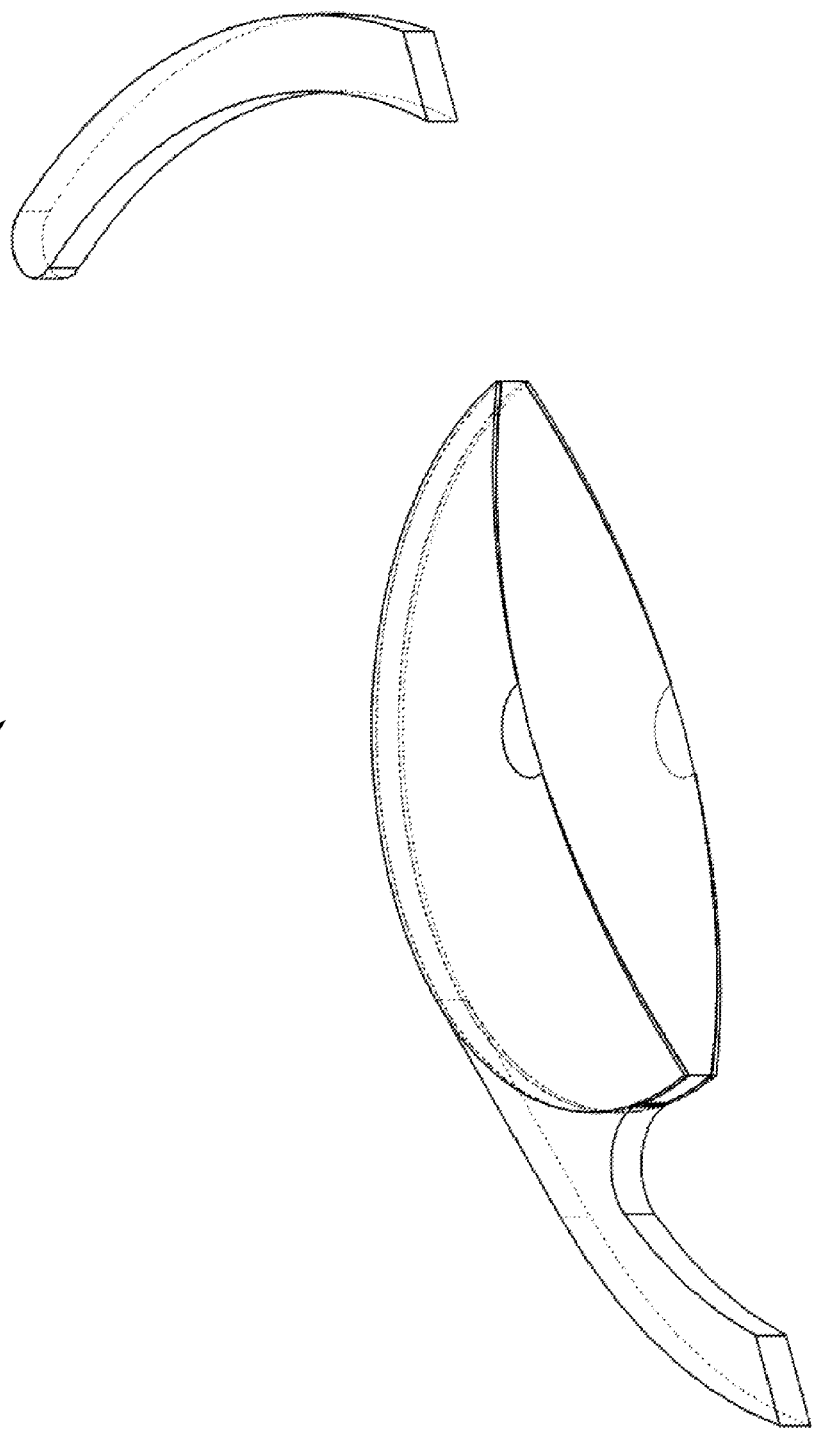
Figure 121:
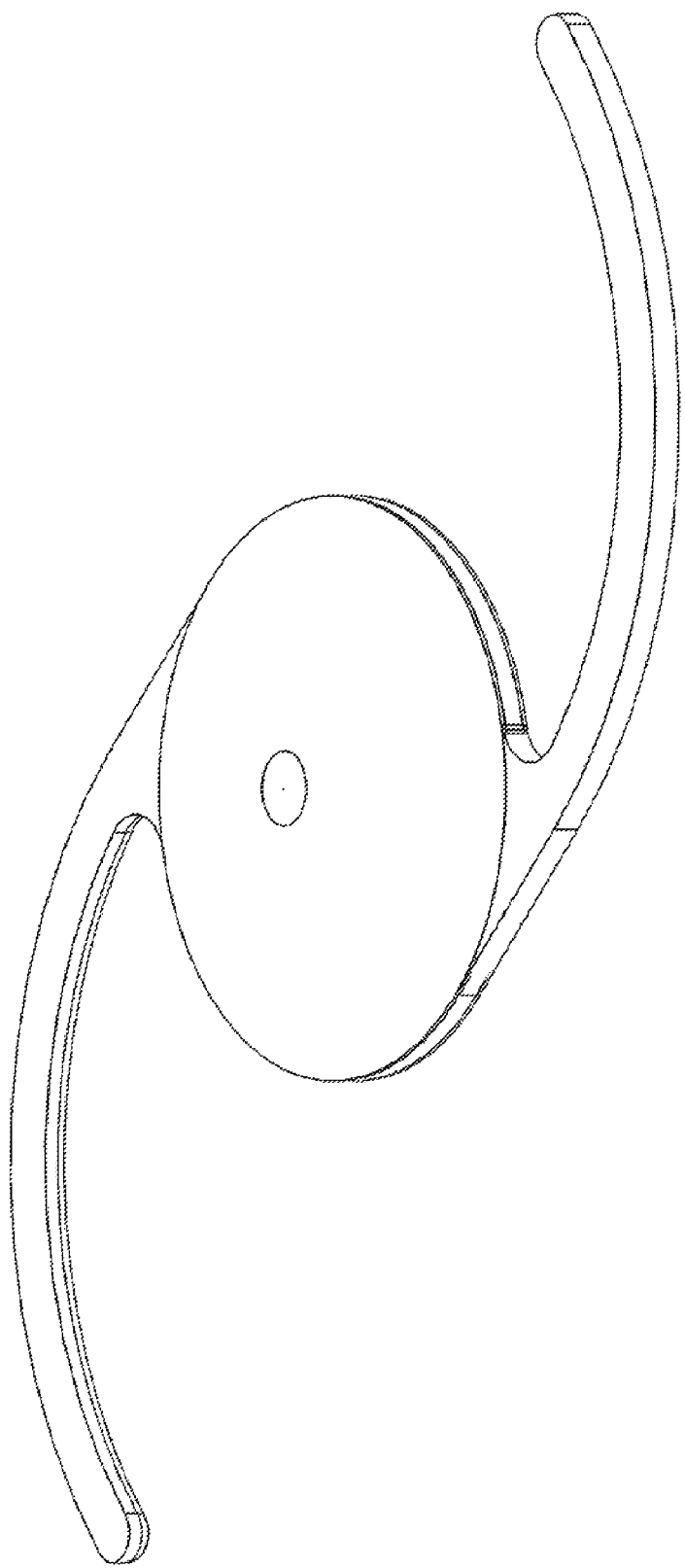

An exemplary optical sculpting method is generally described in the flowcharts depicted in FIG. 33 (3300)-FIG. 36 (3600). While this method is amenable to modification, the general steps involved in fabricating the IOL comprise:
(1) Select and orient a polymeric material slab (PMS) or polymeric material blank (PMB) for processing (3301). As generally depicted in FIG. 41 (4100)-FIG. 42 (4200), a PMS may be used for full slab contouring in which optional top fiducials (4101, 4102, 4103, 4104) and orthogonal bottom fiducials (4201, 4202, 4203, 4204) may be used to orient the PMS during manufacturing, or some variant of pre-formed PMB blank material may be used as generally depicted in FIG. 43 (4300)-FIG. 44 (4400) and FIG. 18 (1800)-FIG. 24 (2400).
(2) Sculpt (cut) the posterior lenticule surface with a femtosecond pulsed laser source (PLS) (3302) (as generally depicted in FIG. 45 (4500)-FIG. 48 (4800));
(3) Cut the side edges of the lens in the PM with the femtosecond pulsed laser source (PLS) (3303) (as generally depicted in FIG. 49 (4900)-FIG. 52 (5200));
(4) Cut the edges of the lens to the posterior PM surface (3304) (as generally depicted in FIG. 53 (5300)-FIG. 56 (5600));
(5) Remove the posterior PM material over the lenticule (3305) (as generally depicted in FIG. 57 (5700)-FIG. 60 (6000));
(6) Sculpt (cut) the anterior lenticule PM surface with the femtosecond pulsed laser source (PLS) (3406) (as generally depicted in FIG. 61 (6100)-FIG. 64 (6400));
(7) Cut the edges of the lens to the anterior PM surface (3407) (as generally depicted in FIG. 65 (6500)-FIG. 68 (6800));
(8) Remove the anterior PM material over the lenticule (3408) (as generally depicted in FIG. 69 (6900)-FIG. 72 (7200));
(9) Cut the left haptic posterior surface with the femtosecond pulsed laser source (PLS) (3409) (as generally depicted in FIG. 73 (7300)-FIG. 76 (7600));
(10) Cut the left haptic side edge surface with the femtosecond pulsed laser source (PLS) (3410) (as generally depicted in FIG. 77 (7700)-FIG. 80 (8000));
(11) Cut the left haptic anterior surface with the femtosecond pulsed laser source (PLS) (3511) (as generally depicted in FIG. 81 (8100)-FIG. 84 (8400));

(12) Remove the left haptic posterior PM material (3512) (as generally depicted in FIG. 85 (8500)-FIG. 88 (8800));
(13) Remove the left haptic anterior PM material (3513) (as generally depicted in FIG. 89 (8900)-FIG. 92 (9200));
(14) Remove the left haptic interior PM material (3514) (as generally depicted in FIG. 93 (9300)-FIG. 96 (9600));
(15) Cut the right haptic posterior surface with the femtosecond pulsed laser source (PLS) (3615) (as generally depicted in FIG. 97 (9700)-FIG. 100 (10000));
(16) Cut the right haptic side edge surface with the femtosecond pulsed laser source (PLS) (3616) (as generally depicted in FIG. 101 (10100)-FIG. 104 (10400));
(17) Cut the right haptic anterior surface with the femtosecond pulsed laser source (PLS) (3617) (as generally depicted in FIG. 105 (10500)-FIG. 108 (10800));
(18) Remove the right haptic posterior PM material (3618) (as generally depicted in FIG. 109 (10900)-FIG. 112 (11200));
(19) Remove the right haptic anterior PM material (3619) (as generally depicted in FIG. 113 (11300)-FIG. 116 (11600));
(20) Remove the right haptic interior PM material (3620) (as generally depicted in FIG. 117 (11700)-FIGS. 120 (12000)); and
(21) Optionally process the edges of the left and the right haptics with the femtosecond pulsed laser source (PLS) (3621) (as generally depicted in FIG. 121 (12100)-FIG. 128 (12800));
wherein:
the PLS is configured to emit pulsed laser radiation (PLR) output at a repetition rate of at least 1 million pulses per second;
the PLS is configured to emit the PLR output with a pulse-width of 900 femtoseconds or less;
the PLS is configured by a computing control device (CCD) to generate a three dimensional cutting pattern (TDP) using at least 7.5 million focused laser pulses within 5 minutes; and
the IOL fabricated comprises an anterior surface, a posterior surface, and one or more haptics.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Generalized Optical Sculpting Process (3700)-(3800)

Figure 37:
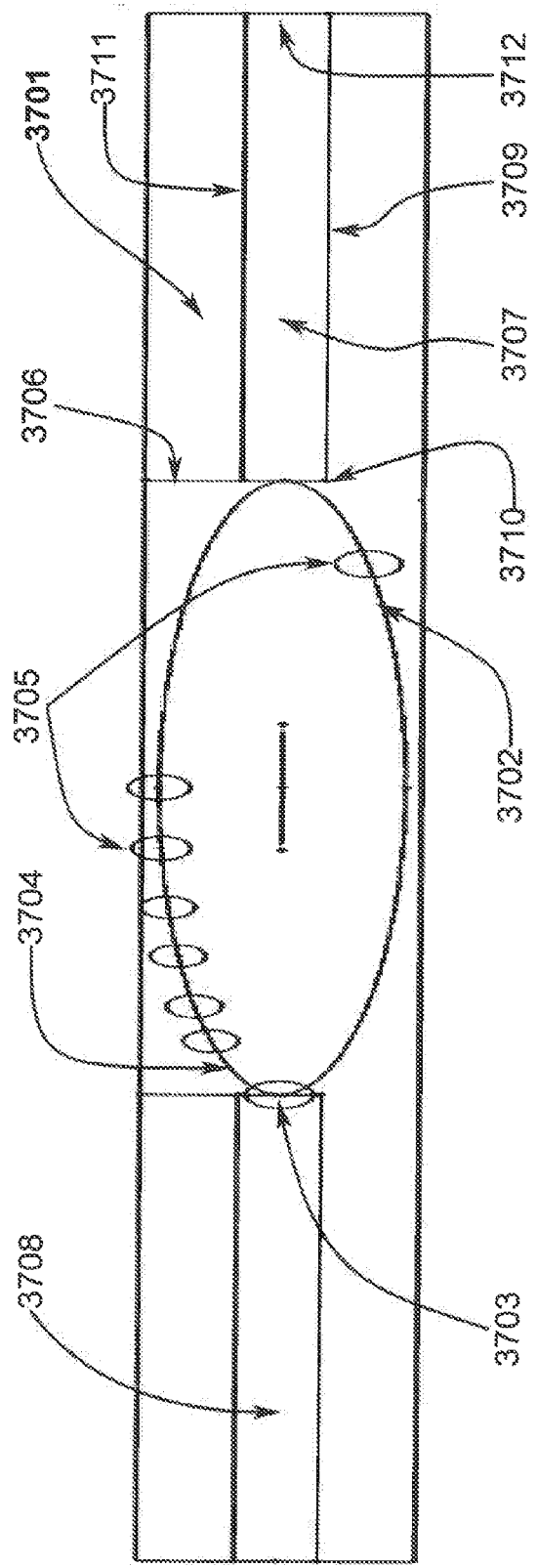
FIG. 37 illustrates a side view of the process of cutting a lens and a haptics by focused femtosecond laser pulses, starting from a blank slab of polymeric material (PMB)

Referencing FIG. 37 (3700), the optical sculpting procedure is generally depicted that creates a complete intraocular lens, including haptics, from a slab of polymeric material (3701) is presented in side view. First, the posterior surface (3702) of the lenticule is sculpted. Then a rim-cut (3703) is performed, sparing the proximal connections of the haptics. Subsequent to the rim-cut (3703), the lenticule anterior surface (3704) is cut. Approximately 5 million laser pulses are employed for cutting the posterior (3702) and respectively the anterior (3704) surfaces of the lenticule. For the rim-cut (3703) approximately one hundred thousand laser pulses are employed. The individual cutting elements (3705) (i.e., so-called cutting pitches) are approximately 2.6 μm in diameter, extending to a cutting depth of approximately 12 μm.

In a second procedural step, a cylindrically shaped peripheral cut (3706) is performed, connecting to the surface of the slab of PMB (3701). In a third procedural step, the slab is repositioned to allow for cutting of a first member (3707) of the haptics (3708). Initially, the posterior surface (3709) of the first member (3707) of the haptics (3708) is sculpted. Then the side-walls (3710) of the first member of the haptics (3708) is sculpted. Finally, the anterior surface (3711) of the first member (3707) of the haptics (3708) is cut. Then, a cylindrically shaped peripheral cut (3712) is performed connecting to the surface of the slab of PMB (3701). In a last procedural step, the second member of the haptics is similarly sculpted.

Figure 38:
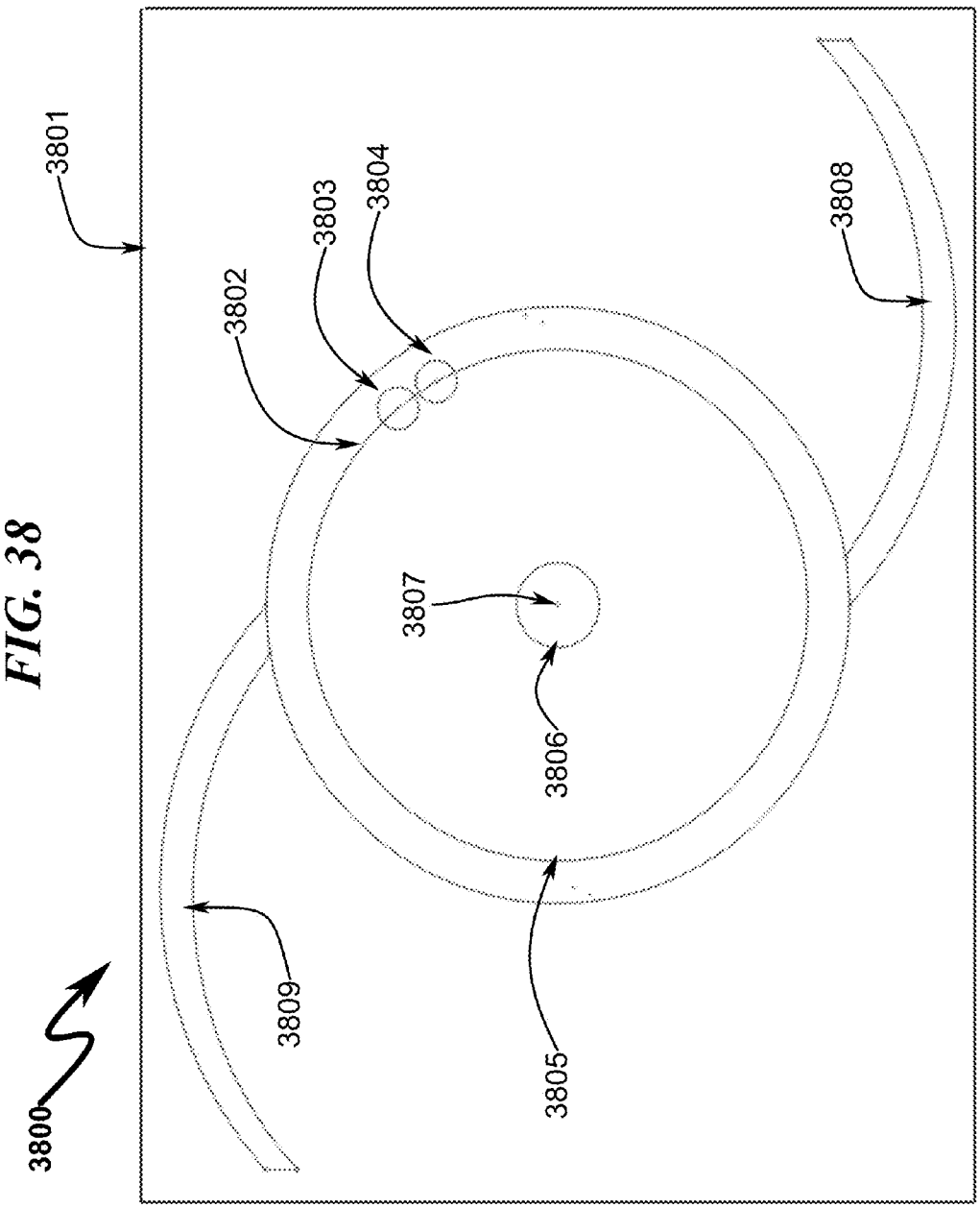
FIG. 38 illustrates a top view of the process of cutting a lens and a haptics by focused femtosecond laser pulses, starting from a blank slab of polymeric material (PMB)

Referencing FIG. 38 (3800), a top view of the sculpting procedure is presented starting with a PMB slab (3801). The spiral cutting pattern (3802) is depicted. The individual laser spots (3803, 3804) are separated by the pixel size of 2.6 μm, resulting in a cutting speed of 2.6 m/sec, at a pulse repetition rate of 1 MHz. The spiral contains approximately 1153 individual 'circular' tracks, with a rotational speed of 50 Hz at the outer perimeter (3805), and a rotational speed of 500 Hz at the track (3806) with a diameter of 1 mm. The rotational speed is kept at 500 Hz for the central cap (3807) of the lenticule, securing a high degree of regularity of the sculpting process. Haptics (3808, 3808) are depicted as cut by the previously described procedure above.

Generalized Spiral Cutting Parameters

Generalized procedural cutting parameters are summarized below for a spiral pattern at a 1 MHz pulse repetition rate:

| Parameter | Value |
| --- | --- |
| Circular-pattern | 50 Hz (6 mm diameter) to 500 Hz (1 mm diameter) |
| Z-Focus | Up to 10 Hz |
| Pixel Rate (AOM) | 2.0 MHz |
| Pixel Size | 2.6 μm |
| Pixel-Dwell-Time | ~1.0 μs |
| Pulses/Pixel (1 MHz) | ~1 |
| Cutting Speed | Up to 2.6 m/s (less in central 1 mm) |

The rotational tracks are facilitated by the galvanometric mirrors, with rotational speeds from 50 Hz to 500 Hz. Two oscillating galvanometrically driven mirrors, which are detuned by a phase-shift of 90 degrees, are providing the circular movement of the laser beam. The z-focus is synchronously adjusted, according to the shape of the surfaces of the sculpted lenticule. Any shape can be programmed, including aspheric and multifocal modalities. A typical sculpting process can be completed in a few seconds.

Sculpting Pattern Dynamics (3900)-(4000)

Figure 39:
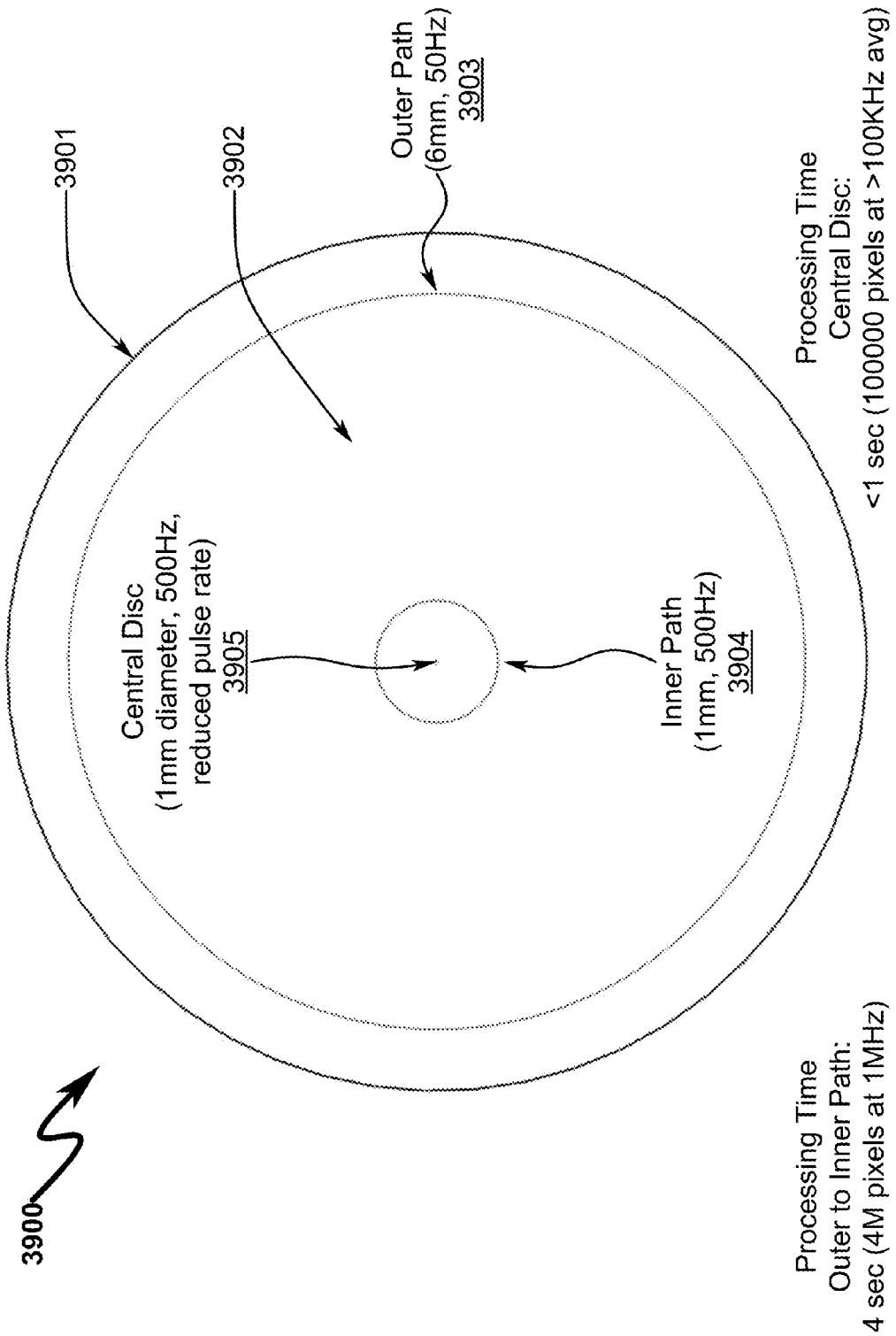
FIG. 39 illustrates a top view of spiral cutting pattern dynamics.
Figure 40:
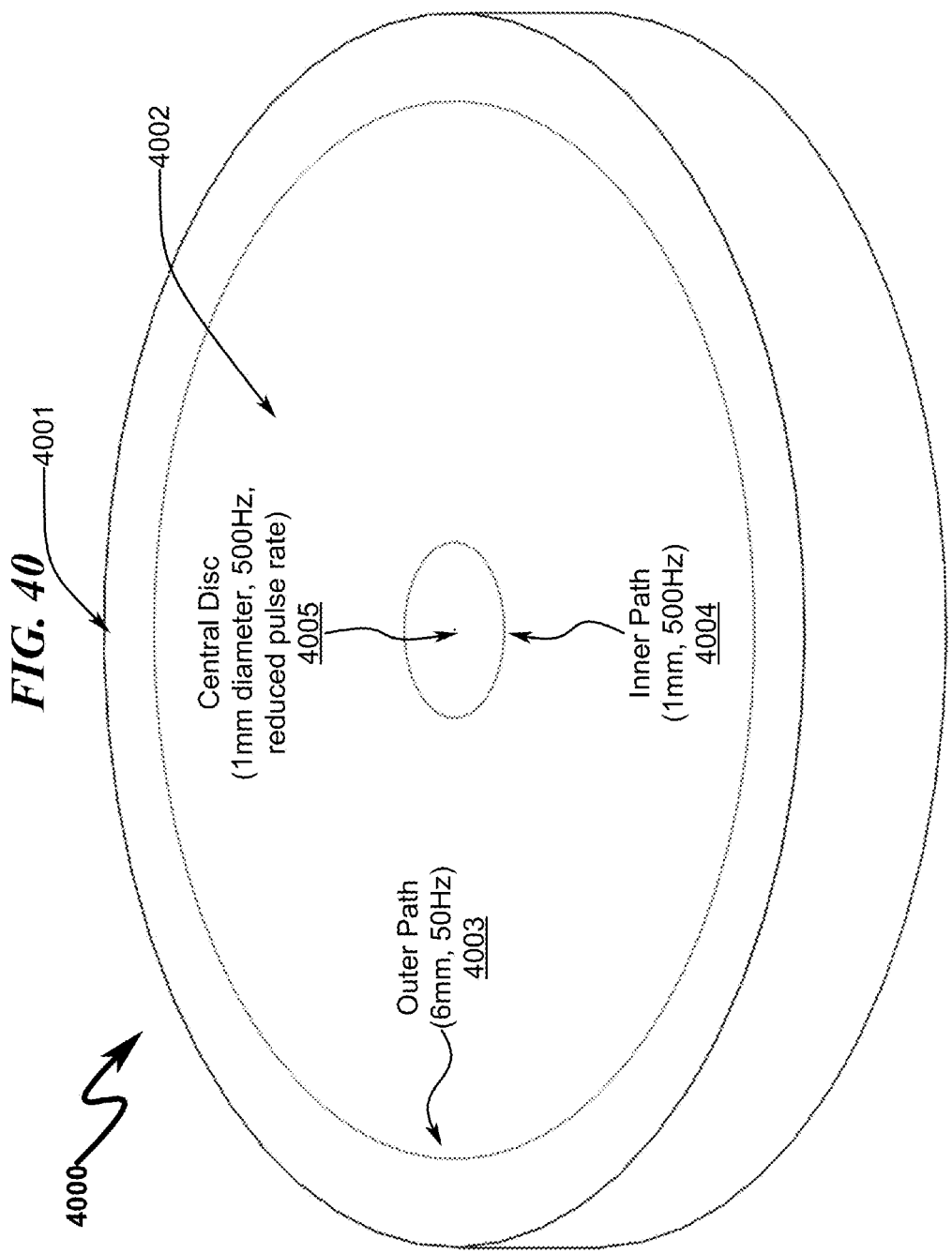
FIG. 40 illustrates a perspective view of spiral cutting pattern dynamics.

FIG. 39 (3900)-FIG. 40 (4000) depict the dynamics of the sculpting pattern on the PMB (3901, 4001), as proposed by the present invention. Due to the limitations of commercially available galvanometrically-driven mirrors, a separation of the sculpting process in two different regimes is required. In a first procedural step, the area (3902, 4002) between an outer diameter (3903, 4003) of 6 mm to an inner diameter (3904, 4004) of 1 mm is sculpted, with rotational speeds from 50 Hz to 500 Hz. The processing time of this area amounts to four seconds, with four million pulses distributed. Then, the central disc (2505, 2605) is processed, with the galvanometrically-driven mirrors set to a fixed speed of 500 Hz. In order to provide an equal spatial distribution of the laser spots at the demanded spacing of 2.6 μm, the pulse rate of the femtosecond laser is continuously diminished, accordingly, by picking the appropriate number of pulses by the acousto-optic modulator. Thus, a processing time for sculpting the central disc of close to 1 second results, putting the overall time for sculpting the posterior or anterior surface of the lenticule to approximately 5 seconds.

Fabrication Sequence (4100)-(12800)

Figure 42:
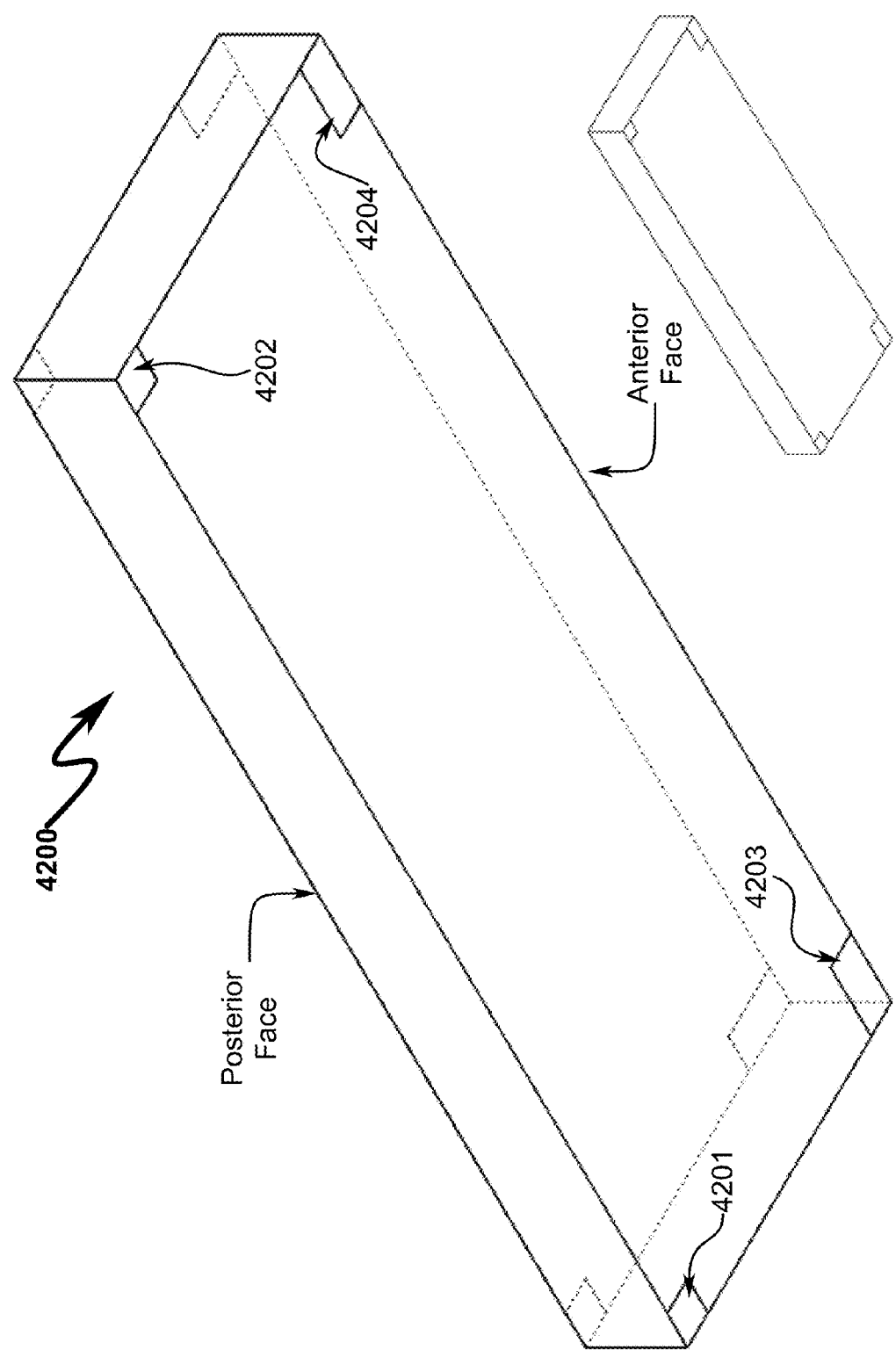
FIG. 42 illustrates a bottom right perspective view of a PMS used in an exemplary present invention IOL fabrication sequence.
Figure 43:
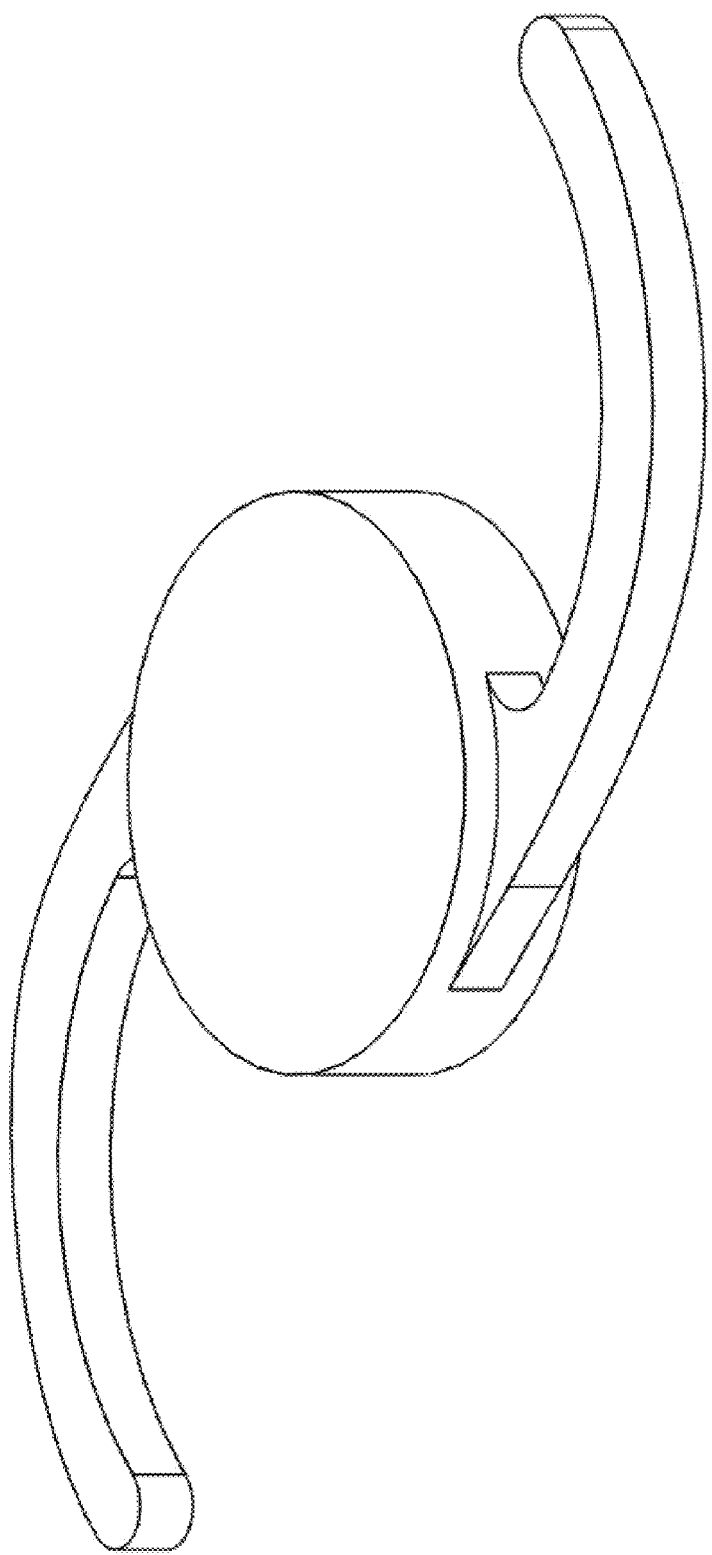
FIG. 43 illustrates a top right perspective view of a PMB used in an exemplary present invention IOL fabrication sequence.
Figure 44:
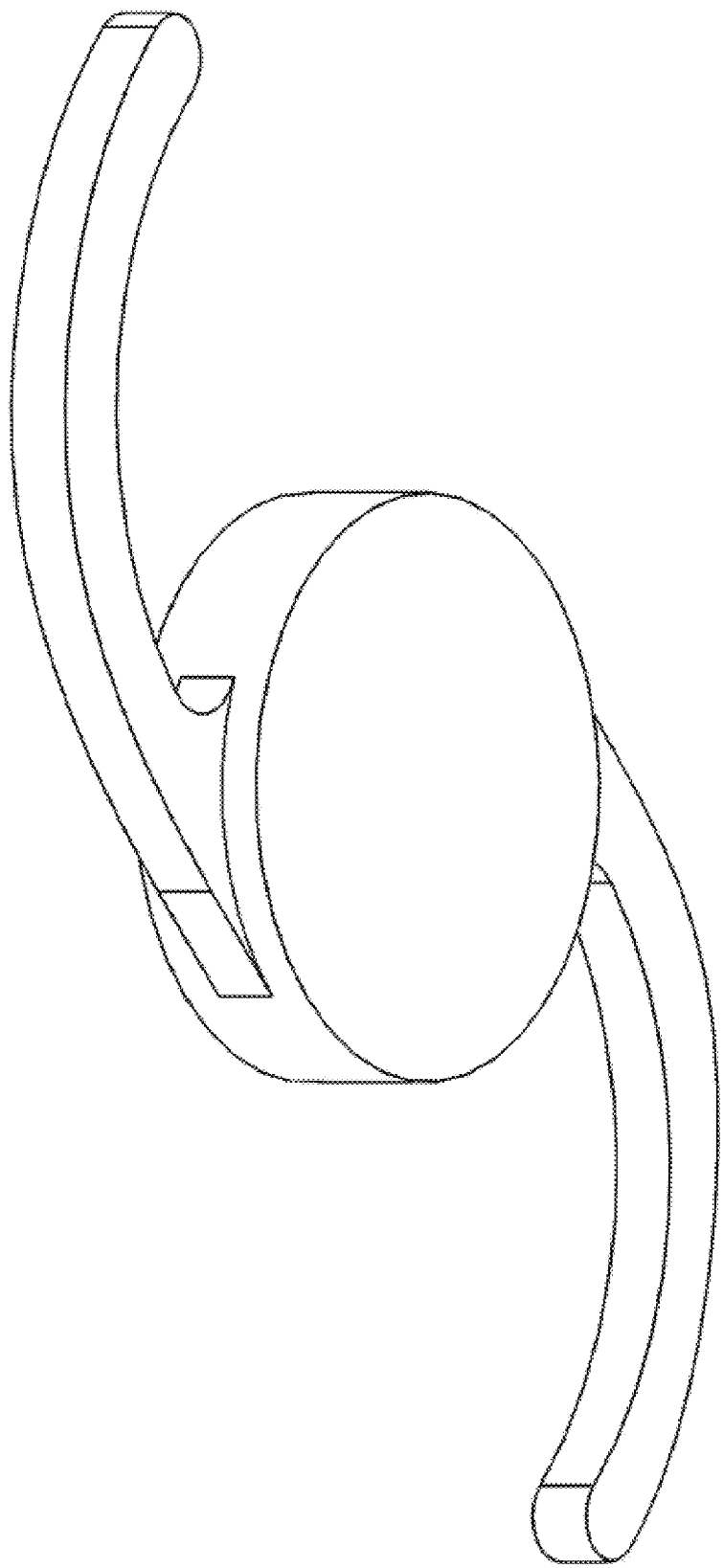
FIG. 44 illustrates a bottom right perspective view of a PMB used in an exemplary present invention IOL fabrication sequence.
Figure 45:
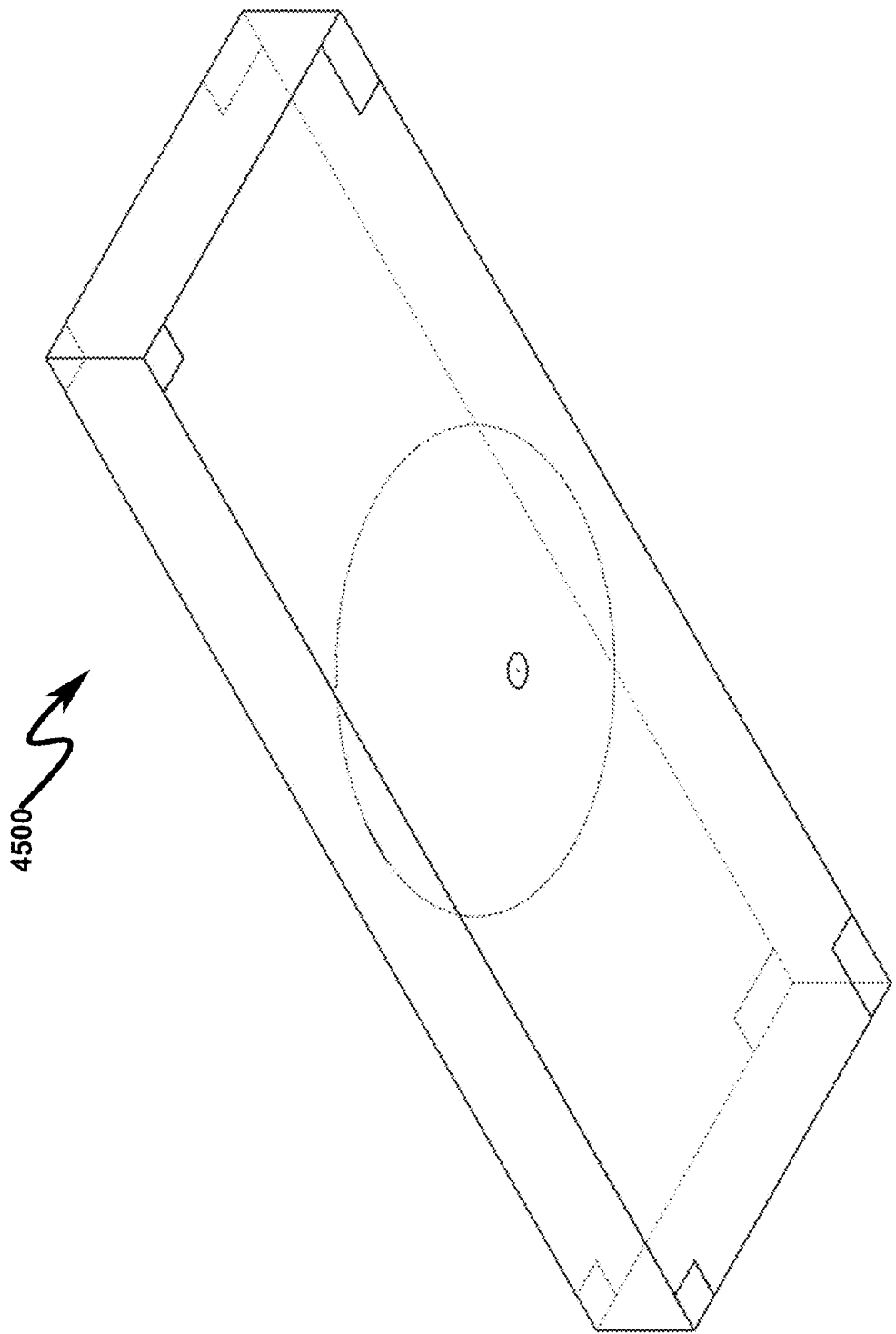
FIG. 45 illustrates a bottom right perspective view of a posterior lens cut in an exemplary present invention IOL fabrication sequence formed using a PMS.
Figure 46:
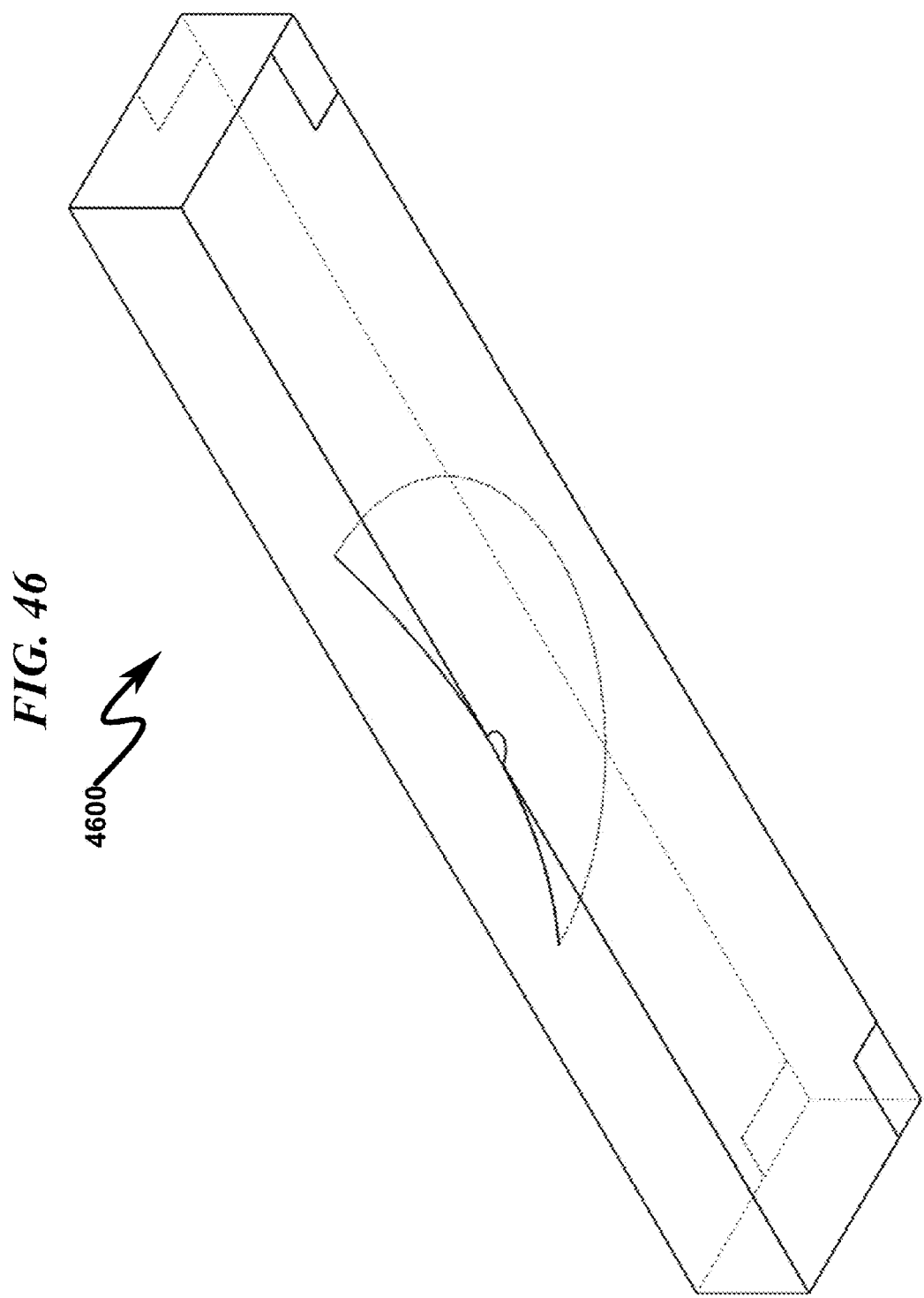
FIG. 46 illustrates a bottom right perspective front section view of a posterior lens cut in an exemplary present invention IOL fabrication sequence formed using a PMS.
Figure 47:
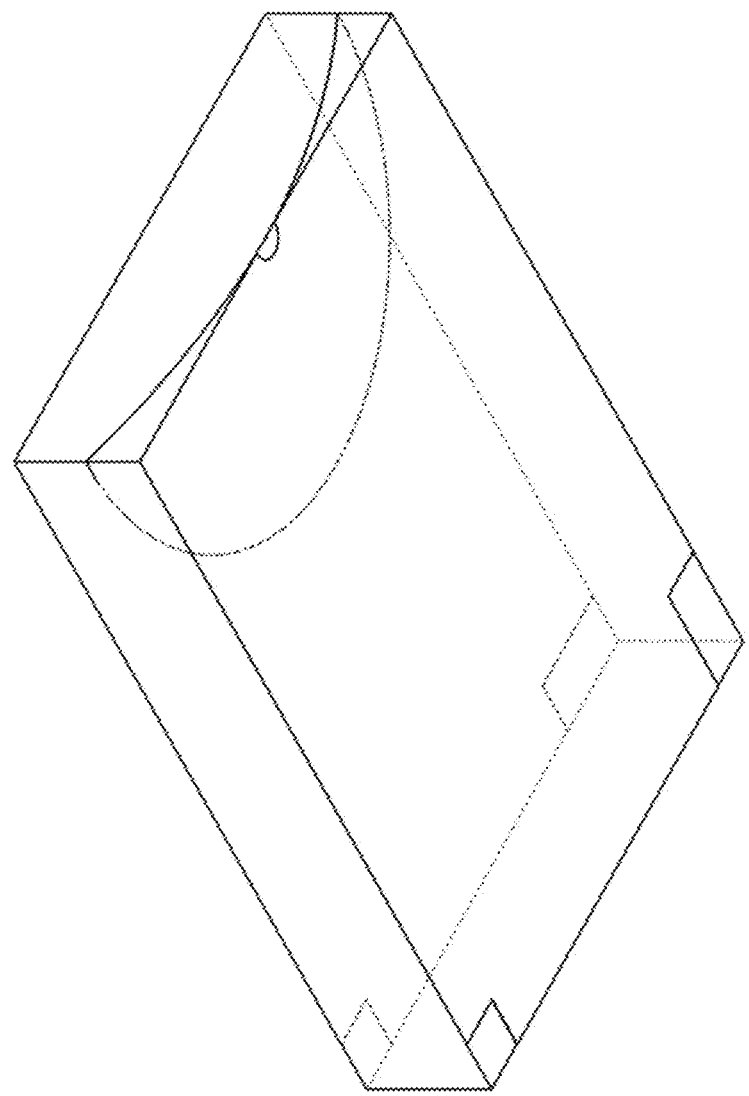
FIG. 47 illustrates a bottom right perspective right section view of a posterior lens cut in an exemplary present invention IOL fabrication sequence formed using a PMS.
Figure 48:
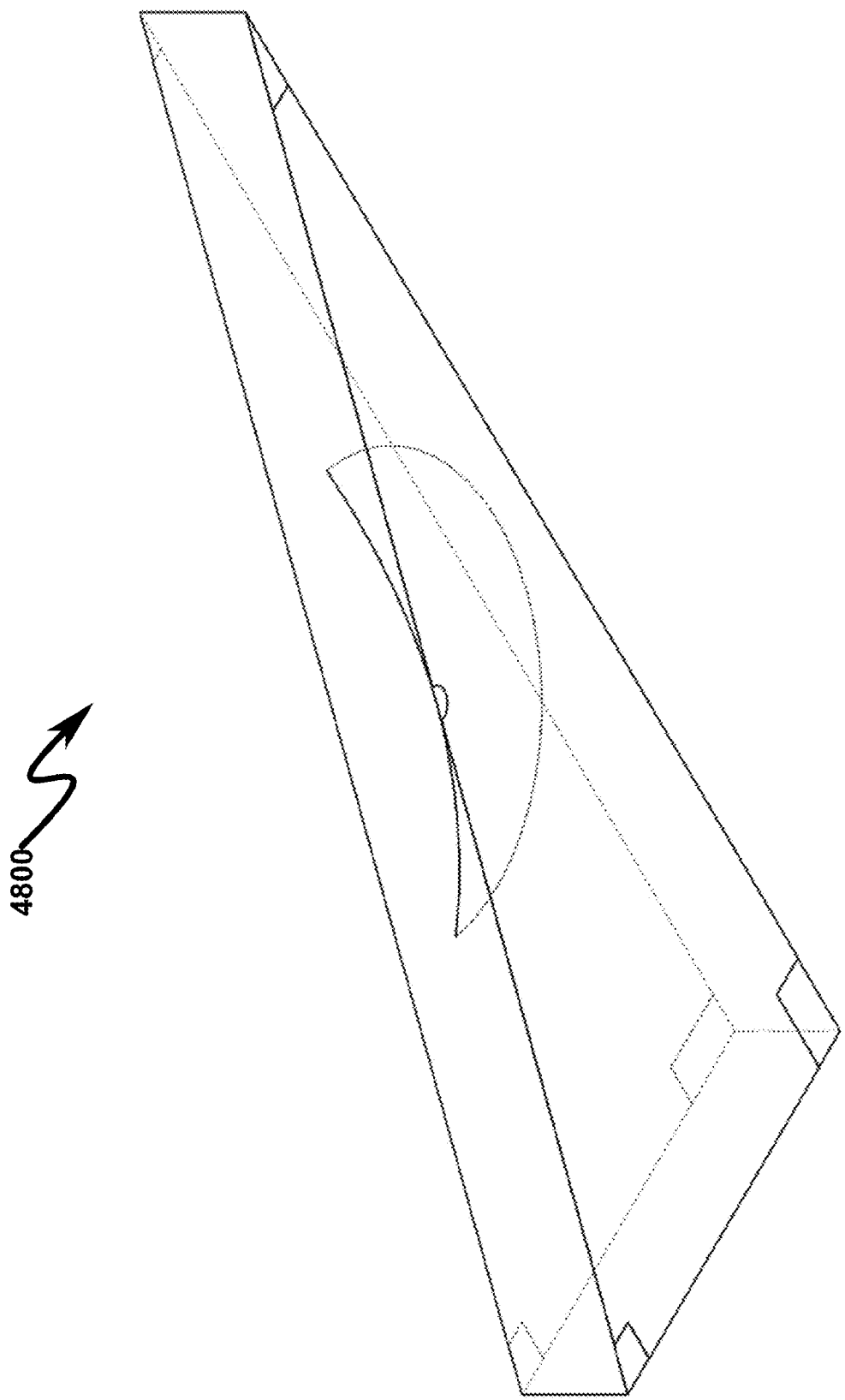
FIG. 48 illustrates a bottom right perspective diagonal section view of a posterior lens cut in an exemplary present invention IOL fabrication sequence formed using a PMS.
Figure 49:
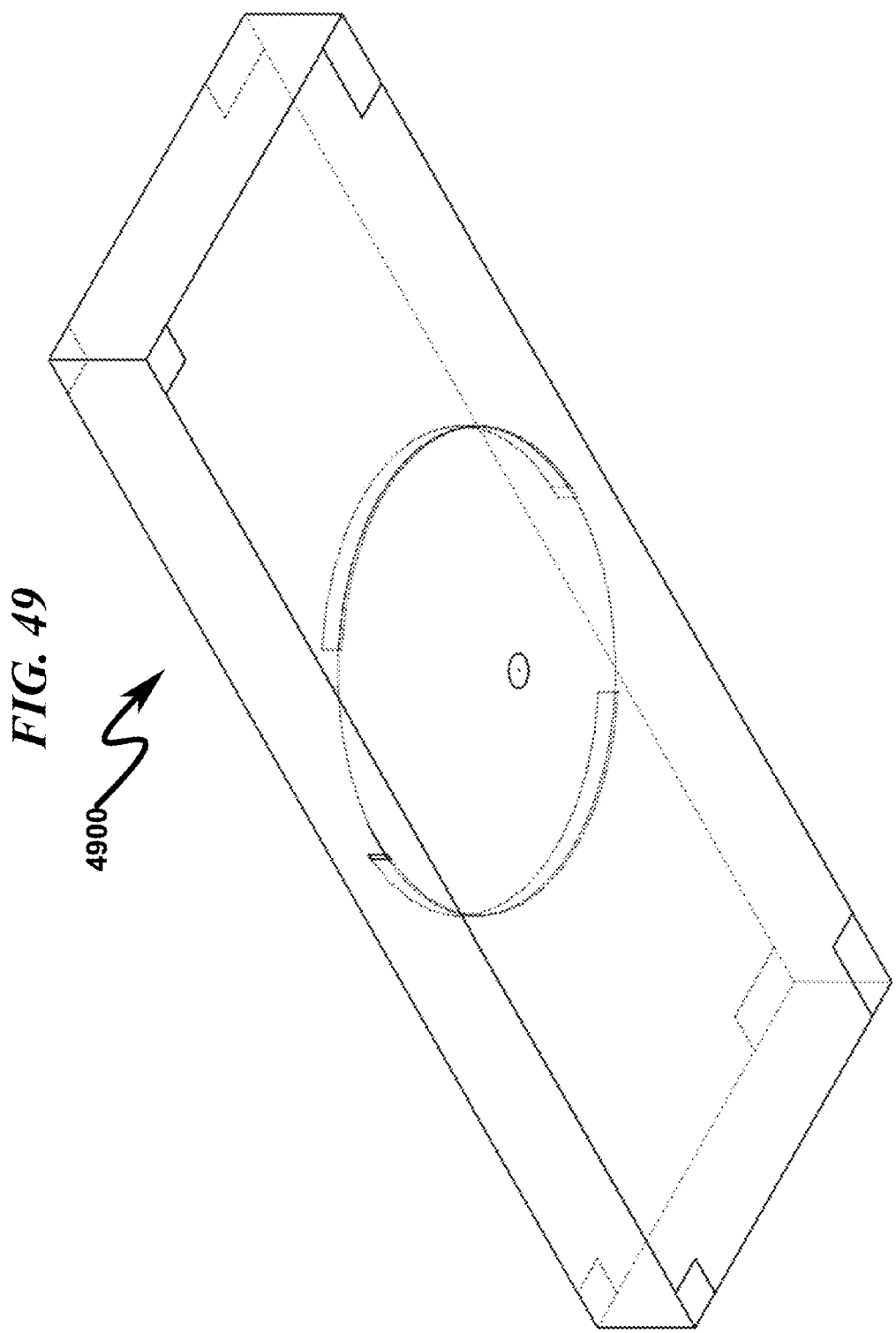
FIG. 49 illustrates a bottom right perspective view of an interior edge lens cut in an exemplary present invention IOL fabrication sequence formed using a PMS.
Figure 50:
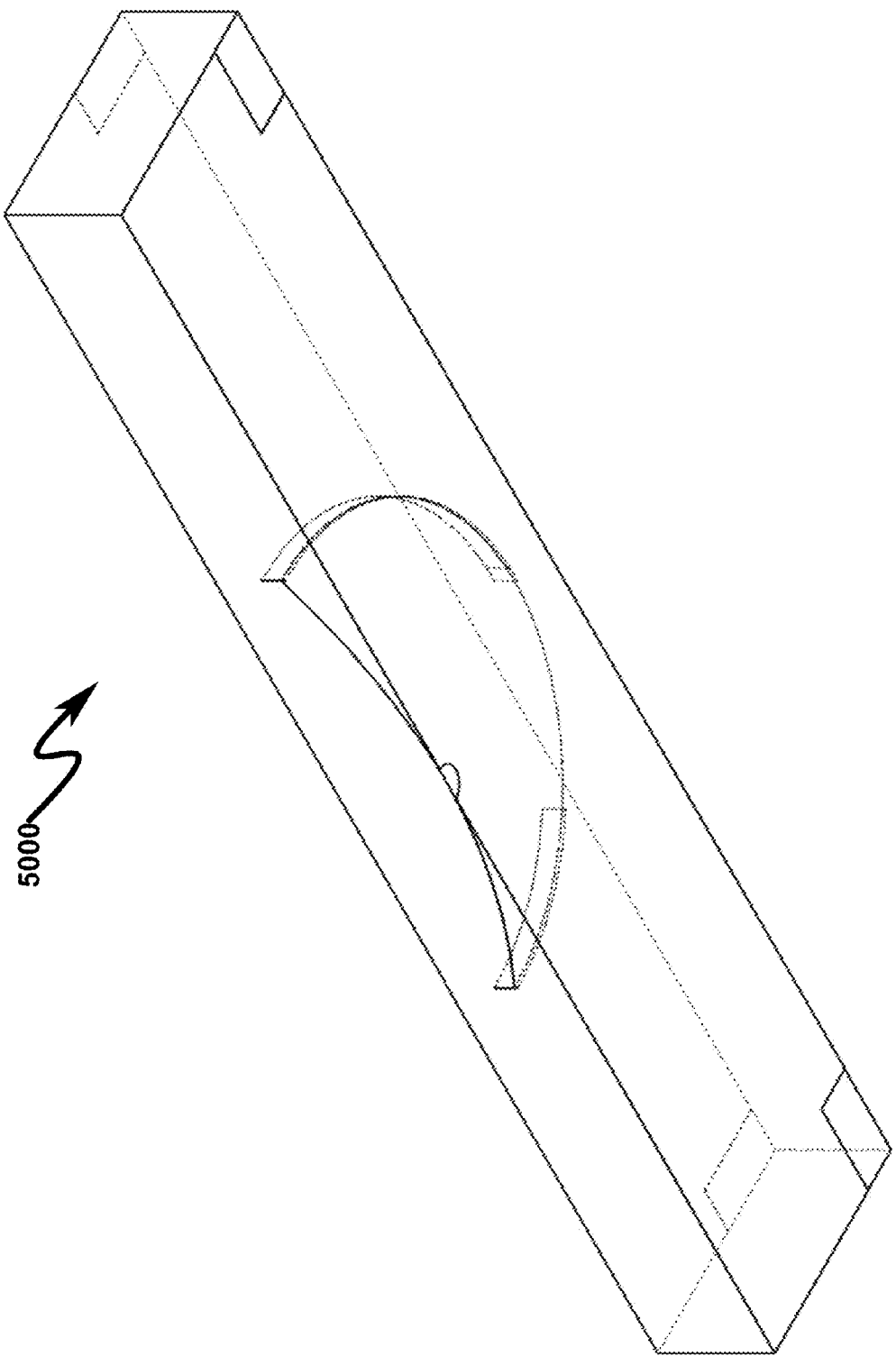
FIG. 50 illustrates a bottom right perspective front section view of an interior edge lens cut in an exemplary present invention IOL fabrication sequence formed using a PMS.
Figure 51:
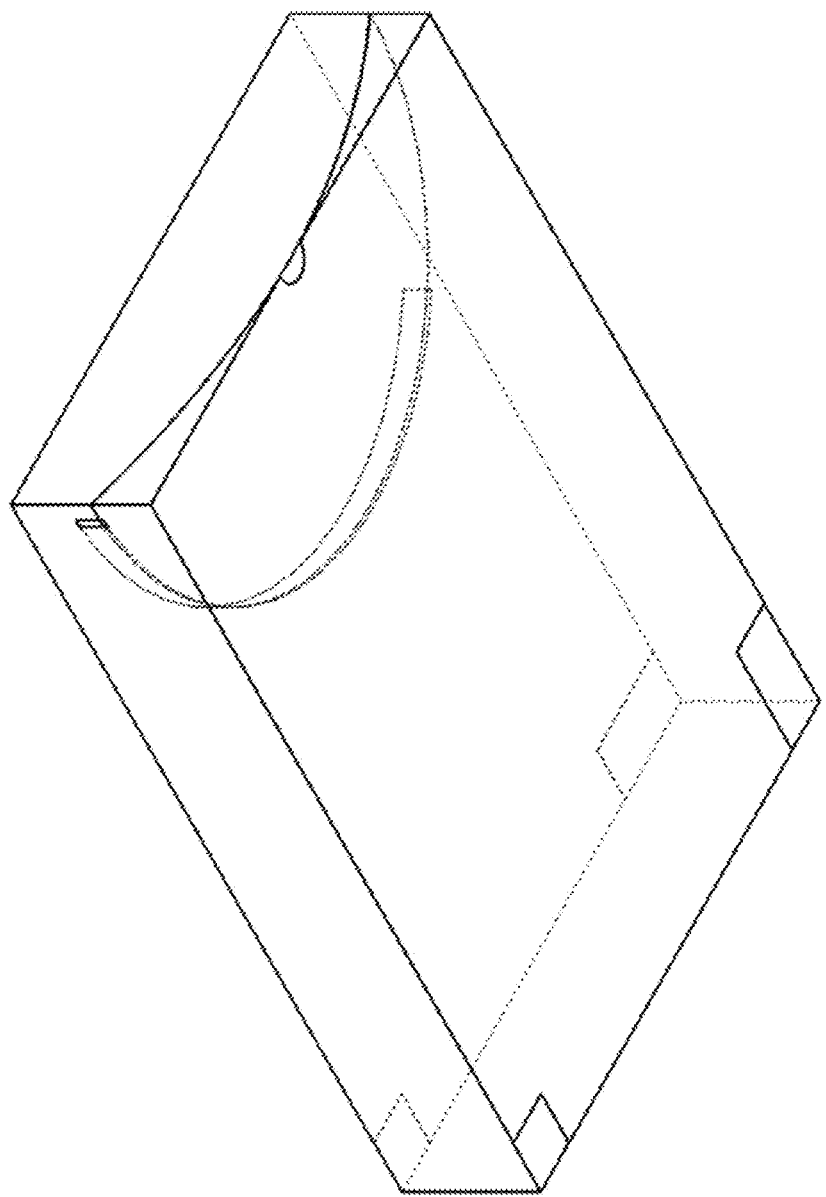
FIG. 51 illustrates a bottom right perspective right section view of an interior edge lens cut in an exemplary present invention IOL fabrication sequence formed using a PMS.
Figure 122:
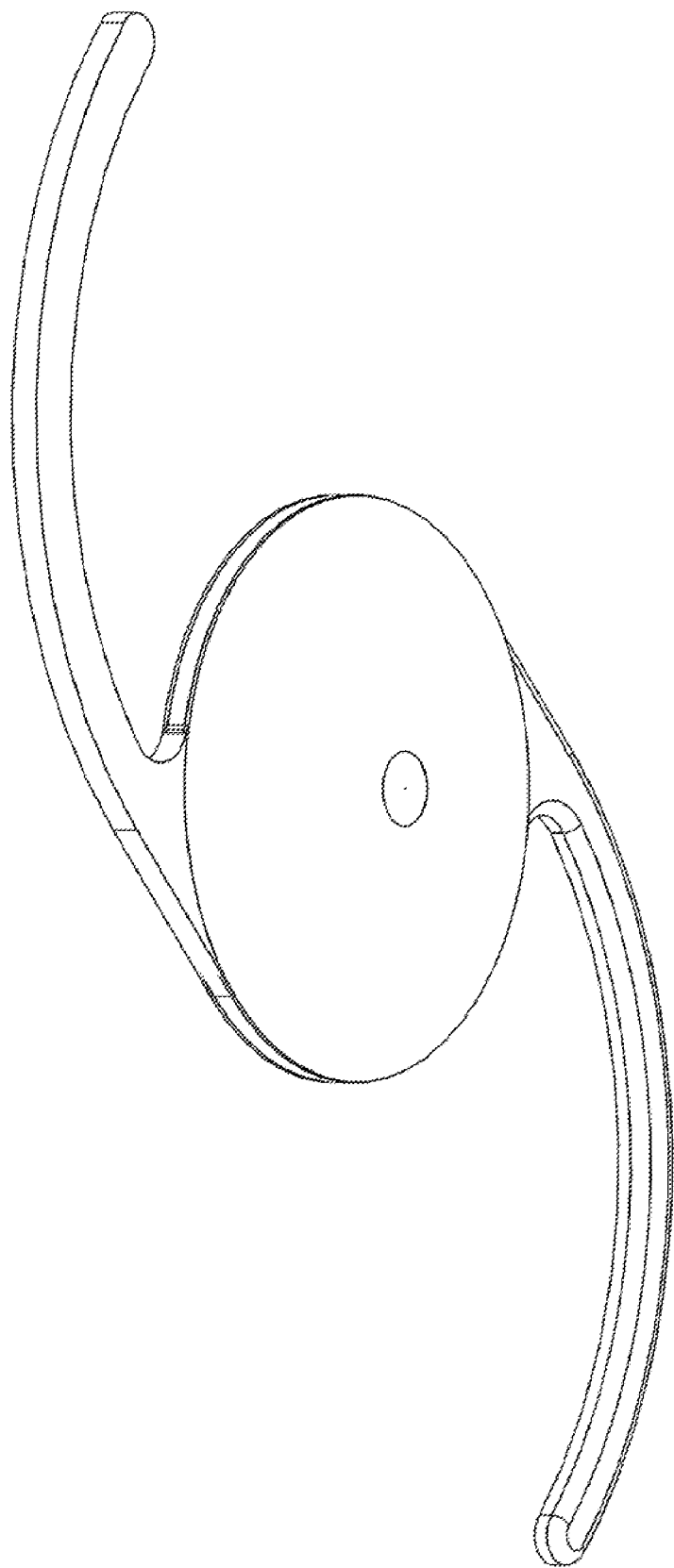
Figure 123:
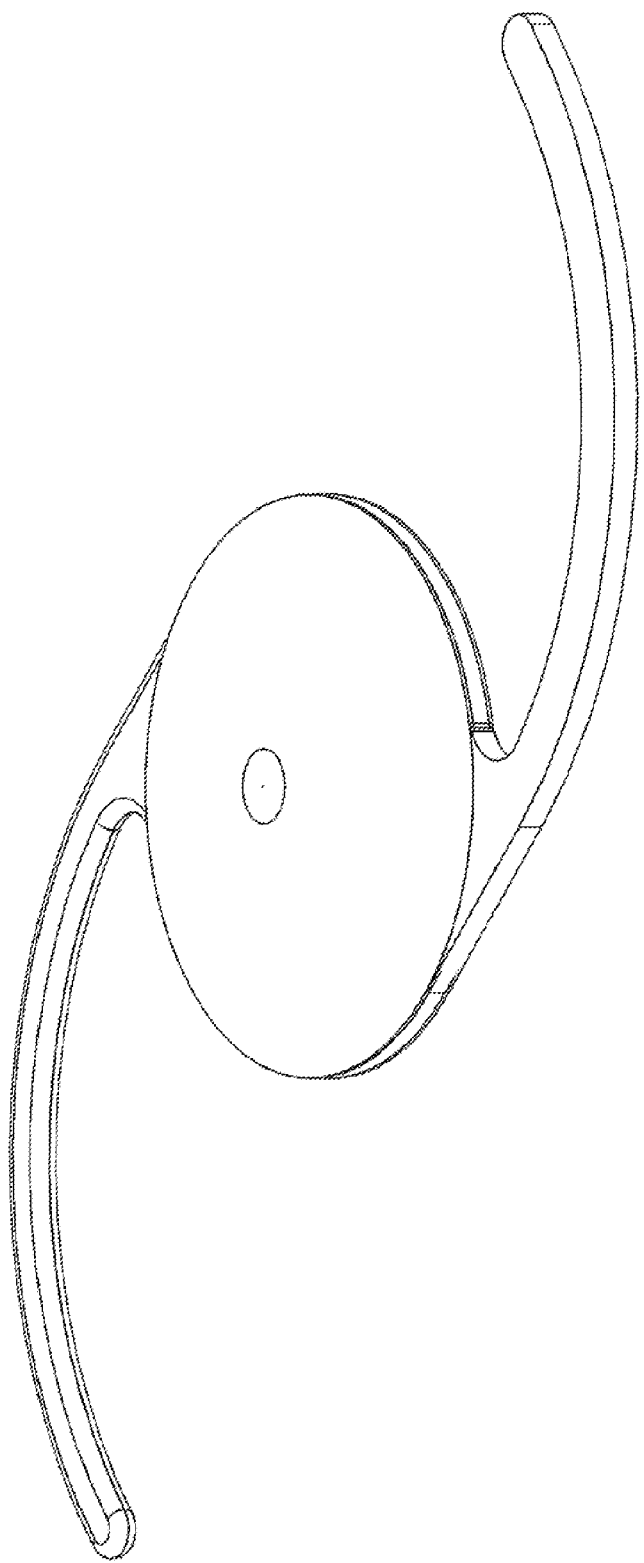
Figure 124:
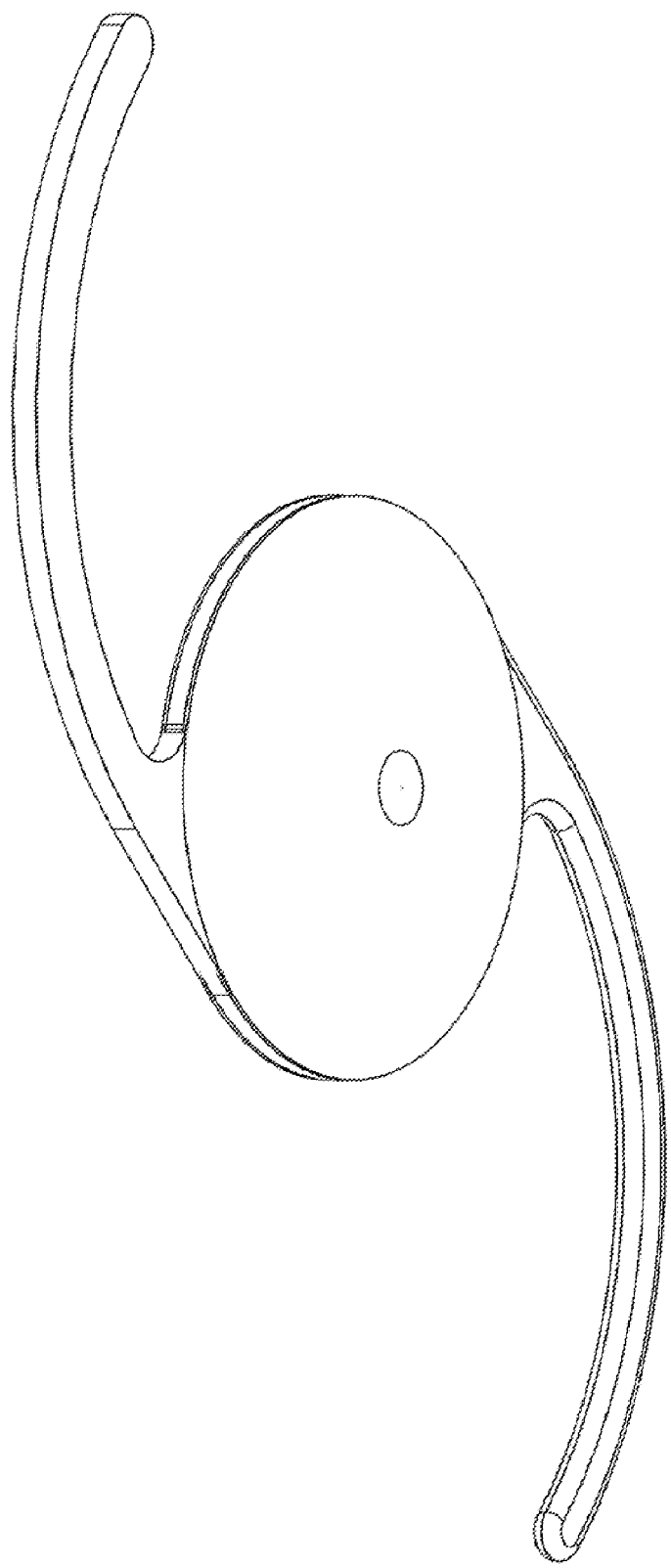
Figure 125:
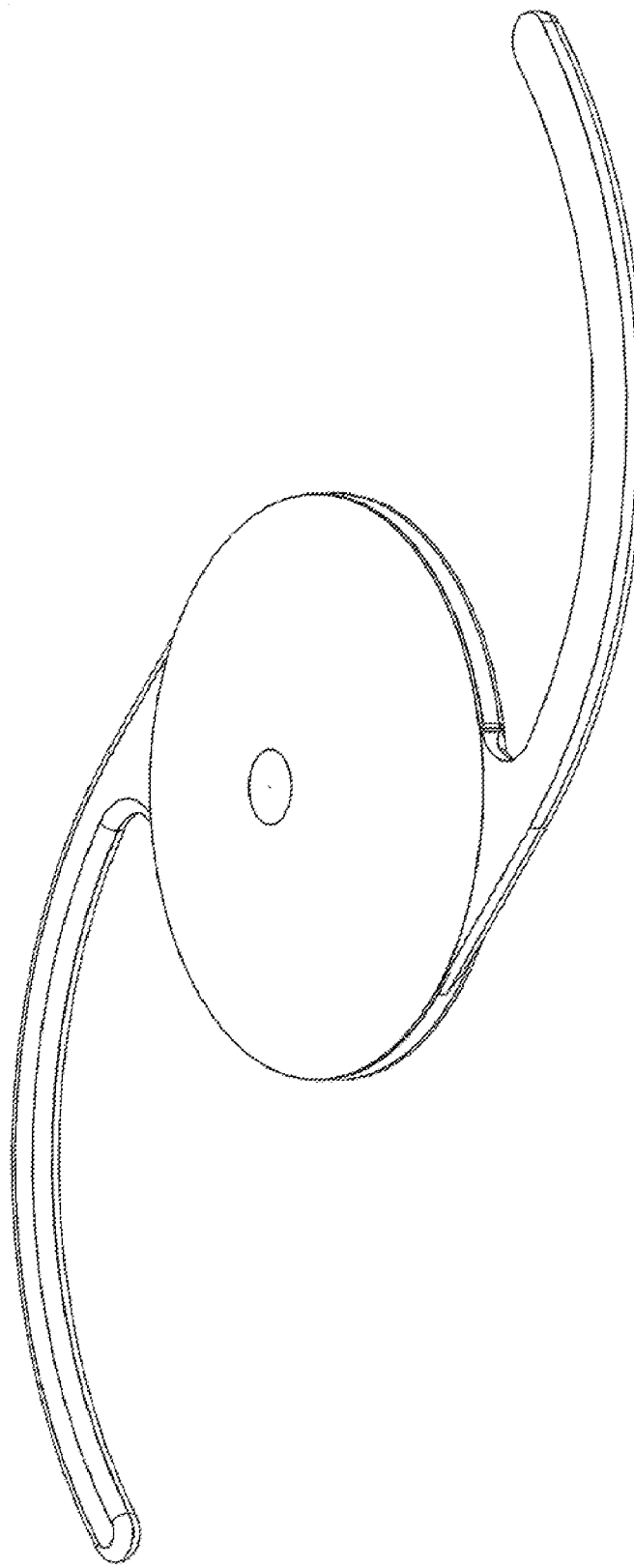
Figure 126:
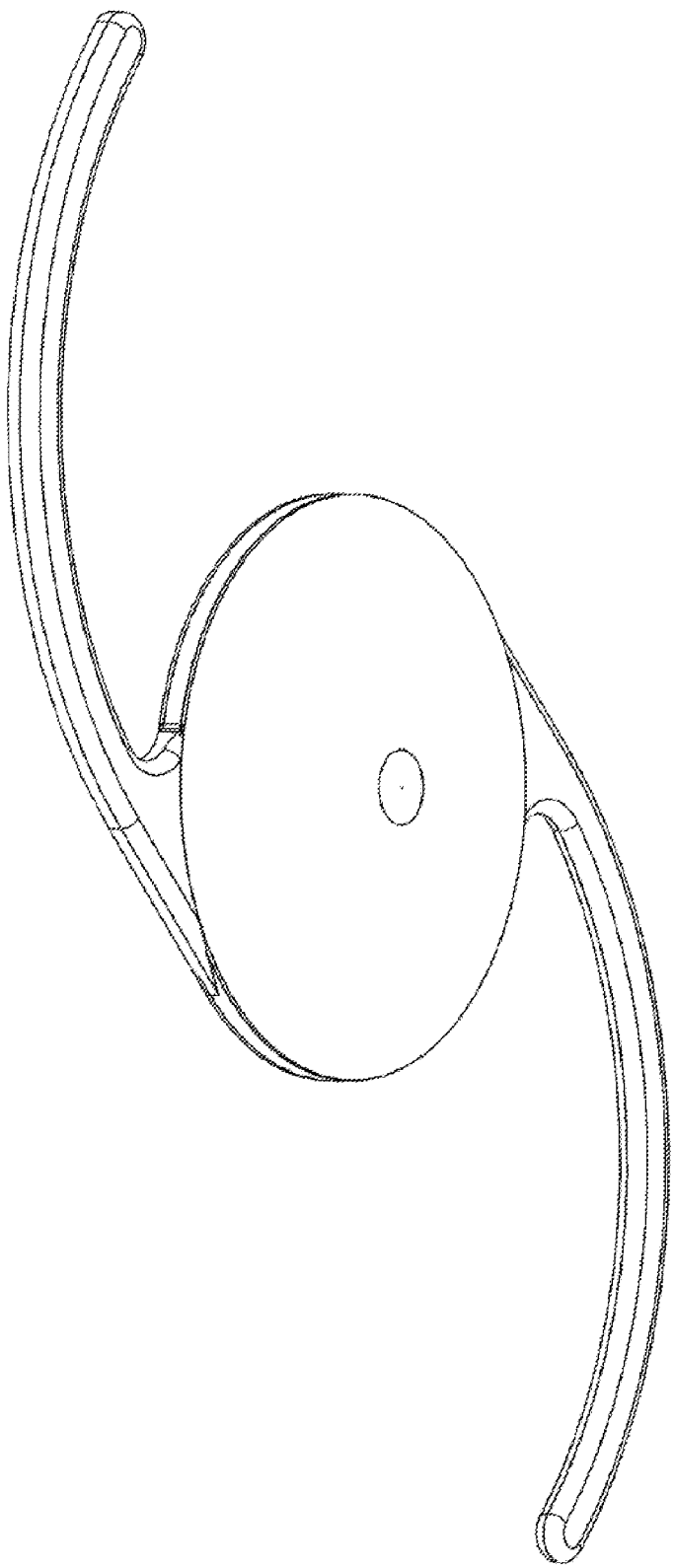
Figure 127:
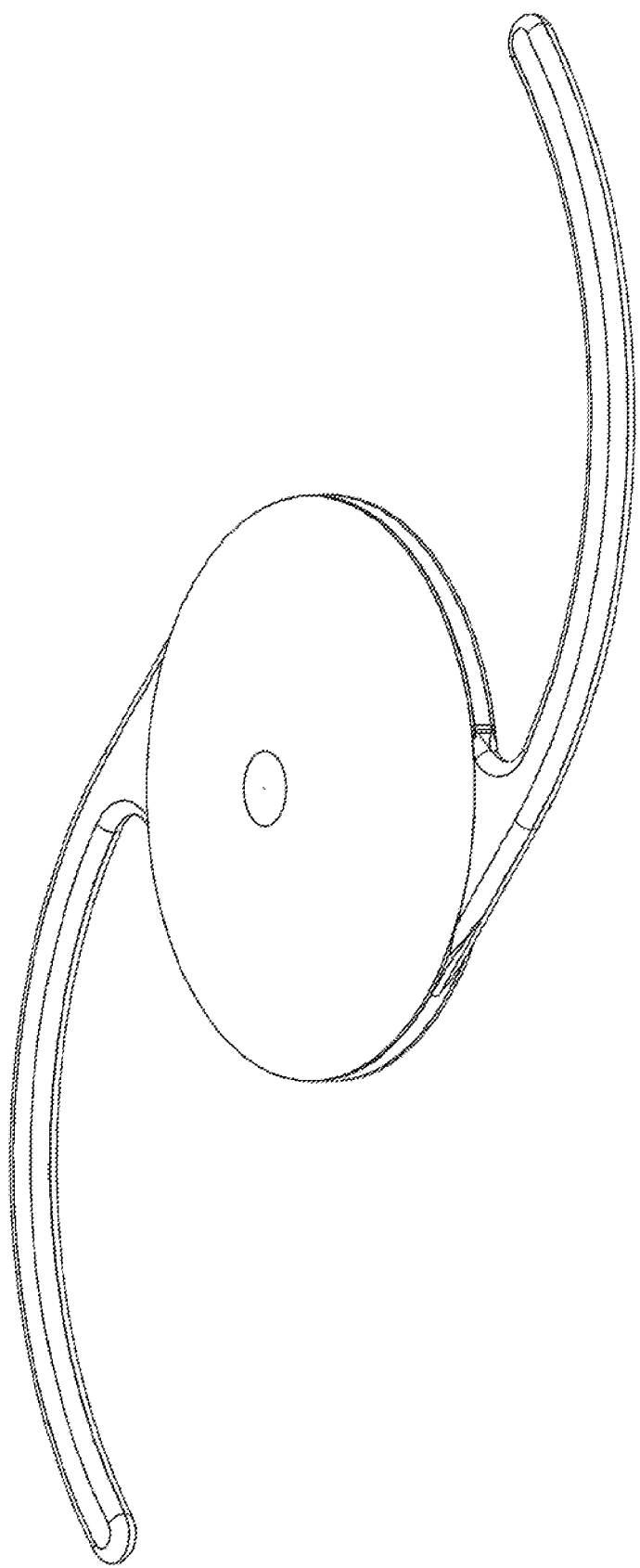

FIG. 41 (4100)-FIG. 128 (12800) depict an exemplary fabrication sequence in which an IOL is constructed starting from a PMS (FIG. 41 (4100)-FIG. 42 (4200)) or optionally a PMB (FIG. 43 (4300)-FIG. 44 (4400)). A general discussion of IOL fabrication using a polymeric material slab (PMS) (FIG. 41 (4100)-FIG. 42 (4200)) will now be presented but it should be noted that the use of a preformed polymeric material blank (PMB) (FIG. 43 (4300)-FIG. 44 (4400)) may result in fewer required cuts in the overall fabrication process. Within the generic PMS fabrication sequence, the following figure sets depicting various manufacturing steps are provided:

FIG. 45 (4500)-FIG. 48 (4800) depict cutting the posterior surface of the lens;
FIG. 49 (4900)-FIG. 52 (5200) depict cutting the side edges of the lens;
FIG. 53 (5300)-FIG. 56 (5600) depict cutting the edges of the lens to the posterior surface of the PMS;
FIG. 57 (5700)-FIG. 60 (6000) depict removal of the PMS material contacting the posterior surface of the lens;
FIG. 61 (6100)-FIG. 64 (6400) depict cutting the anterior surface of the lens;
FIG. 65 (6500)-FIG. 68 (6800) depict cutting the edges of the lens to the anterior surface of the PMS;
FIG. 69 (6900)-FIG. 72 (7200) depict removal of the PMS material contacting the anterior surface of the lens;
FIG. 73 (7300)-FIG. 76 (7600) depict cutting the left haptic posterior surface;
FIG. 77 (7700)-FIG. 80 (8000) depict cutting the left haptic side edge surface;
FIG. 81 (8100)-FIG. 84 (8400) depict cutting the left haptic anterior surface;
FIG. 85 (8500)-FIG. 88 (8800) depict removal of the left haptic posterior PMS material;
FIG. 89 (8900)-FIG. 92 (9200) depict removal of the left haptic anterior PMS material;
FIG. 93 (9300)-FIG. 96 (9600) depict removal of the left haptic interior PMS material;
FIG. 97 (9700)-FIG. 100 (10000) depict cutting the right haptic posterior surface;
FIG. 101 (10100)-FIG. 104 (10400) depict cutting the right haptic side edge surface;
FIG. 105 (10500)-FIG. 108 (10800) depict cutting the right haptic anterior surface;
FIG. 109 (10900)-FIG. 112 (11200) depict removal of the right haptic posterior PMS material;
FIG. 113 (11300)-FIG. 116 (11600) depict removal of the right haptic anterior PMS material;
FIG. 117 (11700)-FIG. 120 (12000) depict removal of the right haptic interior PMS material;
FIG. 121 (12100)-FIG. 122 (12200) depict additional edge processing of the left posterior haptic;
FIG. 123 (12300)-FIG. 124 (12400) depict additional edge processing of the left anterior haptic;
FIG. 125 (12500)-FIG. 126 (12600) depict additional edge processing of the right posterior haptic;
FIG. 127 (12700)-FIG. 128 (12800) depict additional edge processing of the right anterior haptic.

One skilled in the art will recognize that these steps may be rearranged in some invention embodiments without changing the spirit and scope of the invention. Additionally, it should be noted that the additional edge processing of the left and right haptics may be performed as part of the posterior/interior (edge)/anterior surface formation of the haptics. The exact form of the haptics will be application specific and as such only a generic posterior/interior (edge)/anterior cutting sequence has been depicted to illustrate the general concepts of the invention.

System Summary

The present invention system may be broadly generalized as a system for fabricating an intraocular lens (IOL) comprising:
(a) pulsed laser source (PLS);
(b) acoustic-optical modulator (AOM);
(c) focusing laser optics (FLO);
(d) laser scanning device (LSD); and
(e) computing control device (CCD);
wherein:
the PLS is configured to emit a pulsed laser radiation (PLR) output at a repetition rate of at least 0.1 million pulses per second;
the PLS is configured to emit the PLR output with a pulse-width of 900 femtoseconds or less;
the AOM is configured to control the pulse energy and pulse repetition rate of the PLS;
the FLO is configured to receive the PLR and produce a focused pulsed laser beam (FLB);
the LSD is configured to receive the FLB and direct the FLB in three dimensions; Two-dimensional scanning and Z focusing.
the LSD is numerically controlled by the CCD to generate a three-dimensional cutting pattern (TDP) using the PLS on a polymeric material blank (PMB) that is impinged by the FLB; and
the PLS is configured by the CCD to generate the TDP using at least 7.5 million focused laser pulses within 5 minutes.

This general system summary may be augmented by the various elements described herein to produce a wide variety of invention embodiments consistent with this overall design description.

Method Summary

The present invention method may be broadly generalized as a method for fabricating an intraocular lens (IOL) comprising:
(1) generating pulsed laser radiation (PLR) output from a pulsed laser source (PLS);
(2) controlling the pulse energy and pulse repetition rate of the PLS with an acoustic-optical modulator (AOM);
(3) receiving the PLR with focusing laser optics (FLO) and producing a focused pulsed laser beam (FLB);
(4) receiving the FLB with a laser scanning device (LSD) and scanning the FLB in three dimensions;
(5) numerically controlling the LSD with a computing control device (CCD) to generate a three-dimensional cutting pattern (TDP) using the PLS on a polymeric material blank (PMB) that is impinged by the FLB; and (6) sculpting the PMB using the TDP to form an intraocular lens (IOL);

wherein:

the PLS is configured to emit the PLR output at a repetition rate of at least 0.1 million pulses per second;

the PLS is configured to emit the PLR output with a pulse-width of 900 femtoseconds or less;

the PLS is configured by the CCD to generate the TDP using at least 7.5 million focused laser pulses within 5 minutes; and the IOL comprises an anterior surface, a posterior surface, and one or more haptics.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Alternate System Summary

An alternative present invention system may be broadly generalized as a system for fabricating an intraocular lens (IOL) comprising:

(a) pulsed laser source (PLS);
(b) acoustic-optical modulator (AOM);
(c) focusing laser optics (FLO);
(d) laser scanning device (LSD); and
(e) computing control device (CCD);

wherein:

the PLS is configured to emit a pulsed laser radiation (PLR) output at a repetition rate of at least 0.1 million pulses per second;

the PLS is configured to emit the PLR output with a pulse-width of 900 femtoseconds or less;

the AOM is configured to control the pulse energy and pulse repetition rate of the PLS;

the FLO is configured to receive the PLR and produce a focused pulsed laser beam (FLB);

the LSD is configured to receive the FLB and scan the FLB in three dimensions;

the LSD is numerically controlled by the CCD to generate a three-dimensional cutting pattern (TDP) on a polymeric material blank (PMB) that is impinged by the FLB;

the PLS is configured by the CCD to generate the TDP using at least 7.5 million focused laser pulses within 5 minutes;

the LSD is numerically controlled by the CCD to form a refractive index shape (RIS) lens within the PMB by modifying the refractive index within the PMB using the PLS.

This general system summary may be augmented by the various elements described herein to produce a wide variety of invention embodiments consistent with this overall design description.

Alternate Method Summary

An alternate present invention method may be broadly generalized as a method for fabricating an intraocular lens (IOL) comprising:

(1) generating pulsed laser radiation (PLR) output from a pulsed laser source (PLS);

(2) controlling the pulse energy and pulse repetition rate of the PLS with an acoustic-optical modulator (AOM);

(3) receiving the PLR with focusing laser optics (FLO) and producing a focused pulsed laser beam (FLB);

(4) receiving the FLB with a laser scanning device (LSD) and scanning the FLB in three dimensions;

(5) numerically controlling the LSD with a computing control device (CCD) to generate a three-dimensional cutting pattern (TDP) using the PLS on a polymeric material blank (PMB) that is impinged by the FLB;

(6) sculpting the PMB using the TDP to form an intraocular lens (IOL);

(7) numerically controlling the LSD by the CCD to form a refractive index shape (RIS) lens within the PMB by modifying the refractive index within the PMB using the PLS;

wherein:

the PLS is configured to emit the PLR output at a repetition rate of at least 0.1 million pulses per second;

the PLS is configured to emit the PLR output with a pulse-width of 900 femtoseconds or less;

the PLS is configured by the CCD to generate the TDP using at least 7.5 million focused laser pulses within 5 minutes; and the IOL comprises an anterior surface, a posterior surface, and one or more haptics.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method Variations

The present invention anticipates a wide variety of variations in the basic theme of construction. The examples presented previously do not represent the entire scope of possible usages. They are meant to cite a few of the almost limitless possibilities.

This basic system, method, and product-by-process may be augmented with a variety of ancillary embodiments, including but not limited to:

An embodiment wherein the PLS has a wavelength of at least 500 nm/1000 nm.

An embodiment wherein the PLS has a pulse length of 400 femtoseconds or less.

An embodiment wherein the PLS has a repetition rate of at least 100000 pulses per second.

An embodiment wherein the PLS has a pulse energy of at least 1.0 µJ.

An embodiment wherein the PLS has a pulse peak power of at least 5 MW.

An embodiment wherein the PLS has a beam quality factor $M^2$ of 1.2 or less.

An embodiment wherein the FLO has a numerical aperture NA of at NA=0.13 or greater.

An embodiment wherein the FLB has a focal diameter of 3.0 µm or less.

An embodiment wherein the FLB has a depth of focus of 15 µm or less.

An embodiment wherein the FLB has a pulse energy of at least 5.0 µJ.

An embodiment wherein the TDP comprises: a first cut that defines a posterior surface of a lenticule within the PMB; wherein: the first cut is completed within 15 seconds.

An embodiment wherein the TDP comprises: a first cut that defines a posterior surface of a lenticule within the PMB; and a second cut that defines an anterior surface of the PMB; wherein: the first cut and the second cut are completed within 15 seconds.

An embodiment wherein the TDP comprises: a second cut that defines an anterior surface of the PMB; and a third cut that circumferentially extends to a surface of the PMB; wherein: the second cut and the third cut are completed within 15 seconds.

An embodiment wherein the TDP comprises: a first cut that defines a posterior surface of a lenticule within the PMB; a second cut that defines an anterior surface of the PMB; and a third cut that circumferentially extends to a surface of the PMB; wherein: the first cut, the second cut, and the third cut are completed within 15 seconds.

An embodiment wherein the first cut is spherically shaped.

An embodiment wherein the first cut is aspherically shaped.

An embodiment wherein the first cut is cylindrically shaped.

An embodiment wherein the first cut is multifocally shaped.

An embodiment wherein the second cut is spherically shaped.

An embodiment wherein the second cut is aspherically shaped.

An embodiment wherein the second cut is cylindrically shaped.

An embodiment wherein the second cut is multifocally shaped.

An embodiment wherein the PMB is oriented by a PMB positioning table (PMT) configured to permit repositioning of the PMB with respect to the FLB under control of the CCD.

An embodiment wherein the PMT is configured to reposition the PMB under control of the CCD to form one or more haptic members on the PMB using the FLB.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system/method allowing intraocular lens (IOL) fabrication using a femtosecond laser has been disclosed. The system and method generate a stream of pulses at a rate of at least 0.1 million pulses per second and a pulse length of 400 femtoseconds or less to sculpt a polymeric material blank (PMB) to form an IOL. The high repetition rate and short pulse length combine to permit IOL fabrication in less than 10 minutes. During this fabrication procedure a lens may be formed within the IOL by incorporating a refractive index shaping (RIS) structure within the IOL. Additionally, IOL haptics may be formed during this IOL formation process. This combination of physical feature generation and RIS structure generation permits per-patient customization of the IOL as it relates to sphere, cylinder, asphericity, multifocality, and/or higher optical aberrations (HOAs).

CLAIMS INTERPRETATION

The following rules apply when interpreting the CLAIMS of the present invention:

The CLAIM PREAMBLE should be considered as limiting the scope of the claimed invention.

"WHEREIN" clauses should be considered as limiting the scope of the claimed invention.

"WHEREBY" clauses should be considered as limiting the scope of the claimed invention.

"ADAPTED TO" clauses should be considered as limiting the scope of the claimed invention.

"ADAPTED FOR" clauses should be considered as limiting the scope of the claimed invention.

The term "MEANS" specifically invokes the means-plus-function claims limitation recited in 35 U.S.C. §112(f) and such claim shall be construed to cover the corresponding structure, material, or acts described in the specification and equivalents thereof.

The phrase "MEANS FOR" specifically invokes the means-plus-function claims limitation recited in 35 U.S.C. §112(f) and such claim shall be construed to cover the corresponding structure, material, or acts described in the specification and equivalents thereof.

The phrase "STEP FOR" specifically invokes the step-plus-function claims limitation recited in 35 U.S.C. §112(f) and such claim shall be construed to cover the corresponding structure, material, or acts described in the specification and equivalents thereof.

The step-plus-function claims limitation recited in 35 U.S.C. §112(f) shall be construed to cover the corresponding structure, material, or acts described in the specification and equivalents thereof ONLY for such claims including the phrases "MEANS FOR", "MEANS", or "STEP FOR".

The phrase "AND/OR" in the context of an expression "X and/or Y" should be interpreted to define the set of "(X and Y)" in union with the set "(X or Y)" as interpreted by Ex Parte Gross (USPTO Patent Trial and Appeal Board, Appeal 2011-004811, Ser. No. 11/565,411, ("'and/or' covers embodiments having element A alone, B alone, or elements A and B taken together").

The claims presented herein are to be interpreted in light of the specification and drawings presented herein with sufficiently narrow scope such as to not preempt any abstract idea.

The claims presented herein are to be interpreted in light of the specification and drawings presented herein with sufficiently narrow scope such as to not preclude every application of any idea.

The claims presented herein are to be interpreted in light of the specification and drawings presented herein with sufficiently narrow scope such as to preclude any basic mental process that could be performed entirely in the human mind.

The claims presented herein are to be interpreted in light of the specification and drawings presented herein with sufficiently narrow scope such as to preclude any process that could be performed entirely by human manual effort.

What is claimed is:

1. An intraocular lens (IOL) formation system comprising:
    (a) pulsed laser source (PLS);
    (b) acoustic-optical modulator (AOM);
    (c) focusing laser optics (FLO);
    (d) laser scanning device (LSD); and
    (e) computing control device (CCD);
    wherein:
    said PLS is configured to emit a pulsed laser radiation (PLR) output at a repetition rate of at least 0.1 million pulses per second;
    said PLS is configured to emit said PLR output with a pulse-width of 900 femtoseconds or less;
    said AOM is configured to control the pulse energy and pulse repetition rate of said PLS;
    said FLO is configured to receive said PLR and produce a focused pulsed laser beam (FLB);
    said LSD is configured to receive said FLB and scan said FLB in three dimensions, two dimensions using a scan system and the third dimension using a Z stage;
    said LSD is numerically controlled by said CCD to generate a three-dimensional cutting pattern (TDP) using said PLS on a polymeric material blank (PMB) that is impinged by said FLB; and
    said PLS is configured by said CCD to generate said TDP using at least 7.5 million focused laser pulses within 5 minutes.

2. The intraocular lens (IOL) formation system of claim 1 wherein said PLS has a wavelength of less than 550 nm or at least 1000 nm.

3. The intraocular lens (IOL) formation system of claim 1 wherein said PLS has a pulse length of 400 femtoseconds or less.

4. The intraocular lens (IOL) formation system of claim 1 wherein said PLS has a repetition rate of at least 100000 pulses per second.

5. The intraocular lens (IOL) formation system of claim 1 wherein said PLS has a pulse energy of at least 1.0 µJ.

6. The intraocular lens (IOL) formation system of claim 1 wherein said PLS has a pulse peak power of at least 5 MW.

7. The intraocular lens (IOL) formation system of claim 1 wherein said PLS has a beam quality factor $M^2$ of 1.2 or less.

8. The intraocular lens (IOL) formation system of claim 1 wherein said FLO has a numerical aperture NA of NA=0.13 or greater.

9. The intraocular lens (IOL) formation system of claim 1 wherein said FLB has a focal diameter of 4.0 µm or less.

10. The intraocular lens (IOL) formation system of claim 1 wherein said FLB has a depth of focus of 2 µm or more.

11. The intraocular lens (IOL) formation system of claim 1 wherein said FLB has a pulse energy of at least 5.0 µJ.

12. The intraocular lens (IOL) formation system of claim 1 wherein said TDP comprises:
    (a) a first cut that defines a posterior surface of a lenticule within said PMB;
    wherein:
    said first cut is completed within 15 seconds.

13. The intraocular lens (IOL) formation system of claim 1 wherein said TDP comprises:
    (a) a first cut that defines a posterior surface of a lenticule within said PMB; and
    (b) a second cut that defines an anterior surface of said PMB;
    wherein:
    said first cut and said second cut are completed within 15 seconds.

14. The intraocular lens (IOL) formation system of claim 1 wherein said TDP comprises:
    (a) a second cut that defines an anterior surface of said PMB; and
    (b) a third cut that circumferentially extends to a surface of said PMB;
    wherein:
    said second cut and said third cut are completed within 15 seconds.

15. The intraocular lens (IOL) formation system of claim 1 wherein said TDP comprises:
    (a) a first cut that defines a posterior surface of a lenticule within said PMB;
    (b) a second cut that defines an anterior surface of said PMB; and
    (c) a third cut that circumferentially extends to a surface of said PMB;
    wherein:
    said first cut, said second cut, and said third cut are completed within 15 seconds.

16. The intraocular lens (IOL) formation system of claim 1 wherein said first cut is spherically shaped.

17. The intraocular lens (IOL) formation system of claim 1 wherein said first cut is aspherically shaped.

18. The intraocular lens (IOL) formation system of claim 1 wherein said first cut is cylindrically shaped.

19. The intraocular lens (IOL) formation system of claim 1 wherein said first cut is multifocally shaped.

20. The intraocular lens (IOL) formation system of claim 1 wherein said second cut is spherically shaped.

21. The intraocular lens (IOL) formation system of claim 1 wherein said second cut is aspherically shaped.

22. The intraocular lens (IOL) formation system of claim 1 wherein said second cut is cylindrically shaped.

23. The intraocular lens (IOL) formation system of claim 1 wherein said second cut is multifocally shaped.

24. The intraocular lens (IOL) formation system of claim 1 wherein said PMB is oriented by a PMB positioning table (PMT) configured to permit repositioning of said PMB with respect to said FLB under control of said CCD.

25. The intraocular lens (IOL) formation system of claim 24 wherein said PMT is configured to reposition said PMB under control of said CCD to form one or more haptic members on said PMB using said FLB.

26. An intraocular lens (IOL) formation method comprising:
(1) generating pulsed laser radiation (PLR) output from a pulsed laser source (PLS);
(2) controlling the pulse energy and pulse repetition rate of said PLS with an acoustic-optical modulator (AOM);
(3) receiving said PLR with focusing laser optics (FLO) and producing a focused pulsed laser beam (FLB);
(4) receiving said FLB with a laser scanning device (LSD) and scanning said FLB in three dimensions;
(5) numerically controlling said LSD with a computing control device (CCD) to generate a three-dimensional cutting pattern (TDP) using said PLS on a polymeric material blank (PMB) that is impinged by said FLB; and
(6) sculpting said PMB using said TDP to form an intraocular lens (IOL);
wherein:
said PLS is configured to emit said PLR output at a repetition rate of at least 0.1 million pulses per second;
said PLS is configured to emit said PLR output with a pulse-width of 400 femtoseconds or less;
said PLS is configured by said CCD to generate said TDP using at least 7.5 million focused laser pulses within 5 minutes; and
said IOL comprises an anterior surface, a posterior surface, and one or more haptics.

27. The intraocular lens (IOL) formation method of claim 26 wherein said PLS has a wavelength of at least 500 nm/1000 nm.

28. The intraocular lens (IOL) formation method of claim 26 wherein said PLS has a pulse length of 400 femtoseconds or less.

29. The intraocular lens (IOL) formation method of claim 26 wherein said PLS has a repetition rate of at least 100000 pulses per second.

30. The intraocular lens (IOL) formation method of claim 26 wherein said PLS has a pulse energy of at least 1.0 μJ.

31. The intraocular lens (IOL) formation method of claim 26 wherein said PLS has a pulse peak power of at least 5 MW.

32. The intraocular lens (IOL) formation method of claim 26 wherein said PLS has a beam quality factor $M^2$ of 1.2 or less.

33. The intraocular lens (IOL) formation method of claim 26 wherein said FLO has a numerical aperture NA of NA=0.13 or greater.

34. The intraocular lens (IOL) formation method of claim 26 wherein said FLB has a focal diameter of 3.0 μm or less.

35. The intraocular lens (IOL) formation method of claim 26 wherein said FLB has a depth of focus of 15 μm or less.

36. The intraocular lens (IOL) formation method of claim 26 wherein said FLB has a pulse energy of at least 5.0 μJ.

37. The intraocular lens (IOL) formation method of claim 26 wherein said TDP comprises:
(a) a first cut that defines a posterior surface of a lenticule within said PMB;
wherein:
said first cut is completed within 15 seconds.

38. The intraocular lens (IOL) formation method of claim 26 wherein said TDP comprises:
(a) a first cut that defines a posterior surface of a lenticule within said PMB; and
(b) a second cut that defines an anterior surface of said PMB;
wherein:
said first cut and said second cut are completed within 15 seconds.

39. The intraocular lens (IOL) formation method of claim 26 wherein said TDP comprises:
(a) a second cut that defines an anterior surface of said PMB; and
(b) a third cut that circumferentially extends to a surface of said PMB;
wherein:
said second cut and said third cut are completed within 15 seconds.

40. The intraocular lens (IOL) formation method of claim 26 wherein said TDP comprises:
(a) a first cut that defines a posterior surface of a lenticule within said PMB;
(b) a second cut that defines an anterior surface of said PMB; and
(c) a third cut that circumferentially extends to a surface of said PMB;
wherein:
said first cut, said second cut, and said third cut are completed within 15 seconds.

41. The intraocular lens (IOL) formation method of claim 26 wherein said first cut is spherically shaped.

42. The intraocular lens (IOL) formation method of claim 26 wherein said first cut is aspherically shaped.

43. The intraocular lens (IOL) formation method of claim 26 wherein said first cut is cylindrically shaped.

44. The intraocular lens (IOL) formation method of claim 26 wherein said first cut is multifocally shaped.

45. The intraocular lens (IOL) formation method of claim 26 wherein said second cut is spherically shaped.

46. The intraocular lens (IOL) formation method of claim 26 wherein said second cut is aspherically shaped.

47. The intraocular lens (IOL) formation method of claim 26 wherein said second cut is cylindrically shaped.

48. The intraocular lens (IOL) formation method of claim 26 wherein said second cut is multifocally shaped.

49. The intraocular lens (IOL) formation method of claim 26 wherein said PMB is oriented by a PMB positioning table (PMT) configured to permit repositioning of said PMB with respect to said FLB under control of said CCD.

50. The intraocular lens (IOL) formation method of claim 49 wherein said PMT is configured to reposition said PMB under control of said CCD to form one or more haptic members on said PMB using said FLB.

51. An intraocular lens (IOL) formation system comprising:
(a) pulsed laser source (PLS);
(b) acoustic-optical modulator (AOM);
(c) focusing laser optics (FLO);
(d) laser scanning device (LSD); and
(e) computing control device (CCD);
wherein:
said PLS is configured to emit a pulsed laser radiation (PLR) output at a repetition rate of at least 0.1 million pulses per second;

said PLS is configured to emit said PLR output with a pulse-width of 400 femtoseconds or less;

said AOM is configured to control the pulse energy and pulse repetition rate of said PLS;

said FLO is configured to receive said PLR and produce a focused pulsed laser beam (FLB);

said LSD is configured to receive said FLB and scan said FLB in three dimensions;

said LSD is numerically controlled by said CCD to generate a three-dimensional cutting pattern (TDP) on a polymeric material blank (PMB) that is impinged by said FLB;

said PLS is configured by said CCD to generate said TDP using at least 5 million focused laser pulses within 5 minutes;

said LSD is numerically controlled by said CCD to form a refractive index shape (RIS) lens within said PMB by modifying the refractive index within said PMB using said PLS.

52. The intraocular lens (IOL) formation system of claim 51 wherein said PLS has a wavelength of at least 500 nm.

53. The intraocular lens (IOL) formation system of claim 51 wherein said PLS has a pulse length of 150 femtoseconds or less.

54. The intraocular lens (IOL) formation system of claim 51 wherein said PLS has a repetition rate of at least 100000 pulses per second.

55. The intraocular lens (IOL) formation system of claim 51 wherein said PLS has a pulse energy of at least 0.1 µJ.

56. The intraocular lens (IOL) formation system of claim 51 wherein said PLS has a pulse peak power of at least 10 MW.

57. The intraocular lens (IOL) formation system of claim 51 wherein said PLS has a beam quality factor $M^2$ of 1.2 or less.

58. The intraocular lens (IOL) formation system of claim 51 wherein said FLO has a numerical aperture NA of NA=0.13 or greater.

59. The intraocular lens (IOL) formation system of claim 51 wherein said FLB has a focal diameter of 3.0 µm or less.

60. The intraocular lens (IOL) formation system of claim 51 wherein said FLB has a depth of focus of 15 µm or less.

61. The intraocular lens (IOL) formation system of claim 51 wherein said FLB has a pulse energy of 0.5 µJ or less.

62. The intraocular lens (IOL) formation system of claim 51 wherein said TDP comprises:
(a) a first cut that defines a posterior surface of a lenticule within said PMB;
wherein:
said first cut is completed within 15 seconds.

63. The intraocular lens (IOL) formation system of claim 51 wherein said TDP comprises:
(a) a first cut that defines a posterior surface of a lenticule within said PMB; and
(b) a second cut that defines an anterior surface of said PMB;
wherein:
said first cut and said second cut are completed within 15 seconds.

64. The intraocular lens (IOL) formation system of claim 51 wherein said TDP comprises:
(a) a second cut that defines an anterior surface of said PMB; and
(b) a third cut that circumferentially extends to a surface of said PMB;
wherein:
said second cut and said third cut are completed within 15 seconds.

65. The intraocular lens (IOL) formation system of claim 51 wherein said TDP comprises:
(a) a first cut that defines a posterior surface of a lenticule within said PMB;
(b) a second cut that defines an anterior surface of said PMB; and
(c) a third cut that circumferentially extends to a surface of said PMB;
wherein:
said first cut, said second cut, and said third cut are completed within 15 seconds.

66. The intraocular lens (IOL) formation system of claim 51 wherein said first cut is spherically shaped.

67. The intraocular lens (IOL) formation system of claim 51 wherein said first cut is aspherically shaped.

68. The intraocular lens (IOL) formation system of claim 51 wherein said first cut is cylindrically shaped.

69. The intraocular lens (IOL) formation system of claim 51 wherein said first cut is multifocally shaped.

70. The intraocular lens (IOL) formation system of claim 51 wherein said second cut is spherically shaped.

71. The intraocular lens (IOL) formation system of claim 51 wherein said second cut is aspherically shaped.

72. The intraocular lens (IOL) formation system of claim 51 wherein said second cut is cylindrically shaped.

73. The intraocular lens (IOL) formation system of claim 51 wherein said second cut is multifocally shaped.

74. The intraocular lens (IOL) formation system of claim 51 wherein said PMB is oriented by a PMB positioning table (PMT) configured to permit repositioning of said PMB with respect to said FLB under control of said CCD.

75. The intraocular lens (IOL) formation system of claim 74 wherein said PMT is configured to reposition said PMB under control of said CCD to form one or more haptic members on said PMB using said FLB.

76. An intraocular lens (IOL) formation method comprising:
(1) generating pulsed laser radiation (PLR) output from a pulsed laser source (PLS);
(2) controlling the pulse energy and pulse repetition rate of said PLS with an acousto-optical modulator (AOM);
(3) receiving said PLR with focusing laser optics (FLO) and producing a focused pulsed laser beam (FLB);
(4) receiving said FLB with a laser scanning device (LSD) and scanning said FLB in three dimensions;
(5) numerically controlling said LSD with a computing control device (CCD) to generate a three-dimensional cutting pattern (TDP) using said PLS on a polymeric material blank (PMB) that is impinged by said FLB;
(6) sculpting said PMB using said TDP to form an intraocular lens (IOL); and
(7) numerically controlling said LSD by said CCD to form a refractive index shape (RIS) lens within said PMB by modifying the refractive index within said PMB using said PLS;
wherein:
said PLS is configured to emit said PLR output at a repetition rate of at least 1 million pulses per second;
said PLS is configured to emit said PLR output with a pulse-width of 300 femtoseconds or less;
said PLS is configured by said CCD to generate said TDP using at least 5 million focused laser pulses within 5 minutes; and
said IOL comprises an anterior surface, a posterior surface, and one or more haptics.

77. The intraocular lens (IOL) formation method of claim 76 wherein said PLS has a wavelength of at least 1000 nm.

78. The intraocular lens (IOL) formation method of claim 76 wherein said PLS has a pulse length of 200 femtoseconds or less.

79. The intraocular lens (IOL) formation method of claim 76 wherein said PLS has a repetition rate of at least 1000000 pulses per second.

80. The intraocular lens (IOL) formation method of claim 76 wherein said PLS has a pulse energy of at least 1.0 µJ.

81. The intraocular lens (IOL) formation method of claim 76 wherein said PLS has a pulse peak power of at least 5 MW.

82. The intraocular lens (IOL) formation method of claim 76 wherein said PLS has a beam quality factor $M^2$ of 1.2 or less.

83. The intraocular lens (IOL) formation method of claim 76 wherein said FLO has a numerical aperture NA of NA=0.13 or greater.

84. The intraocular lens (IOL) formation method of claim 76 wherein said FLB has a focal diameter of 3.0 µm or less.

85. The intraocular lens (IOL) formation method of claim 76 wherein said FLB has a depth of focus of 15 µm or less.

86. The intraocular lens (IOL) formation method of claim 76 wherein said FLB has a pulse energy of at least 5.0 µJ.

87. The intraocular lens (IOL) formation method of claim 76 wherein said TDP comprises:
  (a) a first cut that defines a posterior surface of a lenticule within said PMB;
  wherein:
  said first cut is completed within 15 seconds.

88. The intraocular lens (IOL) formation method of claim 76 wherein said TDP comprises:
  (a) a first cut that defines a posterior surface of a lenticule within said PMB; and
  (b) a second cut that defines an anterior surface of said PMB;
  wherein:
  said first cut and said second cut are completed within 15 seconds.

89. The intraocular lens (IOL) formation method of claim 76 wherein said TDP comprises:
  (a) a second cut that defines an anterior surface of said PMB; and
  (b) a third cut that circumferentially extends to a surface of said PMB;
  wherein:
  said second cut and said third cut are completed within 15 seconds.

90. The intraocular lens (IOL) formation method of claim 76 wherein said TDP comprises:
  (a) a first cut that defines a posterior surface of a lenticule within said PMB;
  (b) a second cut that defines an anterior surface of said PMB; and
  (c) a third cut that circumferentially extends to a surface of said PMB;
  wherein:
  said first cut, said second cut, and said third cut are completed within 15 seconds.

91. The intraocular lens (IOL) formation method of claim 76 wherein said first cut is spherically shaped.

92. The intraocular lens (IOL) formation method of claim 76 wherein said first cut is aspherically shaped.

93. The intraocular lens (IOL) formation method of claim 76 wherein said first cut is cylindrically shaped.

94. The intraocular lens (IOL) formation method of claim 76 wherein said first cut is multifocally shaped.

95. The intraocular lens (IOL) formation method of claim 76 wherein said second cut is spherically shaped.

96. The intraocular lens (IOL) formation method of claim 76 wherein said second cut is aspherically shaped.

97. The intraocular lens (IOL) formation method of claim 76 wherein said second cut is cylindrically shaped.

98. The intraocular lens (IOL) formation method of claim 76 wherein said second cut is multifocally shaped.

99. The intraocular lens (IOL) formation method of claim 76 wherein said PMB is oriented by a PMB positioning table (PMT) configured to permit repositioning of said PMB with respect to said FLB under control of said CCD.

100. The intraocular lens (IOL) formation method of claim 99 wherein said PMT is configured to reposition said PMB under control of said CCD to form one or more haptic members on said PMB using said FLB.

* * * * *